United States Patent [19]
Kim et al.

[11] Patent Number: 5,766,840
[45] Date of Patent: Jun. 16, 1998

[54] HEPATITIS G VIRUS AND MOLECULAR CLONING THEREOF

[75] Inventors: Jungsuh P. Kim; Kirk E. Fry; LaVonne Marie Young, all of Palo Alto; Jeffrey M. Linnen, Foster City, all of Calif.; John Wages, Corvallis, Oreg.

[73] Assignee: Genelabs Technologies, Inc., Redwood City, Calif.

[21] Appl. No.: 466,033

[22] Filed: Jun. 5, 1995

Related U.S. Application Data

[60] Division of Ser. No. 444,733, May 19, 1995, and a continuation-in-part of Ser. No. 389,886, Feb. 15, 1995, abandoned, which is a continuation-in-part of Ser. No. 357,509, Dec. 16, 1994, abandoned, which is a continuation-in-part of Ser. No. 329,729, Oct. 26, 1994, abandoned, which is a continuation-in-part of Ser. No. 285,558, Aug. 3, 1994, abandoned, and Ser. No. 285,543, Aug. 3, 1994, abandoned, which is a continuation-in-part of Ser. No. 246,985, May 20, 1994, abandoned, said Ser. No. 285,558, is a continuation-in-part of Ser. No. 246,985, said Ser. No. 444,733, is a continuation-in-part of Ser. No. 344,271, Nov. 23, 1994, abandoned, which is a continuation-in-part of Ser. No. 285,561, Aug. 3, 1994, abandoned, which is a continuation-in-part of Ser. No. 246,985.

[51] Int. Cl.$^6$ ............................ C12Q 1/70; C07K 16/10
[52] U.S. Cl. ...................... 435/5; 530/388.3; 530/389.4
[58] Field of Search .......................... 530/388.3, 387.1, 530/389.4; 435/5, 69.3

[56] References Cited

U.S. PATENT DOCUMENTS

| | | | |
|---|---|---|---|
| 4,870,026 | 9/1989 | Wands et al. | 436/548 |
| 5,032,511 | 7/1991 | Takahashi et al. | 435/69.1 |
| 5,077,193 | 12/1991 | Mishiro et al. | 435/5 |
| 5,218,099 | 6/1993 | Reyes et al. | 536/23.72 |
| 5,275,947 | 1/1994 | Arima et al. | 435/252.33 |
| 5,308,750 | 5/1994 | Mehta et al. | 435/5 |
| 5,486,473 | 1/1996 | Fujita et al. | 435/240.2 |

FOREIGN PATENT DOCUMENTS

| | | |
|---|---|---|
| 0 318 216 | 5/1989 | European Pat. Off. . |
| 0 363 025 | 4/1990 | European Pat. Off. . |
| WO 90/00597 | 1/1990 | WIPO . |
| WO 91/06562 | 5/1991 | WIPO . |
| WO 91/15003 | 10/1991 | WIPO . |
| WO 94/18217 | 8/1994 | WIPO . |
| WO 95/21922 | 8/1995 | WIPO . |

OTHER PUBLICATIONS

Murphy, F.A., "Virus Taxonomy" pp. 15–57 in Fields Virology, Third Edition, vol. 1, Lippincott–Raven, Philadelphia 1996.

Bradley, D.W., et al., "Posttransfusion Non–A, Non–B Hepatitis: Physicochemical Properties of Two Distinct Agents," *The Journal of Infectious Diseases* 148(2):254–265 (1983).

Buti, M., et al., "Non–A, Non–B, Non–C, Non–E Acute Hepatitis: Does It Really Exist?" *Journal of Hepatology, The Journal of the European Association for the Study of the Liver*, in Abstracts of the 28th Annual Meeting of the European Association for the Study of the Liver, 1–4 Sep. 1993, Paris, France, 18(Suppl 1):S25 (1993).

Chan, S.W., et al., "Analysis of a new hepatitis C virus type and its phylogenetic relationship to existing variants," *Journal of General Virology*, 73(5):1131–1141 (1992).

Choo, Q–L., et al., "Isolation of a cDNA Clone Derived from a Blood–Borne Non–A, Non–B Viral Hepatitis Genome," *Science*, 244:359–362 (1989).

Jiang, X., et al., "Norwalk Virus Genome Cloning and Characterization," *Science*, 250:1580–1583 (1990).

Jones, W.F., et al., "The Role of Hepatitis C Virus (HCV) and Hepatitis E Virus (HEV) in ACute Hepatitis: Evidence for a Non–A,B,C,D,E Syndrome," *The American Association for the Study of Liver Diseases*, 16(2 Pt. 2):77A (1992).

Karayiannis, P., et al., "Studies of GB Hepatitis Agent in Tamarins," *Hepatology*, 9(2):186–192 (1989).

Matsui, S.M., et al., "The Isolation and Characterization of a Norwalk Virus–specific cDNA," *J. Clin. Invest.*, 87:1456–1461 (1991).

Matsuura, Y., et al., "Expression of the S–coded Genes of Lymphocytic Choriomeningitis Arenavirus using a Baculovirus Vector," *J. Gen. Virol.*, 67:1515–1529 (1986).

Overton, H.A., et al., "Identification of the N and $NS_s$ Proteins Coded by the Ambisense S RNA of Punta Toro Phlebovirus Using Monospecific Antisera Raised to Baculovirus Expressed N and NSs Proteins," *Virology*, 157:338–350 (1987).

Reyes, G.R., et al., "Molecular Biology of Non–A, Non–B Hepatitis C and Hepatitis E Viruses," *Advances in Virus Research*, 40:57–103 (1991).

Reyes, G.R., "New Strategies for Isolation of Low Abundance Viral and Host cDNAs: Application to Cloning of the Hepatitis E Virus and Analysis of Tissue–Specific Transcription," *Seminars in Liver Disease*, 12(3):289–300 (1992).

Reyes, G.R., et al., "Hepatitis E virus (HEV): epitope mapping and detection of strain variation," in Viral Hepatitus C, D, and E. Proceedings of the International Meeting on Non–A, Non–B Hepatitus, Tokyo, 27–30 Sep. 1989, T. Shikata, et al., eds. Elsevier Science Publishers, Amsterdam, NL, Chapter 43:237–245 (1989).

*Primary Examiner*—Marian C. Knode
*Assistant Examiner*—Brenda Glass Brumback
*Attorney, Agent, or Firm*—Gary R. Fabian; Susan T. Evans; Peter J. Dehlinger

[57] ABSTRACT

Polypeptide antigens are disclosed which are immunoreactive with sera from individuals having a non-A, non-B, non-C, non-D, non-E Hepatitis, herein designated Hepatitis G Virus (HGV). Corresponding genomic-fragment clones containing polynucleotides encoding the open reading frame sequences for the antigenic polypeptides are taught. The antigens are useful in diagnostic methods for detecting the presence of HGV in test subjects. The antigens are also useful in vaccine and antibody preparations. In addition, the entire coding sequences of two HGV isolates are disclosed. Methods are presented for nucleic acid-based detection of HGV in samples and also methods for the isolation of further genomic sequences corresponding to HGV.

12 Claims, 17 Drawing Sheets

```
                                         10        20        30
                                                 *....*
HGV                                 lweskktpcaicvDatcfDssiteedvalet
                                     :.  ..: :.. :.. .:. .:.:.:.: .
HoCV   ykwvkqkpvvipgyegktplfqifdkvkkewdqfqnpvavsfDtkawDdtqvttndlelik
           3490      3500      3510      3520      3530      3540

40        50        60        70        80
                                                *.**...*...*
HGV    el--yalasdhpewvrapgkyyasgtmvtpegvpvgerycRsSGvltTsasNc-ltcyik
       ..  :  .  ..  ....  .  ...  ..  ...:..:     .  :.::  .:::.:. :.  ..
HoCV   diqkyyfkkkwhkfidtltmhmsevpvitadgevyirkgqRgSGqpdTsagNsmlnvltm
           3550      3560      3570      3580      3590      3600

90             100       110       120       130       140
                                ***
HGV    vkaacervgl------knvslliaGDDcliicerpvcdpsdalgralasygyacepsyha
       : : :: .:.       . ... . ::: ..: ::..
HoCV   vyafceatgvpyksfdrvakihvcGDDgfliteralgekfaskgvqilyeagkpqkiteg
           3610      3620      3630      3640      3650      3660
```

Fig. 5A

```
                                                    10        20        30
                                                         *....*
HGV                                   lweskktpcaicvDatcfDssiteedvalet
                                       :.:::.: ... :. :::::..::.:. .:.
HCV   vvstlpqvvmgssygfqyspggrveflvntwkskknpmgfsyDtrcfDstvtendirvee
      2600      2610      2620      2630      2640      2650

40        50        60        70        80
                                                  *.**...*...*
HGV   elya---lasdhpewvra-pgkyyasgtmvtpegvpvgerycRsSGvltTsasNcltcyi
      ..:.   :::.. .. ... ... : .:......:   : : ::.::::::: .: ::::.
HCV   siyqccdlapearqaikslterlyiggpltnskggncgyrrcRaSGvltTscgNtltcyl
      2660      2670      2680      2690      2700      2710

90       100       110       120       130       140
                         ***
HGV   kvkaacervglknvslliaGDDcliicerpvcdpsdalgralasygyacepsyhasldta
      :..:::  . :.. ..:..::: ..:::..  . ..:  :....
HCV   kasaacraaklqdctmlvnGDDlvvicesagtqedaaslrvfteamtrysappgdppqpe
      2720      2730      2740      2750      2760      2770
```

Fig. 5B

```
              Thrombin cleavage
   sj26          |  \/  |     |GE3-2----------------------->
    K  S  D  L  V  P  R  G  S  M  V  S  W  D  A  D  A  R  A  P
    *        *        *        *        *        *        *
    1        11       21       31       41       51
   CAAAATCGGATCTGGTTCCGCGTGGTTCCATGGTCTCATGGGACGCGGACGCTCGTGCGC
                                C^CATGG(NcoI)

---------------------------------------------------------->
     A  M  V  Y  G  P  G  Q  S  V  T  I  D  G  E  R  Y  T  L  P
     *        *        *        *        *        *
    61       71       81       91       101      111
   CCGCGATGGTCTATGGCCCTGGGCAAAGTGTTACCATTGACGGGGAGCGCTACACCTTGC
       ^Base mutated to remove NcoI site        AGC^GCT(Eco47III)

---------------------------------------------------------->
      H  Q  L  R  L  R  N  V  A  P  S  E  V  S  S  E  V  S  I  D
      *        *        *        *        *        *
     121      131      141      151      161      171
   CTCATCAACTGAGGCTCAGGAATGTGGCACCCTCTGAGGTTTCATCCGAGGTGTCCATTG

---------------------------------------------------------->
      I  G  T  E  T  E  D  S  E  L  T  E  A  D  L  P  P  A  A  A
      *        *        *        *        *        *
     181      191      201      211      221      231
   ACATTGGGACGGAGACTGAAGACTCAGAACTGACTGAGGCCGATCTGCCGCCGGCGGCTG
                 CTGAAG(Eco57I_16/14->)               GCC^GGC(NaeI)
      CTTCAG(<-14/16_Eco57I)

---------------------------------------------------------->
      A  L  Q  A  I  E  N  A  A  R  I  L  E  P  H  I  D  V  I  M
      *        *        *        *        *        *
     241      251      261      271      281      291
   CTGCTCTCCAAGCGATCGAGAATGCTGCGAGGATTCTTGAACCGCACATTGATGTCATCA
                     CGAT^CG(PvuI)
           GAATGCN^(BsmI)

---------------------------------------------------------->
      E  D  C  S  T  P  S  L  C  G  S  S  R  E  M  P  V  W  G  E
      *        *        *        *        *        *
     301      311      321      331      341      351
   TGGAGGACTGCAGTACACCCTCTCTTTGTGGTAGTAGCCGAGAGATGCCTGTATGGGGAG
            CTGCA^G(PstI)

-------------------END-GE3-2>|         poly His for IMAC
      D  I  P  R  T  P  S  P  A  L  I  G  S  H  H  H  H  H  Z   <-----NOTE
      *        *        *        *        *        *
     361      371      381      391      401      411
   AAGACATCCCCCGTACTCCATCGCCAGCACTTATCGGATCCCACCATCACCATCACCATT
                                         G^GATCC(BamHI)

|pGEX---------------------->
      N  S  S  Z  L  T  D  D  L  P
      *        *        *        *
     421      431      441      451
   AGAATTCATCGTGACTGACTGACGATCTACCT                 Fig. 6
      G^AATTC(EcoRI)
```

Fig. 10B        Fig. 10D        Fig. 10F
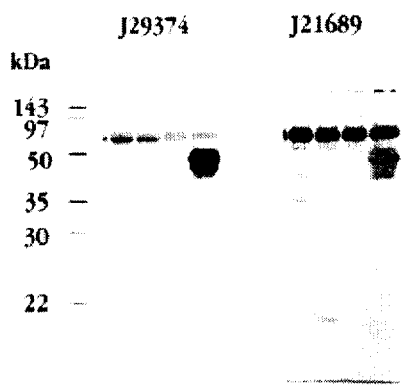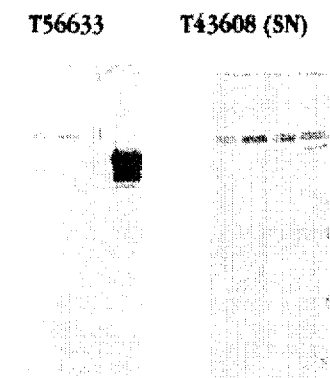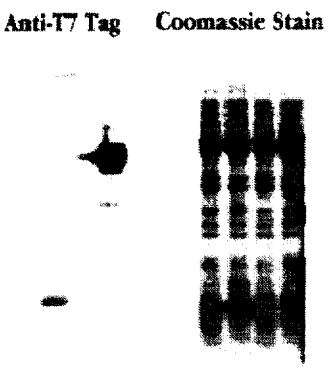
Fig. 10A        Fig. 10C        Fig. 10E

Fig. 14A   Fig. 14B   Fig. 14C   Fig. 14D

Fig. 15B  Fig. 15D
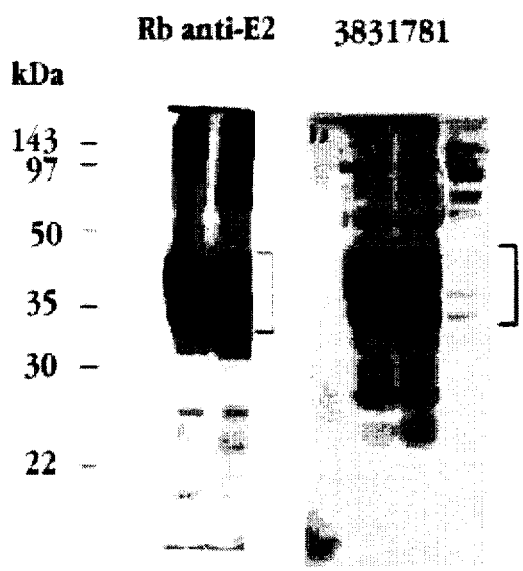
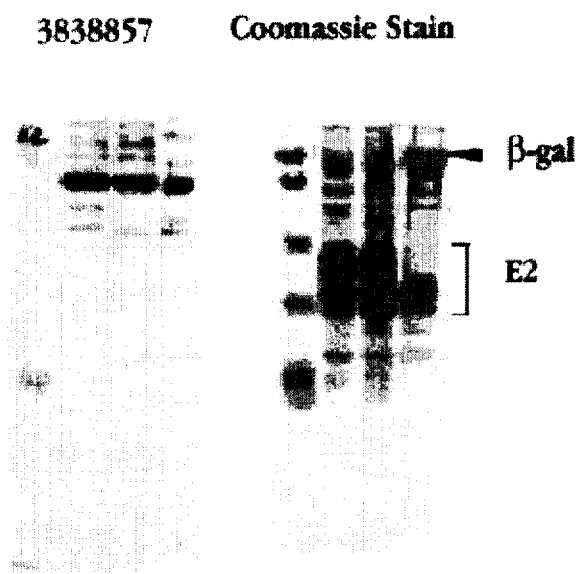
Fig. 15A  Fig. 15C

SEQUENCE LISTING ( 1 ) GENERAL INFORMATION:

( i i i ) NUMBER OF SEQUENCES: 277

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: SISPA primer, top strand Linker AB ( x i ) SEQUENCE DESCRIPTION: SEQ ID NO:1:

GGAATTCGCG GCCGCTCG         18

( 2 ) INFORMATION FOR SEQ ID NO:2:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (iii) HYPOTHETICAL: NO (vi) ORIGINAL SOURCE:
    (C) INDIVIDUAL ISOLATE: Linker AB, bottom strand (xi) SEQUENCE DESCRIPTION: SEQ ID NO:2:

```
CGAGCGGCCG CGAATTCCTT                                                       20
```

(2) INFORMATION FOR SEQ ID NO:3:

(i) SEQUENCE CHARACTERISTICS:
        (A) LENGTH: 237 base pairs
        (B) TYPE: nucleic acid
        (C) STRANDEDNESS: double
        (D) TOPOLOGY: linear (ii) MOLECULE TYPE: DNA (iii) HYPOTHETICAL: NO (vi) ORIGINAL SOURCE:
        (C) INDIVIDUAL ISOLATE: PNF 2161 CLONE 470-20-1

(ix) FEATURE:
        (A) NAME/KEY: CDS
        (B) LOCATION: 1..237

(xi) SEQUENCE DESCRIPTION: SEQ ID NO:3:

```
GAA  TTC  GCG  GCC  GCT  CGG  GCT  GTC  TCG  GAC  TCT  TGG  ATG  ACC  TCG  AAT        48
Glu  Phe  Ala  Ala  Ala  Arg  Ala  Val  Ser  Asp  Ser  Trp  Met  Thr  Ser  Asn
 1              5                        10                       15

GAG  TCA  GAG  GAC  GGG  GTA  TCC  TCC  TGC  GAG  GAG  GAC  ACC  GGC  GGG  GTC        96
Glu  Ser  Glu  Asp  Gly  Val  Ser  Ser  Cys  Glu  Glu  Asp  Thr  Gly  Gly  Val
                 20                       25                       30

TTC  TCA  TCT  GAG  CTG  CTC  TCA  GTA  ACC  GAG  ATA  AGT  GCT  GGC  GAT  GGA       144
Phe  Ser  Ser  Glu  Leu  Leu  Ser  Val  Thr  Glu  Ile  Ser  Ala  Gly  Asp  Gly
            35                       40                       45

GTA  CGG  GGG  ATG  TCT  TCT  CCC  CAT  ACA  GGC  ATC  TCT  CGG  CTA  CTA  CCA       192
Val  Arg  Gly  Met  Ser  Ser  Pro  His  Thr  Gly  Ile  Ser  Arg  Leu  Leu  Pro
       50                       55                       60

CAA  AGA  GAG  GGT  GTA  CTG  CAG  TCC  TCC  ACG  AGC  GGC  CGC  GAA  TTC            237
Gln  Arg  Glu  Gly  Val  Leu  Gln  Ser  Ser  Thr  Ser  Gly  Arg  Glu  Phe
 65                       70                       75
```

(2) INFORMATION FOR SEQ ID NO:4:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO:4:

```
Glu  Phe  Ala  Ala  Ala  Arg  Ala  Val  Ser  Asp  Ser  Trp  Met  Thr  Ser  Asn
 1              5                        10                       15

Glu  Ser  Glu  Asp  Gly  Val  Ser  Ser  Cys  Glu  Glu  Asp  Thr  Gly  Gly  Val
                 20                       25                       30

Phe  Ser  Ser  Glu  Leu  Leu  Ser  Val  Thr  Glu  Ile  Ser  Ala  Gly  Asp  Gly
            35                       40                       45
```

```
Val Arg Gly Met Ser Ser Pro His Thr Gly Ile Ser Arg Leu Leu Pro
 50                  55                  60
Gln Arg Glu Gly Val Leu Gln Ser Ser Thr Ser Gly Arg Glu Phe
 65                  70                  75
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HAV-R1

( x i ) SEQUENCE DESCRIPTION: SEQ ID NO:5:

GTTGACCAAC TGAGTCTGAA GC        22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HAV-F1

( x i ) SEQUENCE DESCRIPTION: SEQ ID NO:6:

GATTGGAAAT CTGATCCGTC CC        22

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HCV- LANR ( x i ) SEQUENCE DESCRIPTION: SEQ ID NO:7:

TCGCGACCCA ACACTACTC        19

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:

(C) INDIVIDUAL ISOLATE: HCV 1532

(xi) SEQUENCE DESCRIPTION: SEQ ID NO:8:

GGGGGCGACA CTCCACCA 18

(2) INFORMATION FOR SEQ ID NO:9:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470- 20-1-77F (xi) SEQUENCE DESCRIPTION: SEQ ID NO:9:

CTCTTTGTGG TAGTAGCCGA GAGAT 25

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470- 20-1-211R (xi) SEQUENCE DESCRIPTION: SEQ ID NO:10:

CGAATGAGTC AGAGGACGGG GTAT 24

(2) INFORMATION FOR SEQ ID NO:11:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer KL- 1

(xi) SEQUENCE DESCRIPTION: SEQ ID NO:11:

GCAGGATCCG AATTCGCATC TAGAGAT 27

(2) INFORMATION FOR SEQ ID NO:12:

(i) SEQUENCE CHARACTERISTICS:
(A) LENGTH: 29 base pairs
(B) TYPE: nucleic acid
(C) STRANDEDNESS: single
(D) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer KL- 2

( x i ) SEQUENCE DESCRIPTION: SEQ ID NO:12:

ATCTCTAGAT GCGAATTCGG ATCCTGCGA    29

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: LAMBDA GT11, REVERSE PRIMER ( x i ) SEQUENCE DESCRIPTION: SEQ ID NO:13:

GGCAGACATG GCCTGCCCGG    20

( 2 ) INFORMATION FOR SEQ ID NO:14:

( i ) SEQUENCE CHARACTERISTICS:
        ( A ) LENGTH: 9392 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: HGV-PNF 2161 Variant ( i x ) FEATURE:
        ( A ) NAME/KEY: CDS
        ( B ) LOCATION: 459..9077

( x i ) SEQUENCE DESCRIPTION: SEQ ID NO:14:

```
ACGTGGGGGA GTTGATCCCC CCCCCCCGGC ACTGGGTGCA AGCCCAGAA  ACCGACGCCT      60
ATCTAAGTAG ACGCAATGAC TCGGCGCCGA CTCGGCGACC GGCCAAAAGG TGGTGGATGG     120
GTGATGACAG GGTTGGTAGG TCGTAAATCC CGGTCACCTT GGTAGCCACT ATAGGTGGGT     180
CTTAAGAGAA GGTTAAGATT CCTCTTGTGC CTGCGGCGAG ACCGCGCACG GTCCACAGGT     240
GTTGGCCCTA CCGGTGGGAA TAAGGGCCCG ACGTCAGGCT CGTCGTTAAA CCGAGCCCGT     300
TACCCACCTG GGCAAACGAC GCCCACGTAC GGTCCACGTC GCCCTTCAAT GTCTCTCTTG     360
ACCAATAGGC GTAGCCGGCG AGTTGACAAG GACCAGTGGG GGCCGGGGGC TTGGAGAGGG     420
ACTCCAAGTC CCGCCCTTCC CGGTGGGCCG GGAAATGC ATG GGG CCA CCC AGC         473
                                          Met Gly Pro Pro Ser
                                           1               5

TCC GCG GCG GCC TGC AGC CGG GGT AGC CCA AGA ATC CTT CGG GTG AGG      521
Ser Ala Ala Ala Cys Ser Arg Gly Ser Pro Arg Ile Leu Arg Val Arg
         10                  15                  20
```

-continued

| | | | | | | | | | | | | | | | | |
|---|---|---|---|---|---|---|---|---|---|---|---|---|---|---|---|---|
| GCG | GGT | GGC | ATT | TCC | TTT | TTC | TAT | ACC | ATC | ATG | GCA | GTC | CTT | CTG | CTC | 569 |
| Ala | Gly | Gly | Ile | Ser | Phe | Phe | Tyr | Thr | Ile | Met | Ala | Val | Leu | Leu | Leu | |
| | | | 25 | | | | | 30 | | | | | 35 | | | |
| CTT | CTC | GTG | GTT | GAG | GCC | GGG | GCC | ATT | CTG | GCC | CCG | GCC | ACC | CAC | GCT | 617 |
| Leu | Leu | Val | Val | Glu | Ala | Gly | Ala | Ile | Leu | Ala | Pro | Ala | Thr | His | Ala | |
| | | 40 | | | | | 45 | | | | | 50 | | | | |
| TGT | CGA | GCG | AAT | GGG | CAA | TAT | TTC | CTC | ACA | AAT | TGT | TGT | GCC | CCG | GAG | 665 |
| Cys | Arg | Ala | Asn | Gly | Gln | Tyr | Phe | Leu | Thr | Asn | Cys | Cys | Ala | Pro | Glu | |
| | 55 | | | | | 60 | | | | | 65 | | | | | |
| GAC | ATC | GGG | TTC | TGC | CTG | GAG | GGT | GGA | TGC | CTG | GTG | GCC | CTG | GGG | TGC | 713 |
| Asp | Ile | Gly | Phe | Cys | Leu | Glu | Gly | Gly | Cys | Leu | Val | Ala | Leu | Gly | Cys | |
| 70 | | | | | 75 | | | | | 80 | | | | | 85 | |
| ACG | ATT | TGC | ACT | GAC | CAA | TGC | TGG | CCA | CTG | TAT | CAG | GCG | GGT | TTG | GCT | 761 |
| Thr | Ile | Cys | Thr | Asp | Gln | Cys | Trp | Pro | Leu | Tyr | Gln | Ala | Gly | Leu | Ala | |
| | | | | 90 | | | | | 95 | | | | | 100 | | |
| GTG | CGG | CCT | GGC | AAG | TCC | GCG | GCC | CAA | CTG | GTG | GGG | GAG | CTG | GGT | AGC | 809 |
| Val | Arg | Pro | Gly | Lys | Ser | Ala | Ala | Gln | Leu | Val | Gly | Glu | Leu | Gly | Ser | |
| | | | | 105 | | | | | 110 | | | | | 115 | | |
| CTA | TAC | GGG | CCC | CTG | TCG | GTC | TCG | GCC | TAT | GTG | GCT | GGG | ATC | CTG | GGC | 857 |
| Leu | Tyr | Gly | Pro | Leu | Ser | Val | Ser | Ala | Tyr | Val | Ala | Gly | Ile | Leu | Gly | |
| | | 120 | | | | | 125 | | | | | 130 | | | | |
| CTG | GGT | GAG | GTG | TAC | TCG | GGT | GTC | CTA | ACG | GTG | GGA | GTC | GCG | TTG | ACG | 905 |
| Leu | Gly | Glu | Val | Tyr | Ser | Gly | Val | Leu | Thr | Val | Gly | Val | Ala | Leu | Thr | |
| | 135 | | | | | 140 | | | | | 145 | | | | | |
| CGC | CGG | GTC | TAC | CCG | GTG | CCT | AAC | CTG | ACG | TGT | GCA | GTC | GCG | TGT | GAG | 953 |
| Arg | Arg | Val | Tyr | Pro | Val | Pro | Asn | Leu | Thr | Cys | Ala | Val | Ala | Cys | Glu | |
| 150 | | | | | 155 | | | | | 160 | | | | | 165 | |
| CTA | AAG | TGG | GAA | AGT | GAG | TTT | TGG | AGA | TGG | ACT | GAA | CAG | CTG | GCC | TCC | 1001 |
| Leu | Lys | Trp | Glu | Ser | Glu | Phe | Trp | Arg | Trp | Thr | Glu | Gln | Leu | Ala | Ser | |
| | | | | 170 | | | | | 175 | | | | | 180 | | |
| AAC | TAC | TGG | ATT | CTG | GAA | TAC | CTC | TGG | AAG | GTC | CCA | TTT | GAT | TTC | TGG | 1049 |
| Asn | Tyr | Trp | Ile | Leu | Glu | Tyr | Leu | Trp | Lys | Val | Pro | Phe | Asp | Phe | Trp | |
| | | | 185 | | | | | 190 | | | | | 195 | | | |
| AGA | GGC | GTG | ATA | AGC | CTG | ACC | CCC | TTG | TTG | GTT | TGC | GTG | GCC | GCA | TTG | 1097 |
| Arg | Gly | Val | Ile | Ser | Leu | Thr | Pro | Leu | Leu | Val | Cys | Val | Ala | Ala | Leu | |
| | | 200 | | | | | 205 | | | | | 210 | | | | |
| CTG | CTG | CTT | GAG | CAA | CGG | ATT | GTC | ATG | GTC | TTC | CTG | TTG | GTG | ACG | ATG | 1145 |
| Leu | Leu | Leu | Glu | Gln | Arg | Ile | Val | Met | Val | Phe | Leu | Leu | Val | Thr | Met | |
| | 215 | | | | | 220 | | | | | 225 | | | | | |
| GCC | GGG | ATG | TCG | CAA | GGC | GCC | CCT | GCC | TCC | GTT | TTG | GGG | TCA | CGC | CCC | 1193 |
| Ala | Gly | Met | Ser | Gln | Gly | Ala | Pro | Ala | Ser | Val | Leu | Gly | Ser | Arg | Pro | |
| 230 | | | | | 235 | | | | | 240 | | | | | 245 | |
| TTT | GAC | TAC | GGG | TTG | ACT | TGG | CAG | ACC | TGC | TCT | TGC | AGG | GCC | AAC | GGT | 1241 |
| Phe | Asp | Tyr | Gly | Leu | Thr | Trp | Gln | Thr | Cys | Ser | Cys | Arg | Ala | Asn | Gly | |
| | | | | 250 | | | | | 255 | | | | | 260 | | |
| TCG | CGT | TTT | TCG | ACT | GGG | GAG | AAG | GTG | TGG | GAC | CGT | GGG | AAC | GTT | ACG | 1289 |
| Ser | Arg | Phe | Ser | Thr | Gly | Glu | Lys | Val | Trp | Asp | Arg | Gly | Asn | Val | Thr | |
| | | | 265 | | | | | 270 | | | | | 275 | | | |
| CTT | CAG | TGT | GAC | TGC | CCT | AAC | GGC | CCC | TGG | GTG | TGG | TTG | CCA | GCC | TTT | 1337 |
| Leu | Gln | Cys | Asp | Cys | Pro | Asn | Gly | Pro | Trp | Val | Trp | Leu | Pro | Ala | Phe | |
| | | 280 | | | | | 285 | | | | | 290 | | | | |
| TGC | CAA | GCA | ATC | GGC | TGG | GGT | GAC | CCC | ATC | ACT | TAT | TGG | AGC | CAC | GGG | 1385 |
| Cys | Gln | Ala | Ile | Gly | Trp | Gly | Asp | Pro | Ile | Thr | Tyr | Trp | Ser | His | Gly | |
| | 295 | | | | | 300 | | | | | 305 | | | | | |
| CAA | AAT | CAG | TGG | CCC | CTT | TCA | TGC | CCC | CAG | TAT | GTC | TAT | GGG | TCT | GCT | 1433 |
| Gln | Asn | Gln | Trp | Pro | Leu | Ser | Cys | Pro | Gln | Tyr | Val | Tyr | Gly | Ser | Ala | |
| 310 | | | | | 315 | | | | | 320 | | | | | 325 | |
| ACA | GTC | ACT | TGC | GTG | TGG | GGT | TCC | GCT | TCT | TGG | TTT | GCC | TCC | ACC | AGT | 1481 |
| Thr | Val | Thr | Cys | Val | Trp | Gly | Ser | Ala | Ser | Trp | Phe | Ala | Ser | Thr | Ser | |
| | | | | 330 | | | | | 335 | | | | | 340 | | |

-continued

| | | | | | | | | | | | | | | | | |
|---|---|---|---|---|---|---|---|---|---|---|---|---|---|---|---|---|
| GGT | CGC | GAC | TCG | AAG | ATA | GAT | GTG | TGG | AGT | TTA | GTG | CCA | GTT | GGC | TCT | 1529 |
| Gly | Arg | Asp | Ser | Lys | Ile | Asp | Val | Trp | Ser | Leu | Val | Pro | Val | Gly | Ser | |
| | | | 345 | | | | 350 | | | | | 355 | | | | |
| GCC | ACC | TGC | ACC | ATA | GCC | GCA | CTT | GGA | TCA | TCG | GAT | CGC | GAC | ACG | GTG | 1577 |
| Ala | Thr | Cys | Thr | Ile | Ala | Ala | Leu | Gly | Ser | Ser | Asp | Arg | Asp | Thr | Val | |
| | | 360 | | | | | 365 | | | | | 370 | | | | |
| CCT | GGG | CTC | TCC | GAG | TGG | GGA | ATC | CCG | TGC | GTG | ACG | TGT | GTT | CTG | GAC | 1625 |
| Pro | Gly | Leu | Ser | Glu | Trp | Gly | Ile | Pro | Cys | Val | Thr | Cys | Val | Leu | Asp | |
| | 375 | | | | | 380 | | | | | 385 | | | | | |
| CGT | CGG | CCT | GCC | TCC | TGC | GGC | ACC | TGT | GTG | AGG | GAC | TGC | TGG | CCC | GAG | 1673 |
| Arg | Arg | Pro | Ala | Ser | Cys | Gly | Thr | Cys | Val | Arg | Asp | Cys | Trp | Pro | Glu | |
| 390 | | | | | 395 | | | | | 400 | | | | | 405 | |
| ACC | GGG | TCG | GTT | AGG | TTC | CCA | TTC | CAT | CGG | TGC | GGC | GTG | GGG | CCT | CGG | 1721 |
| Thr | Gly | Ser | Val | Arg | Phe | Pro | Phe | His | Arg | Cys | Gly | Val | Gly | Pro | Arg | |
| | | | | 410 | | | | | 415 | | | | | 420 | | |
| CTG | ACA | AAG | GAC | TTG | GAA | GCT | GTG | CCC | TTC | GTC | AAC | AGG | ACA | ACT | CCC | 1769 |
| Leu | Thr | Lys | Asp | Leu | Glu | Ala | Val | Pro | Phe | Val | Asn | Arg | Thr | Thr | Pro | |
| | | | 425 | | | | | 430 | | | | | 435 | | | |
| TTC | ACC | ATT | AGG | GGG | CCC | CTG | GGC | AAC | CAG | GGC | CGA | GGC | AAC | CCG | GTG | 1817 |
| Phe | Thr | Ile | Arg | Gly | Pro | Leu | Gly | Asn | Gln | Gly | Arg | Gly | Asn | Pro | Val | |
| | | | 440 | | | | | 445 | | | | | 450 | | | |
| CGG | TCG | CCC | TTG | GGT | TTT | GGG | TCC | TAC | GCC | ATG | ACC | AGG | ATC | CGA | GAT | 1865 |
| Arg | Ser | Pro | Leu | Gly | Phe | Gly | Ser | Tyr | Ala | Met | Thr | Arg | Ile | Arg | Asp | |
| | 455 | | | | | 460 | | | | | 465 | | | | | |
| ACC | CTA | CAT | CTG | GTG | GAG | TGT | CCC | ACA | CCA | GCC | ATT | GAG | CCT | CCC | ACC | 1913 |
| Thr | Leu | His | Leu | Val | Glu | Cys | Pro | Thr | Pro | Ala | Ile | Glu | Pro | Pro | Thr | |
| 470 | | | | | 475 | | | | | 480 | | | | | 485 | |
| GGG | ACG | TTT | GGG | TTC | TTC | CCC | GGG | ACG | CCG | CCT | CTC | AAC | AAC | TGC | ATG | 1961 |
| Gly | Thr | Phe | Gly | Phe | Phe | Pro | Gly | Thr | Pro | Pro | Leu | Asn | Asn | Cys | Met | |
| | | | | 490 | | | | | 495 | | | | | 500 | | |
| CTC | TTG | GGC | ACG | GAA | GTG | TCC | GAG | GCA | CTT | GGG | GGG | GCT | GGC | CTC | ACG | 2009 |
| Leu | Leu | Gly | Thr | Glu | Val | Ser | Glu | Ala | Leu | Gly | Gly | Ala | Gly | Leu | Thr | |
| | | | 505 | | | | | 510 | | | | | 515 | | | |
| GGG | GGG | TTC | TAT | GAA | CCC | CTG | GTG | CGC | AGG | TGT | TCG | AAG | CTG | ATG | GGA | 2057 |
| Gly | Gly | Phe | Tyr | Glu | Pro | Leu | Val | Arg | Arg | Cys | Ser | Lys | Leu | Met | Gly | |
| | | 520 | | | | | 525 | | | | | 530 | | | | |
| AGC | CGA | AAT | CCG | GTT | TGT | CCG | GGG | TTT | GCA | TGG | CTC | TCT | TCG | GGC | AGG | 2105 |
| Ser | Arg | Asn | Pro | Val | Cys | Pro | Gly | Phe | Ala | Trp | Leu | Ser | Ser | Gly | Arg | |
| | 535 | | | | | 540 | | | | | 545 | | | | | |
| CCT | GAT | GGG | TTT | ATA | CAT | GTC | CAG | GGT | CAC | TTG | CAG | GAG | GTG | GAT | GCA | 2153 |
| Pro | Asp | Gly | Phe | Ile | His | Val | Gln | Gly | His | Leu | Gln | Glu | Val | Asp | Ala | |
| 550 | | | | | 555 | | | | | 560 | | | | | 565 | |
| GGC | AAC | TTC | ATC | CCG | CCC | CCG | CGC | TGG | TTG | CTC | TTG | GAC | TTT | GTA | TTT | 2201 |
| Gly | Asn | Phe | Ile | Pro | Pro | Pro | Arg | Trp | Leu | Leu | Leu | Asp | Phe | Val | Phe | |
| | | | | 570 | | | | | 575 | | | | | 580 | | |
| GTC | CTG | TTA | TAC | CTG | ATG | AAG | CTG | GCT | GAG | GCA | CGG | TTG | GTC | CCG | CTG | 2249 |
| Val | Leu | Leu | Tyr | Leu | Met | Lys | Leu | Ala | Glu | Ala | Arg | Leu | Val | Pro | Leu | |
| | | | 585 | | | | | 590 | | | | | 595 | | | |
| ATC | TTG | CTG | CTG | CTA | TGG | TGG | TGG | GTG | AAC | CAG | CTG | GCA | GTC | CTA | GGG | 2297 |
| Ile | Leu | Leu | Leu | Leu | Trp | Trp | Trp | Val | Asn | Gln | Leu | Ala | Val | Leu | Gly | |
| | | 600 | | | | | 605 | | | | | 610 | | | | |
| CTG | CCG | GCT | GTG | GAA | GCC | GCC | GTG | GCA | GGT | GAG | GTC | TTC | GCG | GGC | CCT | 2345 |
| Leu | Pro | Ala | Val | Glu | Ala | Ala | Val | Ala | Gly | Glu | Val | Phe | Ala | Gly | Pro | |
| | 615 | | | | | 620 | | | | | 625 | | | | | |
| GCC | CTG | TCC | TGG | TGT | CTG | GGA | CTC | CCG | GTC | GTC | AGT | ATG | ATA | TTG | GGT | 2393 |
| Ala | Leu | Ser | Trp | Cys | Leu | Gly | Leu | Pro | Val | Val | Ser | Met | Ile | Leu | Gly | |
| 630 | | | | | 635 | | | | | 640 | | | | | 645 | |
| TTG | GCA | AAC | CTG | GTG | CTG | TAC | TTT | AGA | TGG | TTG | GGA | CCC | CAA | CGC | CTG | 2441 |
| Leu | Ala | Asn | Leu | Val | Leu | Tyr | Phe | Arg | Trp | Leu | Gly | Pro | Gln | Arg | Leu | |
| | | | | 650 | | | | | 655 | | | | | 660 | | |

```
ATG TTC CTC GTG TTG TGG AAG CTT GCT CGG GGA GCT TTC CCG CTG GCC    2489
Met Phe Leu Val Leu Trp Lys Leu Ala Arg Gly Ala Phe Pro Leu Ala
            665                 670                 675

CTC TTG ATG GGG ATT TCG GCG ACC CGC GGG CGC ACC TCA GTG CTC GGG    2537
Leu Leu Met Gly Ile Ser Ala Thr Arg Gly Arg Thr Ser Val Leu Gly
            680                 685                 690

GCC GAG TTC TGC TTC GAT GCT ACA TTC GAG GTG GAC ACT TCG GTG TTG    2585
Ala Glu Phe Cys Phe Asp Ala Thr Phe Glu Val Asp Thr Ser Val Leu
            695                 700                 705

GGC TGG GTG GTG GCC AGT GTG GTA GCT TGG GCC ATT GCG CTC CTG AGC    2633
Gly Trp Val Val Ala Ser Val Val Ala Trp Ala Ile Ala Leu Leu Ser
710                 715                 720                 725

TCG ATG AGC GCA GGG GGG TGG AGG CAC AAA GCC GTG ATC TAT AGG ACG    2681
Ser Met Ser Ala Gly Gly Trp Arg His Lys Ala Val Ile Tyr Arg Thr
                730                 735                 740

TGG TGT AAG GGG TAC CAG GCA ATC CGT CAA AGG GTG GTG AGG AGC CCC    2729
Trp Cys Lys Gly Tyr Gln Ala Ile Arg Gln Arg Val Val Arg Ser Pro
                745                 750                 755

CTC GGG GAG GGG CGG CCT GCC AAA CCC CTG ACC TTT GCC TGG TGC TTG    2777
Leu Gly Glu Gly Arg Pro Ala Lys Pro Leu Thr Phe Ala Trp Cys Leu
            760                 765                 770

GCC TCG TAC ATC TGG CCA GAT GCT GTG ATG ATG GTG GTG GTT GCC TTG    2825
Ala Ser Tyr Ile Trp Pro Asp Ala Val Met Met Val Val Val Ala Leu
            775                 780                 785

GTC CTT CTC TTT GGC CTG TTC GAC GCG TTG GAT TGG GCC TTG GAG GAG    2873
Val Leu Leu Phe Gly Leu Phe Asp Ala Leu Asp Trp Ala Leu Glu Glu
790                 795                 800                 805

ATC TTG GTG TCC CGG CCC TCG TTG CGG CGT TTG GCT CGG GTG GTT GAG    2921
Ile Leu Val Ser Arg Pro Ser Leu Arg Arg Leu Ala Arg Val Val Glu
                810                 815                 820

TGC TGT GTG ATG GCG GGT GAG AAG GCC ACA ACC GTC CGG CTG GTC TCC    2969
Cys Cys Val Met Ala Gly Glu Lys Ala Thr Thr Val Arg Leu Val Ser
                825                 830                 835

AAG ATG TGT GCG AGA GGA GCT TAT TTG TTC GAT CAT ATG GGC TCT TTT    3017
Lys Met Cys Ala Arg Gly Ala Tyr Leu Phe Asp His Met Gly Ser Phe
            840                 845                 850

TCG CGT GCT GTC AAG GAG CGC CTG TTG GAA TGG GAC GCA GCT CTT GAA    3065
Ser Arg Ala Val Lys Glu Arg Leu Leu Glu Trp Asp Ala Ala Leu Glu
            855                 860                 865

CCT CTG TCA TTC ACT AGG ACG GAC TGT CGC ATC ATA CGG GAT GCC GCG    3113
Pro Leu Ser Phe Thr Arg Thr Asp Cys Arg Ile Ile Arg Asp Ala Ala
870                 875                 880                 885

AGG ACT TTG TCC TGC GGG CAG TGC GTC ATG GGT TTA CCC GTG GTT GCG    3161
Arg Thr Leu Ser Cys Gly Gln Cys Val Met Gly Leu Pro Val Val Ala
                890                 895                 900

CGC CGT GGT GAT GAG GTT CTC ATC GGC GTC TTC CAG GAT GTG AAT CAT    3209
Arg Arg Gly Asp Glu Val Leu Ile Gly Val Phe Gln Asp Val Asn His
                905                 910                 915

TTG CCT CCC GGG TTT GTT CCG ACC GCG CCT GTT GTC ATC CGA CGG TGC    3257
Leu Pro Pro Gly Phe Val Pro Thr Ala Pro Val Val Ile Arg Arg Cys
            920                 925                 930

GGA AAG GGC TTC TTG GGG GTC ACA AAG GCT GCC TTG ACA GGT CGG GAT    3305
Gly Lys Gly Phe Leu Gly Val Thr Lys Ala Ala Leu Thr Gly Arg Asp
            935                 940                 945

CCT GAC TTA CAT CCA GGG AAC GTC ATG GTG TTG GGG ACG GCT ACG TCG    3353
Pro Asp Leu His Pro Gly Asn Val Met Val Leu Gly Thr Ala Thr Ser
950                 955                 960                 965

CGA AGC ATG GGA ACA TGC TTG AAC GGC CTG CTG TTC ACG ACC TTC CAT    3401
Arg Ser Met Gly Thr Cys Leu Asn Gly Leu Leu Phe Thr Thr Phe His
                970                 975                 980
```

| | | | | | | | | | | | | | | | | |
|---|---|---|---|---|---|---|---|---|---|---|---|---|---|---|---|---|
| GGG | GCT | TCA | TCC | CGA | ACC | ATC | GCC | ACA | CCC | GTG | GGG | GCC | CTT | AAT | CCC | 3449 |
| Gly | Ala | Ser | Ser | Arg | Thr | Ile | Ala | Thr | Pro | Val | Gly | Ala | Leu | Asn | Pro | |
| | | 985 | | | | | 990 | | | | | | 995 | | | |
| AGA | TGG | TGG | TCA | GCC | AGT | GAT | GAT | GTC | ACG | GTG | TAT | CCA | CTC | CCG | GAT | 3497 |
| Arg | Trp | Trp | Ser | Ala | Ser | Asp | Asp | Val | Thr | Val | Tyr | Pro | Leu | Pro | Asp | |
| | | 1000 | | | | | 1005 | | | | | | 1010 | | | |
| GGG | GCT | ACT | TCG | TTA | ACA | CCT | TGT | ACT | TGC | CAG | GCT | GAG | TCC | TGT | TGG | 3545 |
| Gly | Ala | Thr | Ser | Leu | Thr | Pro | Cys | Thr | Cys | Gln | Ala | Glu | Ser | Cys | Trp | |
| | | 1015 | | | | | 1020 | | | | | | 1025 | | | |
| GTC | ATC | AGA | TCC | GAC | GGG | GCC | CTA | TGC | CAT | GGC | TTG | AGC | AAG | GGG | GAC | 3593 |
| Val | Ile | Arg | Ser | Asp | Gly | Ala | Leu | Cys | His | Gly | Leu | Ser | Lys | Gly | Asp | |
| 1030 | | | | | 1035 | | | | | 1040 | | | | | 1045 | |
| AAG | GTG | GAG | CTG | GAT | GTG | GCC | ATG | GAG | GTC | TCT | GAC | TTC | CGT | GGC | TCG | 3641 |
| Lys | Val | Glu | Leu | Asp | Val | Ala | Met | Glu | Val | Ser | Asp | Phe | Arg | Gly | Ser | |
| | | | | 1050 | | | | | 1055 | | | | | 1060 | | |
| TCT | GGC | TCA | CCG | GTC | CTA | TGT | GAC | GAA | GGG | CAC | GCA | GTA | GGA | ATG | CTC | 3689 |
| Ser | Gly | Ser | Pro | Val | Leu | Cys | Asp | Glu | Gly | His | Ala | Val | Gly | Met | Leu | |
| | | | 1065 | | | | | 1070 | | | | | 1075 | | | |
| GTG | TCT | GTG | CTT | CAC | TCC | GGT | GGT | AGG | GTC | ACC | GCG | GCA | CGG | TTC | ACT | 3737 |
| Val | Ser | Val | Leu | His | Ser | Gly | Gly | Arg | Val | Thr | Ala | Ala | Arg | Phe | Thr | |
| | | 1080 | | | | | 1085 | | | | | | 1090 | | | |
| AGG | CCG | TGG | ACC | CAA | GTG | CCA | ACA | GAT | GCC | AAA | ACC | ACT | ACT | GAA | CCC | 3785 |
| Arg | Pro | Trp | Thr | Gln | Val | Pro | Thr | Asp | Ala | Lys | Thr | Thr | Thr | Glu | Pro | |
| | | 1095 | | | | | 1100 | | | | | | 1105 | | | |
| CCT | CCG | GTG | CCG | GCC | AAA | GGA | GTT | TTC | AAA | GAG | GCC | CCG | TTG | TTT | ATG | 3833 |
| Pro | Pro | Val | Pro | Ala | Lys | Gly | Val | Phe | Lys | Glu | Ala | Pro | Leu | Phe | Met | |
| 1110 | | | | | 1115 | | | | | 1120 | | | | | 1125 | |
| CCT | ACG | GGA | GCG | GGA | AAG | AGC | ACT | CGC | GTC | CCG | TTG | GAG | TAC | GAT | AAC | 3881 |
| Pro | Thr | Gly | Ala | Gly | Lys | Ser | Thr | Arg | Val | Pro | Leu | Glu | Tyr | Asp | Asn | |
| | | | 1130 | | | | | 1135 | | | | | 1140 | | | |
| ATG | GGG | CAC | AAG | GTC | TTA | ATC | TTG | AAC | CCC | TCA | GTG | GCC | ACT | GTG | CGG | 3929 |
| Met | Gly | His | Lys | Val | Leu | Ile | Leu | Asn | Pro | Ser | Val | Ala | Thr | Val | Arg | |
| | | | 1145 | | | | | 1150 | | | | | 1155 | | | |
| GCC | ATG | GGC | CCG | TAC | ATG | GAG | CGG | CTG | GCG | GGT | AAA | CAT | CCA | AGT | ATA | 3977 |
| Ala | Met | Gly | Pro | Tyr | Met | Glu | Arg | Leu | Ala | Gly | Lys | His | Pro | Ser | Ile | |
| | | 1160 | | | | | 1165 | | | | | | 1170 | | | |
| TAC | TGT | GGG | CAT | GAT | ACA | ACT | GCT | TTC | ACA | AGG | ATC | ACT | GAC | TCC | CCC | 4025 |
| Tyr | Cys | Gly | His | Asp | Thr | Thr | Ala | Phe | Thr | Arg | Ile | Thr | Asp | Ser | Pro | |
| | | 1175 | | | | | 1180 | | | | | | 1185 | | | |
| CTG | ACG | TAT | TCA | ACC | TAT | GGG | AGG | TTT | TTG | GCC | AAC | CCT | AGG | CAG | ATG | 4073 |
| Leu | Thr | Tyr | Ser | Thr | Tyr | Gly | Arg | Phe | Leu | Ala | Asn | Pro | Arg | Gln | Met | |
| 1190 | | | | | 1195 | | | | | 1200 | | | | | 1205 | |
| CTA | CGG | GGC | GTT | TCG | GTG | GTC | ATT | TGT | GAT | GAG | TGC | CAC | AGT | CAT | GAC | 4121 |
| Leu | Arg | Gly | Val | Ser | Val | Val | Ile | Cys | Asp | Glu | Cys | His | Ser | His | Asp | |
| | | | | 1210 | | | | | 1215 | | | | | 1220 | | |
| TCA | ACC | GTG | CTG | TTA | GGC | ATT | GGG | AGA | GTC | CGG | GAG | CTG | GCG | CGT | GGG | 4169 |
| Ser | Thr | Val | Leu | Leu | Gly | Ile | Gly | Arg | Val | Arg | Glu | Leu | Ala | Arg | Gly | |
| | | | | 1225 | | | | | 1230 | | | | | 1235 | | |
| TGC | GGG | GTG | CAA | CTA | GTG | CTC | TAC | GCC | ACC | GCT | ACA | CCT | CCC | GGA | TCC | 4217 |
| Cys | Gly | Val | Gln | Leu | Val | Leu | Tyr | Ala | Thr | Ala | Thr | Pro | Pro | Gly | Ser | |
| | | | 1240 | | | | | 1245 | | | | | 1250 | | | |
| CCT | ATG | ACG | CAG | CAC | CCT | TCC | ATA | ATT | GAG | ACA | AAA | TTG | GAC | GTG | GGC | 4265 |
| Pro | Met | Thr | Gln | His | Pro | Ser | Ile | Ile | Glu | Thr | Lys | Leu | Asp | Val | Gly | |
| | | 1255 | | | | | 1260 | | | | | | 1265 | | | |
| GAG | ATT | CCC | TTT | TAT | GGG | CAT | GGA | ATA | CCC | CTC | GAG | CGG | ATG | CGA | ACC | 4313 |
| Glu | Ile | Pro | Phe | Tyr | Gly | His | Gly | Ile | Pro | Leu | Glu | Arg | Met | Arg | Thr | |
| 1270 | | | | | 1275 | | | | | 1280 | | | | | 1285 | |
| GGA | AGG | CAC | CTC | GTG | TTC | TGC | CAT | TCT | AAG | GCT | GAG | TGC | GAG | CGC | CTT | 4361 |
| Gly | Arg | His | Leu | Val | Phe | Cys | His | Ser | Lys | Ala | Glu | Cys | Glu | Arg | Leu | |
| | | | | 1290 | | | | | 1295 | | | | | 1300 | | |

| | | | | | | | | | | | | | | | | |
|---|---|---|---|---|---|---|---|---|---|---|---|---|---|---|---|---|
| GCT | GGC | CAG | TTC | TCC | GCT | AGG | GGG | GTC | AAT | GCC | ATT | GCC | TAT | TAT | AGG | 4409 |
| Ala | Gly | Gln | Phe | Ser | Ala | Arg | Gly | Val | Asn | Ala | Ile | Ala | Tyr | Tyr | Arg | |
| | | | | 1305 | | | | 1310 | | | | | 1315 | | | |
| GGT | AAA | GAC | AGT | TCT | ATC | ATC | AAG | GAT | GGG | GAC | CTG | GTG | GTC | TGT | GCT | 4457 |
| Gly | Lys | Asp | Ser | Ser | Ile | Ile | Lys | Asp | Gly | Asp | Leu | Val | Val | Cys | Ala | |
| | 1320 | | | | | 1325 | | | | | 1330 | | | | | |
| ACA | GAC | GCG | CTT | TCC | ACT | GGG | TAC | ACT | GGA | AAT | TTC | GAC | TCC | GTC | ACC | 4505 |
| Thr | Asp | Ala | Leu | Ser | Thr | Gly | Tyr | Thr | Gly | Asn | Phe | Asp | Ser | Val | Thr | |
| | | 1335 | | | | | 1340 | | | | | 1345 | | | | |
| GAC | TGT | GGA | TTA | GTG | GTG | GAG | GAG | GTC | GTT | GAG | GTG | ACC | CTT | GAT | CCC | 4553 |
| Asp | Cys | Gly | Leu | Val | Val | Glu | Glu | Val | Val | Glu | Val | Thr | Leu | Asp | Pro | |
| 1350 | | | | | 1355 | | | | | 1360 | | | | | 1365 | |
| ACC | ATT | ACC | ATC | TCC | CTG | CGG | ACA | GTG | CCT | GCG | TCG | GCT | GAA | CTG | TCG | 4601 |
| Thr | Ile | Thr | Ile | Ser | Leu | Arg | Thr | Val | Pro | Ala | Ser | Ala | Glu | Leu | Ser | |
| | | | | 1370 | | | | | 1375 | | | | | 1380 | | |
| ATG | CAA | AGA | CGA | GGA | CGC | ACG | GGT | AGG | GGC | AGG | TCT | GGA | CGC | TAC | TAC | 4649 |
| Met | Gln | Arg | Arg | Gly | Arg | Thr | Gly | Arg | Gly | Arg | Ser | Gly | Arg | Tyr | Tyr | |
| | | | 1385 | | | | | 1390 | | | | | 1395 | | | |
| TAC | GCG | GGG | GTG | GGC | AAA | GCC | CCT | GCG | GGT | GTG | GTG | CGC | TCA | GGT | CCT | 4697 |
| Tyr | Ala | Gly | Val | Gly | Lys | Ala | Pro | Ala | Gly | Val | Val | Arg | Ser | Gly | Pro | |
| | | 1400 | | | | | 1405 | | | | | 1410 | | | | |
| GTC | TGG | TCG | GCG | GTG | GAA | GCT | GGA | GTG | ACC | TGG | TAC | GGA | ATG | GAA | CCT | 4745 |
| Val | Trp | Ser | Ala | Val | Glu | Ala | Gly | Val | Thr | Trp | Tyr | Gly | Met | Glu | Pro | |
| | 1415 | | | | | 1420 | | | | | 1425 | | | | | |
| GAC | TTG | ACA | GCT | AAC | CTA | CTG | AGA | CTT | TAC | GAC | GAC | TGC | CCT | TAC | ACC | 4793 |
| Asp | Leu | Thr | Ala | Asn | Leu | Leu | Arg | Leu | Tyr | Asp | Asp | Cys | Pro | Tyr | Thr | |
| 1430 | | | | | 1435 | | | | | 1440 | | | | | 1445 | |
| GCA | GCC | GTC | GCG | GCT | GAT | ATC | GGA | GAA | GCC | GCG | GTG | TTC | TTC | TCT | GGG | 4841 |
| Ala | Ala | Val | Ala | Ala | Asp | Ile | Gly | Glu | Ala | Ala | Val | Phe | Phe | Ser | Gly | |
| | | | | 1450 | | | | | 1455 | | | | | 1460 | | |
| CTC | GCC | CCA | TTG | AGG | ATG | CAC | CCT | GAT | GTC | AGC | TGG | GCA | AAA | GTT | CGC | 4889 |
| Leu | Ala | Pro | Leu | Arg | Met | His | Pro | Asp | Val | Ser | Trp | Ala | Lys | Val | Arg | |
| | | | | 1465 | | | | | 1470 | | | | | 1475 | | |
| GGC | GTC | AAC | TGG | CCC | CTC | TTG | GTG | GGT | GTT | CAG | CGG | ACC | ATG | TGT | CGG | 4937 |
| Gly | Val | Asn | Trp | Pro | Leu | Leu | Val | Gly | Val | Gln | Arg | Thr | Met | Cys | Arg | |
| | | | 1480 | | | | | 1485 | | | | | 1490 | | | |
| GAA | ACA | CTG | TCT | CCC | GGC | CCA | TCG | GAT | GAC | CCC | CAA | TGG | GCA | GGT | CTG | 4985 |
| Glu | Thr | Leu | Ser | Pro | Gly | Pro | Ser | Asp | Asp | Pro | Gln | Trp | Ala | Gly | Leu | |
| | | 1495 | | | | | 1500 | | | | | 1505 | | | | |
| AAG | GGC | CCA | AAT | CCT | GTC | CCA | CTC | CTG | CTG | AGG | TGG | GGC | AAT | GAT | TTA | 5033 |
| Lys | Gly | Pro | Asn | Pro | Val | Pro | Leu | Leu | Leu | Arg | Trp | Gly | Asn | Asp | Leu | |
| 1510 | | | | | 1515 | | | | | 1520 | | | | | 1525 | |
| CCA | TCT | AAA | GTG | GCC | GGC | CAC | CAC | ATA | GTG | GAC | GAC | CTG | GTC | CGG | AGA | 5081 |
| Pro | Ser | Lys | Val | Ala | Gly | His | His | Ile | Val | Asp | Asp | Leu | Val | Arg | Arg | |
| | | | | 1530 | | | | | 1535 | | | | | 1540 | | |
| CTC | GGT | GTG | GCG | GAG | GGT | TAC | GTC | CGC | TGC | GAC | GCT | GGG | CCG | ATC | TTG | 5129 |
| Leu | Gly | Val | Ala | Glu | Gly | Tyr | Val | Arg | Cys | Asp | Ala | Gly | Pro | Ile | Leu | |
| | | | | 1545 | | | | | 1550 | | | | | 1555 | | |
| ATG | ATC | GGT | CTA | GCT | ATC | GCG | GGG | GGA | ATG | ATC | TAC | GCG | TCA | TAC | ACC | 5177 |
| Met | Ile | Gly | Leu | Ala | Ile | Ala | Gly | Gly | Met | Ile | Tyr | Ala | Ser | Tyr | Thr | |
| | | | | 1560 | | | | | 1565 | | | | | 1570 | | |
| GGG | TCG | CTA | GTG | GTG | GTG | ACA | GAC | TGG | GAT | GTG | AAG | GGG | GGT | GGC | GCC | 5225 |
| Gly | Ser | Leu | Val | Val | Val | Thr | Asp | Trp | Asp | Val | Lys | Gly | Gly | Gly | Ala | |
| | 1575 | | | | | 1580 | | | | | 1585 | | | | | |
| CCC | CTT | TAT | CGG | CAT | GGA | GAC | CAG | GCC | ACG | CCT | CAG | CCG | GTG | GTG | CAG | 5273 |
| Pro | Leu | Tyr | Arg | His | Gly | Asp | Gln | Ala | Thr | Pro | Gln | Pro | Val | Val | Gln | |
| 1590 | | | | | 1595 | | | | | 1600 | | | | | 1605 | |
| GTT | CCT | CCG | GTA | GAC | CAT | CGG | CCG | GGG | GGT | GAA | TCA | GCA | CCA | TCG | GAT | 5321 |
| Val | Pro | Pro | Val | Asp | His | Arg | Pro | Gly | Gly | Glu | Ser | Ala | Pro | Ser | Asp | |
| | | | | 1610 | | | | | 1615 | | | | | 1620 | | |

| | |
|---|---|
| GCC AAG ACA GTG ACA GAT GCG GTG GCA GCC ATC CAG GTG GAC TGC GAT<br>Ala Lys Thr Val Thr Asp Ala Val Ala Ala Ile Gln Val Asp Cys Asp<br>1625 1630 1635 | 5369 |
| TGG ACT ATC ATG ACT CTG TCG ATC GGA GAA GTG TTG TCC TTG GCT CAG<br>Trp Thr Ile Met Thr Leu Ser Ile Gly Glu Val Leu Ser Leu Ala Gln<br>1640 1645 1650 | 5417 |
| GCT AAG ACG GCC GAG GCC TAC ACA GCA ACC GCC AAG TGG CTC GCT GGC<br>Ala Lys Thr Ala Glu Ala Tyr Thr Ala Thr Ala Lys Trp Leu Ala Gly<br>1655 1660 1665 | 5465 |
| TGC TAT ACG GGG ACG CGG GCC GTT CCC ACT GTA TCC ATT GTT GAC AAG<br>Cys Tyr Thr Gly Thr Arg Ala Val Pro Thr Val Ser Ile Val Asp Lys<br>1670 1675 1680 1685 | 5513 |
| CTC TTC GCC GGA GGG TGG GCG GCT GTG GTG GGC CAT TGC CAC AGC GTG<br>Leu Phe Ala Gly Gly Trp Ala Ala Val Val Gly His Cys His Ser Val<br>1690 1695 1700 | 5561 |
| ATT GCT GCG GCG GTG GCG GCC TAC GGG GCT TCA AGG AGC CCG CCG TTG<br>Ile Ala Ala Ala Val Ala Ala Tyr Gly Ala Ser Arg Ser Pro Pro Leu<br>1705 1710 1715 | 5609 |
| GCA GCC GCG GCT TCC TAC CTG ATG GGG TTG GGC GTT GGA GGC AAC GCT<br>Ala Ala Ala Ala Ser Tyr Leu Met Gly Leu Gly Val Gly Gly Asn Ala<br>1720 1725 1730 | 5657 |
| CAG ACG CGC CTG GCG TCT GCC CTC CTA TTG GGG GCT GCT GGA ACC GCC<br>Gln Thr Arg Leu Ala Ser Ala Leu Leu Leu Gly Ala Ala Gly Thr Ala<br>1735 1740 1745 | 5705 |
| TTG GGC ACT CCT GTC GTG GGC TTG ACC ATG GCA GGT GCG TTC ATG GGG<br>Leu Gly Thr Pro Val Val Gly Leu Thr Met Ala Gly Ala Phe Met Gly<br>1750 1755 1760 1765 | 5753 |
| GGG GCC AGT GTC TCC CCC TCC TTG GTC ACC ATT TTA TTG GGG GCC GTC<br>Gly Ala Ser Val Ser Pro Ser Leu Val Thr Ile Leu Leu Gly Ala Val<br>1770 1775 1780 | 5801 |
| GGA GGT TGG GAG GGT GTT GTC AAC GCG GCG AGC CTA GTC TTT GAC TTC<br>Gly Gly Trp Glu Gly Val Val Asn Ala Ala Ser Leu Val Phe Asp Phe<br>1785 1790 1795 | 5849 |
| ATG GCG GGG AAA CTT TCA TCA GAA GAT CTG TGG TAT GCC ATC CCG GTA<br>Met Ala Gly Lys Leu Ser Ser Glu Asp Leu Trp Tyr Ala Ile Pro Val<br>1800 1805 1810 | 5897 |
| CTG ACC AGC CCG GGG GCG GGC CTT GCG GGG ATC GCT CTC GGG TTG GTT<br>Leu Thr Ser Pro Gly Ala Gly Leu Ala Gly Ile Ala Leu Gly Leu Val<br>1815 1820 1825 | 5945 |
| TTG TAT TCA GCT AAC AAC TCT GGC ACT ACC ACT TGG TTG AAC CGT CTG<br>Leu Tyr Ser Ala Asn Asn Ser Gly Thr Thr Thr Trp Leu Asn Arg Leu<br>1830 1835 1840 1845 | 5993 |
| CTG ACT ACG TTA CCA AGG TCT TCA TGT ATC CCG GAC AGT TAC TTT CAG<br>Leu Thr Thr Leu Pro Arg Ser Ser Cys Ile Pro Asp Ser Tyr Phe Gln<br>1850 1855 1860 | 6041 |
| CAA GTT GAC TAT TGC GAC AAG GTC TCA GCC GTG CTC CGG CGC CTG AGC<br>Gln Val Asp Tyr Cys Asp Lys Val Ser Ala Val Leu Arg Arg Leu Ser<br>1865 1870 1875 | 6089 |
| CTC ACC CGC ACA GTG GTT GCC CTG GTC AAC AGG GAG CCT AAG GTG GAT<br>Leu Thr Arg Thr Val Val Ala Leu Val Asn Arg Glu Pro Lys Val Asp<br>1880 1885 1890 | 6137 |
| GAG GTA CAG GTG GGG TAT GTC TGG GAC CTG TGG GAG TGG ATC ATG CGC<br>Glu Val Gln Val Gly Tyr Val Trp Asp Leu Trp Glu Trp Ile Met Arg<br>1895 1900 1905 | 6185 |
| CAA GTG CGC GTG GTC ATG GCC AGA CTC AGG GCC CTC TGC CCC GTG GTG<br>Gln Val Arg Val Val Met Ala Arg Leu Arg Ala Leu Cys Pro Val Val<br>1910 1915 1920 1925 | 6233 |
| TCA CTA CCC TTG TGG CAT TGC GGG GAG GGG TGG TCC GGG GAA TGG TTG<br>Ser Leu Pro Leu Trp His Cys Gly Glu Gly Trp Ser Gly Glu Trp Leu<br>1930 1935 1940 | 6281 |

| | |
|---|---:|
| CTT GAC GGT CAT GTT GAG AGT CGC TGC CTC TGT GGC TGC GTG ATC ACT<br>Leu Asp Gly His Val Glu Ser Arg Cys Leu Cys Gly Cys Val Ile Thr<br>1945                         1950                    1955 | 6329 |
| GGT GAC GTT CTG AAT GGG CAA CTC AAA GAA CCA GTT TAC TCT ACC AAG<br>Gly Asp Val Leu Asn Gly Gln Leu Lys Glu Pro Val Tyr Ser Thr Lys<br>1960                       1965                   1970 | 6377 |
| CTG TGC CGG CAC TAT TGG ATG GGG ACT GTC CCT GTG AAC ATG CTG GGT<br>Leu Cys Arg His Tyr Trp Met Gly Thr Val Pro Val Asn Met Leu Gly<br>1975                       1980                   1985 | 6425 |
| TAC GGT GAA ACG TCG CCT CTC CTG GCC TCC GAC ACC CCG AAG GTT GTG<br>Tyr Gly Glu Thr Ser Pro Leu Leu Ala Ser Asp Thr Pro Lys Val Val<br>1990                       1995                   2000                 2005 | 6473 |
| CCC TTC GGG ACG TCT GGC TGG GCT GAG GTG GTG GTG ACC ACT ACC CAC<br>Pro Phe Gly Thr Ser Gly Trp Ala Glu Val Val Val Thr Thr Thr His<br>2010                       2015                   2020 | 6521 |
| GTG GTA ATC AGG AGG ACC TCC GCC TAT AAG CTG CTG CGC CAG CAA ATC<br>Val Val Ile Arg Arg Thr Ser Ala Tyr Lys Leu Leu Arg Gln Gln Ile<br>2025                       2030                   2035 | 6569 |
| CTA TCG GCT GCT GTA GCT GAG CCC TAC TAC GTC GAC GGC ATT CCG GTC<br>Leu Ser Ala Ala Val Ala Glu Pro Tyr Tyr Val Asp Gly Ile Pro Val<br>2040                       2045                   2050 | 6617 |
| TCA TGG GAC GCG GAC GCT CGT GCG CCC GCC ATG GTC TAT GGC CCT GGG<br>Ser Trp Asp Ala Asp Ala Arg Ala Pro Ala Met Val Tyr Gly Pro Gly<br>2055                       2060                   2065 | 6665 |
| CAA AGT GTT ACC ATT GAC GGG GAG CGC TAC ACC TTG CCT CAT CAA CTG<br>Gln Ser Val Thr Ile Asp Gly Glu Arg Tyr Thr Leu Pro His Gln Leu<br>2070                       2075                   2080                 2085 | 6713 |
| AGG CTC AGG AAT GTG GCA CCC TCT GAG GTT TCA TCC GAG GTG TCC ATT<br>Arg Leu Arg Asn Val Ala Pro Ser Glu Val Ser Ser Glu Val Ser Ile<br>2090                       2095                   2100 | 6761 |
| GAC ATT GGG ACG GAG ACT GAA GAC TCA GAA CTG ACT GAG GCC GAT CTG<br>Asp Ile Gly Thr Glu Thr Glu Asp Ser Glu Leu Thr Glu Ala Asp Leu<br>2105                       2110                   2115 | 6809 |
| CCG CCG GCG GCT GCT GCT CTC CAA GCG ATC GAG AAT GCT GCG AGG ATT<br>Pro Pro Ala Ala Ala Ala Leu Gln Ala Ile Glu Asn Ala Ala Arg Ile<br>2120                       2125                   2130 | 6857 |
| CTT GAA CCG CAC ATT GAT GTC ATC ATG GAG GAC TGC AGT ACA CCC TCT<br>Leu Glu Pro His Ile Asp Val Ile Met Glu Asp Cys Ser Thr Pro Ser<br>2135                       2140                   2145 | 6905 |
| CTT TGT GGT AGT AGC CGA GAG ATG CCT GTA TGG GGA GAA GAC ATC CCC<br>Leu Cys Gly Ser Ser Arg Glu Met Pro Val Trp Gly Glu Asp Ile Pro<br>2150                       2155                   2160                 2165 | 6953 |
| CGT ACT CCA TCG CCA GCA CTT ATC TCG GTT ACT GAG AGC AGC TCA GAT<br>Arg Thr Pro Ser Pro Ala Leu Ile Ser Val Thr Glu Ser Ser Ser Asp<br>2170                       2175                   2180 | 7001 |
| GAG AAG ACC CCG TCG GTG TCC TCC TCG CAG GAG GAT ACC CCG TCC TCT<br>Glu Lys Thr Pro Ser Val Ser Ser Ser Gln Glu Asp Thr Pro Ser Ser<br>2185                       2190                   2195 | 7049 |
| GAC TCA TTC GAG GTC ATC CAA GAG TCC GAG ACA GCC GAA GGG GAG GAA<br>Asp Ser Phe Glu Val Ile Gln Glu Ser Glu Thr Ala Glu Gly Glu Glu<br>2200                       2205                   2210 | 7097 |
| AGT GTC TTC AAC GTG GCT CTT TCC GTA TTA AAA GCC TTA TTT CCA CAG<br>Ser Val Phe Asn Val Ala Leu Ser Val Leu Lys Ala Leu Phe Pro Gln<br>2215                       2220                   2225 | 7145 |
| AGC GAC GCG ACC AGG AAG CTT ACC GTC AAG ATG TCG TGC TGC GTT GAA<br>Ser Asp Ala Thr Arg Lys Leu Thr Val Lys Met Ser Cys Cys Val Glu<br>2230                       2235                   2240                 2245 | 7193 |
| AAG AGC GTC ACG CGC TTT TTC TCA TTG GGG TTG ACG GTG GCT GAT GTT<br>Lys Ser Val Thr Arg Phe Phe Ser Leu Gly Leu Thr Val Ala Asp Val<br>2250                       2255                   2260 | 7241 |

```
GCT AGC CTG TGT GAG ATG GAA ATC CAG AAC CAT ACA GCC TAT TGT GAC      7289
Ala Ser Leu Cys Glu Met Glu Ile Gln Asn His Thr Ala Tyr Cys Asp
        2265                    2270                    2275

CAG GTG CGC ACT CCG CTT GAA TTG CAG GTT GGG TGC TTG GTG GGC AAT      7337
Gln Val Arg Thr Pro Leu Glu Leu Gln Val Gly Cys Leu Val Gly Asn
        2280                    2285                    2290

GAA CTT ACC TTT GAA TGT GAC AAG TGT GAG GCT AGG CAA GAA ACC TTG      7385
Glu Leu Thr Phe Glu Cys Asp Lys Cys Glu Ala Arg Gln Glu Thr Leu
        2295                    2300                    2305

GCC TCC TTC TCT TAC ATT TGG TCT GGA GTG CCG CTG ACT AGG GCC ACG      7433
Ala Ser Phe Ser Tyr Ile Trp Ser Gly Val Pro Leu Thr Arg Ala Thr
        2310                    2315                    2320            2325

CCG GCC AAG CCT CCC GTG GTG AGG CCG GTT GGC TCT TTG TTA GTG GCC      7481
Pro Ala Lys Pro Pro Val Val Arg Pro Val Gly Ser Leu Leu Val Ala
                2330                    2335                    2340

GAC ACT ACT AAG GTG TAT GTT ACC AAT CCA GAC AAT GTG GGA CGG AGG      7529
Asp Thr Thr Lys Val Tyr Val Thr Asn Pro Asp Asn Val Gly Arg Arg
                2345                    2350                    2355

GTG GAC AAG GTG ACC TTC TGG CGT GCT CCT AGG GTT CAT GAT AAG TAC      7577
Val Asp Lys Val Thr Phe Trp Arg Ala Pro Arg Val His Asp Lys Tyr
        2360                    2365                    2370

CTC GTG GAC TCT ATT GAG CGC GCT AAG AGG GCC GCT CAA GCC TGC CTA      7625
Leu Val Asp Ser Ile Glu Arg Ala Lys Arg Ala Ala Gln Ala Cys Leu
        2375                    2380                    2385

AGC ATG GGT TAC ACT TAT GAG GAA GCA ATA AGG ACT GTA AGG CCA CAT      7673
Ser Met Gly Tyr Thr Tyr Glu Glu Ala Ile Arg Thr Val Arg Pro His
2390                    2395                    2400                    2405

GCT GCC ATG GGC TGG GGA TCT AAG GTG TCG GTT AAG GAC TTA GCC ACC      7721
Ala Ala Met Gly Trp Gly Ser Lys Val Ser Val Lys Asp Leu Ala Thr
        2410                    2415                    2420

CCC GCG GGG AAG ATG GCC GTC CAT GAC CGG CTT CAG GAG ATA CTT GAA      7769
Pro Ala Gly Lys Met Ala Val His Asp Arg Leu Gln Glu Ile Leu Glu
        2425                    2430                    2435

GGG ACT CCG GTC CCC TTT ACT CTT ACT GTG AAA AAG GAG GTG TTC TTC      7817
Gly Thr Pro Val Pro Phe Thr Leu Thr Val Lys Lys Glu Val Phe Phe
        2440                    2445                    2450

AAA GAC CGG AAG GAG GAG AAG GCC CCC CGC CTC ATT GTG TTC CCC CCC      7865
Lys Asp Arg Lys Glu Glu Lys Ala Pro Arg Leu Ile Val Phe Pro Pro
        2455                    2460                    2465

CTG GAC TTC CGG ATA GCT GAA AAG CTC ATC TTG GGA GAC CCA GGC CGG      7913
Leu Asp Phe Arg Ile Ala Glu Lys Leu Ile Leu Gly Asp Pro Gly Arg
2470                    2475                    2480                    2485

GTA GCC AAG GCG GTG TTG GGG GGG GCC TAC GCC TTC CAG TAC ACC CCA      7961
Val Ala Lys Ala Val Leu Gly Gly Ala Tyr Ala Phe Gln Tyr Thr Pro
                2490                    2495                    2500

AAT CAG CGA GTT AAG GAG ATG CTC AAG CTA TGG GAG TCT AAG AAG ACC      8009
Asn Gln Arg Val Lys Glu Met Leu Lys Leu Trp Glu Ser Lys Lys Thr
        2505                    2510                    2515

CCT TGC GCC ATC TGT GTG GAC GCC ACC TGC TTC GAC AGT AGC ATA ACT      8057
Pro Cys Ala Ile Cys Val Asp Ala Thr Cys Phe Asp Ser Ser Ile Thr
        2520                    2525                    2530

GAA GAG GAC GTG GCT TTG GAG ACA GAG CTA TAC GCT CTG GCC TCT GAC      8105
Glu Glu Asp Val Ala Leu Glu Thr Glu Leu Tyr Ala Leu Ala Ser Asp
        2535                    2540                    2545

CAT CCA GAA TGG GTG CGG GCA CTT GGG AAA TAC TAT GCC TCA GGC ACC      8153
His Pro Glu Trp Val Arg Ala Leu Gly Lys Tyr Tyr Ala Ser Gly Thr
        2550                    2555                    2560            2565

ATG GTC ACC CCG GAA GGG GTG CCC GTC GGT GAG AGG TAT TGC AGA TCC      8201
Met Val Thr Pro Glu Gly Val Pro Val Gly Glu Arg Tyr Cys Arg Ser
        2570                    2575                    2580
```

-continued

| | | | | | | | | | | | | | | | | |
|---|---|---|---|---|---|---|---|---|---|---|---|---|---|---|---|---|
| TCG | GGT | GTC | CTA | ACA | ACT | AGC | GCG | AGC | AAC | TGC | TTG | ACC | TGC | TAC | ATC | 8249 |
| Ser | Gly | Val | Leu | Thr | Thr | Ser | Ala | Ser | Asn | Cys | Leu | Thr | Cys | Tyr | Ile | |
| | | | 2585 | | | | 2590 | | | | | 2595 | | | | |
| AAG | GTG | AAA | GCT | GCC | TGT | GAG | AGA | GTG | GGG | CTG | AAA | AAT | GTC | TCT | CTT | 8297 |
| Lys | Val | Lys | Ala | Ala | Cys | Glu | Arg | Val | Gly | Leu | Lys | Asn | Val | Ser | Leu | |
| | | | 2600 | | | | 2605 | | | | | 2610 | | | | |
| CTC | ATA | GCC | GGC | GAT | GAC | TGC | TTG | ATC | ATA | TGT | GAG | CGG | CCA | GTG | TGC | 8345 |
| Leu | Ile | Ala | Gly | Asp | Asp | Cys | Leu | Ile | Ile | Cys | Glu | Arg | Pro | Val | Cys | |
| | | | 2615 | | | | 2620 | | | | | 2625 | | | | |
| GAC | CCA | AGC | GAC | GCT | TTG | GGC | AGA | GCC | CTA | GCG | AGC | TAT | GGG | TAC | GCG | 8393 |
| Asp | Pro | Ser | Asp | Ala | Leu | Gly | Arg | Ala | Leu | Ala | Ser | Tyr | Gly | Tyr | Ala | |
| | 2630 | | | | 2635 | | | | | 2640 | | | | | 2645 | |
| TGC | GAG | CCC | TCA | TAT | CAT | GCA | TCA | TTG | GAC.ACG | GCC | CCC | TTC | TGC | TCC | | 8441 |
| Cys | Glu | Pro | Ser | Tyr | His | Ala | Ser | Leu | Asp | Thr | Ala | Pro | Phe | Cys | Ser | |
| | | | 2650 | | | | 2655 | | | | | 2660 | | | | |
| ACT | TGG | CTT | GCT | GAG | TGC | AAT | GCA | GAT | GGG | AAG | CGC | CAT | TTC | TTC | CTG | 8489 |
| Thr | Trp | Leu | Ala | Glu | Cys | Asn | Ala | Asp | Gly | Lys | Arg | His | Phe | Phe | Leu | |
| | | | 2665 | | | | 2670 | | | | | 2675 | | | | |
| ACC | ACG | GAC | TTC | CGG | AGG | CCG | CTC | GCT | CGC | ATG | TCG | AGT | GAG | TAT | AGT | 8537 |
| Thr | Thr | Asp | Phe | Arg | Arg | Pro | Leu | Ala | Arg | Met | Ser | Ser | Glu | Tyr | Ser | |
| | | | 2680 | | | | 2685 | | | | | 2690 | | | | |
| GAC | CCG | ATG | GCT | TCG | GCG | ATC | GGT | TAC | ATC | CTC | CTT | TAT | CCT | TGG | CAC | 8585 |
| Asp | Pro | Met | Ala | Ser | Ala | Ile | Gly | Tyr | Ile | Leu | Leu | Tyr | Pro | Trp | His | |
| | 2695 | | | | 2700 | | | | | 2705 | | | | | | |
| CCC | ATC | ACA | CGG | TGG | GTC | ATC | ATC | CCT | CAT | GTG | CTA | ACG | TGC | GCA | TTC | 8633 |
| Pro | Ile | Thr | Arg | Trp | Val | Ile | Ile | Pro | His | Val | Leu | Thr | Cys | Ala | Phe | |
| 2710 | | | | 2715 | | | | | 2720 | | | | | 2725 | | |
| AGG | GGT | GGA | GGC | ACA | CCG | TCT | GAT | CCG | GTT | TGG | TGC | CAG | GTG | CAT | GGT | 8681 |
| Arg | Gly | Gly | Gly | Thr | Pro | Ser | Asp | Pro | Val | Trp | Cys | Gln | Val | His | Gly | |
| | | | 2730 | | | | 2735 | | | | | 2740 | | | | |
| AAC | TAC | TAC | AAG | TTT | CCA | CTG | GAC | AAA | CTG | CCT | AAC | ATC | ATC | GTG | GCC | 8729 |
| Asn | Tyr | Tyr | Lys | Phe | Pro | Leu | Asp | Lys | Leu | Pro | Asn | Ile | Ile | Val | Ala | |
| | | | 2745 | | | | 2750 | | | | | 2755 | | | | |
| CTC | CAC | GGA | CCA | GCA | GCG | TTG | AGG | GTT | ACC | GCA | GAC | ACA | ACT | AAA | ACA | 8777 |
| Leu | His | Gly | Pro | Ala | Ala | Leu | Arg | Val | Thr | Ala | Asp | Thr | Thr | Lys | Thr | |
| | | | 2760 | | | | 2765 | | | | | 2770 | | | | |
| AAG | ATG | GAG | GCT | GGT | AAG | GTT | CTG | AGC | GAC | CTC | AAG | CTC | CCT | GGC | TTA | 8825 |
| Lys | Met | Glu | Ala | Gly | Lys | Val | Leu | Ser | Asp | Leu | Lys | Leu | Pro | Gly | Leu | |
| | | | 2775 | | | | 2780 | | | | | 2785 | | | | |
| GCA | GTC | CAC | CGA | AAG | AAG | GCC | GGG | GCG | TTG | CGA | ACA | CGC | ATG | CTC | CGC | 8873 |
| Ala | Val | His | Arg | Lys | Lys | Ala | Gly | Ala | Leu | Arg | Thr | Arg | Met | Leu | Arg | |
| 2790 | | | | 2795 | | | | | 2800 | | | | | 2805 | | |
| TCG | CGC | GGT | TGG | GCT | GAG | TTG | GCT | AGG | GGC | TTG | TTG | TGG | CAT | CCA | GGC | 8921 |
| Ser | Arg | Gly | Trp | Ala | Glu | Leu | Ala | Arg | Gly | Leu | Leu | Trp | His | Pro | Gly | |
| | | | 2810 | | | | 2815 | | | | | 2820 | | | | |
| CTA | CGG | CTT | CCT | CCC | CCT | GAG | ATT | GCT | GGT | ATC | CCG | GGG | GGT | TTC | CCT | 8969 |
| Leu | Arg | Leu | Pro | Pro | Pro | Glu | Ile | Ala | Gly | Ile | Pro | Gly | Gly | Phe | Pro | |
| | | | 2825 | | | | 2830 | | | | | 2835 | | | | |
| CTC | TCC | CCC | CCC | TAT | ATG | GGG | GTG | GTA | CAT | CAA | TTG | GAT | TTC | ACA | AGC | 9017 |
| Leu | Ser | Pro | Pro | Tyr | Met | Gly | Val | Val | His | Gln | Leu | Asp | Phe | Thr | Ser | |
| | | | 2840 | | | | 2845 | | | | | 2850 | | | | |
| CAG | AGG | AGT | CGC | TGG | CGG | TGG | TTG | GGG | TTC | TTA | GCC | CTG | CTC | ATC | GTA | 9065 |
| Gln | Arg | Ser | Arg | Trp | Arg | Trp | Leu | Gly | Phe | Leu | Ala | Leu | Leu | Ile | Val | |
| | | | 2855 | | | | 2860 | | | | | 2865 | | | | |
| GCC | CTC | TTC | GGG | TGAACTAAAT | TCATCTGTTG | CGGCAAGGTC | TGGTGACTGA | | | | | | | | | 9117 |
| Ala | Leu | Phe | Gly | | | | | | | | | | | | | |
| 2870 | | | | | | | | | | | | | | | | |

| | | | | |
|---|---|---|---|---|
| TCATCACCGG | AGGAGGTTCC | CGCCCTCCCC | GCCCCAGGGG | TCTCCCCGCT | GGGTAAAAAG | 9177 |
| GGCCCGGCCT | TGGGAGGCAT | GGTGGTTACT | AACCCCCTGG | CAGGGTCAAA | GCCTGATGGT | 9237 |

```
GCTAATGCAC TGCCACTTCG GTGGCGGGTC GCTACCTTAT AGCGTAATCC GTGACTACGG      9297

GCTGCTCGCA GAGCCCTCCC CGGATGGGGC ACAGTGCACT GTGATCTGAA GGGGTGCACC      9357

CCGGGAAGAG CTCGGCCCGA AGGCCGGSTT CTACT                                9392
```

( 2 ) INFORMATION FOR SEQ ID NO:15:

( i ) SEQUENCE CHARACTERISTICS:
        ( A ) LENGTH: 2873 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Gly  Pro  Pro  Ser  Ser  Ala  Ala  Ala  Cys  Ser  Arg  Gly  Ser  Pro  Arg
 1                   5                        10                      15

Ile  Leu  Arg  Val  Arg  Ala  Gly  Gly  Ile  Ser  Phe  Phe  Tyr  Thr  Ile  Met
           20                        25                       30

Ala  Val  Leu  Leu  Leu  Leu  Leu  Val  Val  Glu  Ala  Gly  Ala  Ile  Leu  Ala
                35                        40                       45

Pro  Ala  Thr  His  Ala  Cys  Arg  Ala  Asn  Gly  Gln  Tyr  Phe  Leu  Thr  Asn
      50                        55                       60

Cys  Cys  Ala  Pro  Glu  Asp  Ile  Gly  Phe  Cys  Leu  Glu  Gly  Gly  Cys  Leu
65                        70                       75                      80

Val  Ala  Leu  Gly  Cys  Thr  Ile  Cys  Thr  Asp  Gln  Cys  Trp  Pro  Leu  Tyr
                85                        90                       95

Gln  Ala  Gly  Leu  Ala  Val  Arg  Pro  Gly  Lys  Ser  Ala  Ala  Gln  Leu  Val
               100                       105                      110

Gly  Glu  Leu  Gly  Ser  Leu  Tyr  Gly  Pro  Leu  Ser  Val  Ser  Ala  Tyr  Val
               115                       120                      125

Ala  Gly  Ile  Leu  Gly  Leu  Gly  Glu  Val  Tyr  Ser  Gly  Val  Leu  Thr  Val
          130                       135                      140

Gly  Val  Ala  Leu  Thr  Arg  Arg  Val  Tyr  Pro  Val  Pro  Asn  Leu  Thr  Cys
145                       150                       155                     160

Ala  Val  Ala  Cys  Glu  Leu  Lys  Trp  Glu  Ser  Glu  Phe  Trp  Arg  Trp  Thr
                165                       170                      175

Glu  Gln  Leu  Ala  Ser  Asn  Tyr  Trp  Ile  Leu  Glu  Tyr  Leu  Trp  Lys  Val
               180                       185                      190

Pro  Phe  Asp  Phe  Trp  Arg  Gly  Val  Ile  Ser  Leu  Thr  Pro  Leu  Leu  Val
          195                       200                      205

Cys  Val  Ala  Ala  Leu  Leu  Leu  Leu  Glu  Gln  Arg  Ile  Val  Met  Val  Phe
     210                       215                      220

Leu  Leu  Val  Thr  Met  Ala  Gly  Met  Ser  Gln  Gly  Ala  Pro  Ala  Ser  Val
225                       230                       235                     240

Leu  Gly  Ser  Arg  Pro  Phe  Asp  Tyr  Gly  Leu  Thr  Trp  Gln  Thr  Cys  Ser
                245                       250                      255

Cys  Arg  Ala  Asn  Gly  Ser  Arg  Phe  Ser  Thr  Gly  Glu  Lys  Val  Trp  Asp
               260                       265                      270

Arg  Gly  Asn  Val  Thr  Leu  Gln  Cys  Asp  Cys  Pro  Asn  Gly  Pro  Trp  Val
          275                       280                      285

Trp  Leu  Pro  Ala  Phe  Cys  Gln  Ala  Ile  Gly  Trp  Gly  Asp  Pro  Ile  Thr
     290                       295                      300

Tyr  Trp  Ser  His  Gly  Gln  Asn  Gln  Trp  Pro  Leu  Ser  Cys  Pro  Gln  Tyr
305                       310                       315                     320

Val  Tyr  Gly  Ser  Ala  Thr  Val  Thr  Cys  Val  Trp  Gly  Ser  Ala  Ser  Trp
                325                       330                      335
```

-continued

| | | | | | | | | | | | | | |
|---|---|---|---|---|---|---|---|---|---|---|---|---|---|
| Phe | Ala | Ser | Thr 340 | Ser | Gly | Arg | Asp | Ser 345 | Lys | Ile | Asp | Val | Trp Ser 350 | Leu |
| Val | Pro | Val 355 | Gly | Ser | Ala | Thr | Cys 360 | Thr | Ile | Ala | Ala | Leu 365 | Gly | Ser | Ser |
| Asp | Arg 370 | Asp | Thr | Val | Pro | Gly 375 | Leu | Ser | Glu | Trp 380 | Gly | Ile | Pro | Cys | Val |
| Thr 385 | Cys | Val | Leu | Asp | Arg 390 | Arg | Pro | Ala | Ser | Cys 395 | Gly | Thr | Cys | Val | Arg 400 |
| Asp | Cys | Trp | Pro | Glu 405 | Thr | Gly | Ser | Val | Arg 410 | Phe | Pro | Phe | His | Arg 415 | Cys |
| Gly | Val | Gly | Pro 420 | Arg | Leu | Thr | Lys | Asp 425 | Leu | Glu | Ala | Val | Pro 430 | Phe | Val |
| Asn | Arg | Thr 435 | Thr | Pro | Phe | Thr | Ile 440 | Arg | Gly | Pro | Leu | Gly 445 | Asn | Gln | Gly |
| Arg | Gly 450 | Asn | Pro | Val | Arg | Ser 455 | Pro | Leu | Gly | Phe | Gly 460 | Ser | Tyr | Ala | Met |
| Thr 465 | Arg | Ile | Arg | Asp | Thr 470 | Leu | His | Leu | Val | Glu 475 | Cys | Pro | Thr | Pro | Ala 480 |
| Ile | Glu | Pro | Pro | Thr 485 | Gly | Thr | Phe | Gly | Phe 490 | Phe | Pro | Gly | Thr | Pro 495 | Pro |
| Leu | Asn | Asn | Cys 500 | Met | Leu | Leu | Gly | Thr 505 | Glu | Val | Ser | Glu | Ala 510 | Leu | Gly |
| Gly | Ala | Gly 515 | Leu | Thr | Gly | Gly | Phe 520 | Tyr | Glu | Pro | Leu | Val 525 | Arg | Arg | Cys |
| Ser | Lys 530 | Leu | Met | Gly | Ser | Arg 535 | Asn | Pro | Val | Cys | Pro 540 | Gly | Phe | Ala | Trp |
| Leu 545 | Ser | Ser | Gly | Arg | Pro 550 | Asp | Gly | Phe | Ile | His 555 | Val | Gln | Gly | His | Leu 560 |
| Gln | Glu | Val | Asp | Ala 565 | Gly | Asn | Phe | Ile | Pro 570 | Pro | Pro | Arg | Trp | Leu 575 | Leu |
| Leu | Asp | Phe | Val 580 | Phe | Val | Leu | Leu | Tyr 585 | Leu | Met | Lys | Leu | Ala 590 | Glu | Ala |
| Arg | Leu | Val 595 | Pro | Leu | Ile | Leu | Leu 600 | Leu | Leu | Trp | Trp | Trp 605 | Val | Asn | Gln |
| Leu | Ala 610 | Val | Leu | Gly | Leu | Pro 615 | Ala | Val | Glu | Ala | Ala 620 | Val | Ala | Gly | Glu |
| Val 625 | Phe | Ala | Gly | Pro | Ala 630 | Leu | Ser | Trp | Cys | Leu 635 | Gly | Leu | Pro | Val 640 | Val |
| Ser | Met | Ile | Leu | Gly 645 | Leu | Ala | Asn | Leu | Val 650 | Leu | Tyr | Phe | Arg | Trp 655 | Leu |
| Gly | Pro | Gln | Arg 660 | Leu | Met | Phe | Leu | Val 665 | Leu | Trp | Lys | Leu | Ala 670 | Arg | Gly |
| Ala | Phe | Pro 675 | Leu | Ala | Leu | Leu | Met 680 | Gly | Ile | Ser | Ala | Thr 685 | Arg | Gly | Arg |
| Thr | Ser 690 | Val | Leu | Gly | Ala | Glu 695 | Phe | Cys | Phe | Asp | Ala 700 | Thr | Phe | Glu | Val |
| Asp 705 | Thr | Ser | Val | Leu | Gly 710 | Trp | Val | Val | Ala | Ser 715 | Val | Val | Ala | Trp | Ala 720 |
| Ile | Ala | Leu | Leu | Ser 725 | Ser | Met | Ser | Ala | Gly 730 | Gly | Trp | Arg | His | Lys 735 | Ala |
| Val | Ile | Tyr | Arg 740 | Thr | Trp | Cys | Lys | Gly 745 | Tyr | Gln | Ala | Ile | Arg 750 | Gln | Arg |
| Val | Val | Arg | Ser | Pro | Leu | Gly | Glu | Gly | Arg | Pro | Ala | Lys | Pro | Leu | Thr |

|     |     |     |     |     | 755 |     |     |     | 760 |     |     |     | 765 |     |
|---|---|---|---|---|---|---|---|---|---|---|---|---|---|---|
| Phe | Ala | Trp | Cys | Leu | Ala | Ser | Tyr | Ile | Trp | Pro | Asp | Ala | Val | Met | Met |
|     | 770 |     |     |     |     | 775 |     |     |     | 780 |     |     |     |     |     |
| Val | Val | Val | Ala | Leu | Val | Leu | Leu | Phe | Gly | Leu | Phe | Asp | Ala | Leu | Asp |
| 785 |     |     |     |     | 790 |     |     |     |     | 795 |     |     |     |     | 800 |
| Trp | Ala | Leu | Glu | Glu | Ile | Leu | Val | Ser | Arg | Pro | Ser | Leu | Arg | Arg | Leu |
|     |     |     |     | 805 |     |     |     |     | 810 |     |     |     |     | 815 |     |
| Ala | Arg | Val | Val | Glu | Cys | Cys | Val | Met | Ala | Gly | Glu | Lys | Ala | Thr | Thr |
|     |     |     | 820 |     |     |     |     | 825 |     |     |     |     | 830 |     |     |
| Val | Arg | Leu | Val | Ser | Lys | Met | Cys | Ala | Arg | Gly | Ala | Tyr | Leu | Phe | Asp |
|     |     | 835 |     |     |     |     | 840 |     |     |     |     | 845 |     |     |     |
| His | Met | Gly | Ser | Phe | Ser | Arg | Ala | Val | Lys | Glu | Arg | Leu | Leu | Glu | Trp |
|     | 850 |     |     |     |     | 855 |     |     |     |     | 860 |     |     |     |     |
| Asp | Ala | Ala | Leu | Glu | Pro | Leu | Ser | Phe | Thr | Arg | Thr | Asp | Cys | Arg | Ile |
| 865 |     |     |     |     | 870 |     |     |     |     | 875 |     |     |     |     | 880 |
| Ile | Arg | Asp | Ala | Ala | Arg | Thr | Leu | Ser | Cys | Gly | Gln | Cys | Val | Met | Gly |
|     |     |     |     | 885 |     |     |     |     | 890 |     |     |     |     | 895 |     |
| Leu | Pro | Val | Val | Ala | Arg | Arg | Gly | Asp | Glu | Val | Leu | Ile | Gly | Val | Phe |
|     |     |     | 900 |     |     |     |     | 905 |     |     |     |     | 910 |     |     |
| Gln | Asp | Val | Asn | His | Leu | Pro | Pro | Gly | Phe | Val | Pro | Thr | Ala | Pro | Val |
|     |     | 915 |     |     |     |     | 920 |     |     |     |     | 925 |     |     |     |
| Val | Ile | Arg | Arg | Cys | Gly | Lys | Gly | Phe | Leu | Gly | Val | Thr | Lys | Ala | Ala |
|     | 930 |     |     |     |     | 935 |     |     |     |     | 940 |     |     |     |     |
| Leu | Thr | Gly | Arg | Asp | Pro | Asp | Leu | His | Pro | Gly | Asn | Val | Met | Val | Leu |
| 945 |     |     |     |     | 950 |     |     |     |     | 955 |     |     |     |     | 960 |
| Gly | Thr | Ala | Thr | Ser | Arg | Ser | Met | Gly | Thr | Cys | Leu | Asn | Gly | Leu | Leu |
|     |     |     |     | 965 |     |     |     |     | 970 |     |     |     |     | 975 |     |
| Phe | Thr | Thr | Phe | His | Gly | Ala | Ser | Ser | Arg | Thr | Ile | Ala | Thr | Pro | Val |
|     |     |     | 980 |     |     |     |     | 985 |     |     |     |     | 990 |     |     |
| Gly | Ala | Leu | Asn | Pro | Arg | Trp | Trp | Ser | Ala | Ser | Asp | Asp | Val | Thr | Val |
|     |     | 995 |     |     |     |     | 1000 |     |     |     |     | 1005 |     |     |     |
| Tyr | Pro | Leu | Pro | Asp | Gly | Ala | Thr | Ser | Leu | Thr | Pro | Cys | Thr | Cys | Gln |
|     |     | 1010 |     |     |     |     | 1015 |     |     |     |     | 1020 |     |     |     |
| Ala | Glu | Ser | Cys | Trp | Val | Ile | Arg | Ser | Asp | Gly | Ala | Leu | Cys | His | Gly |
| 1025 |     |     |     |     | 1030 |     |     |     |     | 1035 |     |     |     |     | 1040 |
| Leu | Ser | Lys | Gly | Asp | Lys | Val | Glu | Leu | Asp | Val | Ala | Met | Glu | Val | Ser |
|     |     |     |     | 1045 |     |     |     |     | 1050 |     |     |     |     | 1055 |     |
| Asp | Phe | Arg | Gly | Ser | Ser | Gly | Ser | Pro | Val | Leu | Cys | Asp | Glu | Gly | His |
|     |     |     | 1060 |     |     |     |     | 1065 |     |     |     |     | 1070 |     |     |
| Ala | Val | Gly | Met | Leu | Val | Ser | Val | Leu | His | Ser | Gly | Gly | Arg | Val | Thr |
|     |     | 1075 |     |     |     |     | 1080 |     |     |     |     | 1085 |     |     |     |
| Ala | Ala | Arg | Phe | Thr | Arg | Pro | Trp | Thr | Gln | Val | Pro | Thr | Asp | Ala | Lys |
|     | 1090 |     |     |     |     | 1095 |     |     |     |     | 1100 |     |     |     |     |
| Thr | Thr | Thr | Glu | Pro | Pro | Pro | Val | Pro | Ala | Lys | Gly | Val | Phe | Lys | Glu |
| 1105 |     |     |     |     | 1110 |     |     |     |     | 1115 |     |     |     |     | 1120 |
| Ala | Pro | Leu | Phe | Met | Pro | Thr | Gly | Ala | Gly | Lys | Ser | Thr | Arg | Val | Pro |
|     |     |     |     | 1125 |     |     |     |     | 1130 |     |     |     |     | 1135 |     |
| Leu | Glu | Tyr | Asp | Asn | Met | Gly | His | Lys | Val | Leu | Ile | Leu | Asn | Pro | Ser |
|     |     |     | 1140 |     |     |     |     | 1145 |     |     |     |     | 1150 |     |     |
| Val | Ala | Thr | Val | Arg | Ala | Met | Gly | Pro | Tyr | Met | Glu | Arg | Leu | Ala | Gly |
|     |     | 1155 |     |     |     |     | 1160 |     |     |     |     | 1165 |     |     |     |
| Lys | His | Pro | Ser | Ile | Tyr | Cys | Gly | His | Asp | Thr | Thr | Ala | Phe | Thr | Arg |
|     | 1170 |     |     |     |     | 1175 |     |     |     |     | 1180 |     |     |     |     |

```
Ile  Thr  Asp  Ser  Pro  Leu  Thr  Tyr  Ser  Thr  Tyr  Gly  Arg  Phe  Leu  Ala
1185                1190                1195                          1200

Asn  Pro  Arg  Gln  Met  Leu  Arg  Gly  Val  Ser  Val  Val  Ile  Cys  Asp  Glu
                         1205                     1210                     1215

Cys  His  Ser  His  Asp  Ser  Thr  Val  Leu  Leu  Gly  Ile  Gly  Arg  Val  Arg
               1220                     1225                    1230

Glu  Leu  Ala  Arg  Gly  Cys  Gly  Val  Gln  Leu  Val  Leu  Tyr  Ala  Thr  Ala
          1235                    1240                         1245

Thr  Pro  Pro  Gly  Ser  Pro  Met  Thr  Gln  His  Pro  Ser  Ile  Ile  Glu  Thr
          1250                    1255                         1260

Lys  Leu  Asp  Val  Gly  Glu  Ile  Pro  Phe  Tyr  Gly  His  Gly  Ile  Pro  Leu
1265                1270                     1275                          1280

Glu  Arg  Met  Arg  Thr  Gly  Arg  His  Leu  Val  Phe  Cys  His  Ser  Lys  Ala
                    1285                     1290                         1295

Glu  Cys  Glu  Arg  Leu  Ala  Gly  Gln  Phe  Ser  Ala  Arg  Gly  Val  Asn  Ala
               1300                    1305                         1310

Ile  Ala  Tyr  Tyr  Arg  Gly  Lys  Asp  Ser  Ser  Ile  Ile  Lys  Asp  Gly  Asp
               1315                    1320                         1325

Leu  Val  Val  Cys  Ala  Thr  Asp  Ala  Leu  Ser  Thr  Gly  Tyr  Thr  Gly  Asn
               1330                    1335                         1340

Phe  Asp  Ser  Val  Thr  Asp  Cys  Gly  Leu  Val  Val  Glu  Glu  Val  Val  Glu
1345                1350                     1355                          1360

Val  Thr  Leu  Asp  Pro  Thr  Ile  Thr  Ile  Ser  Leu  Arg  Thr  Val  Pro  Ala
                    1365                     1370                         1375

Ser  Ala  Glu  Leu  Ser  Met  Gln  Arg  Arg  Gly  Arg  Thr  Gly  Arg  Gly  Arg
               1380                    1385                         1390

Ser  Gly  Arg  Tyr  Tyr  Tyr  Ala  Gly  Val  Gly  Lys  Ala  Pro  Ala  Gly  Val
               1395                    1400                         1405

Val  Arg  Ser  Gly  Pro  Val  Trp  Ser  Ala  Val  Glu  Ala  Gly  Val  Thr  Trp
          1410                    1415                         1420

Tyr  Gly  Met  Glu  Pro  Asp  Leu  Thr  Ala  Asn  Leu  Leu  Arg  Leu  Tyr  Asp
1425                1430                     1435                          1440

Asp  Cys  Pro  Tyr  Thr  Ala  Ala  Val  Ala  Ala  Asp  Ile  Gly  Glu  Ala  Ala
               1445                    1450                         1455

Val  Phe  Phe  Ser  Gly  Leu  Ala  Pro  Leu  Arg  Met  His  Pro  Asp  Val  Ser
               1460                    1465                         1470

Trp  Ala  Lys  Val  Arg  Gly  Val  Asn  Trp  Pro  Leu  Leu  Val  Gly  Val  Gln
          1475                    1480                         1485

Arg  Thr  Met  Cys  Arg  Glu  Thr  Leu  Ser  Pro  Gly  Pro  Ser  Asp  Asp  Pro
          1490                    1495                         1500

Gln  Trp  Ala  Gly  Leu  Lys  Gly  Pro  Asn  Pro  Val  Pro  Leu  Leu  Leu  Arg
1505                1510                     1515                          1520

Trp  Gly  Asn  Asp  Leu  Pro  Ser  Lys  Val  Ala  Gly  His  His  Ile  Val  Asp
                    1525                     1530                         1535

Asp  Leu  Val  Arg  Arg  Leu  Gly  Val  Ala  Glu  Gly  Tyr  Val  Arg  Cys  Asp
                    1540                     1545                         1550

Ala  Gly  Pro  Ile  Leu  Met  Ile  Gly  Leu  Ala  Ile  Ala  Gly  Gly  Met  Ile
               1555                    1560                         1565

Tyr  Ala  Ser  Tyr  Thr  Gly  Ser  Leu  Val  Val  Val  Thr  Asp  Trp  Asp  Val
               1570                    1575                         1580

Lys  Gly  Gly  Gly  Ala  Pro  Leu  Tyr  Arg  His  Gly  Asp  Gln  Ala  Thr  Pro
1585                1590                     1595                          1600

Gln  Pro  Val  Val  Gln  Val  Pro  Pro  Val  Asp  His  Arg  Pro  Gly  Gly  Glu
                    1605                     1610                         1615
```

Ser Ala Pro Ser Asp Ala Lys Thr Val Thr Asp Ala Val Ala Ala Ile
            1620                1625               1630

Gln Val Asp Cys Asp Trp Thr Ile Met Thr Leu Ser Ile Gly Glu Val
            1635                1640               1645

Leu Ser Leu Ala Gln Ala Lys Thr Ala Glu Ala Tyr Thr Ala Thr Ala
            1650                1655               1660

Lys Trp Leu Ala Gly Cys Tyr Thr Gly Thr Arg Ala Val Pro Thr Val
1665                1670                1675               1680

Ser Ile Val Asp Lys Leu Phe Ala Gly Gly Trp Ala Ala Val Val Gly
                1685                1690               1695

His Cys His Ser Val Ile Ala Ala Ala Val Ala Ala Tyr Gly Ala Ser
            1700                1705               1710

Arg Ser Pro Pro Leu Ala Ala Ala Ala Ser Tyr Leu Met Gly Leu Gly
            1715                1720               1725

Val Gly Gly Asn Ala Gln Thr Arg Leu Ala Ser Ala Leu Leu Leu Gly
            1730                1735               1740

Ala Ala Gly Thr Ala Leu Gly Thr Pro Val Val Gly Leu Thr Met Ala
1745                1750                1755               1760

Gly Ala Phe Met Gly Gly Ala Ser Val Ser Pro Ser Leu Val Thr Ile
                1765                1770               1775

Leu Leu Gly Ala Val Gly Gly Trp Glu Gly Val Val Asn Ala Ala Ser
            1780                1785               1790

Leu Val Phe Asp Phe Met Ala Gly Lys Leu Ser Ser Glu Asp Leu Trp
            1795                1800               1805

Tyr Ala Ile Pro Val Leu Thr Ser Pro Gly Ala Gly Leu Ala Gly Ile
            1810                1815               1820

Ala Leu Gly Leu Val Leu Tyr Ser Ala Asn Asn Ser Gly Thr Thr Thr
1825                1830                1835               1840

Trp Leu Asn Arg Leu Leu Thr Thr Leu Pro Arg Ser Ser Cys Ile Pro
            1845                1850               1855

Asp Ser Tyr Phe Gln Gln Val Asp Tyr Cys Asp Lys Val Ser Ala Val
            1860                1865               1870

Leu Arg Arg Leu Ser Leu Thr Arg Thr Val Val Ala Leu Val Asn Arg
            1875                1880               1885

Glu Pro Lys Val Asp Glu Val Gln Val Gly Tyr Val Trp Asp Leu Trp
            1890                1895               1900

Glu Trp Ile Met Arg Gln Val Arg Val Val Met Ala Arg Leu Arg Ala
1905                1910                1915               1920

Leu Cys Pro Val Val Ser Leu Pro Leu Trp His Cys Gly Glu Gly Trp
                1925                1930               1935

Ser Gly Glu Trp Leu Leu Asp Gly His Val Glu Ser Arg Cys Leu Cys
            1940                1945               1950

Gly Cys Val Ile Thr Gly Asp Val Leu Asn Gly Gln Leu Lys Glu Pro
            1955                1960               1965

Val Tyr Ser Thr Lys Leu Cys Arg His Tyr Trp Met Gly Thr Val Pro
            1970                1975               1980

Val Asn Met Leu Gly Tyr Gly Glu Thr Ser Pro Leu Leu Ala Ser Asp
1985                1990                1995               2000

Thr Pro Lys Val Val Pro Phe Gly Thr Ser Gly Trp Ala Glu Val Val
                2005                2010               2015

Val Thr Thr Thr His Val Val Ile Arg Arg Thr Ser Ala Tyr Lys Leu
            2020                2025               2030

Leu Arg Gln Gln Ile Leu Ser Ala Ala Val Ala Glu Pro Tyr Tyr Val

|     |     |     |     | 2035 |     |     |     | 2040 |     |     |     | 2045 |     |     |
| --- | --- | --- | --- | --- | --- | --- | --- | --- | --- | --- | --- | --- | --- | --- |

Asp Gly Ile Pro Val Ser Trp Asp Ala Asp Ala Arg Ala Pro Ala Met
    2050                2055                2060

Val Tyr Gly Pro Gly Gln Ser Val Thr Ile Asp Gly Glu Arg Tyr Thr
2065            2070                2075                2080

Leu Pro His Gln Leu Arg Leu Arg Asn Val Ala Pro Ser Glu Val Ser
                2085                2090                2095

Ser Glu Val Ser Ile Asp Ile Gly Thr Glu Thr Glu Asp Ser Glu Leu
            2100                2105                2110

Thr Glu Ala Asp Leu Pro Pro Ala Ala Ala Leu Gln Ala Ile Glu
        2115                2120                2125

Asn Ala Ala Arg Ile Leu Glu Pro His Ile Asp Val Ile Met Glu Asp
    2130                2135                2140

Cys Ser Thr Pro Ser Leu Cys Gly Ser Ser Arg Glu Met Pro Val Trp
2145                2150                .2155                2160

Gly Glu Asp Ile Pro Arg Thr Pro Ser Pro Ala Leu Ile Ser Val Thr
                2165                2170                2175

Glu Ser Ser Ser Asp Glu Lys Thr Pro Ser Val Ser Ser Ser Gln Glu
            2180                2185                2190

Asp Thr Pro Ser Ser Asp Ser Phe Glu Val Ile Gln Glu Ser Glu Thr
        2195                2200                2205

Ala Glu Gly Glu Glu Ser Val Phe Asn Val Ala Leu Ser Val Leu Lys
    2210                2215                2220

Ala Leu Phe Pro Gln Ser Asp Ala Thr Arg Lys Leu Thr Val Lys Met
2225                2230                2235                2240

Ser Cys Cys Val Glu Lys Ser Val Thr Arg Phe Phe Ser Leu Gly Leu
                2245                2250                2255

Thr Val Ala Asp Val Ala Ser Leu Cys Glu Met Glu Ile Gln Asn His
            2260                2265                2270

Thr Ala Tyr Cys Asp Gln Val Arg Thr Pro Leu Glu Leu Gln Val Gly
        2275                2280                2285

Cys Leu Val Gly Asn Glu Leu Thr Phe Glu Cys Asp Lys Cys Glu Ala
    2290                2295                2300

Arg Gln Glu Thr Leu Ala Ser Phe Ser Tyr Ile Trp Ser Gly Val Pro
2305                2310                2315                2320

Leu Thr Arg Ala Thr Pro Ala Lys Pro Pro Val Val Arg Pro Val Gly
                2325                2330                2335

Ser Leu Leu Val Ala Asp Thr Thr Lys Val Tyr Val Thr Asn Pro Asp
            2340                2345                2350

Asn Val Gly Arg Arg Val Asp Lys Val Thr Phe Trp Arg Ala Pro Arg
        2355                2360                2365

Val His Asp Lys Tyr Leu Val Asp Ser Ile Glu Arg Ala Lys Arg Ala
    2370                2375                2380

Ala Gln Ala Cys Leu Ser Met Gly Tyr Thr Tyr Glu Glu Ala Ile Arg
2385                2390                2395                2400

Thr Val Arg Pro His Ala Ala Met Gly Trp Gly Ser Lys Val Ser Val
                2405                2410                2415

Lys Asp Leu Ala Thr Pro Ala Gly Lys Met Ala Val His Asp Arg Leu
            2420                2425                2430

Gln Glu Ile Leu Glu Gly Thr Pro Val Pro Phe Thr Leu Thr Val Lys
        2435                2440                2445

Lys Glu Val Phe Phe Lys Asp Arg Lys Glu Glu Lys Ala Pro Arg Leu
    2450                2455                2460

```
Ile Val Phe Pro Pro Leu Asp Phe Arg Ile Ala Glu Lys Leu Ile Leu
2465                 2470                2475                2480

Gly Asp Pro Gly Arg Val Ala Lys Ala Val Leu Gly Gly Ala Tyr Ala
                2485                2490                2495

Phe Gln Tyr Thr Pro Asn Gln Arg Val Lys Glu Met Leu Lys Leu Trp
            2500                2505                2510

Glu Ser Lys Lys Thr Pro Cys Ala Ile Cys Val Asp Ala Thr Cys Phe
        2515                2520                2525

Asp Ser Ser Ile Thr Glu Glu Asp Val Ala Leu Glu Thr Glu Leu Tyr
    2530                2535                2540

Ala Leu Ala Ser Asp His Pro Glu Trp Val Arg Ala Leu Gly Lys Tyr
2545                2550                2555                2560

Tyr Ala Ser Gly Thr Met Val Thr Pro Glu Gly Val Pro Val Gly Glu
                2565                2570                2575

Arg Tyr Cys Arg Ser Ser Gly Val Leu Thr Thr Ser Ala Ser Asn Cys
            2580                2585                2590

Leu Thr Cys Tyr Ile Lys Val Lys Ala Ala Cys Glu Arg Val Gly Leu
        2595                2600                2605

Lys Asn Val Ser Leu Leu Ile Ala Gly Asp Asp Cys Leu Ile Ile Cys
    2610                2615                2620

Glu Arg Pro Val Cys Asp Pro Ser Asp Ala Leu Gly Arg Ala Leu Ala
2625                2630                2635                2640

Ser Tyr Gly Tyr Ala Cys Glu Pro Ser Tyr His Ala Ser Leu Asp Thr
                2645                2650                2655

Ala Pro Phe Cys Ser Thr Trp Leu Ala Glu Cys Asn Ala Asp Gly Lys
            2660                2665                2670

Arg His Phe Phe Leu Thr Thr Asp Phe Arg Arg Pro Leu Ala Arg Met
        2675                2680                2685

Ser Ser Glu Tyr Ser Asp Pro Met Ala Ser Ala Ile Gly Tyr Ile Leu
    2690                2695                2700

Leu Tyr Pro Trp His Pro Ile Thr Arg Trp Val Ile Ile Pro His Val
2705                2710                2715                2720

Leu Thr Cys Ala Phe Arg Gly Gly Gly Thr Pro Ser Asp Pro Val Trp
                2725                2730                2735

Cys Gln Val His Gly Asn Tyr Tyr Lys Phe Pro Leu Asp Lys Leu Pro
            2740                2745                2750

Asn Ile Ile Val Ala Leu His Gly Pro Ala Ala Leu Arg Val Thr Ala
        2755                2760                2765

Asp Thr Thr Lys Thr Lys Met Glu Ala Gly Lys Val Leu Ser Asp Leu
    2770                2775                2780

Lys Leu Pro Gly Leu Ala Val His Arg Lys Lys Ala Gly Ala Leu Arg
2785                2790                2795                2800

Thr Arg Met Leu Arg Ser Arg Gly Trp Ala Glu Leu Ala Arg Gly Leu
                2805                2810                2815

Leu Trp His Pro Gly Leu Arg Leu Pro Pro Glu Ile Ala Gly Ile
            2820                2825                2830

Pro Gly Gly Phe Pro Leu Ser Pro Pro Tyr Met Gly Val Val His Gln
        2835                2840                2845

Leu Asp Phe Thr Ser Gln Arg Ser Arg Trp Arg Trp Leu Gly Phe Leu
    2850                2855                2860

Ala Leu Leu Ile Val Ala Leu Phe Gly
2865                2870
```

( 2 ) INFORMATION FOR SEQ ID NO:16:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: PROBE 470-20- 1-152F ( x i ) SEQUENCE DESCRIPTION: SEQ ID NO:16:

TCGGTTACTG AGAGCAGCTC AGATGAG 27

( 2 ) INFORMATION FOR SEQ ID NO:17:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: JML-A, PRIMER ( x i ) SEQUENCE DESCRIPTION: SEQ ID NO:17:

AGGAATTCAG CGGCCGCGAG 20

( 2 ) INFORMATION FOR SEQ ID NO:18:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: JML-B, PRIMER ( x i ) SEQUENCE DESCRIPTION: SEQ ID NO:18:

CTCGCGGCCG CTGAATTCCT TT 22

( 2 ) INFORMATION FOR SEQ ID NO:19:

( i ) SEQUENCE CHARACTERISTICS:
  ( A ) LENGTH: 203 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( v i ) ORIGINAL SOURCE:
  ( C ) INDIVIDUAL ISOLATE: 470-20-1 CLONE, WITHOUT SISPA
    LINKERS ( i x ) FEATURE:
  ( A ) NAME/KEY: CDS
  ( B ) LOCATION: 2..203

( x i ) SEQUENCE DESCRIPTION: SEQ ID NO:19:

| G | GCT | GTC | TCG | GAC | TCT | TGG | ATG | ACC | TCG | AAT | GAG | TCA | GAG | GAC | GGG | 46 |
|---|---|---|---|---|---|---|---|---|---|---|---|---|---|---|---|---|
|   | Ala | Val | Ser | Asp | Ser | Trp | Met | Thr | Ser | Asn | Glu | Ser | Glu | Asp | Gly |  |
|   | 1 |   |   |   | 5 |   |   |   |   | 10 |   |   |   |   | 15 |  |

| GTA | TCC | TCC | TGC | GAG | GAG | GAC | ACC | GGC | GGG | GTC | TTC | TCA | TCT | GAG | CTG | 94 |
|---|---|---|---|---|---|---|---|---|---|---|---|---|---|---|---|---|
| Val | Ser | Ser | Cys | Glu | Glu | Asp | Thr | Gly | Gly | Val | Phe | Ser | Ser | Glu | Leu |  |
|   |   |   |   | 20 |   |   |   |   | 25 |   |   |   |   | 30 |   |  |

| CTC | TCA | GTA | ACC | GAG | ATA | AGT | GCT | GGC | GAT | GGA | GTA | CGG | GGG | ATG | TCT | 142 |
|---|---|---|---|---|---|---|---|---|---|---|---|---|---|---|---|---|
| Leu | Ser | Val | Thr | Glu | Ile | Ser | Ala | Gly | Asp | Gly | Val | Arg | Gly | Met | Ser |  |
|   |   |   | 35 |   |   |   |   | 40 |   |   |   |   | 45 |   |   |  |

| TCT | CCC | CAT | ACA | GGC | ATC | TCT | CGG | CTA | CTA | CCA | CAA | AGA | GAG | GGT | GTA | 190 |
|---|---|---|---|---|---|---|---|---|---|---|---|---|---|---|---|---|
| Ser | Pro | His | Thr | Gly | Ile | Ser | Arg | Leu | Leu | Pro | Gln | Arg | Glu | Gly | Val |  |
|   |   | 50 |   |   |   |   |   | 55 |   |   |   | 60 |   |   |   |  |

| CTG | CAG | TCC | TCC | A | 203 |
|---|---|---|---|---|---|
| Leu | Gln | Ser | Ser |   |   |
|   | 65 |   |   |   |   |

( 2 ) INFORMATION FOR SEQ ID NO:20:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| Ala | Val | Ser | Asp | Ser | Trp | Met | Thr | Ser | Asn | Glu | Ser | Glu | Asp | Gly | Val |
|---|---|---|---|---|---|---|---|---|---|---|---|---|---|---|---|
| 1 |   |   |   | 5 |   |   |   |   | 10 |   |   |   |   | 15 |   |

| Ser | Ser | Cys | Glu | Glu | Asp | Thr | Gly | Gly | Val | Phe | Ser | Ser | Glu | Leu | Leu |
|---|---|---|---|---|---|---|---|---|---|---|---|---|---|---|---|
|   |   |   | 20 |   |   |   |   | 25 |   |   |   |   | 30 |   |   |

| Ser | Val | Thr | Glu | Ile | Ser | Ala | Gly | Asp | Gly | Val | Arg | Gly | Met | Ser | Ser |
|---|---|---|---|---|---|---|---|---|---|---|---|---|---|---|---|
|   |   | 35 |   |   |   |   | 40 |   |   |   |   | 45 |   |   |   |

| Pro | His | Thr | Gly | Ile | Ser | Arg | Leu | Leu | Pro | Gln | Arg | Glu | Gly | Val | Leu |
|---|---|---|---|---|---|---|---|---|---|---|---|---|---|---|---|
|   | 50 |   |   |   |   | 55 |   |   |   |   | 60 |   |   |   |   |

| Gln | Ser | Ser |
|---|---|---|
| 65 |   |   |

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 470-20-1- 152R ( x i ) SEQUENCE DESCRIPTION: SEQ ID NO:21:

CTCATCTGAG CTGCTCTCAG TAACCGA        27

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: OLIGONUCLEOTIDE B ( x i ) SEQUENCE DESCRIPTION: SEQ ID NO:22:

CTGTCTCGGA CTCTTGGATG ACCT     24

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: COGNATE OLIGONUCLEOTIDE 211R'

( x i ) SEQUENCE DESCRIPTION: SEQ ID NO:23:

ATACCCCGTC CTCTGACTCA TTCG     24

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: COGNATE OLIGONUCLEOTIDE B'

( x i ) SEQUENCE DESCRIPTION: SEQ ID NO:24:

AGGTCATCCA AGAGTCCGAG ACAG     24

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: LAMBDA GT 11 FORWARD PRIMER, 20mer ( x i ) SEQUENCE DESCRIPTION: SEQ ID NO:25:

CACATGGCTG AATATCGACG     20

( 2 ) INFORMATION FOR SEQ ID NO:26:

( i ) SEQUENCE CHARACTERISTICS:
        ( A ) LENGTH: 180 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 4E3

( x i ) SEQUENCE DESCRIPTION: SEQ ID NO:26:

```
GCGAGCCTAG  TCTTTGACTT  CATGGCGGGG  AAACTTTCAT  CAGAAGATCT  GTGGTATGCC      60
ATCCCGGTAC  TGACCAGCCC  GGGGGCGGGC  CTTGCGGGGA  TCGCTCTCGG  GTTGGTTTTG     120
TATTCAGCTA  ACAACTCTGG  CACTACCACT  TGGTTGAACC  GTCTGCTGAC  TACGTTACCA     180
```

( 2 ) INFORMATION FOR SEQ ID NO:27:

( i ) SEQUENCE CHARACTERISTICS:
        ( A ) LENGTH: 430 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 3E3

( x i ) SEQUENCE DESCRIPTION: SEQ ID NO:27:

```
GGCACTACCA  CTTGGTTGAA  CCGTCTGCTG  ACTACGTTAC  CAAGGTCTTC  ATGTATCCCG      60
GACAGTTACT  TTCAGCAAGT  TGACTATTGC  GACAAGGTCT  CAGCCGTGCT  CCGGCGCCTG     120
AGCCTCACCC  GCACAGTGGT  TGCCCTGGTC  AACAGGGAGC  CTAAGGTGGA  TGAGGTACAG     180
GTGGGGTATG  TCTGGGACCT  GTGGGAGTGG  ATCATGCGCC  AAGTGCGCGT  GGTCATGGCC     240
AGACTCAGGG  CCCTCTGCCC  CGTGGTGTCA  CTACCCTTGT  GGCATTGCGG  GGAGGGGTGG     300
TCCGGGGAAT  GGTTGCTTGA  CGGTCATGTT  GAGAGTCGCT  GCCTCTGTGG  CTGCGTGATC     360
ACTGGTGACG  TTCTGAATGG  GCAACTCAAA  GAACCAGTTT  ACTCTACCAA  GCTGTGCCGG     420
CACTATTGGA                                                                 430
```

( 2 ) INFORMATION FOR SEQ ID NO:28:

( i ) SEQUENCE CHARACTERISTICS:
        ( A ) LENGTH: 180 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 2E5

( x i ) SEQUENCE DESCRIPTION: SEQ ID NO:28:

| | | | | | |
|---|---|---|---|---|---|
| CTTACCGTCA | AGATGTCGTG | CTGCGTTGAA | AAGAGCGTCA | CGCGCTTTTT | CTCATTGGGG | 60 |
| TTGACGGTGG | CTGATGTTGC | TAGCCTGTGT | GAGATGGAAA | TCCAGAACCA | TACAGCCTAT | 120 |
| TGTGACCAGG | TGCGCACTCC | GCTTGAATTG | CAGGTTGGGT | GCTTGGTGGG | CAATGAACTT | 180 |

( 2 ) INFORMATION FOR SEQ ID NO:29:

( i ) SEQUENCE CHARACTERISTICS:
        ( A ) LENGTH: 344 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 1E5

( x i ) SEQUENCE DESCRIPTION: SEQ ID NO:29:

| | | | | | |
|---|---|---|---|---|---|
| CTTCTCTTTG | TGGTAGTAGC | CGAGAGATGC | CTGTATGGGG | AGAAGACATC | CCCCGTACTC | 60 |
| CATCGCCAGC | ACTTATCTCG | GTTACTGAGA | GCAGCTCAGA | TGAGAAGACC | CCGTCGGTGT | 120 |
| CCTCCTCGCA | GGAGGATACC | CCGTCCTCTG | ACTCATTCGA | GGTCATCCAA | GAGTCCGAGA | 180 |
| CAGCCGAAGG | GGAGGAAAGT | GTCTTCAACG | TGGCTCTTTC | CGTATTAAAA | GCCTTATTTC | 240 |
| CACAGAGCGA | CGCGACCAGG | AAGCTTACCG | TCAAGATGTC | GTGCTGCGTT | GAAAAGAGCG | 300 |
| TCACGCGCTT | TTTCTCATTG | GGGTTGACGG | TGGCTGATGT | TGCT | | 344 |

( 2 ) INFORMATION FOR SEQ ID NO:30:

( i ) SEQUENCE CHARACTERISTICS:
        ( A ) LENGTH: 423 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 4E5

( x i ) SEQUENCE DESCRIPTION: SEQ ID NO:30:

| | | | | | |
|---|---|---|---|---|---|
| GTAAGGCCAC | ATGCTGCCAT | GGGCTGGGGA | TCTAAGGTGT | CGGTTAAGGA | CTTAGCCACC | 60 |
| CCCGCGGGA | AGATGGCCGT | CCATGACCGG | CTTCAGGAGA | TACTTGAAGG | GACTCCGGTC | 120 |
| CCCTTTACTC | TTACTGTGAA | AAAGGAGGTG | TTCTTCAAAG | ACCGGAAGGA | GGAGAAGGCC | 180 |
| CCCCGCCTCA | TTGTGTTCCC | CCCCCTGGAC | TTCCGGATAG | CTGAAAAGCT | CATCTTGGGA | 240 |
| GACCCAGGCC | GGGTAGCCAA | GGCGGTGTTG | GGGGGGGCCT | ACGCCTTCCA | GTACACCCCA | 300 |
| AATCAGCGAG | TTAAGGAGAT | GCTCAAGCTA | TGGGAGTCTA | AGAAGACCCC | TTGCGCCATC | 360 |
| TGTGTGGACG | CCACCTGCTT | CGACAGTAGC | ATAACTGAAG | AGGACGTGGC | TTTGGAGACA | 420 |
| GAG | | | | | | 423 |

( 2 ) INFORMATION FOR SEQ ID NO:31:

( i ) SEQUENCE CHARACTERISTICS:

(A) LENGTH: 516 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 3E5

(xi) SEQUENCE DESCRIPTION: SEQ ID NO:31:

| | | | | | | |
|---|---|---|---|---|---|---|
| TACAGCCTAT | TGTGACCAGG | TGCGCACTCC | GCTTGAATTG | CAGGTTGGGT | GCTTGGTGGG | 60 |
| CAATGAACTT | ACCTTTGAAT | GTGACAAGTG | TGAGGCTAGG | CAAGAAACCT | TGGCCTCCTT | 120 |
| CTCTTACATT | TGGTCTGGAG | TGCCGCTGAC | TAGGGCCACG | CCGGCCAAGC | CTCCCGTGGT | 180 |
| GAGGCCGGTT | GGCTCTTTGT | TAGTGGCCGA | CACTACTAAG | GTGTATGTTA | CCAATCCAGA | 240 |
| CAATGTGGGA | CGGAGGGTGG | ACAAGGTGAC | CTTCTGGCGT | GCTCCTAGGG | TTCATGATAA | 300 |
| GTACCTCGTG | GACTCTATTG | AGCGCGCTAA | GAGGGCCGCT | CAAGCCTGCC | TAAGCATGGG | 360 |
| TTACACTTAT | GAGGAAGCAA | TAAGGACTGT | AAGGCCACAT | GCTGCCATGG | GCTGGGGATC | 420 |
| TAAGGTGTCG | GTTAAGGACT | TAGCCACCCC | CGCGGGGAAG | ATGGCCGTCC | ATGACCGGCT | 480 |
| TCAGGAGATA | CTTGAAGGGA | CTCCGGTCCC | CTTTAC | | | 516 |

(2) INFORMATION FOR SEQ ID NO:32:

(i) SEQUENCE CHARACTERISTICS:
(A) LENGTH: 518 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 2E3

(xi) SEQUENCE DESCRIPTION: SEQ ID NO:32:

| | | | | | | |
|---|---|---|---|---|---|---|
| GAATGGGCAA | CTCAAAGAAC | CAGTTTACTC | TACCAAGCTG | TGCCGGCACT | ATTGGATGGG | 60 |
| GACTGTCCCT | GTGAACATGC | TGGGTTACGG | TGAAACGTCG | CCTCTCCTGG | CCTCCGACAC | 120 |
| CCCGAAGGTT | GTGCCCTTCG | GGACGTCTGG | CTGGGCTGAG | GTGGTGGTGA | CCACTACCCA | 180 |
| CGTGGTAATC | AGGAGGACCT | CCGCCTATAA | GCTGCTGCGC | CAGCAAATCC | TATCGGCTGC | 240 |
| TGTAGCTGAG | CCCTACTACG | TCGACGGCAT | TCCGGTCTCA | TGGGACGCGG | ACGCTCGTGC | 300 |
| GCCCGCCATG | GTCTATGGCC | CTGGGCAAAG | TGTTACCATT | GACGGGAGC | GCTACACCTT | 360 |
| GCCTCATCAA | CTGAGGCTCA | GGAATGTGGC | ACCCTCTGAG | GTTTCATCCG | AGGTGTCCAT | 420 |
| TGACATTGGG | ACGGAGACTG | AAGACTCAGA | ACTGACTGAG | GCCGATCTGC | CGCCGGCGGC | 480 |
| TGCTGCTCTC | CAAGCGATCG | AGAATGCTGC | GAGGATTC | | | 518 |

(2) INFORMATION FOR SEQ ID NO:33:

(i) SEQUENCE CHARACTERISTICS:
(A) LENGTH: 268 base pairs
(B) TYPE: nucleic acid
(C) STRANDEDNESS: both
(D) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Consensus Sequence 1E3

( x i ) SEQUENCE DESCRIPTION: SEQ ID NO:33:

| | | | | | | |
|---|---|---|---|---|---|---|
| CTTACTGAGG | CCGATCTGCC | GCCGGCGGCT | GCTGCTCTCC | AAGCGATCGA | GAATGCTGCG | 60 |
| AGGATTCTTG | AACCGCACAT | TGATGTCATC | ATGGAGGACT | GCAGTACACC | CTCTCTTTGT | 120 |
| GGTAGTAGCC | GAGAGATGCC | TGTATGGGGA | GAAGACATCC | CCCGTACTCC | ATCGCCAGCA | 180 |
| CTTATCTCGG | TTACTGAGAG | CAGCTCAGAT | GAGAAGACCC | CGTCGGTGTC | CTCCTCGCAG | 240 |
| GAGGATACCC | CGTCCTCTGA | CTCATTCG | | | | 268 |

( 2 ) INFORMATION FOR SEQ ID NO:34:

( i ) SEQUENCE CHARACTERISTICS:
        ( A ) LENGTH: 781 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: INDIVIDUAL CLONE 4E5-20

( x i ) SEQUENCE DESCRIPTION: SEQ ID NO:34:

| | | | | | | |
|---|---|---|---|---|---|---|
| GTAAGGCCAC | ATGCTGCCAT | GGGCTGGGGA | TCTAAGGTGT | CGGTTAAGGA | CTTAGCCACC | 60 |
| CCCGCGGGGA | AGATGGCCGT | CCATGACCGG | CTTCAGGAGA | TACTTGAAGG | GACTCCGGTC | 120 |
| CCCTTTACTC | TTACTGTGAA | AAAGGAGGTG | TTCTTCAAAG | ACCGGAAGGA | GGAGAAGGCC | 180 |
| CCCCGCCTCA | TTGTGTTCCC | CCCCCTGGAC | TTCGGATAG | CTGAAAAGCT | CATCTTGGGA | 240 |
| GACCCAGGCC | GGGTAGCCAA | GGCGGTGTTG | GGGGGGGCCT | ACGCCTTCCA | GTACACCCA | 300 |
| AATCAGCGAG | TTAAGGAGAT | GCTCAAGCTA | TGGGAGTCTA | AGAAGACCCC | TTGCGCCATC | 360 |
| TGTGTGGACG | CCACCTGCTT | CGACAGTAGC | ATAACTGAAG | AGGACGTGGC | TTTGGAGACA | 420 |
| GAGTTATACG | CTCTGGCCTC | TGACCATCCA | GAATGGGTGC | GGGCACCTGG | GAAATACTAT | 480 |
| GCCTCAGGCA | CCATGGTCAC | CCCGGAAGGG | GTGCCCGTCG | GTGAGAGGTA | TTGCAGATCC | 540 |
| TCGGGTGTCC | TAACAACTAG | CGCGAGCAAC | TGCCTGACCT | GCTACATCAA | GGTGAAAGCT | 600 |
| GCCTGTGAGA | GAGTGGGGCT | GAAAAATGTC | TCTCTTCTCA | TAGCCGGCGA | TGACTGCTTG | 660 |
| ATCATATGTG | AGCGGCCAGT | GTGCGACCCA | AGCGACGCTT | TGGGCAGAGC | CCTAGCGAGC | 720 |
| TATGGGTACG | CGTGCGAGCC | CTCATATCAT | GCATCATTGG | ACACGGCCCC | CTTCTGCTCC | 780 |
| A | | | | | | 781 |

( 2 ) INFORMATION FOR SEQ ID NO:35:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: PROBE 470- 201-1-142R ( x i ) SEQUENCE DESCRIPTION: SEQ ID NO:35:

```
TCGGTTACTG AGAGCAGCTC AGATGAG                                                    27
```

( 2 ) INFORMATION FOR SEQ ID NO:36:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PROBE 470-20- 1-152F ( x i ) SEQUENCE DESCRIPTION: SEQ ID NO:36:

```
TCGGTTACTG AGAGCAGCTC AGATGAG                                                    27
```

( 2 ) INFORMATION FOR SEQ ID NO:37:

( i ) SEQUENCE CHARACTERISTICS:
        ( A ) LENGTH: 570 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Clone 470EXP1

( i x ) FEATURE:
        ( A ) NAME/KEY: CDS
        ( B ) LOCATION: 1..570

( x i ) SEQUENCE DESCRIPTION: SEQ ID NO:37:

```
GCT  GTA  TGG  TTC  TGG  ATT  TCC  ATC  TCA  CAC  AGG  CTA  GCA  ACA  TCA  GCC    48
Ala  Val  Trp  Phe  Trp  Ile  Ser  Ile  Ser  His  Arg  Leu  Ala  Thr  Ser  Ala
 1              5                   10                  15

ACC  GTC  AAC  CCC  AAT  GAG  AAA  AAG  CGC  GTG  ACG  CTC  TTT  TCA  ACG  CAG    96
Thr  Val  Asn  Pro  Asn  Glu  Lys  Lys  Arg  Val  Thr  Leu  Phe  Ser  Thr  Gln
             20                   25                       30

CAC  GAC  ATC  TTG  ACG  GTA  AGC  TTC  CTG  GTC  GCG  TCG  CTC  TGT  GGA  AAT   144
His  Asp  Ile  Leu  Thr  Val  Ser  Phe  Leu  Val  Ala  Ser  Leu  Cys  Gly  Asn
              35                       40                   45

AAG  GCT  TTT  AAT  ACG  GAA  AGA  GCC  ACG  TTG  AAG  ACA  CTT  TCC  TCC  CCT   192
Lys  Ala  Phe  Asn  Thr  Glu  Arg  Ala  Thr  Leu  Lys  Thr  Leu  Ser  Ser  Pro
         50                       55                   60

TCG  GCT  GTC  TCG  GAC  TCT  TGG  ATG  ACC  TCG  AAT  GAG  TCA  GAG  GAC  GGG   240
Ser  Ala  Val  Ser  Asp  Ser  Trp  Met  Thr  Ser  Asn  Glu  Ser  Glu  Asp  Gly
 65                  70                       75                       80

GTA  TCC  TCC  TGC  GAG  GAG  GAC  ACC  GAC  GGG  GTC  TTC  TCA  TCT  GAG  CTG   288
Val  Ser  Ser  Cys  Glu  Glu  Asp  Thr  Asp  Gly  Val  Phe  Ser  Ser  Glu  Leu
```

```
CTC TCA GTA ACC GAG ATA AGT GCT GGC GAT GGA GTA CGG GGG ATG TCT        336
Leu Ser Val Thr Glu Ile Ser Ala Gly Asp Gly Val Arg Gly Met Ser
            100                 105                 110

TCT CCC CAT ACA GGC ATC TCT CGG CTA CTA CCA CAA AGA GAG GGT GTA        384
Ser Pro His Thr Gly Ile Ser Arg Leu Leu Pro Gln Arg Glu Gly Val
        115                 120                 125

CTG CAG TCC TCC ATG ATG ACA TCA ATG TGC GGT TCA AGA ATC CTC GCA        432
Leu Gln Ser Ser Met Met Thr Ser Met Cys Gly Ser Arg Ile Leu Ala
130                     135                 140

GCA TTC TCG ATC GCT TGG AGA GCA GCA GCC GCC GGC GGC AGA TCG GCC        480
Ala Phe Ser Ile Ala Trp Arg Ala Ala Ala Ala Gly Gly Arg Ser Ala
145                 150                 155                 160

TCA GTC AGT TCT GAG TCT TCA GTC TCC GTC CCA ATG TCA ATG GAC ACC        528
Ser Val Ser Ser Glu Ser Ser Val Ser Val Pro Met Ser Met Asp Thr
                165                 170                 175

TCG GAT GAA ACC TCA GAG GGT GCC ACA TTC CTG AGC CTC AGT              570
Ser Asp Glu Thr Ser Glu Gly Ala Thr Phe Leu Ser Leu Ser
            180                 185                 190
```

( 2 ) INFORMATION FOR SEQ ID NO:38:

( i ) SEQUENCE CHARACTERISTICS:
        ( A ) LENGTH: 190 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Ala Val Trp Phe Trp Ile Ser Ile Ser His Arg Leu Ala Thr Ser Ala
 1               5                   10                  15

Thr Val Asn Pro Asn Glu Lys Lys Arg Val Thr Leu Phe Ser Thr Gln
                20                  25                  30

His Asp Ile Leu Thr Val Ser Phe Leu Val Ala Ser Leu Cys Gly Asn
            35                  40                  45

Lys Ala Phe Asn Thr Glu Arg Ala Thr Leu Lys Thr Leu Ser Ser Pro
 50                  55                  60

Ser Ala Val Ser Asp Ser Trp Met Thr Ser Asn Glu Ser Glu Asp Gly
 65              70                  75                      80

Val Ser Ser Cys Glu Glu Asp Thr Asp Gly Val Phe Ser Ser Glu Leu
                85                  90                  95

Leu Ser Val Thr Glu Ile Ser Ala Gly Asp Gly Val Arg Gly Met Ser
            100                 105                 110

Ser Pro His Thr Gly Ile Ser Arg Leu Leu Pro Gln Arg Glu Gly Val
        115                 120                 125

Leu Gln Ser Ser Met Met Thr Ser Met Cys Gly Ser Arg Ile Leu Ala
130                 135                 140

Ala Phe Ser Ile Ala Trp Arg Ala Ala Ala Ala Gly Gly Arg Ser Ala
145                 150                 155                 160

Ser Val Ser Ser Glu Ser Ser Val Ser Val Pro Met Ser Met Asp Thr
                165                 170                 175

Ser Asp Glu Thr Ser Glu Gly Ala Thr Phe Leu Ser Leu Ser
            180                 185                 190
```

( 2 ) INFORMATION FOR SEQ ID NO:39:

( i ) SEQUENCE CHARACTERISTICS:
        ( A ) LENGTH: 1288 base pairs
        ( B ) TYPE: nucleic acid (C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 5E3

(xi) SEQUENCE DESCRIPTION: SEQ ID NO:39:

| | | | | | | |
|---|---|---|---|---|---|---|
| ACGGGTAGGG | GCAGGTCTGG | ACGCTACTAC | TACGCGGGGG | TGGGCAAAGC | CCCTGCGGGT | 60 |
| GTGGTGCGCT | CAGGTCCTGT | CTGGTCGGCG | GTGGAAGCTG | GAGTGACCTG | GTACGGAATG | 120 |
| GAACCTGACT | TGACAGCTAA | CCTACTGAGA | CTTTACGACG | ACTGCCCTTA | CACCGCAGCC | 180 |
| GTCGCGGCTG | ATATCGGAGA | AGCCGCGGTG | TTCTTCTCTG | GGCTCGCCCC | ATTGAGGATG | 240 |
| CACCCTGATG | TCAGCTGGGC | AAAAGTTCGC | GGCGTCAACT | GGCCCTCTT | GGTGGGTGTT | 300 |
| CAGCGGACCA | TGTGTCGGGA | AACACTGTCT | CCCGGCCCAT | CGGATGACCC | CCAATGGGCA | 360 |
| GGTCTGAAGG | GCCCAAATCC | TGTCCCACTC | CTGCTGAGGT | GGGGCAATGA | TTTACCATCT | 420 |
| AAAGTGGCCG | GCCACCACAT | AGTGGACGAC | CTGGTCCGGA | GACTCGGTGT | GGCGGAGGGT | 480 |
| TACGTCCGCT | GCGACGCTGG | GCCGATCTTG | ATGATCGGTC | TAGCTATCGC | GGGGGGAATG | 540 |
| ATCTACGCGT | CATACACCGG | GTCGCTAGTG | GTGGTGACAG | ACTGGGATGT | GAAGGGGGT | 600 |
| GGCGCCCCCC | TTTATCGGCA | TGGAGACCAG | GCCACGCCTC | AGCCGGTGGT | GCAGGTTCCT | 660 |
| CCGGTAGACC | ATCGGCCGGG | GGGTGAATCA | GCACCATCGG | ATGCCAAGAC | AGTGACAGAT | 720 |
| GCGGTGGCAG | CCATCCAGGT | GGACTGCGAT | TGGACTATCA | TGACTCTGTC | GATCGGAGAA | 780 |
| GTGTTGTCCT | TGGCTCAGGC | TAAGACGGCC | GAGGCCTACA | CAGCAACCGC | CAAGTGGCTC | 840 |
| GCTGGCTGCT | ATACGGGGAC | GCGGGCCGTT | CCCACTGTAT | CCATTGTTGA | CAAGCTCTTC | 900 |
| GCCGGAGGGT | GGGCGGCTGT | GGTGGGCCAT | TGCCACAGCG | TGATTGCTGC | GGCGGTGGCG | 960 |
| GCCTACGGGG | CTTCAAGGAG | CCCGCCGTTG | GCAGCCGCGG | CTTCCTACCT | GATGGGGTTG | 1020 |
| GGCGTTGGAG | GCAACGCTCA | GACGCGCCTG | GCGTCTGCCC | TCCTATTGGG | GGCTGCTGGA | 1080 |
| ACCGCCTTGG | GCACTCCTGT | CGTGGGCTTG | ACCATGGCAG | GTGCGTTCAT | GGGGGGGCC | 1140 |
| AGTGTCTCCC | CCTCCTTGGT | CACCATTTTA | TTGGGGGCCG | TCGGAGGTTG | GGAGGGTGTT | 1200 |
| GTCAACGCGG | CGAGCCTAGT | CTTTGACTTC | ATGGCGGGGA | AACTTTCATC | AGAAGATCTG | 1260 |
| TGGTATGCCA | TCCCGGTACT | GACCAGCC | | | | 1288 |

(2) INFORMATION FOR SEQ ID NO:40:

(i) SEQUENCE CHARACTERISTICS:
(A) LENGTH: 862 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 6E3

(xi) SEQUENCE DESCRIPTION: SEQ ID NO:40:

| | | | | | | |
|---|---|---|---|---|---|---|
| ACGGCAACAT | GGGGCACAAG | GTCTTAATCT | TGAACCCCTC | AGTGGCCACT | GTGCGGGCCA | 60 |

|          |          |          |          |          |          |     |
|----------|----------|----------|----------|----------|----------|-----|
| TGGGCCCGTA | CATGGAGCGG | CTGGCGGGTA | AACATCCAAG | TATATACTGT | GGGCATGATA | 120 |
| CAACTGCTTT | CACAAGGATC | ACTGACTCCC | CCCTGACGTA | TTCAACCTAT | GGGAGGTTTT | 180 |
| TGGCCAACCC | TAGGCAGATG | CTACGGGGCG | TTTCGGTGGT | CATTTGTGAT | GAGTGCCACA | 240 |
| GTCATGACTC | AACCGTGCTG | TTAGGCATTG | GGAGAGTTCG | GGAGCTGGCG | CGTGGGTGCG | 300 |
| GAGTGCAACT | AGTGCTCTAC | GCCACCGCTA | CACCTCCCGG | ATCCCCTATG | ACGCAGCACC | 360 |
| CTTCCATAAT | TGAGACAAAA | TTGGACGTGG | GCGAGATTCC | CTTTTATGGG | CATGGAATAC | 420 |
| CCCTCGAGCG | GATGCGAACC | GGAAGGCACC | TCGTGTTCTG | CCATTCTAAG | GCTGAGTGCG | 480 |
| AGCGCCTTGC | TGGCCAGTTC | TCCGCTAGGG | GGTCAATGC  | CATTGCCTAT | TATAGGGGTA | 540 |
| AAGACAGTTC | TATCATCAAG | GATGGGACC  | TGGTGGTCTG | TGCTACAGAC | GCGCTTTCCA | 600 |
| CTGGGTACAC | TGGAAATTTC | GACTCCGTCA | CCGACTGTGG | ATTAGTGGTG | GAGGAGGTCG | 660 |
| TTGAGGTGAC | CCTTGATCCC | ACCATTACCA | TCTCCCTGCG | GACAGTGCCT | GCGTCGGCTG | 720 |
| AACTGTCGAT | GCAAGACGA  | GGACGCACGG | GTAGGGGCAG | GTCTGGACGC | TACTACTACG | 780 |
| CGGGGGTGGG | CAAAGCCCCT | GCGGGTGTGG | TGCGCTCAGG | TCCTGTCTGG | TCGGCGGTGG | 840 |
| AAGCTGGAGT | GACCTCGTAC | GG         |            |            |            | 862 |

( 2 ) INFORMATION FOR SEQ ID NO:41:

( i ) SEQUENCE CHARACTERISTICS:
        ( A ) LENGTH: 865 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Individual Clone GE3L-11

( x i ) SEQUENCE DESCRIPTION: SEQ ID NO:41:

|          |          |          |          |          |          |     |
|----------|----------|----------|----------|----------|----------|-----|
| AGTACGGCAA | CATGGGGCAC | AAGGTCTTAA | TCTTGAACCC | CTCAGTGGCC | ACTGTGCGGG | 60  |
| CCATGGGCCC | GTACATGGAG | CGGCTGGCGG | GTAAACATCC | AAGTATATAC | TGTGGGCATG | 120 |
| ATACAACTGC | TTTCACAAGG | ATCACTGACT | CCCCCCTGAC | GTATTCAACC | TATGGGAGGT | 180 |
| TTTTGGCCAA | CCCTAGGCAG | ATGCTACGGG | GCGTTTCGGT | GGTCATTTGT | GATGAGTGCC | 240 |
| ACAGTCATGA | CTCAACCGTG | CTGTTAGGCA | TTGGGAGAGT | CCGGGAGCTG | GCGCGTGGGT | 300 |
| GCGGGGTGCA | ACTAGTGCTC | TACGCCACCG | CTACACCTCC | CGGATCCCCT | ATGACGCAGC | 360 |
| ACCCTTCCAT | AATTGAGACA | AAATTGGACG | TGGGCGAGAT | TCCCTTTTAT | GGACATGGAA | 420 |
| TACCCCTCGA | GCGGATGCGA | ACCGGAAGGC | ACCTCGTGTT | CTGCCATTCT | AAGGCTGAGT | 480 |
| GCGAGCGCCT | TGCTGGCCAG | TTCTCCGCTA | GGGGGTCAA  | TGCCATTGCC | TATTATAGGG | 540 |
| GTAAAGACAG | TTCTATCATC | AAGGATGGGG | ACCTGGTGGT | CTGTGCTACA | GACGCGCTTT | 600 |
| CCACTGGGTA | CACTGGAAAT | TTCGACTCCG | TCACCGACTG | TGGATTAGTG | GTGGAGGAGG | 660 |
| TCGTTGAGGT | GACCCTTGAT | CCCACCATTA | CCATCTCCCT | GCGGACAGTG | CCTGCGTCGG | 720 |
| CTGAACTGTC | GATGCAAAGA | CGAGGACGCA | CGGGTAGGGG | CAGGTCTGGA | CGCTACTACT | 780 |
| ACGCGGGGGT | GGGCAAAGCC | CCTGCGGGTG | TGGTGCGCTC | AGGTCCTGTC | TGGTCGGCGG | 840 |
| TGGAAGCTGG | AGTGACCTCG | TACGG      |            |            |            | 865 |

( 2 ) INFORMATION FOR SEQ ID NO:42:

( i ) SEQUENCE CHARACTERISTICS:
  ( A ) LENGTH: 596 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( C ) INDIVIDUAL ISOLATE: Consensus Sequence 7E3

( x i ) SEQUENCE DESCRIPTION: SEQ ID NO:42:

| | | | | | | |
|---|---|---|---|---|---|---|
| AGCATGGGAA | CATGCTTGAA | CGGCCTGCTG | TTCACGACCT | TCCATGGGC | TTCATCCCGA | 60 |
| ACCATCGCCA | CACCCGTGGG | GGCCCTTAAT | CCCAGATGGT | GGTCAGCCAG | TGATGATGTC | 120 |
| ACGGTGTATC | CACTCCCGGA | TGGGGCTACT | TCGTTAACAC | CTTGTACTTG | CCAGGCTGAG | 180 |
| TCCTGTTGGG | TCATCAGATC | CGACGGGGCC | CTATGCCATG | GCTTGAGCAA | GGGGGACAAG | 240 |
| GTGGAGCTGG | ATGTGGCCAT | GGAGGTCTCT | GACTTCCGTG | GCTCGTCTGG | CTCACCGGTC | 300 |
| CTATGTGACG | AAGGGCACGC | AGTAGGAATG | CTCGTGTCTG | TGCTTCACTC | CGGTGGTAGG | 360 |
| GTCACCGCGG | CACGGTTCAC | TAGGCCGTGG | ACCCAAGTGC | CAACAGATGC | CAAAACCACT | 420 |
| ACTGAACCCC | CTCCGGTGCC | GGCCAAAGGA | GTTTTCAAAG | AGGCCCCGTT | GTTTATGCCT | 480 |
| ACGGGAGCGG | GAAAGAGCAC | TCGCGTCCCG | TTGGAGTACG | ATAACATGGG | GCACAAGGTC | 540 |
| TTAATCTTGA | ACCCCTCAGT | GGCCACTGTG | CGGGCCATGG | GCCCGTACAT | GGAGCG | 596 |

( 2 ) INFORMATION FOR SEQ ID NO:43:

( i ) SEQUENCE CHARACTERISTICS:
  ( A ) LENGTH: 586 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( C ) INDIVIDUAL ISOLATE: Consensus Sequence 5E5

( x i ) SEQUENCE DESCRIPTION: SEQ ID NO:43:

| | | | | | | |
|---|---|---|---|---|---|---|
| GAGCTATGGG | TACGCGTGCG | AGCCCTCATA | TCATGCATCA | TTGGACACGG | CCCCCTTCTG | 60 |
| CTCCACTTGG | CTTGCTGAGT | GCAATGCAGA | TGGGAAGCGC | CATTTCTTCC | TGACCACGGA | 120 |
| CTTCCGGAGG | CCGCTCGCTC | GCATGTCGAG | TGAGTATAGT | GACCCGATGG | CTTCGGCGAT | 180 |
| CGGTTACATC | CTCCTTTATC | CTTGGCACCC | CATCACACGG | TGGGTCATCA | TCCCTCATGT | 240 |
| GCTAACGTGC | GCATTCAGGG | GTGGAGGCAC | ACCGTCTGAT | CCGGTTTGGT | GCCAGGTGCA | 300 |
| TGGTAACTAC | TACAAGTTTC | CACTGGACAA | ACTGCCTAAC | ATCATCGTGG | CCCTCCACGG | 360 |
| ACCAGCAGCG | TTGAGGGTTA | CCGCAGACAC | AACTAAAACA | AAGATGGAGG | CTGGTAAGGT | 420 |
| TCTGAGCGAC | CTCAAGCTCC | CTGGCTTAGC | AGTCCACCGA | AAGAAGGCCG | GGCGTTGCG | 480 |
| AACACGCATG | CTCCGCTCGC | GCGGTTGGGC | TGAGTTGGCT | AGGGGCTTGT | TGTGGCATCC | 540 |
| AGGCCTACGG | CTTCCTCCCC | CTGAGATTGC | TGGTATCCCG | GGGGGT | | 586 |

( 2 ) INFORMATION FOR SEQ ID NO:44:

( i ) SEQUENCE CHARACTERISTICS:
: ( A ) LENGTH: 242 base pairs
: ( B ) TYPE: nucleic acid
: ( C ) STRANDEDNESS: both
: ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
: ( C ) INDIVIDUAL ISOLATE: Consensus Sequence 6E5 (44F)

( x i ) SEQUENCE DESCRIPTION: SEQ ID NO:44:

```
CGAACGCGCA TGCTCCGCTC GCGCGGTTGG GCTGAGTTGG CTAGGGGCTT GTTGTGGCAT        60
CCAGGCCTAC GGCTTCCTCC CCCTGAGATT GCTGGTATCC CGGGGGGTTT CCCTCTCTCC       120
CCCCCCTATA TGGGGGTGGT ACACCAATTG GATTTCACAA GCCAGAGGAG TCGCTGGCGG       180
TGGTTGGGGT TCTTAGCCCT GCTCATCGTA GCCCTCTTCG GGTGAACTAA ATTCATCTGT       240
TG                                                                      242
```

( 2 ) INFORMATION FOR SEQ ID NO:45:

( i ) SEQUENCE CHARACTERISTICS:
: ( A ) LENGTH: 27 base pairs
: ( B ) TYPE: nucleic acid
: ( C ) STRANDEDNESS: both
: ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
: ( C ) INDIVIDUAL ISOLATE: Primer Gt11 rev-JL ( x i ) SEQUENCE DESCRIPTION: SEQ ID NO:45:

```
TGGTAATGGT AGCGACCGGC GCTCAGC                                            27
```

( 2 ) INFORMATION FOR SEQ ID NO:46:

( i ) SEQUENCE CHARACTERISTICS:
: ( A ) LENGTH: 45 base pairs
: ( B ) TYPE: nucleic acid
: ( C ) STRANDEDNESS: both
: ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
: ( C ) INDIVIDUAL ISOLATE: Primer GE- 3F ( x i ) SEQUENCE DESCRIPTION: SEQ ID NO:46:

```
GCCGCCATGG TCTCATGGGA CGCGGACGCT CGTGCGCCCG CGATG                        45
```

( 2 ) INFORMATION FOR SEQ ID NO:47:

( i ) SEQUENCE CHARACTERISTICS:
: ( A ) LENGTH: 34 base pairs
: ( B ) TYPE: nucleic acid
: ( C ) STRANDEDNESS: both
: ( D ) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Primer GE- 3R (x i) SEQUENCE DESCRIPTION: SEQ ID NO:47:

GCGCGGATCC GATAAGTGCT GGCGATGGAG TACG    34

(2) INFORMATION FOR SEQ ID NO:48:

(i) SEQUENCE CHARACTERISTICS:
 (A) LENGTH: 22 base pairs
 (B) TYPE: nucleic acid
 (C) STRANDEDNESS: both
 (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Primer GE- 9F (x i) SEQUENCE DESCRIPTION: SEQ ID NO:48:

GGCACCATGG TCACCCCGGA AG    22

(2) INFORMATION FOR SEQ ID NO:49:

(i) SEQUENCE CHARACTERISTICS:
 (A) LENGTH: 28 base pairs
 (B) TYPE: nucleic acid
 (C) STRANDEDNESS: both
 (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Primer GE- 9R (x i) SEQUENCE DESCRIPTION: SEQ ID NO:49:

GCTCGGATCC GGAGCAGAAG GGGGCCGT    28

(2) INFORMATION FOR SEQ ID NO:50:

(i) SEQUENCE CHARACTERISTICS:
 (A) LENGTH: 364 base pairs
 (B) TYPE: nucleic acid
 (C) STRANDEDNESS: both
 (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: GE3-2

(i x) FEATURE:
 (A) NAME/KEY: CDS
 (B) LOCATION: 2..364

( x i ) SEQUENCE DESCRIPTION: SEQ ID NO:50:

```
G GTC TCA TGG GAC GCG GAC GCT CGT GCG CCC GCG ATG GTC TAT GGC         46
  Val Ser Trp Asp Ala Asp Ala Arg Ala Pro Ala Met Val Tyr Gly
  1             5                   10                  15

CCT GGG CAA AGT GTT ACC ATT GAC GGG GAG CGC TAC ACC TTG CCT CAT       94
Pro Gly Gln Ser Val Thr Ile Asp Gly Glu Arg Tyr Thr Leu Pro His
              20                  25                  30

CAA CTG AGG CTC AGG AAT GTG GCA CCC TCT GAG GTT TCA TCC GAG GTG      142
Gln Leu Arg Leu Arg Asn Val Ala Pro Ser Glu Val Ser Ser Glu Val
            35                  40                  45

TCC ATT GAC ATT GGG ACG GAG ACT GAA GAC TCA GAA CTG ACT GAG GCC      190
Ser Ile Asp Ile Gly Thr Glu Thr Glu Asp Ser Glu Leu Thr Glu Ala
        50                  55                  60

GAT CTG CCG CCG GCG GCT GCT GCT CTC CAA GCG ATC GAG AAT GCT GCG      238
Asp Leu Pro Pro Ala Ala Ala Ala Leu Gln Ala Ile Glu Asn Ala Ala
    65                  70                  75

AGG ATT CTT GAA CCG CAC ATT GAT GTC ATC ATG GAG GAC TGC AGT ACA      286
Arg Ile Leu Glu Pro His Ile Asp Val Ile Met Glu Asp Cys Ser Thr
80                  85                  90                  95

CCC TCT CTT TGT GGT AGT AGC CGA GAG ATG CCT GTA TGG GGA GAA GAC      334
Pro Ser Leu Cys Gly Ser Ser Arg Glu Met Pro Val Trp Gly Glu Asp
                100                 105                 110

ATC CCC CGT ACT CCA TCG CCA GCA CTT ATC                              364
Ile Pro Arg Thr Pro Ser Pro Ala Leu Ile
                115                 120
```

( 2 ) INFORMATION FOR SEQ ID NO:51:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Val Ser Trp Asp Ala Asp Ala Arg Ala Pro Ala Met Val Tyr Gly Pro
1               5                   10                  15

Gly Gln Ser Val Thr Ile Asp Gly Glu Arg Tyr Thr Leu Pro His Gln
              20                  25                  30

Leu Arg Leu Arg Asn Val Ala Pro Ser Glu Val Ser Ser Glu Val Ser
            35                  40                  45

Ile Asp Ile Gly Thr Glu Thr Glu Asp Ser Glu Leu Thr Glu Ala Asp
        50                  55                  60

Leu Pro Ala Ala Ala Ala Leu Gln Ala Ile Glu Asn Ala Ala Arg
65                  70                  75                  80

Ile Leu Glu Pro His Ile Asp Val Ile Met Glu Asp Cys Ser Thr Pro
                85                  90                  95

Ser Leu Cys Gly Ser Ser Arg Glu Met Pro Val Trp Gly Glu Asp Ile
                100                 105                 110

Pro Arg Thr Pro Ser Pro Ala Leu Ile
                115                 120
```

( 2 ) INFORMATION FOR SEQ ID NO:52:

( i ) SEQUENCE CHARACTERISTICS:
        ( A ) LENGTH: 290 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Clone GE9- 2

( i x ) FEATURE:
    ( A ) NAME/KEY: CDS
    ( B ) LOCATION: 3..290

( x i ) SEQUENCE DESCRIPTION: SEQ ID NO:52:

```
CC ATG GTC ACC CCG GAA GGG GTG CCC GTT GGT GAG AGG TAT TGC AGA        47
   Met Val Thr Pro Glu Gly Val Pro Val Gly Glu Arg Tyr Cys Arg
   1               5                   10                  15

TCC TCG GGT GTC CTA ACA ACT AGC GCG AGC AAC TGC TTG ACC TGC TAC        95
Ser Ser Gly Val Leu Thr Thr Ser Ala Ser Asn Cys Leu Thr Cys Tyr
                20                  25                  30

ATC AAG GTG AAA GCC GCC TGT GAG AGG GTG GGG CTG AAA AAT GTC TCT       143
Ile Lys Val Lys Ala Ala Cys Glu Arg Val Gly Leu Lys Asn Val Ser
            35                  40                  45

CTT CTC ATA GCC GGC GAT GAC TGC TTG ATC ATA TGT GAG CGG CCA GTG       191
Leu Leu Ile Ala Gly Asp Asp Cys Leu Ile Ile Cys Glu Arg Pro Val
        50                  55                  60

TGC GAC CCA AGC GAC GCT TTG GGC AGA GCC CTA GCG AGC TAT GGG TAC       239
Cys Asp Pro Ser Asp Ala Leu Gly Arg Ala Leu Ala Ser Tyr Gly Tyr
    65                  70                  75

GCG TGC GAG CCC TCA TAT TAT GCA TGC TCG GAC ACG GCC CCC TTC TGC       287
Ala Cys Glu Pro Ser Tyr Tyr Ala Cys Ser Asp Thr Ala Pro Phe Cys
80                  85                  90                  95

TCC                                                                    290
Ser
```

( 2 ) INFORMATION FOR SEQ ID NO:53:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

```
Met Val Thr Pro Glu Gly Val Pro Val Gly Glu Arg Tyr Cys Arg Ser
1               5                   10                  15

Ser Gly Val Leu Thr Thr Ser Ala Ser Asn Cys Leu Thr Cys Tyr Ile
                20                  25                  30

Lys Val Lys Ala Ala Cys Glu Arg Val Gly Leu Lys Asn Val Ser Leu
            35                  40                  45

Leu Ile Ala Gly Asp Asp Cys Leu Ile Ile Cys Glu Arg Pro Val Cys
        50                  55                  60

Asp Pro Ser Asp Ala Leu Gly Arg Ala Leu Ala Ser Tyr Gly Tyr Ala
65                  70                  75                  80

Cys Glu Pro Ser Tyr Tyr Ala Cys Ser Asp Thr Ala Pro Phe Cys Ser
                85                  90                  95
```

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: linear (  i i  ) MOLECULE TYPE: DNA (  i i i  ) HYPOTHETICAL: NO (  i v  ) ANTI-SENSE: NO (  v i  ) ORIGINAL SOURCE:
    (  C  ) INDIVIDUAL ISOLATE: JML-A SISPA Primer (  x i  ) SEQUENCE DESCRIPTION: SEQ ID NO:54:

AGGAATTCAG CGGCCGCGAG 20

( 2 ) INFORMATION FOR SEQ ID NO:55:

(  i  ) SEQUENCE CHARACTERISTICS:
        (  A  ) LENGTH: 22 base pairs
        (  B  ) TYPE: nucleic acid
        (  C  ) STRANDEDNESS: both
        (  D  ) TOPOLOGY: linear (  i i  ) MOLECULE TYPE: DNA (  i i i  ) HYPOTHETICAL: NO (  i v  ) ANTI-SENSE: NO (  v i  ) ORIGINAL SOURCE:
    (  C  ) INDIVIDUAL ISOLATE: JML-B SISPA Primer (  x i  ) SEQUENCE DESCRIPTION: SEQ ID NO:55:

CTCGCGGCCG CTGAATTCCT TT 22

( 2 ) INFORMATION FOR SEQ ID NO:56:

(  i  ) SEQUENCE CHARACTERISTICS:
        (  A  ) LENGTH: 32 base pairs
        (  B  ) TYPE: nucleic acid
        (  C  ) STRANDEDNESS: both
        (  D  ) TOPOLOGY: linear (  i i  ) MOLECULE TYPE: DNA (  i i i  ) HYPOTHETICAL: NO (  i v  ) ANTI-SENSE: NO (  v i  ) ORIGINAL SOURCE:
    (  C  ) INDIVIDUAL ISOLATE: 470ep-f1 Primer (  x i  ) SEQUENCE DESCRIPTION: SEQ ID NO:56:

GCGAATTCGC CATGGCGGGG AGACTTTCAT CA 32

( 2 ) INFORMATION FOR SEQ ID NO:57:

(  i  ) SEQUENCE CHARACTERISTICS:
        (  A  ) LENGTH: 35 base pairs
        (  B  ) TYPE: nucleic acid
        (  C  ) STRANDEDNESS: both
        (  D  ) TOPOLOGY: linear (  i i  ) MOLECULE TYPE: DNA (  i i i  ) HYPOTHETICAL: NO (  i v  ) ANTI-SENSE: NO (  v i  ) ORIGINAL SOURCE:
    (  C  ) INDIVIDUAL ISOLATE: 470ep-R1 Primer (  x i  ) SEQUENCE DESCRIPTION: SEQ ID NO:57:

GCGAATTCGG ATCCAGGGCC ATAGACCATC GCGGG 35

( 2 ) INFORMATION FOR SEQ ID NO:58:

( i ) SEQUENCE CHARACTERISTICS:
    ( A ) LENGTH: 26 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: 470ep-f2 Primer ( x i ) SEQUENCE DESCRIPTION: SEQ ID NO:58:

GCGAATTCCG TGCGCCCGCC ATGGTC                                            26

( 2 ) INFORMATION FOR SEQ ID NO:59:

( i ) SEQUENCE CHARACTERISTICS:
    ( A ) LENGTH: 32 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: 470ep-R3 Primer ( x i ) SEQUENCE DESCRIPTION: SEQ ID NO:59:

GCGAATTCGG ATCCCAAGGT TTCTTGCCTA GC                                     32

( 2 ) INFORMATION FOR SEQ ID NO:60:

( i ) SEQUENCE CHARACTERISTICS:
    ( A ) LENGTH: 26 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: 470ep-f4 Primer ( x i ) SEQUENCE DESCRIPTION: SEQ ID NO:60:

GCGAATTCAA GTGTGAGGCT AGGCAA                                            26

( 2 ) INFORMATION FOR SEQ ID NO:61:

( i ) SEQUENCE CHARACTERISTICS:
    ( A ) LENGTH: 35 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO -continued (v i) ORIGINAL SOURCE:
    (C) INDIVIDUAL ISOLATE: 470ep-R4 Primer (x i) SEQUENCE DESCRIPTION: SEQ ID NO:61:

GCGAATTCGG ATCCCCACAC AGATGGCGCA AGGGG   35

(2) INFORMATION FOR SEQ ID NO:62:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: KL-1 SISPA Primer (x i) SEQUENCE DESCRIPTION: SEQ ID NO:62:

GCAGGATCCG AATTCGCATC TAGAGAT   27

(2) INFORMATION FOR SEQ ID NO:63:

(i) SEQUENCE CHARACTERISTICS:
        (A) LENGTH: 29 base pairs
        (B) TYPE: nucleic acid
        (C) STRANDEDNESS: both
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: KL-2 SISPA Primer (x i) SEQUENCE DESCRIPTION: SEQ ID NO:63:

ATCTCTAGAT GCGAATTCGG ATCCTGCGA   29

(2) INFORMATION FOR SEQ ID NO:64:

(i) SEQUENCE CHARACTERISTICS:
        (A) LENGTH: 186 base pairs
        (B) TYPE: nucleic acid
        (C) STRANDEDNESS: both
        (D) TOPOLOGY: linear (i i) MOLECULE TYPE: cDNA (i i i) HYPOTHETICAL: NO (i v) ANTI-SENSE: NO (v i) ORIGINAL SOURCE:
        (C) INDIVIDUAL ISOLATE: Clone Y5-10

(i x) FEATURE:
        (A) NAME/KEY: CDS
        (B) LOCATION: 1..186

(x i) SEQUENCE DESCRIPTION: SEQ ID NO:64:

| CGT | GCG | CCC | GCC | ATG | GTC | TAT | GGC | CCT | GGG | CAA | AGT | GTT | GCC | ATT | GAC | 48 |
| Arg | Ala | Pro | Ala | Met | Val | Tyr | Gly | Pro | Gly | Gln | Ser | Val | Ala | Ile | Asp | |
| 1 | | | | 5 | | | | | 10 | | | | | 15 | | |

GGG GAG CGC TAC ACC TTG CCT CAT CAA CTG AGG CTC AGG AAT GTG GCA   96

```
Gly Glu Arg Tyr Thr Leu Pro His Gln Leu Arg Leu Arg Asn Val Ala
             20                  25                  30

CCC TCT GAG GTT TCA TCC GAG GTG TCC ATT GAC ATT GGG ACG GAG GCT       144
Pro Ser Glu Val Ser Ser Glu Val Ser Ile Asp Ile Gly Thr Glu Ala
             35                  40                  45

GAA AAC TCA GAA CTG ACT GAG GCC GAT CTG CCG CCG GCG GCT               186
Glu Asn Ser Glu Leu Thr Glu Ala Asp Leu Pro Pro Ala Ala
 50                      55                  60
```

(2) INFORMATION FOR SEQ ID NO:65:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:65:

```
Arg Ala Pro Ala Met Val Tyr Gly Pro Gly Gln Ser Val Ala Ile Asp
 1               5                  10                  15

Gly Glu Arg Tyr Thr Leu Pro His Gln Leu Arg Leu Arg Asn Val Ala
             20                  25                  30

Pro Ser Glu Val Ser Ser Glu Val Ser Ile Asp Ile Gly Thr Glu Ala
             35                  40                  45

Glu Asn Ser Glu Leu Thr Glu Ala Asp Leu Pro Pro Ala Ala
 50                      55                  60
```

(2) INFORMATION FOR SEQ ID NO:66:

(i) SEQUENCE CHARACTERISTICS:
        (A) LENGTH: 282 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-12

(ix) FEATURE:
        (A) NAME/KEY: CDS
        (B) LOCATION: 1..282

(xi) SEQUENCE DESCRIPTION: SEQ ID NO:66:

```
CGT GCG CCC GCC ATG GTC TAT GGC CCT GGG CAA AGT GTT ACC ATT GAC       48
Arg Ala Pro Ala Met Val Tyr Gly Pro Gly Gln Ser Val Thr Ile Asp
 1               5                  10                  15

GGG GAG CGC TAC ACC TTG CCT CAT CAA CTG AGG CTC AGG AAT GTG GCA       96
Gly Glu Arg Tyr Thr Leu Pro His Gln Leu Arg Leu Arg Asn Val Ala
             20                  25                  30

CCC TCT GAG GTT TCA TCC GAG GTG TCC ATT GAC ATT GGG ACG GAG ACT      144
Pro Ser Glu Val Ser Ser Glu Val Ser Ile Asp Ile Gly Thr Glu Thr
             35                  40                  45

GAA GAC TCA GAA CTG ACT GAG GCC GAT CTG CCG CCG GCG GCT GCT GCT      192
Glu Asp Ser Glu Leu Thr Glu Ala Asp Leu Pro Pro Ala Ala Ala Ala
 50                      55                  60

CTC CAA GCG ATC GAG AAT GCT GCG AGG ATT CTT GAA CCG CAC ATT GAT      240
Leu Gln Ala Ile Glu Asn Ala Ala Arg Ile Leu Glu Pro His Ile Asp
 65                      70                  75                  80

GTC ATC ATG GAG GAC TGC AGT ACA CCC TCT CTT TGT GGT AGT              282
```

```
Val Ile Met Glu Asp Cys Ser Thr Pro Ser Leu Cys Gly Ser
             85                      90
```

( 2 ) INFORMATION FOR SEQ ID NO:67:

( i ) SEQUENCE CHARACTERISTICS:
        ( A ) LENGTH: 94 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

```
Arg Ala Pro Ala Met Val Tyr Gly Pro Gly Gln Ser Val Thr Ile Asp
 1               5                  10                      15

Gly Glu Arg Tyr Thr Leu Pro His Gln Leu Arg Leu Arg Asn Val Ala
             20                      25                  30

Pro Ser Glu Val Ser Ser Glu Val Ser Ile Asp Ile Gly Thr Glu Thr
             35                      40                  45

Glu Asp Ser Glu Leu Thr Glu Ala Asp Leu Pro Pro Ala Ala Ala Ala
         50                  55                  60

Leu Gln Ala Ile Glu Asn Ala Ala Arg Ile Leu Glu Pro His Ile Asp
 65                      70                  75                  80

Val Ile Met Glu Asp Cys Ser Thr Pro Ser Leu Cys Gly Ser
                 85                      90
```

( 2 ) INFORMATION FOR SEQ ID NO:68:

( i ) SEQUENCE CHARACTERISTICS:
        ( A ) LENGTH: 279 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5-26

( i x ) FEATURE:
        ( A ) NAME/KEY: CDS
        ( B ) LOCATION: 1..279

( x i ) SEQUENCE DESCRIPTION: SEQ ID NO:68:

```
CGT GCG CCC GCC ATG GTC TAT GGC CCT GGG CAA AGT GTT TCC ATT GAC    48
Arg Ala Pro Ala Met Val Tyr Gly Pro Gly Gln Ser Val Ser Ile Asp
 1               5                  10                      15

GGG GAG CGC TAC ACC TTG CCT CAT CAA CTG AGG CTC AGG AAT GTG GCA    96
Gly Glu Arg Tyr Thr Leu Pro His Gln Leu Arg Leu Arg Asn Val Ala
             20                      25                  30

CCC TCT GAG GTT TCA TCC GAG GTG TCC ATT GAC ATT GGG ACG GAG ACT   144
Pro Ser Glu Val Ser Ser Glu Val Ser Ile Asp Ile Gly Thr Glu Thr
             35                      40                  45

GAA GAC TCA GAA CTG ACT GAG GCC GAC CTG CCG CCG GCG GCT GCT GCT   192
Glu Asp Ser Glu Leu Thr Glu Ala Asp Leu Pro Pro Ala Ala Ala Ala
         50                  55                  60

CTC CAA GCG ATC GAG AAT GCT GCG AGG ATT CTT GAA CCG CAC ATC GAT   240
Leu Gln Ala Ile Glu Asn Ala Ala Arg Ile Leu Glu Pro His Ile Asp
 65                      70                  75                  80

GTC ATC ATG GAG GAC TGC AGT ACA CCC TCT CTT TGT GGT                279
Val Ile Met Glu Asp Cys Ser Thr Pro Ser Leu Cys Gly
                 85                      90
```

( 2 ) INFORMATION FOR SEQ ID NO:69:

( i ) SEQUENCE CHARACTERISTICS:
    ( A ) LENGTH: 93 amino acids
    ( B ) TYPE: amino acid
    ( D ) TOPOLOGY: linear ( i i ) MOLECULE TYPE: protein ( x i ) SEQUENCE DESCRIPTION: SEQ ID NO:69:

```
Arg Ala Pro Ala Met Val Tyr Gly Pro Gly Gln Ser Val Ser Ile Asp
 1               5                  10                  15

Gly Glu Arg Tyr Thr Leu Pro His Gln Leu Arg Leu Arg Asn Val Ala
             20                  25                  30

Pro Ser Glu Val Ser Ser Glu Val Ser Ile Asp Ile Gly Thr Glu Thr
         35                  40                  45

Glu Asp Ser Glu Leu Thr Glu Ala Asp Leu Pro Pro Ala Ala Ala Ala
         50                  55                  60

Leu Gln Ala Ile Glu Asn Ala Ala Arg Ile Leu Glu Pro His Ile Asp
 65                  70                  75                  80

Val Ile Met Glu Asp Cys Ser Thr Pro Ser Leu Cys Gly
                 85                  90
```

( 2 ) INFORMATION FOR SEQ ID NO:70:

( i ) SEQUENCE CHARACTERISTICS:
    ( A ) LENGTH: 108 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Clone Y5- 5

( i x ) FEATURE:
    ( A ) NAME/KEY: CDS
    ( B ) LOCATION: 1..108

( x i ) SEQUENCE DESCRIPTION: SEQ ID NO:70:

```
GCC TAT TGT GAC AAG GTG CGC ACT CCG CTT GAA TTG CAG GTT GGG TGC    48
Ala Tyr Cys Asp Lys Val Arg Thr Pro Leu Glu Leu Gln Val Gly Cys
 1               5                  10                  15

TTG GTG GGC AAT GAA CTT ACC TTT GAA TGT GAC AAG TGT GAG GCT AGG    96
Leu Val Gly Asn Glu Leu Thr Phe Glu Cys Asp Lys Cys Glu Ala Arg
             20                  25                  30

CAA GAA ACC TTG                                                   108
Gln Glu Thr Leu
         35
```

( 2 ) INFORMATION FOR SEQ ID NO:71:

( i ) SEQUENCE CHARACTERISTICS:
    ( A ) LENGTH: 36 amino acids
    ( B ) TYPE: amino acid
    ( D ) TOPOLOGY: linear ( i i ) MOLECULE TYPE: protein ( x i ) SEQUENCE DESCRIPTION: SEQ ID NO:71:

```
Ala Tyr Cys Asp Lys Val Arg Thr Pro Leu Glu Leu Gln Val Gly Cys
```

|   | 1 |   |   |   | 5 |   |   |   |   | 10 |   |   |   |   | 15 |
|---|---|---|---|---|---|---|---|---|---|---|---|---|---|---|---|

Leu Val Gly Asn Glu Leu Thr Phe Glu Cys Asp Lys Cys Glu Ala Arg
                    20                      25                      30

Gln Glu Thr Leu
            35

( 2 ) INFORMATION FOR SEQ ID NO:72:

( i ) SEQUENCE CHARACTERISTICS:
        ( A ) LENGTH: 132 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 3

( i x ) FEATURE:
        ( A ) NAME/KEY: CDS
        ( B ) LOCATION: 1..132

( x i ) SEQUENCE DESCRIPTION: SEQ ID NO:72:

GAG ATG GAA ATC CAG AAC CAT ACA GCC TAT TGT GAC AAG GTG CGC ACT    48
Glu Met Glu Ile Gln Asn His Thr Ala Tyr Cys Asp Lys Val Arg Thr
 1               5                  10                  15

CCG CTT GAA TTG CAG GTT GGG TGC TTG GTG GGC AAT GAA CTT ACC TTT    96
Pro Leu Glu Leu Gln Val Gly Cys Leu Val Gly Asn Glu Leu Thr Phe
             20                  25                  30

GAA TGT GAC AAG TGT GAG GCT AGG CAA GAA ACC TTG    132
Glu Cys Asp Lys Cys Glu Ala Arg Gln Glu Thr Leu
             35                  40

( 2 ) INFORMATION FOR SEQ ID NO:73:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: protein ( x i ) SEQUENCE DESCRIPTION: SEQ ID NO:73:

Glu Met Glu Ile Gln Asn His Thr Ala Tyr Cys Asp Lys Val Arg Thr
 1               5                  10                  15

Pro Leu Glu Leu Gln Val Gly Cys Leu Val Gly Asn Glu Leu Thr Phe
             20                  25                  30

Glu Cys Asp Lys Cys Glu Ala Arg Gln Glu Thr Leu
             35                  40

( 2 ) INFORMATION FOR SEQ ID NO:74:

( i ) SEQUENCE CHARACTERISTICS:
        ( A ) LENGTH: 258 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO (v i) ORIGINAL SOURCE:
  (C) INDIVIDUAL ISOLATE: Clone Y5-27

(i x) FEATURE:
  (A) NAME/KEY: CDS
  (B) LOCATION: 1..258

(x i) SEQUENCE DESCRIPTION: SEQ ID NO:74:

```
AAA GCC TTA TTT CCA CAG AGC GAC GCG ACC AGG AAG CTT ACC GTC AAG      48
Lys Ala Leu Phe Pro Gln Ser Asp Ala Thr Arg Lys Leu Thr Val Lys
 1               5                  10                  15

ATG TCA TGC TGC GTT GAA AAG AGC GTC ACG CGC TTT TTC TCA TTG GGG      96
Met Ser Cys Cys Val Glu Lys Ser Val Thr Arg Phe Phe Ser Leu Gly
             20                  25                  30

TTG ACG GTG GCT GAT GTT GCT AGC CTG TGT GAG ATG GAA ATC CAG AAC     144
Leu Thr Val Ala Asp Val Ala Ser Leu Cys Glu Met Glu Ile Gln Asn
         35                  40                  45

CAT ATA GCC TAT TGT GAC AAG GTG CGC ACT CCG CTT GAA TTG CAG GTT     192
His Ile Ala Tyr Cys Asp Lys Val Arg Thr Pro Leu Glu Leu Gln Val
     50                  55                  60

GGG TGC TTG GTG GGC AAT GAA CTC ACC TTT GAA TGT GAC AAG TGT GAG     240
Gly Cys Leu Val Gly Asn Glu Leu Thr Phe Glu Cys Asp Lys Cys Glu
 65                  70                  75                  80

GCT AGG CAA GAA ACC TTG                                             258
Ala Arg Gln Glu Thr Leu
                 85
```

(2) INFORMATION FOR SEQ ID NO:75:

(i) SEQUENCE CHARACTERISTICS:
    (A) LENGTH: 86 amino acids
    (B) TYPE: amino acid
    (D) TOPOLOGY: linear (i i) MOLECULE TYPE: protein (x i) SEQUENCE DESCRIPTION: SEQ ID NO:75:

```
Lys Ala Leu Phe Pro Gln Ser Asp Ala Thr Arg Lys Leu Thr Val Lys
 1               5                  10                  15

Met Ser Cys Cys Val Glu Lys Ser Val Thr Arg Phe Phe Ser Leu Gly
             20                  25                  30

Leu Thr Val Ala Asp Val Ala Ser Leu Cys Glu Met Glu Ile Gln Asn
         35                  40                  45

His Ile Ala Tyr Cys Asp Lys Val Arg Thr Pro Leu Glu Leu Gln Val
     50                  55                  60

Gly Cys Leu Val Gly Asn Glu Leu Thr Phe Glu Cys Asp Lys Cys Glu
 65                  70                  75                  80

Ala Arg Gln Glu Thr Leu
                 85
```

(2) INFORMATION FOR SEQ ID NO:76:

(i) SEQUENCE CHARACTERISTICS:
    (A) LENGTH: 108 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (v i) ORIGINAL SOURCE:
    (C) INDIVIDUAL ISOLATE: Clone Y5-25

( i x ) FEATURE:
   ( A ) NAME/KEY: CDS
   ( B ) LOCATION: 1..108

( x i ) SEQUENCE DESCRIPTION: SEQ ID NO:76:

```
ACC TAT TGT GAC AAG GTG CGC ACT CCG CTT GAA TTG CAG GTT GGG TGC    48
Thr Tyr Cys Asp Lys Val Arg Thr Pro Leu Glu Leu Gln Val Gly Cys
 1           5                  10                  15

TTG GTG GGC AAT GAA CTT ACC TTT GAA TGT GAC AAG TGT GAG GCT AGG    96
Leu Val Gly Asn Glu Leu Thr Phe Glu Cys Asp Lys Cys Glu Ala Arg
             20                  25                  30

CAA GAA ACC TTG                                                   108
Gln Glu Thr Leu
         35
```

( 2 ) INFORMATION FOR SEQ ID NO:77:

( i ) SEQUENCE CHARACTERISTICS:
    ( A ) LENGTH: 36 amino acids
    ( B ) TYPE: amino acid
    ( D ) TOPOLOGY: linear ( i i ) MOLECULE TYPE: protein ( x i ) SEQUENCE DESCRIPTION: SEQ ID NO:77:

```
Thr Tyr Cys Asp Lys Val Arg Thr Pro Leu Glu Leu Gln Val Gly Cys
 1           5                  10                  15

Leu Val Gly Asn Glu Leu Thr Phe Glu Cys Asp Lys Cys Glu Ala Arg
             20                  25                  30

Gln Glu Thr Leu
         35
```

( 2 ) INFORMATION FOR SEQ ID NO:78:

( i ) SEQUENCE CHARACTERISTICS:
    ( A ) LENGTH: 108 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( C ) INDIVIDUAL ISOLATE: Clone Y5-20

( i x ) FEATURE:
    ( A ) NAME/KEY: CDS
    ( B ) LOCATION: 52..108

( x i ) SEQUENCE DESCRIPTION: SEQ ID NO:78:

```
GCCGACACTA CTAAGGTGTA TGTTACCAAT CCAGACAATG TGGGACGAAG G GTG GGC   57
                                                         Val Gly
                                                          1

AAT GAA CTT ACC TTT GAA TGT GAC AAG TGT GAG GCT AGG CAA GAA ACC  105
Asn Glu Leu Thr Phe Glu Cys Asp Lys Cys Glu Ala Arg Gln Glu Thr
         5                  10                  15

TTG                                                              108
Leu
```

( 2 ) INFORMATION FOR SEQ ID NO:79:

( i ) SEQUENCE CHARACTERISTICS:
    ( A ) LENGTH: 19 amino acids ( B ) TYPE: amino acid
( D ) TOPOLOGY: linear ( i i ) MOLECULE TYPE: protein ( x i ) SEQUENCE DESCRIPTION: SEQ ID NO:79:

| Val | Gly | Asn | Glu | Leu | Thr | Phe | Glu | Cys | Asp | Lys | Cys | Glu | Ala | Arg | Gln |
|---|---|---|---|---|---|---|---|---|---|---|---|---|---|---|---|
| 1 | | | | 5 | | | | | 10 | | | | | 15 | |

| Glu | Thr | Leu |
|---|---|---|

( 2 ) INFORMATION FOR SEQ ID NO:80:

( i ) SEQUENCE CHARACTERISTICS:
( A ) LENGTH: 168 base pairs
( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( C ) INDIVIDUAL ISOLATE: Clone Y5-16

( i x ) FEATURE:
( A ) NAME/KEY: CDS
( B ) LOCATION: 1..168

( x i ) SEQUENCE DESCRIPTION: SEQ ID NO:80:

| TTG | GGG | TTG | ACG | GTG | GCT | GAT | GTT | GCT | AGC | CTG | TGT | GAG | ATG | GAA | ATC | 48 |
|---|---|---|---|---|---|---|---|---|---|---|---|---|---|---|---|---|
| Leu | Gly | Leu | Thr | Val | Ala | Asp | Val | Ala | Ser | Leu | Cys | Glu | Met | Glu | Ile | |
| 1 | | | | 5 | | | | | 10 | | | | | 15 | | |

| CAG | AAC | CAT | ACA | GCC | TAT | TGT | GAC | AAG | GTG | CGC | ACT | CCG | CTT | GAA | TTG | 96 |
|---|---|---|---|---|---|---|---|---|---|---|---|---|---|---|---|---|
| Gln | Asn | His | Thr | Ala | Tyr | Cys | Asp | Lys | Val | Arg | Thr | Pro | Leu | Glu | Leu | |
| | | | 20 | | | | | 25 | | | | | 30 | | | |

| CAG | GTT | GGG | TGC | TTG | GTG | GGC | AAT | GAA | CTT | ACC | TTT | GAA | TGT | GAC | AAG | 144 |
|---|---|---|---|---|---|---|---|---|---|---|---|---|---|---|---|---|
| Gln | Val | Gly | Cys | Leu | Val | Gly | Asn | Glu | Leu | Thr | Phe | Glu | Cys | Asp | Lys | |
| | | 35 | | | | | 40 | | | | | 45 | | | | |

| TGT | GAG | GCT | AGG | CAA | GAA | ACC | TTG | 168 |
|---|---|---|---|---|---|---|---|---|
| Cys | Glu | Ala | Arg | Gln | Glu | Thr | Leu | |
| 50 | | | | | 55 | | | |

( 2 ) INFORMATION FOR SEQ ID NO:81:

( i ) SEQUENCE CHARACTERISTICS:
( A ) LENGTH: 56 amino acids
( B ) TYPE: amino acid
( D ) TOPOLOGY: linear ( i i ) MOLECULE TYPE: protein ( x i ) SEQUENCE DESCRIPTION: SEQ ID NO:81:

| Leu | Gly | Leu | Thr | Val | Ala | Asp | Val | Ala | Ser | Leu | Cys | Glu | Met | Glu | Ile |
|---|---|---|---|---|---|---|---|---|---|---|---|---|---|---|---|
| 1 | | | | 5 | | | | | 10 | | | | | 15 | |

| Gln | Asn | His | Thr | Ala | Tyr | Cys | Asp | Lys | Val | Arg | Thr | Pro | Leu | Glu | Leu |
|---|---|---|---|---|---|---|---|---|---|---|---|---|---|---|---|
| | | | 20 | | | | | 25 | | | | | 30 | | |

| Gln | Val | Gly | Cys | Leu | Val | Gly | Asn | Glu | Leu | Thr | Phe | Glu | Cys | Asp | Lys |
|---|---|---|---|---|---|---|---|---|---|---|---|---|---|---|---|
| | | 35 | | | | | 40 | | | | | 45 | | | |

| Cys | Glu | Ala | Arg | Gln | Glu | Thr | Leu |
|---|---|---|---|---|---|---|---|
| 50 | | | | | 55 | | |

( 2 ) INFORMATION FOR SEQ ID NO:82:

( i ) SEQUENCE CHARACTERISTICS:

( A ) LENGTH: 313 base pairs
( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( C ) INDIVIDUAL ISOLATE: Clone Y5- 50

( i x ) FEATURE:
( A ) NAME/KEY: CDS
( B ) LOCATION: 1..313

( x i ) SEQUENCE DESCRIPTION: SEQ ID NO:82:

```
ATC  ACC  GTC  AAC  CCC  AAT  GAG  AAA  AAG  CGC  GTG  ACG  CTC  TTT  TCA  ACG    48
Ile  Thr  Val  Asn  Pro  Asn  Glu  Lys  Lys  Arg  Val  Thr  Leu  Phe  Ser  Thr
 1              5                        10                       15

CAG  CAC  GAC  ATC  TTG  ACG  GTA  AGC  TTC  CTG  GTC  GCG  TCG  CTC  TGT  GGA    96
Gln  His  Asp  Ile  Leu  Thr  Val  Ser  Phe  Leu  Val  Ala  Ser  Leu  Cys  Gly
              20                       25                       30

AAT  AAG  GCT  TTT  AAT  ACG  GAA  AGA  GCC  ACG  TTG  AAG  ACA  CTT  TCC  TCC   144
Asn  Lys  Ala  Phe  Asn  Thr  Glu  Arg  Ala  Thr  Leu  Lys  Thr  Leu  Ser  Ser
         35                       40                       45

CCT  TCG  GCT  GTC  TCG  GAC  TCT  TGG  ATG  ACC  TCG  AAT  GAG  TCA  GAG  GAC   192
Pro  Ser  Ala  Val  Ser  Asp  Ser  Trp  Met  Thr  Ser  Asn  Glu  Ser  Glu  Asp
    50                       55                       60

GGG  GTA  TCC  TCC  TGC  GAG  GAG  GAC  ACC  GAC  GGG  GTC  TTC  TCA  TCT  GAG   240
Gly  Val  Ser  Ser  Cys  Glu  Glu  Asp  Thr  Asp  Gly  Val  Phe  Ser  Ser  Glu
 65                       70                       75                       80

CTG  CTC  TCA  GTA  ACC  GAG  ATA  AGT  GCT  GGC  GAT  GGA  GTA  CGG  GGG  ATG   288
Leu  Leu  Ser  Val  Thr  Glu  Ile  Ser  Ala  Gly  Asp  Gly  Val  Arg  Gly  Met
                   85                       90                       95

TCT  TCT  CCC  CAT  ACA  GGC  ATC  TCT  C                                        313
Ser  Ser  Pro  His  Thr  Gly  Ile  Ser
              100
```

( 2 ) INFORMATION FOR SEQ ID NO:83:

( i ) SEQUENCE CHARACTERISTICS:
( A ) LENGTH: 104 amino acids
( B ) TYPE: amino acid
( D ) TOPOLOGY: linear ( i i ) MOLECULE TYPE: protein ( x i ) SEQUENCE DESCRIPTION: SEQ ID NO:83:

```
Ile  Thr  Val  Asn  Pro  Asn  Glu  Lys  Lys  Arg  Val  Thr  Leu  Phe  Ser  Thr
 1              5                        10                       15

Gln  His  Asp  Ile  Leu  Thr  Val  Ser  Phe  Leu  Val  Ala  Ser  Leu  Cys  Gly
              20                       25                       30

Asn  Lys  Ala  Phe  Asn  Thr  Glu  Arg  Ala  Thr  Leu  Lys  Thr  Leu  Ser  Ser
         35                       40                       45

Pro  Ser  Ala  Val  Ser  Asp  Ser  Trp  Met  Thr  Ser  Asn  Glu  Ser  Glu  Asp
    50                       55                       60

Gly  Val  Ser  Ser  Cys  Glu  Glu  Asp  Thr  Asp  Gly  Val  Phe  Ser  Ser  Glu
 65                       70                       75                       80

Leu  Leu  Ser  Val  Thr  Glu  Ile  Ser  Ala  Gly  Asp  Gly  Val  Arg  Gly  Met
                   85                       90                       95

Ser  Ser  Pro  His  Thr  Gly  Ile  Ser
              100
```

( 2 ) INFORMATION FOR SEQ ID NO:84:

( i ) SEQUENCE CHARACTERISTICS:
        ( A ) LENGTH: 89 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 52

( i x ) FEATURE:
        ( A ) NAME/KEY: CDS
        ( B ) LOCATION: 28..87

( x i ) SEQUENCE DESCRIPTION: SEQ ID NO:84:

```
ACTGAGAGCA GCTCAGATGA GAAGACC CCT TCG GCT GTC TCG GAC TCT TGG         51
                                Pro Ser Ala Val Ser Asp Ser Trp
                                 1                   5

ATG ACC TCG AAT GAG TCA GAG GAC GGG GTA TCC TCG CA                    89
Met Thr Ser Asn Glu Ser Glu Asp Gly Val Ser Ser
     10              15                  20
```

( 2 ) INFORMATION FOR SEQ ID NO:85:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:85:

```
Pro Ser Ala Val Ser Asp Ser Trp Met Thr Ser Asn Glu Ser Glu Asp
 1               5                  10                  15

Gly Val Ser Ser
         20
```

( 2 ) INFORMATION FOR SEQ ID NO:86:

( i ) SEQUENCE CHARACTERISTICS:
        ( A ) LENGTH: 214 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 53

( i x ) FEATURE:
        ( A ) NAME/KEY: CDS
        ( B ) LOCATION: 1..100

( x i ) SEQUENCE DESCRIPTION: SEQ ID NO:86:

```
AAT AAG GCT TTT AAT ACG GAA AGA GCC ACG TTG AAG ACA CTT TCC TCC       48
Asn Lys Ala Phe Asn Thr Glu Arg Ala Thr Leu Lys Thr Leu Ser Ser
 1               5                  10                  15

CCT TCG GCT GTC TCG GAC TCT TGG ATG ACC TCG AAT GAG TCA GAG GAC       96
```

```
Pro  Ser  Ala  Val  Ser  Asp  Ser  Trp  Met  Thr  Ser  Asn  Glu  Ser  Glu  Asp
              20                       25                       30
```

```
GGG  G ATCTCTAGAT  GCGAATTCAA  GTGTGAGGCT  AGGCAAGAAA  CCTTGGCCTC         150
Gly
```

```
CTTCTCTTAC  ATTTGGTCTG  GAGTGCCGCT  GACTAGGGCC  ACGCCGGCCA  AGCCTCCCGT    210
```

```
GGTG                                                                      214
```

( 2 ) INFORMATION FOR SEQ ID NO:87:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:87:

```
Asn  Lys  Ala  Phe  Asn  Thr  Glu  Arg  Ala  Thr  Leu  Lys  Thr  Leu  Ser  Ser
 1                   5                        10                      15

Pro  Ser  Ala  Val  Ser  Asp  Ser  Trp  Met  Thr  Ser  Asn  Glu  Ser  Glu  Asp
              20                       25                       30

Gly
```

( 2 ) INFORMATION FOR SEQ ID NO:88:

( i ) SEQUENCE CHARACTERISTICS:
        ( A ) LENGTH: 113 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 55

( i x ) FEATURE:
        ( A ) NAME/KEY: CDS
        ( B ) LOCATION: 52..113

( x i ) SEQUENCE DESCRIPTION: SEQ ID NO:88:

```
CCATCGCCAG  CACTTATCTC  GGTTACTGAG  AGCAGCTCAG  ATCAGAAGAC  C  CCT  TCG      57
                                                              Pro  Ser
                                                               1

GCT  GTC  TCG  GAC  TCT  TGG  ATG  ACC  TCG  AAT  GAG  TCA  GAG  GAC  GGG  GTA   105
Ala  Val  Ser  Asp  Ser  Trp  Met  Thr  Ser  Asn  Glu  Ser  Glu  Asp  Gly  Val
          5                        10                       15

TCC  TCG  CA                                                                     113
Ser  Ser
     20
```

( 2 ) INFORMATION FOR SEQ ID NO:89:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:89:

```
Pro  Ser  Ala  Val  Ser  Asp  Ser  Trp  Met  Thr  Ser  Asn  Glu  Ser  Glu  Asp
 1                   5                        10                      15
```

Gly Val Ser Ser
                20

(2) INFORMATION FOR SEQ ID NO:90:

(i) SEQUENCE CHARACTERISTICS:
        (A) LENGTH: 330 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-56

(ix) FEATURE:
        (A) NAME/KEY: CDS
        (B) LOCATION: 1..330

(xi) SEQUENCE DESCRIPTION: SEQ ID NO:90:

```
ACG TTG AAG ACA CTT TCC TCC CCT TCG GCT GTC TCG GAC TCT TGG ATG      48
Thr Leu Lys Thr Leu Ser Ser Pro Ser Ala Val Ser Asp Ser Trp Met
 1               5                  10                  15

ACC TCG AAT GAG TCA GAG GAC GGG GTA TCC TCC TGC GAG GAG GAC ACC      96
Thr Ser Asn Glu Ser Glu Asp Gly Val Ser Ser Cys Glu Glu Asp Thr
                20                  25                  30

GAC GGG GTC TTC TCA TCT GAG CTG CTC TCA GTA ACC GAG ATA AGT GCT     144
Asp Gly Val Phe Ser Ser Glu Leu Leu Ser Val Thr Glu Ile Ser Ala
             35                  40                  45

GGC GAT GGA GTA CGG GGG ATG TCT TCT CCC CAT ACA GGC ATC TCT CGG     192
Gly Asp Gly Val Arg Gly Met Ser Ser Pro His Thr Gly Ile Ser Arg
         50                  55                  60

CTA CTA CCA CAA AGA GAG GGT GTA CTG CAG TCC TCC ATG ATG ACA TCA     240
Leu Leu Pro Gln Arg Glu Gly Val Leu Gln Ser Ser Met Met Thr Ser
 65                  70                  75                  80

ATG TGC GGT TCA AGA ATC CTC GCA GCA TTC TCG ATC GCT TGG AGA GCA     288
Met Cys Gly Ser Arg Ile Leu Ala Ala Phe Ser Ile Ala Trp Arg Ala
                 85                  90                  95

GCA GCC GCC GGC GGC AGA TCG GCC TCA GTC AGT TCT GAG TCT             330
Ala Ala Ala Gly Gly Arg Ser Ala Ser Val Ser Ser Glu Ser
                100                 105                 110
```

(2) INFORMATION FOR SEQ ID NO:91:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:91:

```
Thr Leu Lys Thr Leu Ser Ser Pro Ser Ala Val Ser Asp Ser Trp Met
 1               5                  10                  15

Thr Ser Asn Glu Ser Glu Asp Gly Val Ser Ser Cys Glu Glu Asp Thr
                20                  25                  30

Asp Gly Val Phe Ser Ser Glu Leu Leu Ser Val Thr Glu Ile Ser Ala
             35                  40                  45

Gly Asp Gly Val Arg Gly Met Ser Ser Pro His Thr Gly Ile Ser Arg
         50                  55                  60
```

| | | | | | | | | | | | | | | | |
|---|---|---|---|---|---|---|---|---|---|---|---|---|---|---|---|
| Leu | Leu | Pro | Gln | Arg | Glu | Gly | Val | Leu | Gln | Ser | Ser | Met | Met | Thr | Ser |
| 65 | | | | 70 | | | | | 75 | | | | | | 80 |
| Met | Cys | Gly | Ser | Arg | Ile | Leu | Ala | Ala | Phe | Ser | Ile | Ala | Trp | Arg | Ala |
| | | | | 85 | | | | | 90 | | | | | 95 | |
| Ala | Ala | Ala | Gly | Gly | Arg | Ser | Ala | Ser | Val | Ser | Ser | Glu | Ser | | |
| | | | 100 | | | | | 105 | | | | | 110 | | |

(2) INFORMATION FOR SEQ ID NO:92:

(i) SEQUENCE CHARACTERISTICS:
        (A) LENGTH: 195 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: Clone Y5-57

(ix) FEATURE:
        (A) NAME/KEY: CDS
        (B) LOCATION: 1..195

(xi) SEQUENCE DESCRIPTION: SEQ ID NO:92:

| | | | | | | | | | | | | | | | | |
|---|---|---|---|---|---|---|---|---|---|---|---|---|---|---|---|---|
| ACG | GAA | AGA | GCC | ACG | TTG | AAG | ACA | CTT | TCC | TCC | CCT | TCG | GCT | GCC | TCG | 48 |
| Thr | Glu | Arg | Ala | Thr | Leu | Lys | Thr | Leu | Ser | Ser | Pro | Ser | Ala | Ala | Ser | |
| 1 | | | | 5 | | | | | 10 | | | | | 15 | | |
| GAC | TCT | TGG | ATG | ACC | TCG | AAT | GAG | TCG | GAG | GAC | GGG | GTA | TCC | TCC | TGC | 96 |
| Asp | Ser | Trp | Met | Thr | Ser | Asn | Glu | Ser | Glu | Asp | Gly | Val | Ser | Ser | Cys | |
| | | | 20 | | | | | 25 | | | | | 30 | | | |
| GAA | GAG | GAC | ACC | GAC | GGG | GTC | TTC | TCA | TCT | GAG | CTG | CTC | TCA | GTA | ACC | 144 |
| Glu | Glu | Asp | Thr | Asp | Gly | Val | Phe | Ser | Ser | Glu | Leu | Leu | Ser | Val | Thr | |
| | | 35 | | | | | 40 | | | | | 45 | | | | |
| GAG | ATA | AGT | GCT | GGC | GGT | GGA | GTA | CGG | GGG | ATG | TCT | TCT | CCC | CAT | ACG | 192 |
| Glu | Ile | Ser | Ala | Gly | Gly | Gly | Val | Arg | Gly | Met | Ser | Ser | Pro | His | Thr | |
| | 50 | | | | | 55 | | | | | 60 | | | | | |
| GGC | | | | | | | | | | | | | | | | 195 |
| Gly | | | | | | | | | | | | | | | | |
| 65 | | | | | | | | | | | | | | | | |

(2) INFORMATION FOR SEQ ID NO:93:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO:93:

| | | | | | | | | | | | | | | | |
|---|---|---|---|---|---|---|---|---|---|---|---|---|---|---|---|
| Thr | Glu | Arg | Ala | Thr | Leu | Lys | Thr | Leu | Ser | Ser | Pro | Ser | Ala | Ala | Ser |
| 1 | | | | 5 | | | | | 10 | | | | | 15 | |
| Asp | Ser | Trp | Met | Thr | Ser | Asn | Glu | Ser | Glu | Asp | Gly | Val | Ser | Ser | Cys |
| | | | 20 | | | | | 25 | | | | | 30 | | |
| Glu | Glu | Asp | Thr | Asp | Gly | Val | Phe | Ser | Ser | Glu | Leu | Leu | Ser | Val | Thr |
| | | 35 | | | | | 40 | | | | | 45 | | | |
| Glu | Ile | Ser | Ala | Gly | Gly | Gly | Val | Arg | Gly | Met | Ser | Ser | Pro | His | Thr |
| | 50 | | | | | 55 | | | | | 60 | | | | |
| Gly | | | | | | | | | | | | | | | |
| 65 | | | | | | | | | | | | | | | |

( 2 ) INFORMATION FOR SEQ ID NO:94:

( i ) SEQUENCE CHARACTERISTICS:
        ( A ) LENGTH: 115 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 60

( i x ) FEATURE:
        ( A ) NAME/KEY: CDS
        ( B ) LOCATION: 1..115

( x i ) SEQUENCE DESCRIPTION: SEQ ID NO:94:

```
AAG ACA CTT TCC TCC CCT TCG GCT GTC TCG GAC TCT TGG ATG ACC TCG    48
Lys Thr Leu Ser Ser Pro Ser Ala Val Ser Asp Ser Trp Met Thr Ser
 1               5                   10                  15

AAT GAG TCA GAG GAC GGG GTA TCC TCC TGC GAG GAG GAC ACC GAC TGG    96
Asn Glu Ser Glu Asp Gly Val Ser Ser Cys Glu Glu Asp Thr Asp Trp
             20                  25                  30

GTC TTC TCA TCT GAG CTG C                                        115
Val Phe Ser Ser Glu Leu
         35
```

( 2 ) INFORMATION FOR SEQ ID NO:95:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:95:

```
Lys Thr Leu Ser Ser Pro Ser Ala Val Ser Asp Ser Trp Met Thr Ser
 1               5                   10                  15

Asn Glu Ser Glu Asp Gly Val Ser Ser Cys Glu Glu Asp Thr Asp Trp
             20                  25                  30

Val Phe Ser Ser Glu Leu
         35
```

( 2 ) INFORMATION FOR SEQ ID NO:96:

( i ) SEQUENCE CHARACTERISTICS:
        ( A ) LENGTH: 93 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Clone Y5- 63

( i x ) FEATURE:
        ( A ) NAME/KEY: CDS
        ( B ) LOCATION: 19..93

( x i ) SEQUENCE DESCRIPTION: SEQ ID NO:96:

```
GAGAGCAGCT CAGATGAG AAG ACA CTT TCC TCC CCT TCG GCT GTC TCG GAC        51
                    Lys Thr Leu Ser Ser Pro Ser Ala Val Ser Asp
                    1               5                   10

TCT TGG ATG ACC TCG AAT GAG TCA GAG GAC GGG GTA TCC TCG                93
Ser Trp Met Thr Ser Asn Glu Ser Glu Asp Gly Val Ser Ser
            15              20                      25
```

( 2 ) INFORMATION FOR SEQ ID NO:97:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
Lys Thr Leu Ser Ser Pro Ser Ala Val Ser Asp Ser Trp Met Thr Ser
1               5                   10                      15

Asn Glu Ser Glu Asp Gly Val Ser Ser
            20                  25
```

( 2 ) INFORMATION FOR SEQ ID NO:98:

( i ) SEQUENCE CHARACTERISTICS:
        ( A ) LENGTH: 1181 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 8E3

( x i ) SEQUENCE DESCRIPTION: SEQ ID NO:98:

```
GCTGGCTGAG GCACGGTTGG TCCCGCTGAT CTTGCTGCTG CTATGGTGGT GGGTGAACCA       60
GCTGGCAGTC CTAGGGCTGC CGGCTGTGGA AGCCGCCGTG GCAGGTGAGG TCTTCGCGGG      120
CCCTGCCCTG TCCTGGTGTC TGGGACTCCC GGTCGTCAGT ATGATATTGG GTTTGGCAAA      180
CCTGGTGCTG TACTTTAGAT GGTTGGGACC CCAACGCCTG ATGTTCCTCG TGTTGTGGAA      240
GCTTGCTCGG GGAGCTTTCC CGCTGGCCCT CTTGATGGGG ATTTCGGCGA CCCGCGGGCG      300
CACCTCAGTG CTCGGGGCCG AGTTCTGCTT CGATGCTACA TTCGAGGTGG ACACTTCGGT      360
GTTGGGCTGG GTGGTGGCCA GTGTGGTAGC TTGGGCCATT GCGCTCCTGA GCTCGATGAG      420
CGCAGGGGGG TGGAGGCACA AAGCCGTGAT CTATAGGACG TGGTGTAAGG GGTACCAGGC      480
AATCCGTCAA AGGGTGGTGA GGAGCCCCCT CGGGGAGGGG CGGCCTGCCA AACCCCTGAC      540
CTTTGCCTGG TGCTTGGCCT CGTACATCTG GCCAGATGCT GTGATGATGG TGGTGGTTGC      600
CTTGGTCCTT CTCTTTGGCC TGTTCGACGC GTTGGATTGG GCCTTGGAGG AGATCTTGGT      660
GTCCGGCCC TCGTTGCGGC GTTTGGCTCG GGTGGTTGAG TGCTGTGTGA TGGCGGGTGA      720
GAAGGCCACA ACCGTCCGGC TGGTCTCCAA GATGTGTGCG AGAGGAGCTT ATTTGTTCGA      780
TCATATGGGC TCTTTTCGC GTGCTGTCAA GGAGCGCCTG TTGGAATGGG ACGCAGCTCT      840
TGAACCTCTG TCATTCACTA GGACGGACTG TCGCATCATA CGGGATGCCG CGAGGACTTT      900
GTCCTGCGGG CAGTGCGTCA TGGGTTTACC CGTGGTTGCG CGCCGTGGTG ATGAGGTTCT      960
CATCGGCGTC TTCCAGGATG TGAATCATTT GCCTCCCGGG TTTGTTCCGA CCGCGCCTGT     1020
```

| | | | | | |
|---|---|---|---|---|---|
| TGTCATCCGA | CGGTGCGGAA | AGGGCTTCTT | GGGGGTCACA | AAGGCTGCCT | TGACAGGTCG | 1080
| GGATCCTGAC | TTACATCCAG | GGAACGTCAT | GGTGTTGGGG | ACGGCTACGT | CGCGAAGCAT | 1140
| GGGAACATGC | TTGAACGGCC | TGCTGTTCAC | GACCTTCCAT | G | | 1181

( 2 ) INFORMATION FOR SEQ ID NO:99:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5-10- F1

( x i ) SEQUENCE DESCRIPTION: SEQ ID NO:99:

TCAGCCATGG CTCGTGCGCC CGCGATGGTC        30

( 2 ) INFORMATION FOR SEQ ID NO:100:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5-10- R1

( x i ) SEQUENCE DESCRIPTION: SEQ ID NO:100:

CGAGGATCCA GCCGCCGGCG GCAGATC        27

( 2 ) INFORMATION FOR SEQ ID NO:101:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5- 16F1

( x i ) SEQUENCE DESCRIPTION: SEQ ID NO:101:

GATTCCATGG GTTTGGGGTT GACGGTGGCT GA        32

( 2 ) INFORMATION FOR SEQ ID NO:102:

( i ) SEQUENCE CHARACTERISTICS:
        ( A ) LENGTH: 32 base pairs
        ( B ) TYPE: nucleic acid
        ( C ) STRANDEDNESS: both -continued ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
     ( C ) INDIVIDUAL ISOLATE: Primer 470EP- R3

( x i ) SEQUENCE DESCRIPTION: SEQ ID NO:102:

GCGAATTCGG ATCCCAAGGT TTCTTGCCTA GC               32

( 2 ) INFORMATION FOR SEQ ID NO:103:

( i ) SEQUENCE CHARACTERISTICS:
     ( A ) LENGTH: 27 base pairs
     ( B ) TYPE: nucleic acid
     ( C ) STRANDEDNESS: both
     ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
     ( C ) INDIVIDUAL ISOLATE: Primer Y5-5- F1

( x i ) SEQUENCE DESCRIPTION: SEQ ID NO:103:

GAGGCCATGG CCTATTGTGA CAAGGTG                27

( 2 ) INFORMATION FOR SEQ ID NO:104:

( i ) SEQUENCE CHARACTERISTICS:
     ( A ) LENGTH: 17 base pairs
     ( B ) TYPE: nucleic acid
     ( C ) STRANDEDNESS: both
     ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
     ( C ) INDIVIDUAL ISOLATE: Primer PGEX- R ( x i ) SEQUENCE DESCRIPTION: SEQ ID NO:104:

GACCGTCTCC GGGAGCT                   17

( 2 ) INFORMATION FOR SEQ ID NO:105:

( i ) SEQUENCE CHARACTERISTICS:
     ( A ) LENGTH: 326 base pairs
     ( B ) TYPE: nucleic acid
     ( C ) STRANDEDNESS: both
     ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
     ( C ) INDIVIDUAL ISOLATE: Clone GE15

( i x ) FEATURE:
     ( A ) NAME/KEY: CDS
     ( B ) LOCATION: 3..326

( x i ) SEQUENCE DESCRIPTION: SEQ ID NO:105:

```
CC ATG GAG GTC TCT GAC TTC CGT GGC TCG TCT GGC TCA CCG GTC CTA        47
   Met Glu Val Ser Asp Phe Arg Gly Ser Ser Gly Ser Pro Val Leu
   1               5                   10                  15

TGT GAC GAA GGG CAC GCA GTA GGA ATG CTC GTG TCT GTG CTT CAC TCC        95
Cys Asp Glu Gly His Ala Val Gly Met Leu Val Ser Val Leu His Ser
                    20                  25                  30

GGT GGT AGG GTC ACC GCG GCA CGG TTC ACT AGG CCG TGG ACC CAA GTG       143
Gly Gly Arg Val Thr Ala Ala Arg Phe Thr Arg Pro Trp Thr Gln Val
                35                  40                  45

CCA ACA GAT GCC AAA ACC ACC ACT GAA CCC CCT CCG GTG CCG GCC AAA       191
Pro Thr Asp Ala Lys Thr Thr Thr Glu Pro Pro Pro Val Pro Ala Lys
            50                  55                  60

GGA GTT TTC AAA GAG GCC CCG TTG TTT ATG CCT ACG GGA GCG GGA AAG       239
Gly Val Phe Lys Glu Ala Pro Leu Phe Met Pro Thr Gly Ala Gly Lys
        65                  70                  75

AGC ACT CGC GTC CCG TTG GAG TAC GGC AAC ATG GGG CAC AAG GTC TTA       287
Ser Thr Arg Val Pro Leu Glu Tyr Gly Asn Met Gly His Lys Val Leu
80                  85                  90                  95

ATC TTG AAC CCC TCA GTG GCC ACT GTG CGG GCG ATG GGC                   326
Ile Leu Asn Pro Ser Val Ala Thr Val Arg Ala Met Gly
                100                 105
```

( 2 ) INFORMATION FOR SEQ ID NO:106:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:106:

```
Met Glu Val Ser Asp Phe Arg Gly Ser Ser Gly Ser Pro Val Leu Cys
1               5                   10                  15

Asp Glu Gly His Ala Val Gly Met Leu Val Ser Val Leu His Ser Gly
                20                  25                  30

Gly Arg Val Thr Ala Ala Arg Phe Thr Arg Pro Trp Thr Gln Val Pro
            35                  40                  45

Thr Asp Ala Lys Thr Thr Thr Glu Pro Pro Pro Val Pro Ala Lys Gly
        50                  55                  60

Val Phe Lys Glu Ala Pro Leu Phe Met Pro Thr Gly Ala Gly Lys Ser
65                  70                  75                  80

Thr Arg Val Pro Leu Glu Tyr Gly Asn Met Gly His Lys Val Leu Ile
                85                  90                  95

Leu Asn Pro Ser Val Ala Thr Val Arg Ala Met Gly
            100                 105
```

( 2 ) INFORMATION FOR SEQ ID NO:107:

( i ) SEQUENCE CHARACTERISTICS:
        ( A ) LENGTH: 138 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

( C ) INDIVIDUAL ISOLATE: Clone GE17

( i x ) FEATURE:
    ( A ) NAME/KEY: CDS
    ( B ) LOCATION: 1..138

( x i ) SEQUENCE DESCRIPTION: SEQ ID NO:107:

```
GGT GAT GAG GTT CTC ATC GGC GTC TTC CAG GAT GTG AAT CAT TTG CCT      48
Gly Asp Glu Val Leu Ile Gly Val Phe Gln Asp Val Asn His Leu Pro
 1               5                  10                  15

CCC GGG TTT GTT CCG ACC GCG CCT GTT GTC ATC CGA CGG TGC GGA AAG      96
Pro Gly Phe Val Pro Thr Ala Pro Val Val Ile Arg Arg Cys Gly Lys
             20                  25                  30

GGC TTC TTG GGG GTC ACA AAG GCT GCC TTG ACA GGT CGG GAT             138
Gly Phe Leu Gly Val Thr Lys Ala Ala Leu Thr Gly Arg Asp
         35                  40                  45
```

( 2 ) INFORMATION FOR SEQ ID NO:108:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( x i ) SEQUENCE DESCRIPTION: SEQ ID NO:108:

```
Gly Asp Glu Val Leu Ile Gly Val Phe Gln Asp Val Asn His Leu Pro
 1               5                  10                  15

Pro Gly Phe Val Pro Thr Ala Pro Val Val Ile Arg Arg Cys Gly Lys
             20                  25                  30

Gly Phe Leu Gly Val Thr Lys Ala Ala Leu Thr Gly Arg Asp
         35                  40                  45
```

( 2 ) INFORMATION FOR SEQ ID NO:109:

( i ) SEQUENCE CHARACTERISTICS:
        ( A ) LENGTH: 395 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 9E3

( x i ) SEQUENCE DESCRIPTION: SEQ ID NO:109:

```
TGTATTTGTC CTGTTATACC TGATGAAGCT GGCTGAGGCA CGGTTGGTCC CGCTGATCTT    60
GCTGCTGCTA TGGTGGTGGG TGAACCAGCT GGCAGTCCTA GGGCTGCCGG CTGTGGAAGC   120
CGCCGTGGCA GGTGAGGTCT TCGCGGGCCC TGCCCTGTCC TGGTGTCTGG GACTCCCGGT   180
CGTCAGTATG ATATTGGGTT TGGCAAACCT AGTGCTGTAC TTTAGATGGT TGGGACCCCA   240
ACGCCTGATG TTCCTCGTGT TGTGGAAGCT TGCTCGGGGA GCTTTCCCGC TGGCCCTCTT   300
GATGGGGATT TCGGCGACCC GCGGGCGCAC CTCAGTGCTC GGGGCCGAGT TCTGCTTCGA   360
TGCTACATTC GAGGTGGACA CTTCGGTGTT GGGCT                             395
```

( 2 ) INFORMATION FOR SEQ ID NO:110:

( i ) SEQUENCE CHARACTERISTICS:
        ( A ) LENGTH: 460 base pairs (B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 10E3

(xi) SEQUENCE DESCRIPTION: SEQ ID NO:110:

| | | | | | |
|---|---|---|---|---|---|
| GCCCCTGGGC | AACCAGGGCC | GAGGCAACCC | GGTGCGGTCG | CCCTTGGGTT | TTGGGTCCTA | 60
| CGCCATGACC | AGGATCCGAG | ATACCCTACA | TCTGGTGGAG | TGTCCCACAC | CAGCCATTGA | 120
| GCCTCCCACC | GGGACGTTTG | GGTTCTTCCC | CGGGACGCCG | CCTCTCAACA | ACTGCATGCT | 180
| CTTGGGCACG | GAAGTGTCCG | AGGCACTTGG | GGGGGCTGGC | CTCACGGGGG | GGTTCTATGA | 240
| ACCCCTGGTG | CGCAGGTGTT | CGAAGCTGAT | GGGAAGCCGA | AATCCGGTTT | GTCCGGGGTT | 300
| TGCATGGCTC | TCTTCGGGCA | GGCCTGATGG | GTTTATACAT | GTCCAGGGTC | ACTTGCAGGA | 360
| GGTGGATGCA | GGCAACTTCA | TCCCGCCCCC | GCGCTGGTTG | CTCTTGGACT | TTGTATTTGT | 420
| CCTGTTATAC | CTGATGAAGC | TGGCTGAGGC | ACGGTTGGTC | | | 460

(2) INFORMATION FOR SEQ ID NO:111:

(i) SEQUENCE CHARACTERISTICS:
(A) LENGTH: 28 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GE15F (xi) SEQUENCE DESCRIPTION: SEQ ID NO:111:

GCCGCCATGG AGGTCTCTGA CTTCCGTG 28

(2) INFORMATION FOR SEQ ID NO:112:

(i) SEQUENCE CHARACTERISTICS:
(A) LENGTH: 31 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GE15R (xi) SEQUENCE DESCRIPTION: SEQ ID NO:112:

GCGCGGATCC GCCCATCGCC CGCACAGTGG C 31

(2) INFORMATION FOR SEQ ID NO:113:

(i) SEQUENCE CHARACTERISTICS:
(A) LENGTH: 31 base pairs ( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GE17F ( x i ) SEQUENCE DESCRIPTION: SEQ ID NO:113:

| | | |
|---|---|---|
| CGCTCCATGG GTGATGAGGT TCTCATCGGC G | | 31 |

( 2 ) INFORMATION FOR SEQ ID NO:114:

( i ) SEQUENCE CHARACTERISTICS:
( A ) LENGTH: 28 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GE17R ( x i ) SEQUENCE DESCRIPTION: SEQ ID NO:114:

GTAAGTCAGG ATCCCGACCT GTCAAGGC                          28

( 2 ) INFORMATION FOR SEQ ID NO:115:

( i ) SEQUENCE CHARACTERISTICS:
( A ) LENGTH: 452 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( C ) INDIVIDUAL ISOLATE: NcoI/EcoRI- containing fragment of
pGEX-HISb- GE3-s HGV plasmid ( x i ) SEQUENCE DESCRIPTION: SEQ ID NO:115:

CAAAATCGGA TCTGGTTCCG CGTGGTTCCA TGGTCTCATG GGACGCGGAC GCTCGTGCGC     60

CCGCGATGGT CTATGGCCCT GGGCAAAGTG TTACCATTGA CGGGGAGCGC TACACCTTGC    120

CTCATCAACT GAGGCTCAGG AATGTGGCAC CCTCTGAGGT TTCATCCGAG GTGTCCATTG    180

ACATTGGGAC GGAGACTGAA GACTCAGAAC TGACTGAGGC CGATCTGCCG CCGGCGGCTG    240

CTGCTCTCCA AGCGATCGAG AATGCTGCGA GGATTCTTGA ACCGCACATT GATGTCATCA    300

TGGAGGACTG CAGTACACCC TCTCTTTGTG GTAGTAGCCG AGAGATGCCT GTATGGGGAG    360

AAGACATCCC CCGTACTCCA TCGCCAGCAC TTATCGGATC CCACCATCAC CATCACCATT    420

AGAATTCATC GTGACTGACT GACGATCTAC CT                                   452

( 2 ) INFORMATION FOR SEQ ID NO:116:

( i ) SEQUENCE CHARACTERISTICS:

-continued (A) LENGTH: 590 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 11E3

(xi) SEQUENCE DESCRIPTION: SEQ ID NO:116:

| | | | | | |
|---|---|---|---|---|---|
| AGCAATCGGC | TGGGGTGACC | CCATCACTTA | TTGGAGCCAC | GGGCAAAATC | AGTGGCCCCT | 60 |
| TTCATGCCCC | CAGTATGTCT | ATGGGTCTGC | TACAGTCACT | TGCGTGTGGG | GTTCCGCTTC | 120 |
| TTGGTTTGCC | TCCACCAGTG | GTCGCGACTC | GAAGATAGAT | GTGTGGAGTT | TAGTGCCAGT | 180 |
| TGGCTCTGCC | ACCTGCACCA | TAGCCGCACT | TGGATCATCG | GATCGCGACA | CGGTGCCTGG | 240 |
| GCTCTCCGAG | TGGGGAATCC | CGTGCGTGAC | GTGTGTTCTG | GACCGTCGGC | CTGCCTCCTG | 300 |
| CGGCACCTGT | GTGAGGGACT | GCTGGCCCGA | GACCGGGTCG | GTTAGGTTCC | CATTCCATCG | 360 |
| GTGCGGCGTG | GGGCCTCGGC | TGACAAAGGA | CTTGGAAGCT | GTGCCCTTCG | TCAACAGGAC | 420 |
| AACTCCCTTC | ACCATTAGGG | GGCCCCTGGG | CAACCAGGGC | CGAGGCAACC | CGGTGCGGTC | 480 |
| GCCCTTGGGT | TTTGGGTCCT | ACGCCATGAC | CAGGATCCGA | GATACCCTAC | ATCTGGTGGA | 540 |
| GTGTCCCACA | CCAGCCATCG | AGCCTCCCAC | CGGGACGTTT | GGGTTCTTCC | | 590 |

(2) INFORMATION FOR SEQ ID NO:117:

(i) SEQUENCE CHARACTERISTICS:
(A) LENGTH: 29 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Probe E3- 111PROB (xi) SEQUENCE DESCRIPTION: SEQ ID NO:117:

TGGTGAAGGG AGTTGTCCTA TTGACGAAG 29

(2) INFORMATION FOR SEQ ID NO:118:

(i) SEQUENCE CHARACTERISTICS:
(A) LENGTH: 735 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Consensus Sequence 12E3

(xi) SEQUENCE DESCRIPTION: SEQ ID NO:118:

ATTGTTGTGC CCCGGAGGAC ATCGGGTTCT GCCTGGAGGG TGGATGCCTG GTGGCCCTGG 60

-continued

| | | | | | |
|---|---|---|---|---|---|
| GGTGCACGAT | TTGCACTGAC | CAATGCTGGC | CACTGTATCA | GGCGGGTTTG | GCTGTGCGGC | 120 |
| CTGGCAAGTC | CGCGGCCCAA | CTGGTGGGGG | AGCTGGGTAG | CCTATACGGG | CCCCTGTCGG | 180 |
| TCTCGGCCTA | TGTGGCTGGG | ATCCTGGGCC | TGGGTGAGGT | GTACTCGGGT | GTCCTAACGG | 240 |
| TGGGAGTCGC | GTTGACGCGC | CGGGTCTACC | CGGTGCCTAA | CCTGACGTGT | GCAGTCGCGT | 300 |
| GTGAGCTAAA | GTGGGAAAGT | GAGTTTTGGA | GATGGACTGA | ACAGCTGGCC | TCCAACTACT | 360 |
| GGATTCTGGA | ATACCTCTGG | AAGGTCCCAT | TTGATTTCTG | GAGAGGCGTG | ATAAGCCTGA | 420 |
| CCCCCTTGTT | GGTTTGCGTG | GCCGCATTGC | TGCTGCTTGA | GCAACGGATT | GTCATGGTCT | 480 |
| TCCTGTTGGT | GACGATGGCC | GGGATGTCGC | AAGGCGCCCC | TGCCTCCGTT | TTGGGGTCAC | 540 |
| GCCCCTTTGA | CTACGGGTTG | ACTTGGCAGA | CCTGCTCTTG | CAGGGCCAAC | GGTTCGCGTT | 600 |
| TTTCGACTGG | GGAGAAGGTG | TGGGACCGTG | GGAACGTTAC | GCTTCAGTGT | GACTGCCCTA | 660 |
| ACGGCCCCTG | GGTGTGGTTG | CCAGCCTTTT | GCCAAGCAAT | CGGCTGGGGT | GACCCCATCA | 720 |
| CTTATTGGAG | CCACG | | | | | 735 |

( 2 ) INFORMATION FOR SEQ ID NO:119:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer 470EXT4-2189R ( x i ) SEQUENCE DESCRIPTION: SEQ ID NO:119:

ATCTGTGGTA TGCCATCCCG GT        22

( 2 ) INFORMATION FOR SEQ ID NO:120:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer 470EXT4-29F ( x i ) SEQUENCE DESCRIPTION: SEQ ID NO:120:

GTTATGCTAC TGTCGAAGCA GGT        23

( 2 ) INFORMATION FOR SEQ ID NO:121:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO (iv) ANTI-SENSE: NO (vi) ORIGINAL SOURCE:
    (C) INDIVIDUAL ISOLATE: NS5 Primer GV57-4512 MF (xi) SEQUENCE DESCRIPTION: SEQ ID NO:121:

GGACTTCCGG ATAGCTGARA AGCT                    24

(2) INFORMATION FOR SEQ ID NO:122:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: NS5 Primer GV57-4657 MR (xi) SEQUENCE DESCRIPTION: SEQ ID NO:122:

GCRTCCACAC AGATGGCGCA                         20

(2) INFORMATION FOR SEQ ID NO:123:

(i) SEQUENCE CHARACTERISTICS:
        (A) LENGTH: 28 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: NS5 Probe GV22dc-89 MF (xi) SEQUENCE DESCRIPTION: SEQ ID NO:123:

CYCGCTGRTT TGGGGTGTAC TGGAAGGC                28

(2) INFORMATION FOR SEQ ID NO:124:

(i) SEQUENCE CHARACTERISTICS:
        (A) LENGTH: 31 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: 5'-UTR Primer FV94-22F (xi) SEQUENCE DESCRIPTION: SEQ ID NO:124:

GAAAGCCCCA GAAACCGACG CCTATCTAAG T            31

(2) INFORMATION FOR SEQ ID NO:125:

(i) SEQUENCE CHARACTERISTICS:

(A) LENGTH: 26 base pairs
            (B) TYPE: nucleic acid
            (C) STRANDEDNESS: both
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: 5'UTR Primer FV94-724R (xi) SEQUENCE DESCRIPTION: SEQ ID NO:125:

GCACAGCCAA ACCCGCCTGA TACAGT                                    26

(2) INFORMATION FOR SEQ ID NO:126:

(i) SEQUENCE CHARACTERISTICS:
            (A) LENGTH: 28 base pairs
            (B) TYPE: nucleic acid
            (C) STRANDEDNESS: both
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: 5'-UTR Primer FV94-94F (xi) SEQUENCE DESCRIPTION: SEQ ID NO:126:

GTGGTGGATG GGTGATGACA GGGTTGGT                                  28

(2) INFORMATION FOR SEQ ID NO:127:

(i) SEQUENCE CHARACTERISTICS:
            (A) LENGTH: 29 base pairs
            (B) TYPE: nucleic acid
            (C) STRANDEDNESS: both
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: 5'-UTR Primer FV94-912R (xi) SEQUENCE DESCRIPTION: SEQ ID NO:127:

TAACTCACAC GCGACTGCAC ACGTCAGGT                                 29

(2) INFORMATION FOR SEQ ID NO:128:

(i) SEQUENCE CHARACTERISTICS:
            (A) LENGTH: 30 base pairs
            (B) TYPE: nucleic acid
            (C) STRANDEDNESS: both
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: ENV Library Primer GEP-F15

( x i ) SEQUENCE DESCRIPTION: SEQ ID NO:128:

GCGGCCATGG TGCCCTTCGT CAATAGGACA 30

( 2 ) INFORMATION FOR SEQ ID NO:129:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: ENV Library Primer GEP-R15

( x i ) SEQUENCE DESCRIPTION: SEQ ID NO:129:

CTTGCCATGG CCAGCTGGTT CACCCACCA 29

( 2 ) INFORMATION FOR SEQ ID NO:130:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GEP- F17

( x i ) SEQUENCE DESCRIPTION: SEQ ID NO:130:

GCAGGATCCC CTCTGGAAGG TCCCATTTGA 30

( 2 ) INFORMATION FOR SEQ ID NO:131:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GEP- R16

( x i ) SEQUENCE DESCRIPTION: SEQ ID NO:131:

TGCGAATCCT CGGCCCTGGT TGCCCAG 27

( 2 ) INFORMATION FOR SEQ ID NO:132:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA (iii) HYPOTHETICAL: NO (iv) ANTI-SENSE: NO (vi) ORIGINAL SOURCE:
                        (C) INDIVIDUAL ISOLATE: Primer 470ep-F9

(xi) SEQUENCE DESCRIPTION: SEQ ID NO:132:

GCTAGATCTG GCAACATGGG GCACAAGGTC                    30

(2) INFORMATION FOR SEQ ID NO:133:

(i) SEQUENCE CHARACTERISTICS:
                (A) LENGTH: 30 base pairs
                (B) TYPE: nucleic acid
                (C) STRANDEDNESS: both
                (D) TOPOLOGY: linear (ii) MOLECULE TYPE: DNA (iii) HYPOTHETICAL: NO (iv) ANTI-SENSE: NO (vi) ORIGINAL SOURCE:
                (C) INDIVIDUAL ISOLATE: Primer 470ep-R9

(xi) SEQUENCE DESCRIPTION: SEQ ID NO:133:

CACAGATCTC GCGTAGTAGT AGCGTCCAGA                    30

(2) INFORMATION FOR SEQ ID NO:134:

(i) SEQUENCE CHARACTERISTICS:
                (A) LENGTH: 38 base pairs
                (B) TYPE: nucleic acid
                (C) STRANDEDNESS: both
                (D) TOPOLOGY: linear (ii) MOLECULE TYPE: DNA (iii) HYPOTHETICAL: NO (iv) ANTI-SENSE: NO (vi) ORIGINAL SOURCE:
                (C) INDIVIDUAL ISOLATE: AP Primer for Race PCR (xi) SEQUENCE DESCRIPTION: SEQ ID NO:134:

CTGGTTCGGC CCACCTCTGA AGGTTCCAGA ATCGATAG           38

(2) INFORMATION FOR SEQ ID NO:135:

(i) SEQUENCE CHARACTERISTICS:
                (A) LENGTH: 30 base pairs
                (B) TYPE: nucleic acid
                (C) STRANDEDNESS: both
                (D) TOPOLOGY: linear (ii) MOLECULE TYPE: DNA (iii) HYPOTHETICAL: NO (iv) ANTI-SENSE: NO (vi) ORIGINAL SOURCE:
                (C) INDIVIDUAL ISOLATE: Primer GEP-F10

(xi) SEQUENCE DESCRIPTION: SEQ ID NO:135:

GCTGGATCCA GCATGGGAAC ATGCTTGAAC                    30

(2) INFORMATION FOR SEQ ID NO:136:

( i ) SEQUENCE CHARACTERISTICS:
    ( A ) LENGTH: 30 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer GEP- R10

( x i ) SEQUENCE DESCRIPTION: SEQ ID NO:136:

CGCGGATCCC ACAGTGGCCA CTGAGGGGTT    30

( 2 ) INFORMATION FOR SEQ ID NO:137:

( i ) SEQUENCE CHARACTERISTICS:
    ( A ) LENGTH: 27 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer EXY10- F1

( x i ) SEQUENCE DESCRIPTION: SEQ ID NO:137:

GCCCATATGG TGATCACTGG TGACGTT    27

( 2 ) INFORMATION FOR SEQ ID NO:138:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer EXY10- F2

( x i ) SEQUENCE DESCRIPTION: SEQ ID NO:138:

GCCCATATGC TGGGTTACGG TGAA    24

( 2 ) INFORMATION FOR SEQ ID NO:139:

( i ) SEQUENCE CHARACTERISTICS:
    ( A ) LENGTH: 27 base pairs
    ( B ) TYPE: nucleic acid
    ( C ) STRANDEDNESS: both
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:

( C ) INDIVIDUAL ISOLATE: Primer EXY10- F3

( x i ) SEQUENCE DESCRIPTION: SEQ ID NO:139:

GCCCATATGA CCTCCGCCTA TAAGCTG 27

( 2 ) INFORMATION FOR SEQ ID NO:140:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer EXY10- R1

( x i ) SEQUENCE DESCRIPTION: SEQ ID NO:140:

GCCCATATGA GCCGCCGGCG GCAGATC 27

( 2 ) INFORMATION FOR SEQ ID NO:141:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer EXY5- R1

( x i ) SEQUENCE DESCRIPTION: SEQ ID NO:141:

TGCGGATCCC ACATTGTCTG GATT 24

( 2 ) INFORMATION FOR SEQ ID NO:142:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Y5-5- F1

( x i ) SEQUENCE DESCRIPTION: SEQ ID NO:142:

TCGGCCATGG CCTATTGTGA CAAGGTG 27

( 2 ) INFORMATION FOR SEQ ID NO:143:

( i ) SEQUENCE CHARACTERISTICS:
        ( A ) LENGTH: 219 base pairs
        ( B ) TYPE: nucleic acid
        ( C ) STRANDEDNESS: both
        ( D ) TOPOLOGY: linear (i i) MOLECULE TYPE: cDNA (i i i) HYPOTHETICAL: NO (i v) ANTI-SENSE: NO (v i) ORIGINAL SOURCE:
        (C) INDIVIDUAL ISOLATE: Antigen Clone Q7-12-1

(i x) FEATURE:
        (A) NAME/KEY: CDS
        (B) LOCATION: 1..219

(x i) SEQUENCE DESCRIPTION: SEQ ID NO:143:

| GTG | CCC | TTC | GTC | AAT | AGG | ACA | ACT | CTC | TTC | ACC | ATT | AGG | GGG | CCC | CTG | 48 |
| Val | Pro | Phe | Val | Asn | Arg | Thr | Thr | Leu | Phe | Thr | Ile | Arg | Gly | Pro | Leu | |
| 1 | | | | 5 | | | | | 10 | | | | | 15 | | |

| GGC | AAC | CAG | GGC | CGA | GGC | AAC | CCG | GTG | CGG | TCG | CCC | TTG | GGT | TTT | GGG | 96 |
| Gly | Asn | Gln | Gly | Arg | Gly | Asn | Pro | Val | Arg | Ser | Pro | Leu | Gly | Phe | Gly | |
| | | | 20 | | | | | 25 | | | | | 30 | | | |

| TCC | TAC | GCC | ATG | ACC | AGG | ATC | CGA | GAT | ACC | CTA | CAT | CTG | GTG | GAG | TGT | 144 |
| Ser | Tyr | Ala | Met | Thr | Arg | Ile | Arg | Asp | Thr | Leu | His | Leu | Val | Glu | Cys | |
| | | 35 | | | | | 40 | | | | | 45 | | | | |

| CCC | ACA | CCA | GCC | ATC | GAG | CCT | CCC | ACC | GGG | ACG | TCT | GGG | TTC | TTC | CCC | 192 |
| Pro | Thr | Pro | Ala | Ile | Glu | Pro | Pro | Thr | Gly | Thr | Ser | Gly | Phe | Phe | Pro | |
| | 50 | | | | | 55 | | | | | 60 | | | | | |

| GGG | ACG | CCG | CCT | CTC | AAC | AGC | TGC | ATG | | | | | | | | 219 |
| Gly | Thr | Pro | Pro | Leu | Asn | Ser | Cys | Met | | | | | | | | |
| 65 | | | | | 70 | | | | | | | | | | | |

(2) INFORMATION FOR SEQ ID NO:144:

(i) SEQUENCE CHARACTERISTICS:
        (A) LENGTH: 73 amino acids
        (B) TYPE: amino acid
        (D) TOPOLOGY: linear (i i) MOLECULE TYPE: protein (x i) SEQUENCE DESCRIPTION: SEQ ID NO:144:

| Val | Pro | Phe | Val | Asn | Arg | Thr | Thr | Leu | Phe | Thr | Ile | Arg | Gly | Pro | Leu |
| 1 | | | | 5 | | | | | 10 | | | | | 15 | |

| Gly | Asn | Gln | Gly | Arg | Gly | Asn | Pro | Val | Arg | Ser | Pro | Leu | Gly | Phe | Gly |
| | | | 20 | | | | | 25 | | | | | 30 | | |

| Ser | Tyr | Ala | Met | Thr | Arg | Ile | Arg | Asp | Thr | Leu | His | Leu | Val | Glu | Cys |
| | | 35 | | | | | 40 | | | | | 45 | | | |

| Pro | Thr | Pro | Ala | Ile | Glu | Pro | Pro | Thr | Gly | Thr | Ser | Gly | Phe | Phe | Pro |
| | 50 | | | | | 55 | | | | | 60 | | | | |

| Gly | Thr | Pro | Pro | Leu | Asn | Ser | Cys | Met |
| 65 | | | | | 70 | | | |

(2) INFORMATION FOR SEQ ID NO:145:

(i) SEQUENCE CHARACTERISTICS:
        (A) LENGTH: 264 base pairs
        (B) TYPE: nucleic acid
        (C) STRANDEDNESS: both
        (D) TOPOLOGY: linear (i i) MOLECULE TYPE: cDNA (i i i) HYPOTHETICAL: NO (i v) ANTI-SENSE: NO (v i) ORIGINAL SOURCE:
        (C) INDIVIDUAL ISOLATE: Antigen Clone Y12-10-3

( i x ) FEATURE:
    ( A ) NAME/KEY: CDS
    ( B ) LOCATION: 1..264

( x i ) SEQUENCE DESCRIPTION: SEQ ID NO:145:

| CCC | CTC | GAG | CGG | ATG | CGA | ACC | GGA | AGG | CAC | CTC | GTG | TTC | TGC | CAT | TCT | 48 |
| Pro | Leu | Glu | Arg | Met | Arg | Thr | Gly | Arg | His | Leu | Val | Phe | Cys | His | Ser | |
| 1 | | | | 5 | | | | | 10 | | | | | 15 | | |

| AAG | GCT | GAG | TGC | GAG | CGC | CTT | GCT | GGC | CAG | TTC | TCC | GCT | AGG | GGG | GTC | 96 |
| Lys | Ala | Glu | Cys | Glu | Arg | Leu | Ala | Gly | Gln | Phe | Ser | Ala | Arg | Gly | Val | |
| | | | 20 | | | | | 25 | | | | | 30 | | | |

| AAT | GCC | ATT | GCC | TAT | TAT | AGG | GGT | AAA | GAC | AGC | TCT | ATC | ATC | AAG | GAT | 144 |
| Asn | Ala | Ile | Ala | Tyr | Tyr | Arg | Gly | Lys | Asp | Ser | Ser | Ile | Ile | Lys | Asp | |
| | | 35 | | | | | 40 | | | | | 45 | | | | |

| GGG | GAC | CTG | GTG | GTC | TGT | GCT | ACA | GAC | GCG | CTT | TCC | ACT | GGG | TAC | ACT | 192 |
| Gly | Asp | Leu | Val | Val | Cys | Ala | Thr | Asp | Ala | Leu | Ser | Thr | Gly | Tyr | Thr | |
| 50 | | | | | 55 | | | | | 60 | | | | | | |

| GGA | AAT | TTC | GAC | TCC | GTC | ACC | GAC | TGT | GGA | TTA | GTG | GTG | GAG | GAG | GTC | 240 |
| Gly | Asn | Phe | Asp | Ser | Val | Thr | Asp | Cys | Gly | Leu | Val | Val | Glu | Glu | Val | |
| 65 | | | | | 70 | | | | | 75 | | | | | 80 | |

| GTT | GAG | GTG | ACC | CTT | GAT | CCC | ACC | | | | | | | | | 264 |
| Val | Glu | Val | Thr | Leu | Asp | Pro | Thr | | | | | | | | | |
| | | | | 85 | | | | | | | | | | | | |

( 2 ) INFORMATION FOR SEQ ID NO:146:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: protein ( x i ) SEQUENCE DESCRIPTION: SEQ ID NO:146:

| Pro | Leu | Glu | Arg | Met | Arg | Thr | Gly | Arg | His | Leu | Val | Phe | Cys | His | Ser |
| 1 | | | | 5 | | | | | 10 | | | | | 15 | |

| Lys | Ala | Glu | Cys | Glu | Arg | Leu | Ala | Gly | Gln | Phe | Ser | Ala | Arg | Gly | Val |
| | | | 20 | | | | | 25 | | | | | 30 | | |

| Asn | Ala | Ile | Ala | Tyr | Tyr | Arg | Gly | Lys | Asp | Ser | Ser | Ile | Ile | Lys | Asp |
| | | 35 | | | | | 40 | | | | | 45 | | | |

| Gly | Asp | Leu | Val | Val | Cys | Ala | Thr | Asp | Ala | Leu | Ser | Thr | Gly | Tyr | Thr |
| 50 | | | | | 55 | | | | | 60 | | | | | |

| Gly | Asn | Phe | Asp | Ser | Val | Thr | Asp | Cys | Gly | Leu | Val | Val | Glu | Glu | Val |
| 65 | | | | | 70 | | | | | 75 | | | | | 80 |

| Val | Glu | Val | Thr | Leu | Asp | Pro | Thr |
| | | | | 85 | | | |

( 2 ) INFORMATION FOR SEQ ID NO:147:

( i ) SEQUENCE CHARACTERISTICS:
        ( A ) LENGTH: 205 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone Y12-15-1

( i x ) FEATURE:

( A ) NAME/KEY: CDS
( B ) LOCATION: 1..205

( x i ) SEQUENCE DESCRIPTION: SEQ ID NO:147:

| GCT | AGA | TCT | GGC | AAC | ATG | GGG | CAC | AAG | GTC | TTA | ATC | TTG | AAC | CCC | TCA | 48 |
|---|---|---|---|---|---|---|---|---|---|---|---|---|---|---|---|---|
| Ala | Arg | Ser | Gly | Asn | Met | Gly | His | Lys | Val | Leu | Ile | Leu | Asn | Pro | Ser | |
| 1 | | | | 5 | | | | | 10 | | | | | 15 | | |

| GTG | GCC | ACT | GTG | CGG | GCC | ATG | GGC | CCG | TAC | ATG | GAG | CGG | CTG | GCG | GGT | 96 |
|---|---|---|---|---|---|---|---|---|---|---|---|---|---|---|---|---|
| Val | Ala | Thr | Val | Arg | Ala | Met | Gly | Pro | Tyr | Met | Glu | Arg | Leu | Ala | Gly | |
| | | | 20 | | | | | 25 | | | | | 30 | | | |

| AAA | CAT | CCA | AGT | ATA | TAC | TGT | GGG | CAT | GAT | ACA | ACT | GCT | TTC | ACA | AGG | 144 |
|---|---|---|---|---|---|---|---|---|---|---|---|---|---|---|---|---|
| Lys | His | Pro | Ser | Ile | Tyr | Cys | Gly | His | Asp | Thr | Thr | Ala | Phe | Thr | Arg | |
| | | 35 | | | | | 40 | | | | | 45 | | | | |

| ATC | ACT | GAC | TCC | CCC | CTG | ACG | TAT | TCA | ACC | TAT | GGG | AGG | TTT | TTG | GCC | 192 |
|---|---|---|---|---|---|---|---|---|---|---|---|---|---|---|---|---|
| Ile | Thr | Asp | Ser | Pro | Leu | Thr | Tyr | Ser | Thr | Tyr | Gly | Arg | Phe | Leu | Ala | |
| | 50 | | | | | 55 | | | | | 60 | | | | | |

| AAC | CCT | AGG | CAG | A | | | | | | | | | | | | 205 |
|---|---|---|---|---|---|---|---|---|---|---|---|---|---|---|---|---|
| Asn | Pro | Arg | Gln | | | | | | | | | | | | | |
| 65 | | | | | | | | | | | | | | | | |

( 2 ) INFORMATION FOR SEQ ID NO:148:

( i ) SEQUENCE CHARACTERISTICS:
( A ) LENGTH: 68 amino acids
( B ) TYPE: amino acid
( D ) TOPOLOGY: linear ( i i ) MOLECULE TYPE: protein ( x i ) SEQUENCE DESCRIPTION: SEQ ID NO:148:

| Ala | Arg | Ser | Gly | Asn | Met | Gly | His | Lys | Val | Leu | Ile | Leu | Asn | Pro | Ser |
|---|---|---|---|---|---|---|---|---|---|---|---|---|---|---|---|
| 1 | | | | 5 | | | | | 10 | | | | | 15 | |

| Val | Ala | Thr | Val | Arg | Ala | Met | Gly | Pro | Tyr | Met | Glu | Arg | Leu | Ala | Gly |
|---|---|---|---|---|---|---|---|---|---|---|---|---|---|---|---|
| | | | 20 | | | | | 25 | | | | | 30 | | |

| Lys | His | Pro | Ser | Ile | Tyr | Cys | Gly | His | Asp | Thr | Thr | Ala | Phe | Thr | Arg |
|---|---|---|---|---|---|---|---|---|---|---|---|---|---|---|---|
| | | 35 | | | | | 40 | | | | | 45 | | | |

| Ile | Thr | Asp | Ser | Pro | Leu | Thr | Tyr | Ser | Thr | Tyr | Gly | Arg | Phe | Leu | Ala |
|---|---|---|---|---|---|---|---|---|---|---|---|---|---|---|---|
| | 50 | | | | | 55 | | | | | 60 | | | | |

Asn Pro Arg Gln
65

( 2 ) INFORMATION FOR SEQ ID NO:149:

( i ) SEQUENCE CHARACTERISTICS:
( A ) LENGTH: 32 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GE4F ( x i ) SEQUENCE DESCRIPTION: SEQ ID NO:149:

GCCGCCATGG CTCTCCAAGC GATCGAGAAT GC     32

( 2 ) INFORMATION FOR SEQ ID NO:150:

( i ) SEQUENCE CHARACTERISTICS:
( A ) LENGTH: 31 base pairs
( B ) TYPE: nucleic acid (C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer GE4R (xi) SEQUENCE DESCRIPTION: SEQ ID NO:150:

GCGCGGATCC CAACCCCAAT GAGAAAAAGC G  31

(2) INFORMATION FOR SEQ ID NO:151:

(i) SEQUENCE CHARACTERISTICS:
(A) LENGTH: 23 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470EXP3F (xi) SEQUENCE DESCRIPTION: SEQ ID NO:151:

CCGCCATGGG ACGCGGACGC TCG  23

(2) INFORMATION FOR SEQ ID NO:152:

(i) SEQUENCE CHARACTERISTICS:
(A) LENGTH: 28 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer 470EXP3R (xi) SEQUENCE DESCRIPTION: SEQ ID NO:152:

CGCGGATCCT TACTGTCTTA TTGCTTCC  28

(2) INFORMATION FOR SEQ ID NO:153:

(i) SEQUENCE CHARACTERISTICS:
(A) LENGTH: 34 base pairs
(B) TYPE: nucleic acid
(C) STRANDEDNESS: both
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer FV94-2888F (xi) SEQUENCE DESCRIPTION: SEQ ID NO:153:

```
GCGGAATTCT TGGCTCGGGT GGTTGAGTGC TGTG                                     34
```

( 2 ) INFORMATION FOR SEQ ID NO:154:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer FV94- 3216R ( x i ) SEQUENCE DESCRIPTION: SEQ ID NO:154:

```
GCGAAGCTTC CGTCGGATGA CAACAGGCGC GG                                       32
```

( 2 ) INFORMATION FOR SEQ ID NO:155:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer FV94- 6521F ( x i ) SEQUENCE DESCRIPTION: SEQ ID NO:155:

```
GCGGAATTCA CCTCCGCCTA TAAGCTGCTG CGCCAG                                   36
```

( 2 ) INFORMATION FOR SEQ ID NO:156:

( i ) SEQUENCE CHARACTERISTICS:
        ( A ) LENGTH: 42 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer FV94- 7483R ( x i ) SEQUENCE DESCRIPTION: SEQ ID NO:156:

```
GCTGCGGCCG CCCTCCGTCC CACATTGTCT GGATTGGTAA CA                            42
```

( 2 ) INFORMATION FOR SEQ ID NO:157:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer T7F ( x i ) SEQUENCE DESCRIPTION: SEQ ID NO:157:

ATTAATACGA CTCACTATAG GG                                                          22

( 2 ) INFORMATION FOR SEQ ID NO:158:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer T7R ( x i ) SEQUENCE DESCRIPTION: SEQ ID NO:158:

CAAGGGGTTA TGCTAGTTAT TG                                                          22

( 2 ) INFORMATION FOR SEQ ID NO:159:

( i ) SEQUENCE CHARACTERISTICS:
        ( A ) LENGTH: 402 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone GE4-8

( i x ) FEATURE:
        ( A ) NAME/KEY: CDS
        ( B ) LOCATION: 1..402

( x i ) SEQUENCE DESCRIPTION: SEQ ID NO:159:

```
GCT CTC CAA GCG ATC GAG AAT GCT GCG AGG ATT CTT GAA CCG CAC ATT           48
Ala Leu Gln Ala Ile Glu Asn Ala Ala Arg Ile Leu Glu Pro His Ile
 1               5                  10                  15

GAT GTC ATC ATG GAG GAC TGC AGT ACA CCC TCT CTT TGT GGT AGT AGC           96
Asp Val Ile Met Glu Asp Cys Ser Thr Pro Ser Leu Cys Gly Ser Ser
             20                  25                  30

CGA GAG ATG CCT GTA TGG GGA GAA GAC ATC CCC CGT ACT CCA TCG CCA          144
Arg Glu Met Pro Val Trp Gly Glu Asp Ile Pro Arg Thr Pro Ser Pro
         35                  40                  45

GCA CTT ATC TCG GTT ACT GAG AGC AGC TCA GAT GAG AAG ACC CCG TCG          192
Ala Leu Ile Ser Val Thr Glu Ser Ser Ser Asp Glu Lys Thr Pro Ser
     50                  55                  60

GTG TCC TCC TCG CAG GAG GAT ACC CCG TCC TCT GAC TCA TTC GAG GTC          240
Val Ser Ser Ser Gln Glu Asp Thr Pro Ser Ser Asp Ser Phe Glu Val
 65                  70                  75                  80

ATC CAA GAG TCC GAG ACA GCC GAA GGG GAG GAA AGT GTC TTC AAC GTG          288
Ile Gln Glu Ser Glu Thr Ala Glu Gly Glu Glu Ser Val Phe Asn Val
                 85                  90                  95
```

```
GCT CTT TCC GTA TTA AAA GCC TTA TTT CCA CAG AGC GAC GCG ACC AGG        336
Ala Leu Ser Val Leu Lys Ala Leu Phe Pro Gln Ser Asp Ala Thr Arg
            100             105             110

AAG CTT ACC GTC AAG ATG TCG TGC TGC GTT GAA AAG AGC GTC ACG CGC        384
Lys Leu Thr Val Lys Met Ser Cys Cys Val Glu Lys Ser Val Thr Arg
            115             120             125

TTT TTC TCA TTG GGG TTG                                                402
Phe Phe Ser Leu Gly Leu
130
```

( 2 ) INFORMATION FOR SEQ ID NO:160:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:160:

```
Ala Leu Gln Ala Ile Glu Asn Ala Ala Arg Ile Leu Glu Pro His Ile
1               5                   10                  15

Asp Val Ile Met Glu Asp Cys Ser Thr Pro Ser Leu Cys Gly Ser Ser
                20                  25                  30

Arg Glu Met Pro Val Trp Gly Glu Asp Ile Pro Arg Thr Pro Ser Pro
            35                  40                  45

Ala Leu Ile Ser Val Thr Glu Ser Ser Asp Glu Lys Thr Pro Ser
    50                  55                  60

Val Ser Ser Ser Gln Glu Asp Thr Pro Ser Ser Asp Ser Phe Glu Val
65                  70                  75                  80

Ile Gln Glu Ser Glu Thr Ala Glu Gly Glu Glu Ser Val Phe Asn Val
                85                  90                  95

Ala Leu Ser Val Leu Lys Ala Leu Phe Pro Gln Ser Asp Ala Thr Arg
            100             105             110

Lys Leu Thr Val Lys Met Ser Cys Cys Val Glu Lys Ser Val Thr Arg
            115             120             125

Phe Phe Ser Leu Gly Leu
130
```

( 2 ) INFORMATION FOR SEQ ID NO:161:

( i ) SEQUENCE CHARACTERISTICS:
        ( A ) LENGTH: 1011 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone EXP3-7

( i x ) FEATURE:
        ( A ) NAME/KEY: CDS
        ( B ) LOCATION: 1..1011

( x i ) SEQUENCE DESCRIPTION: SEQ ID NO:161:

```
ATG GTC TAT GGC CCT GGG CAA AGT GTT ACC ATT GAC GGG GAG CGC TAC        48
Met Val Tyr Gly Pro Gly Gln Ser Val Thr Ile Asp Gly Glu Arg Tyr
1               5                   10                  15

ACC TTG CCT CAT CAA CTG AGG CTC AGG AAT GTG GCA CCC TCT GAG GTT        96
```

-continued

| | | | | Thr | Leu | Pro | His | Gln | Leu | Arg | Leu | Arg | Asn | Val | Ala | Pro | Ser | Glu | Val | |
| --- | --- | --- | --- | --- | --- | --- | --- | --- | --- | --- | --- | --- | --- | --- | --- | --- | --- | --- | --- | --- |
| | | | | | | 20 | | | | | 25 | | | | | 30 | | | | |
| TCA | TCC | GAG | GTG | TCC | ATT | GAC | ATT | GGG | ACG | GAG | ACT | GAA | GAC | TCA | GAA | | | | | 144 |
| Ser | Ser | Glu | Val | Ser | Ile | Asp | Ile | Gly | Thr | Glu | Thr | Glu | Asp | Ser | Glu | | | | | |
| | | 35 | | | | | 40 | | | | | 45 | | | | | | | | |
| CTG | ACT | GAG | GCC | GAT | CTG | CCG | CCG | GCG | GCT | GCT | GCT | CTC | CAA | GCG | ATC | | | | | 192 |
| Leu | Thr | Glu | Ala | Asp | Leu | Pro | Pro | Ala | Ala | Ala | Ala | Leu | Gln | Ala | Ile | | | | | |
| | 50 | | | | | 55 | | | | | 60 | | | | | | | | | |
| GAG | AAT | GCT | GCG | AGG | ATT | CTT | GAA | CCG | CAC | ATT | GAT | GTC | ATC | ATG | GAG | | | | | 240 |
| Glu | Asn | Ala | Ala | Arg | Ile | Leu | Glu | Pro | His | Ile | Asp | Val | Ile | Met | Glu | | | | | |
| 65 | | | | | 70 | | | | | 75 | | | | | 80 | | | | | |
| GAC | TGC | AGT | ACA | CCC | TCT | CTT | TGT | GGT | AGT | AGC | CGA | GAG | ATG | CCT | GTA | | | | | 288 |
| Asp | Cys | Ser | Thr | Pro | Ser | Leu | Cys | Gly | Ser | Ser | Arg | Glu | Met | Pro | Val | | | | | |
| | | | | 85 | | | | | 90 | | | | | 95 | | | | | | |
| TGG | GGA | GAA | GAC | ATC | CCC | CGT | ACT | CCA | TCG | CCA | GCA | CTT | ATC | TCG | GTT | | | | | 336 |
| Trp | Gly | Glu | Asp | Ile | Pro | Arg | Thr | Pro | Ser | Pro | Ala | Leu | Ile | Ser | Val | | | | | |
| | | | 100 | | | | | 105 | | | | | 110 | | | | | | | |
| ACT | GAG | AGC | AGC | TCA | GAT | GAG | AAG | ACC | CCG | TCG | GTG | TCC | TCC | TCG | CAG | | | | | 384 |
| Thr | Glu | Ser | Ser | Ser | Asp | Glu | Lys | Thr | Pro | Ser | Val | Ser | Ser | Ser | Gln | | | | | |
| | | 115 | | | | | 120 | | | | | 125 | | | | | | | | |
| GAG | GAT | ACC | CCG | TCC | TCT | GAC | TCA | TTC | GAG | GTC | ATC | CAA | GAG | TCC | GAG | | | | | 432 |
| Glu | Asp | Thr | Pro | Ser | Ser | Asp | Ser | Phe | Glu | Val | Ile | Gln | Glu | Ser | Glu | | | | | |
| | 130 | | | | | 135 | | | | | 140 | | | | | | | | | |
| ACA | GCC | GAA | GGG | GAG | GAA | AGT | GTC | TTC | AAC | GTG | GCT | CTT | TCC | GTA | TTA | | | | | 480 |
| Thr | Ala | Glu | Gly | Glu | Glu | Ser | Val | Phe | Asn | Val | Ala | Leu | Ser | Val | Leu | | | | | |
| 145 | | | | | 150 | | | | | 155 | | | | | 160 | | | | | |
| AAA | GCC | TTA | TTT | CCA | CAG | AGC | GAC | GCG | ACC | AGG | AAG | CTT | ACC | GTC | AAG | | | | | 528 |
| Lys | Ala | Leu | Phe | Pro | Gln | Ser | Asp | Ala | Thr | Arg | Lys | Leu | Thr | Val | Lys | | | | | |
| | | | | 165 | | | | | 170 | | | | | 175 | | | | | | |
| ATG | TCG | TGC | TGC | GTT | GAA | AAG | AGC | GTC | ACG | CGC | TTT | TTC | TCA | TTG | GGG | | | | | 576 |
| Met | Ser | Cys | Cys | Val | Glu | Lys | Ser | Val | Thr | Arg | Phe | Phe | Ser | Leu | Gly | | | | | |
| | | | 180 | | | | | 185 | | | | | 190 | | | | | | | |
| TTG | ACG | GTG | GCT | GAT | GTT | GCT | AGC | CTG | TGT | GAG | ATG | GAA | ATC | CAG | AAC | | | | | 624 |
| Leu | Thr | Val | Ala | Asp | Val | Ala | Ser | Leu | Cys | Glu | Met | Glu | Ile | Gln | Asn | | | | | |
| | | 195 | | | | | 200 | | | | | 205 | | | | | | | | |
| CAT | ACA | GCC | TAT | TGT | GAC | CAG | GTG | CGC | ACT | CCG | CTT | GAA | TTG | CAG | GTT | | | | | 672 |
| His | Thr | Ala | Tyr | Cys | Asp | Gln | Val | Arg | Thr | Pro | Leu | Glu | Leu | Gln | Val | | | | | |
| | 210 | | | | | 215 | | | | | 220 | | | | | | | | | |
| GGG | TGC | TTG | GTG | GGC | AAT | GAA | CTT | ACC | TTT | GAA | TGT | GAC | AAG | TGT | GAG | | | | | 720 |
| Gly | Cys | Leu | Val | Gly | Asn | Glu | Leu | Thr | Phe | Glu | Cys | Asp | Lys | Cys | Glu | | | | | |
| 225 | | | | | 230 | | | | | 235 | | | | | 240 | | | | | |
| GCT | AGG | CAA | GAA | ACC | TTG | GCC | TCC | TTC | TCT | TAC | ATT | TGG | TCT | GGA | GTG | | | | | 768 |
| Ala | Arg | Gln | Glu | Thr | Leu | Ala | Ser | Phe | Ser | Tyr | Ile | Trp | Ser | Gly | Val | | | | | |
| | | | | 245 | | | | | 250 | | | | | 255 | | | | | | |
| CCG | CTG | ACT | AGG | GCC | ACG | CCG | GCC | AAG | CCT | CCC | GTG | GTG | AGG | CCG | GTT | | | | | 816 |
| Pro | Leu | Thr | Arg | Ala | Thr | Pro | Ala | Lys | Pro | Pro | Val | Val | Arg | Pro | Val | | | | | |
| | | 260 | | | | | 265 | | | | | 270 | | | | | | | | |
| GGC | TCT | TTG | TTA | GTG | GCC | GAC | ACT | ACT | AAG | GTG | TAT | GTT | ACC | AAT | CCA | | | | | 864 |
| Gly | Ser | Leu | Leu | Val | Ala | Asp | Thr | Thr | Lys | Val | Tyr | Val | Thr | Asn | Pro | | | | | |
| | | 275 | | | | | 280 | | | | | 285 | | | | | | | | |
| GAC | AAT | GTG | GGA | CGG | AGG | GTG | GAC | AAG | GTG | ACC | TTC | TGG | CGT | GCT | CCT | | | | | 912 |
| Asp | Asn | Val | Gly | Arg | Arg | Val | Asp | Lys | Val | Thr | Phe | Trp | Arg | Ala | Pro | | | | | |
| | 290 | | | | | 295 | | | | | 300 | | | | | | | | | |
| AGG | GTT | CAT | GAT | AAG | TAC | CTC | GTG | GAC | TCT | ATT | GAG | CGC | GCT | AAG | AGG | | | | | 960 |
| Arg | Val | His | Asp | Lys | Tyr | Leu | Val | Asp | Ser | Ile | Glu | Arg | Ala | Lys | Arg | | | | | |
| 305 | | | | | 310 | | | | | 315 | | | | | 320 | | | | | |
| GCC | GCT | CAA | GCC | TGC | CTA | AGC | ATG | GGT | TAC | ACT | TAT | GAG | GAA | GCA | ATA | | | | | 1008 |
| Ala | Ala | Gln | Ala | Cys | Leu | Ser | Met | Gly | Tyr | Thr | Tyr | Glu | Glu | Ala | Ile | | | | | |
| | | | | 325 | | | | | 330 | | | | | 335 | | | | | | |
| AGG | | | | | | | | | | | | | | | | | | | | 1011 |

Arg (2) INFORMATION FOR SEQ ID NO:162:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:162:

```
Met Val Tyr Gly Pro Gly Gln Ser Val Thr Ile Asp Gly Glu Arg Tyr
 1               5                  10                  15
Thr Leu Pro His Gln Leu Arg Leu Arg Asn Val Ala Pro Ser Glu Val
             20                  25                  30
Ser Ser Glu Val Ser Ile Asp Ile Gly Thr Glu Thr Glu Asp Ser Glu
         35                  40                  45
Leu Thr Glu Ala Asp Leu Pro Ala Ala Ala Ala Leu Gln Ala Ile
     50                  55                  60
Glu Asn Ala Ala Arg Ile Leu Glu Pro His Ile Asp Val Ile Met Glu
 65                  70                  75                  80
Asp Cys Ser Thr Pro Ser Leu Cys Gly Ser Ser Arg Glu Met Pro Val
                 85                  90                  95
Trp Gly Glu Asp Ile Pro Arg Thr Pro Ser Pro Ala Leu Ile Ser Val
            100                 105                 110
Thr Glu Ser Ser Ser Asp Glu Lys Thr Pro Ser Val Ser Ser Ser Gln
        115                 120                 125
Glu Asp Thr Pro Ser Ser Asp Ser Phe Glu Val Ile Gln Glu Ser Glu
    130                 135                 140
Thr Ala Glu Gly Glu Glu Ser Val Phe Asn Val Ala Leu Ser Val Leu
145                 150                 155                 160
Lys Ala Leu Phe Pro Gln Ser Asp Ala Thr Arg Lys Leu Thr Val Lys
                165                 170                 175
Met Ser Cys Cys Val Glu Lys Ser Val Thr Arg Phe Phe Ser Leu Gly
            180                 185                 190
Leu Thr Val Ala Asp Val Ala Ser Leu Cys Glu Met Glu Ile Gln Asn
        195                 200                 205
His Thr Ala Tyr Cys Asp Gln Val Arg Thr Pro Leu Glu Leu Gln Val
    210                 215                 220
Gly Cys Leu Val Gly Asn Glu Leu Thr Phe Glu Cys Asp Lys Cys Glu
225                 230                 235                 240
Ala Arg Gln Glu Thr Leu Ala Ser Phe Ser Tyr Ile Trp Ser Gly Val
                245                 250                 255
Pro Leu Thr Arg Ala Thr Pro Ala Lys Pro Pro Val Val Arg Pro Val
            260                 265                 270
Gly Ser Leu Leu Val Ala Asp Thr Thr Lys Val Tyr Val Thr Asn Pro
        275                 280                 285
Asp Asn Val Gly Arg Arg Val Asp Lys Val Thr Phe Trp Arg Ala Pro
    290                 295                 300
Arg Val His Asp Lys Tyr Leu Val Asp Ser Ile Glu Arg Ala Lys Arg
305                 310                 315                 320
Ala Ala Gln Ala Cys Leu Ser Met Gly Tyr Thr Tyr Glu Glu Ala Ile
                325                 330                 335
Arg
```

( 2 ) INFORMATION FOR SEQ ID NO:163:

( i ) SEQUENCE CHARACTERISTICS:
        ( A ) LENGTH: 351 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone GENS2b-1

( i x ) FEATURE:
        ( A ) NAME/KEY: CDS
        ( B ) LOCATION: 1..351

( x i ) SEQUENCE DESCRIPTION: SEQ ID NO:163:

```
TTG  GCT  CGG  GTG  GTT  GAG  TGC  TGT  GTG  ATG  GCG  GGT  GAG  AAG  GCC  ACA      48
Leu  Ala  Arg  Val  Val  Glu  Cys  Cys  Val  Met  Ala  Gly  Glu  Lys  Ala  Thr
 1                  5                       10                      15

ACC  GTC  CGG  CTG  GTC  TCC  AAG  ATG  TGT  GCG  AGA  GGA  GCT  TAT  TTG  TTC      96
Thr  Val  Arg  Leu  Val  Ser  Lys  Met  Cys  Ala  Arg  Gly  Ala  Tyr  Leu  Phe
             20                       25                      30

GAT  CAT  ATG  GGC  TCT  TTT  TCG  CGT  GCT  GTC  AAG  GAG  CGC  CTG  TTG  GAA     144
Asp  His  Met  Gly  Ser  Phe  Ser  Arg  Ala  Val  Lys  Glu  Arg  Leu  Leu  Glu
             35                       40                      45

TGG  GAC  GCA  GCT  CTT  GAA  CCT  CTG  TCA  TTC  ACT  AGG  ACG  GAC  TGT  CGC     192
Trp  Asp  Ala  Ala  Leu  Glu  Pro  Leu  Ser  Phe  Thr  Arg  Thr  Asp  Cys  Arg
             50                       55                      60

ATC  ATA  CGG  GAT  GCC  GCG  AGG  ACT  TTG  TCC  TGC  GGG  CAG  TGC  GTC  ATG     240
Ile  Ile  Arg  Asp  Ala  Ala  Arg  Thr  Leu  Ser  Cys  Gly  Gln  Cys  Val  Met
 65                      70                      75                      80

GGT  TTA  CCC  GTG  GTT  GCG  CGC  CGT  GGT  GAT  GAG  GTT  CTC  ATC  GGC  GTC     288
Gly  Leu  Pro  Val  Val  Ala  Arg  Arg  Gly  Asp  Glu  Val  Leu  Ile  Gly  Val
                  85                      90                      95

TTC  CAG  GAT  GTG  AAT  CAT  TTG  CCT  CCC  GGG  TTT  GTT  CCG  ACC  GCG  CCT     336
Phe  Gln  Asp  Val  Asn  His  Leu  Pro  Pro  Gly  Phe  Val  Pro  Thr  Ala  Pro
             100                      105                     110

GTT  GTC  ATC  CGA  CGG                                                            351
Val  Val  Ile  Arg  Arg
             115
```

( 2 ) INFORMATION FOR SEQ ID NO:164:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: protein ( x i ) SEQUENCE DESCRIPTION: SEQ ID NO:164:

```
Leu  Ala  Arg  Val  Val  Glu  Cys  Cys  Val  Met  Ala  Gly  Glu  Lys  Ala  Thr
 1                  5                       10                      15

Thr  Val  Arg  Leu  Val  Ser  Lys  Met  Cys  Ala  Arg  Gly  Ala  Tyr  Leu  Phe
             20                       25                      30

Asp  His  Met  Gly  Ser  Phe  Ser  Arg  Ala  Val  Lys  Glu  Arg  Leu  Leu  Glu
             35                       40                      45

Trp  Asp  Ala  Ala  Leu  Glu  Pro  Leu  Ser  Phe  Thr  Arg  Thr  Asp  Cys  Arg
             50                       55                      60

Ile  Ile  Arg  Asp  Ala  Ala  Arg  Thr  Leu  Ser  Cys  Gly  Gln  Cys  Val  Met
```

|  |  |  |  |  |  |  |  |  |  |  |  |  |  |  |  |  |
|---|---|---|---|---|---|---|---|---|---|---|---|---|---|---|---|---|
| 65 |  |  |  |  | 70 |  |  |  |  | 75 |  |  |  |  | 80 |  |
| Gly | Leu | Pro | Val | Val | Ala | Arg | Arg | Gly | Asp | Glu | Val | Leu | Ile | Gly | Val |  |
|  |  |  |  | 85 |  |  |  |  | 90 |  |  |  |  | 95 |  |  |
| Phe | Gln | Asp | Val | Asn | His | Leu | Pro | Pro | Gly | Phe | Val | Pro | Thr | Ala | Pro |  |
|  |  |  | 100 |  |  |  |  | 105 |  |  |  |  | 110 |  |  |  |
| Val | Val | Ile | Arg | Arg |  |  |  |  |  |  |  |  |  |  |  |  |
|  |  |  | 115 |  |  |  |  |  |  |  |  |  |  |  |  |  |

( 2 ) INFORMATION FOR SEQ ID NO:165:

( i ) SEQUENCE CHARACTERISTICS:
        ( A ) LENGTH: 993 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Antigen Clone GENS5a-3

( i x ) FEATURE:
        ( A ) NAME/KEY: CDS
        ( B ) LOCATION: 1..993

( x i ) SEQUENCE DESCRIPTION: SEQ ID NO:165:

| ACC | TCC | GCC | TAT | AAG | CTG | CTG | CGC | CAG | CAA | ATC | CTA | TCG | GCT | GCT | GTA | 48 |
|---|---|---|---|---|---|---|---|---|---|---|---|---|---|---|---|---|
| Thr | Ser | Ala | Tyr | Lys | Leu | Leu | Arg | Gln | Gln | Ile | Leu | Ser | Ala | Ala | Val |  |
| 1 |  |  |  | 5 |  |  |  |  | 10 |  |  |  |  | 15 |  |  |
| GCT | GAG | CCC | TAC | TAC | GTC | GAC | GGC | ATT | CCG | GTC | TCA | TGG | GAC | GCG | GAC | 96 |
| Ala | Glu | Pro | Tyr | Tyr | Val | Asp | Gly | Ile | Pro | Val | Ser | Trp | Asp | Ala | Asp |  |
|  |  | 20 |  |  |  |  | 25 |  |  |  |  | 30 |  |  |  |  |
| GCT | CGT | GCG | CCC | GCC | ATG | GTC | TAT | GGC | CCT | GGG | CAA | AGT | GTT | ACC | ATT | 144 |
| Ala | Arg | Ala | Pro | Ala | Met | Val | Tyr | Gly | Pro | Gly | Gln | Ser | Val | Thr | Ile |  |
|  | 35 |  |  |  |  | 40 |  |  |  |  | 45 |  |  |  |  |  |
| GAC | GGG | GAG | CGC | TAC | ACC | TTG | CCT | CAT | CAA | CTG | AGG | CTC | AGG | AAT | GTG | 192 |
| Asp | Gly | Glu | Arg | Tyr | Thr | Leu | Pro | His | Gln | Leu | Arg | Leu | Arg | Asn | Val |  |
| 50 |  |  |  |  | 55 |  |  |  |  | 60 |  |  |  |  |  |  |
| GCA | CCC | TCT | GAG | GTT | TCA | TCC | GAG | GTG | TCC | ATT | GAC | ATT | GGG | ACG | GAG | 240 |
| Ala | Pro | Ser | Glu | Val | Ser | Ser | Glu | Val | Ser | Ile | Asp | Ile | Gly | Thr | Glu |  |
| 65 |  |  |  |  | 70 |  |  |  |  | 75 |  |  |  |  | 80 |  |
| ACT | GAA | GAC | TCA | GAA | CTG | ACT | GAG | GCC | GAT | CTG | CCG | CCG | GCG | GCT | GCT | 288 |
| Thr | Glu | Asp | Ser | Glu | Leu | Thr | Glu | Ala | Asp | Leu | Pro | Pro | Ala | Ala | Ala |  |
|  |  |  |  | 85 |  |  |  |  | 90 |  |  |  |  | 95 |  |  |
| GCT | CTC | CAA | GCG | ATC | GAG | AAT | GCT | GCG | AGG | ATT | CTT | GAA | CCG | CAC | ATT | 336 |
| Ala | Leu | Gln | Ala | Ile | Glu | Asn | Ala | Ala | Arg | Ile | Leu | Glu | Pro | His | Ile |  |
|  |  |  | 100 |  |  |  |  | 105 |  |  |  |  | 110 |  |  |  |
| GAT | GTC | ATC | ATG | GAG | GAC | TGC | AGT | ACA | CCC | TCT | CTT | TGT | GGT | AGT | AGC | 384 |
| Asp | Val | Ile | Met | Glu | Asp | Cys | Ser | Thr | Pro | Ser | Leu | Cys | Gly | Ser | Ser |  |
|  |  | 115 |  |  |  |  | 120 |  |  |  |  | 125 |  |  |  |  |
| CGA | GAG | ATG | CCT | GTA | TGG | GGA | GAA | GAC | ATC | CCC | CGT | ACT | CCA | TCG | CCA | 432 |
| Arg | Glu | Met | Pro | Val | Trp | Gly | Glu | Asp | Ile | Pro | Arg | Thr | Pro | Ser | Pro |  |
| 130 |  |  |  |  | 135 |  |  |  |  | 140 |  |  |  |  |  |  |
| GCA | CTT | ATC | TCG | GTT | ACT | GAG | AGC | AGC | TCA | GAT | GAG | AAG | ACC | CCG | TCG | 480 |
| Ala | Leu | Ile | Ser | Val | Thr | Glu | Ser | Ser | Ser | Asp | Glu | Lys | Thr | Pro | Ser |  |
| 145 |  |  |  |  | 150 |  |  |  |  | 155 |  |  |  |  | 160 |  |
| GTG | TCC | TCC | TCG | CAG | GAG | GAT | ACC | CCG | TCC | TCT | GAC | TCA | TTC | GAG | GTC | 528 |
| Val | Ser | Ser | Ser | Gln | Glu | Asp | Thr | Pro | Ser | Ser | Asp | Ser | Phe | Glu | Val |  |
|  |  |  |  | 165 |  |  |  |  | 170 |  |  |  |  | 175 |  |  |
| ATC | CAA | GAG | TCC | GAG | ACA | GCC | GAA | GGG | GAG | GAA | AGT | GTC | TTC | AAC | GTG | 576 |

| | | | | | | | | | | | | | | | |
|---|---|---|---|---|---|---|---|---|---|---|---|---|---|---|---|
| Ile | Gln | Glu | Ser | Glu | Thr | Ala | Glu | Gly | Glu | Glu | Ser | Val | Phe | Asn | Val |
| | | | 180 | | | | 185 | | | | | 190 | | | |

| GCT | CTT | TCC | GTA | TTA | AAA | GCC | TTA | TTT | CCA | CAG | AGC | GAC | GCG | ACC | AGG | 624 |
|---|---|---|---|---|---|---|---|---|---|---|---|---|---|---|---|---|
| Ala | Leu | Ser | Val | Leu | Lys | Ala | Leu | Phe | Pro | Gln | Ser | Asp | Ala | Thr | Arg | |
| | | 195 | | | | 200 | | | | | 205 | | | | | |

| AAG | CTT | ACC | GTC | AAG | ATG | TCG | TGC | TGC | GTT | GAA | AAG | AGC | GTC | ACG | CGC | 672 |
|---|---|---|---|---|---|---|---|---|---|---|---|---|---|---|---|---|
| Lys | Leu | Thr | Val | Lys | Met | Ser | Cys | Cys | Val | Glu | Lys | Ser | Val | Thr | Arg | |
| | 210 | | | | | 215 | | | | | 220 | | | | | |

| TTT | TTC | TCA | TTG | GGG | TTG | ACG | GTG | GCT | GAT | GTT | GCT | AGC | CTG | TGT | GAG | 720 |
|---|---|---|---|---|---|---|---|---|---|---|---|---|---|---|---|---|
| Phe | Phe | Ser | Leu | Gly | Leu | Thr | Val | Ala | Asp | Val | Ala | Ser | Leu | Cys | Glu | |
| 225 | | | | | 230 | | | | | 235 | | | | | 240 | |

| ATG | GAA | ATC | CAG | AAC | CAT | ACA | GCC | TAT | TGT | GAC | CAG | GTG | CGC | ACT | CCG | 768 |
|---|---|---|---|---|---|---|---|---|---|---|---|---|---|---|---|---|
| Met | Glu | Ile | Gln | Asn | His | Thr | Ala | Tyr | Cys | Asp | Gln | Val | Arg | Thr | Pro | |
| | | | | 245 | | | | | 250 | | | | | 255 | | |

| CTT | GAA | TTG | CAG | GTT | GGG | TGC | TTG | GTG | GGC | AAT | GAA | CTT | ACC | TTT | GAA | 816 |
|---|---|---|---|---|---|---|---|---|---|---|---|---|---|---|---|---|
| Leu | Glu | Leu | Gln | Val | Gly | Cys | Leu | Val | Gly | Asn | Glu | Leu | Thr | Phe | Glu | |
| | | | 260 | | | | | 265 | | | | | 270 | | | |

| TGT | GAC | AAG | TGT | GAG | GCT | AGG | CAA | GAA | ACC | TTG | GCC | TCC | TTC | TCT | TAC | 864 |
|---|---|---|---|---|---|---|---|---|---|---|---|---|---|---|---|---|
| Cys | Asp | Lys | Cys | Glu | Ala | Arg | Gln | Glu | Thr | Leu | Ala | Ser | Phe | Ser | Tyr | |
| | | 275 | | | | | 280 | | | | | 285 | | | | |

| ATT | TGG | TCT | GGA | GTG | CCG | CTG | ACT | AGG | GCC | ACG | CCG | GCC | AAG | CCT | CCC | 912 |
|---|---|---|---|---|---|---|---|---|---|---|---|---|---|---|---|---|
| Ile | Trp | Ser | Gly | Val | Pro | Leu | Thr | Arg | Ala | Thr | Pro | Ala | Lys | Pro | Pro | |
| | 290 | | | | | 295 | | | | | 300 | | | | | |

| GTG | GTG | AGG | CCG | GTT | GGC | TCT | TTG | TTA | GTG | GCC | GAC | ACT | ACT | AAG | GTG | 960 |
|---|---|---|---|---|---|---|---|---|---|---|---|---|---|---|---|---|
| Val | Val | Arg | Pro | Val | Gly | Ser | Leu | Leu | Val | Ala | Asp | Thr | Thr | Lys | Val | |
| 305 | | | | | 310 | | | | | 315 | | | | | 320 | |

| TAT | GTT | ACC | AAT | CCA | GAC | AAT | GTG | GGA | CGG | AGG | | | | | | 993 |
|---|---|---|---|---|---|---|---|---|---|---|---|---|---|---|---|---|
| Tyr | Val | Thr | Asn | Pro | Asp | Asn | Val | Gly | Arg | Arg | | | | | | |
| | | | | 325 | | | | | 330 | | | | | | | |

( 2 ) INFORMATION FOR SEQ ID NO:166:

( i ) SEQUENCE CHARACTERISTICS:
      ( A ) LENGTH: 331 amino acids
      ( B ) TYPE: amino acid
      ( D ) TOPOLOGY: linear ( i i ) MOLECULE TYPE: protein ( x i ) SEQUENCE DESCRIPTION: SEQ ID NO:166:

| Thr | Ser | Ala | Tyr | Lys | Leu | Leu | Arg | Gln | Gln | Ile | Leu | Ser | Ala | Ala | Val |
|---|---|---|---|---|---|---|---|---|---|---|---|---|---|---|---|
| 1 | | | | 5 | | | | | 10 | | | | | 15 | |

| Ala | Glu | Pro | Tyr | Tyr | Val | Asp | Gly | Ile | Pro | Val | Ser | Trp | Asp | Ala | Asp |
|---|---|---|---|---|---|---|---|---|---|---|---|---|---|---|---|
| | | | | 20 | | | | | 25 | | | | | 30 | |

| Ala | Arg | Ala | Pro | Ala | Met | Val | Tyr | Gly | Pro | Gly | Gln | Ser | Val | Thr | Ile |
|---|---|---|---|---|---|---|---|---|---|---|---|---|---|---|---|
| | | | 35 | | | | | 40 | | | | | 45 | | |

| Asp | Gly | Glu | Arg | Tyr | Thr | Leu | Pro | His | Gln | Leu | Arg | Leu | Arg | Asn | Val |
|---|---|---|---|---|---|---|---|---|---|---|---|---|---|---|---|
| | 50 | | | | | 55 | | | | | 60 | | | | |

| Ala | Pro | Ser | Glu | Val | Ser | Ser | Glu | Val | Ser | Ile | Asp | Ile | Gly | Thr | Glu |
|---|---|---|---|---|---|---|---|---|---|---|---|---|---|---|---|
| 65 | | | | | 70 | | | | | 75 | | | | | 80 |

| Thr | Glu | Asp | Ser | Glu | Leu | Thr | Glu | Ala | Asp | Leu | Pro | Pro | Ala | Ala | Ala |
|---|---|---|---|---|---|---|---|---|---|---|---|---|---|---|---|
| | | | | 85 | | | | | 90 | | | | | 95 | |

| Ala | Leu | Gln | Ala | Ile | Glu | Asn | Ala | Ala | Arg | Ile | Leu | Glu | Pro | His | Ile |
|---|---|---|---|---|---|---|---|---|---|---|---|---|---|---|---|
| | | | | 100 | | | | | 105 | | | | | 110 | |

| Asp | Val | Ile | Met | Glu | Asp | Cys | Ser | Thr | Pro | Ser | Leu | Cys | Gly | Ser | Ser |
|---|---|---|---|---|---|---|---|---|---|---|---|---|---|---|---|
| | | | 115 | | | | | 120 | | | | | 125 | | |

| Arg | Glu | Met | Pro | Val | Trp | Gly | Glu | Asp | Ile | Pro | Arg | Thr | Pro | Ser | Pro |
|---|---|---|---|---|---|---|---|---|---|---|---|---|---|---|---|
| | | | 130 | | | | | 135 | | | | | 140 | | |

| Ala | Leu | Ile | Ser | Val | Thr | Glu | Ser | Ser | Ser | Asp | Glu | Lys | Thr | Pro | Ser |
|---|---|---|---|---|---|---|---|---|---|---|---|---|---|---|---|
| 145 | | | | | 150 | | | | | 155 | | | | | 160 |

| | | | | | | | | | | | | | |
|---|---|---|---|---|---|---|---|---|---|---|---|---|---|
|Val|Ser|Ser|Ser|Gln 165|Glu|Asp|Thr|Pro|Ser 170|Asp|Ser|Phe|Glu Val 175|
|Ile|Gln|Glu|Ser 180|Glu|Thr|Ala|Glu|Gly 185|Glu|Glu|Ser|Val|Phe Asn Val 190|
|Ala|Leu|Ser 195|Val|Leu|Lys|Ala|Leu 200|Phe|Pro|Gln|Ser|Ala 205|Thr Arg|
|Lys|Leu 210|Thr|Val|Lys|Met|Ser 215|Cys|Cys|Val|Glu|Lys 220|Ser|Val Thr Arg|
|Phe 225|Phe|Ser|Leu|Gly|Leu 230|Thr|Val|Ala|Asp|Val 235|Ala|Ser|Leu Cys Glu 240|
|Met|Glu|Ile|Gln|Asn 245|His|Thr|Ala|Tyr|Cys 250|Asp|Gln|Val|Arg Thr Pro 255|
|Leu|Glu|Leu|Gln 260|Val|Gly|Cys|Leu|Val 265|Gly|Asn|Glu|Leu|Thr Phe Glu 270|
|Cys|Asp|Lys 275|Cys|Glu|Ala|Arg|Gln 280|Glu|Thr|Leu|Ala|Ser 285|Phe Ser Tyr|
|Ile|Trp 290|Ser|Gly|Val|Pro|Leu 295|Thr|Arg|Ala|Thr|Pro 300|Ala|Lys Pro Pro|
|Val 305|Val|Arg|Pro|Val|Gly 310|Ser|Leu|Leu|Val|Ala 315|Asp|Thr|Thr Lys Val 320|
|Tyr|Val|Thr|Asn|Pro 325|Asp|Asn|Val|Gly|Arg 330|Arg| | | |

(2) INFORMATION FOR SEQ ID NO:167:

(i) SEQUENCE CHARACTERISTICS:
    (A) LENGTH: 536 base pairs
    (B) TYPE: nucleic acid
    (C) STRANDEDNESS: both
    (D) TOPOLOGY: linear (ii) MOLECULE TYPE: cDNA (iii) HYPOTHETICAL: NO (iv) ANTI-SENSE: NO (vi) ORIGINAL SOURCE:
    (C) INDIVIDUAL ISOLATE: Consensus Sequence 3'-end (xi) SEQUENCE DESCRIPTION: SEQ ID NO:167:

```
CTGAGCGACC TCAAGCTCCC TGGCTTAGCA GTCCACCGAA AGAAGGCCGG GGCGTTGCGA      60
ACACGCATGC TCCGCTCGCG CGGTTGGGCT GAGTTGGCTA GGGGCTTGTT GTGGCATCCA     120
GGCCTACGGC TTCCTCCCCC TGAGATTGCT GGTATCCCGG GGGGTTTCCC TCTCTCCCCC     180
CCCTATATGG GGGTGGTACA TCAATTGGAT TTCACAAGCC AGAGGAGTCG CTGGCGGTGG     240
TTGGGGTTCT TAGCCCTGCT CATCGTAGCC CTCTTCGGGT GAACTAAATT CATCTGTTGC     300
GGCAAGGTCT GGTGACTGAT CATCACCGGA GGAGGTTCCC GCCCTCCCCG CCCCAGGGGT     360
CTCCCCGCTG GGTAAAAAGG GCCCGGCCTT GGGAGGCATG GTGGTTACTA ACCCCCTGGC     420
AGGGTCAAAG CCTGATGGTG CTAATGCACT GCCACTTCGG TGGCGGGTCG CTACCTTATA     480
GCGTAATCCG TGACTACGGG CTGCTCGCAG AGCCCTCCCC GGATGGGGCA CAGTGC        536
```

(2) INFORMATION FOR SEQ ID NO:168:

(i) SEQUENCE CHARACTERISTICS:
    (A) LENGTH: 594 base pairs
    (B) TYPE: nucleic acid
    (C) STRANDEDNESS: both
    (D) TOPOLOGY: linear (ii) MOLECULE TYPE: cDNA (iii) HYPOTHETICAL: NO (iv) ANTI-SENSE: NO (vi) ORIGINAL SOURCE:
 (C) INDIVIDUAL ISOLATE: Individual Clone MP3-3

(xi) SEQUENCE DESCRIPTION: SEQ ID NO:168:

| | | | | | | |
|---|---|---|---|---|---|---|
| CTGAGCGACC | TCAAGCTCCC | TGGCTTAGCA | GTCCACCGAA | AGAAGGCCGG | GGCGTTGCGA | 60 |
| ACACGCATGC | TCCGCTCGCG | CGGTTGGGCT | GAGTTGGCTA | GGGGCTTGTT | GTGGCATCCA | 120 |
| GGCCTACGGC | TTCCTCCCCC | TGAGATTGCT | GGTATCCCGG | GGGGTTTCCC | TCTCTCCCCC | 180 |
| CCCTATATGG | GGGTGGTACA | CCAATTGGAT | TTCACAAGCC | AGAGGAGTCG | CTGGCGGTGG | 240 |
| TTGGGGTTCT | TAGCCCTGCT | CATCGTAGCC | CTCTTCGGGT | GAACTAAATT | CATCTGTTGC | 300 |
| GGCAAGGTCT | GGTGACTGAT | CATCACCGGA | GGAGGTTCCC | GCCCTCCCCG | CCCCAGGGGT | 360 |
| CTCCCCGCTG | GGTAAAAAGG | GCCCGGCCTT | GGGAGGCATG | GTGGTTACTA | ACCCCCTGGC | 420 |
| AGGGTCAAAG | CCTGATGGTG | CTAATGCACT | GCCACTTCGG | TGGCGGGTCG | CTACCTTATA | 480 |
| GCGTAATCCG | TGACTACGGG | CTGCTCGCAG | AGCCCTCCCC | GGATGGGGCA | CAGTGCACTG | 540 |
| TGATCTGAAG | GGGTGCACCC | CGGGAAGAGC | TCGGCCCGAA | GGCCGGCTTC | TACT | 594 |

(2) INFORMATION FOR SEQ ID NO:169:

(i) SEQUENCE CHARACTERISTICS:
  (A) LENGTH: 594 base pairs
  (B) TYPE: nucleic acid
  (C) STRANDEDNESS: both
  (D) TOPOLOGY: linear (ii) MOLECULE TYPE: cDNA (iii) HYPOTHETICAL: NO (iv) ANTI-SENSE: NO (vi) ORIGINAL SOURCE:
 (C) INDIVIDUAL ISOLATE: Individual Clone MP3-7

(xi) SEQUENCE DESCRIPTION: SEQ ID NO:169:

| | | | | | | |
|---|---|---|---|---|---|---|
| CTGAGCGACC | TCAAGCTCCC | TGGCTTAGCA | GTCCACCGAA | AGAAGGCCGG | GGCGTTGCGA | 60 |
| ACACGCATGC | TCCGCTCGCG | CGGTTGGGCT | GAGTTGGCTA | GGGGCTTGTT | GTGGCATCCA | 120 |
| GGCCTACGGC | TTCCTCCCCC | TGAGATTGCT | GGTGTCCCGG | GGGGTTTCCC | TCTCTCCCCC | 180 |
| CCCTATATGG | GGGTGGTACA | CCAATTGGAT | TTCACAAGCC | AGAGGAGTCG | CTGGCGGTGG | 240 |
| TTGGGGTTCT | TAGCCCTGCT | CATCGTAGCC | CTCTTCGGGT | GAACTAAATT | CATCTGTTGC | 300 |
| GGCAAGGTCT | GGTGACTGAT | CATCACCGGA | GGAGGTTCCC | GCCCTCCCCG | CCCCAGGGGT | 360 |
| CTCCCCGCTG | GGTAAAAAGG | GCCCGGCCTT | GGGAGGCATG | GTGGTTACTA | ACCCCCTGGC | 420 |
| AGGGTCAAAG | CCTGATGGTG | CTAATGCACT | GCCACTTCGG | TGGCGGGTCG | CTACCTTATA | 480 |
| GCGTAATCCG | TGACTACGGG | CTGCTCGCAG | AGCCCTCCCC | GGATGGGGCA | CAGTGCACTG | 540 |
| TGATCTGAAG | GGGTGCACCC | CGGTAAGAGC | TCGGCCCGAA | GGCCGGGTTC | TACT | 594 |

(2) INFORMATION FOR SEQ ID NO:170:

(i) SEQUENCE CHARACTERISTICS:
  (A) LENGTH: 39 base pairs
  (B) TYPE: nucleic acid
  (C) STRANDEDNESS: both
  (D) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer GV5446IRT ( x i ) SEQUENCE DESCRIPTION: SEQ ID NO:170:

```
CGGTCCCTCG AACTCCAGCG AGTCTTTTTT TTTTTTTT                                    39
```

( 2 ) INFORMATION FOR SEQ ID NO:171:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GV59- 5446F ( x i ) SEQUENCE DESCRIPTION: SEQ ID NO:171:

```
CTGAGCGACC TCAAGCTCCC TGGC                                                   24
```

( 2 ) INFORMATION FOR SEQ ID NO:172:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GV- 5446IR ( x i ) SEQUENCE DESCRIPTION: SEQ ID NO:172:

```
CGGTCCCTCG AACTCCAGCG AGTC                                                   24
```

( 2 ) INFORMATION FOR SEQ ID NO:173:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Probe E5-7- PRB ( x i ) SEQUENCE DESCRIPTION: SEQ ID NO:173:

```
CGTAGCCCTC GGGTGAACTA AAT                                                    23
```

( 2 ) INFORMATION FOR SEQ ID NO:174:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Race Anchor Sequence ( x i ) SEQUENCE DESCRIPTION: SEQ ID NO:174:

```
CACGAATTCA CTATCGATTC TGGAACCTTC AGAGG                                    35
```

( 2 ) INFORMATION FOR SEQ ID NO:175:

( i ) SEQUENCE CHARACTERISTICS:
        ( A ) LENGTH: 736 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: Consensus Sequence 5'-end ( x i ) SEQUENCE DESCRIPTION: SEQ ID NO:175:

```
ACGTGGGGA  GTTGATCCCC  CCCCCCGGC  ACTGGGTGCA  AGCCCAGAA  ACCGACGCCT      60
ATCTAAGTAG  ACGCAATGAC  TCGGCGCCGA  CTCGGCGACC  GGCCAAAAGG  TGGTGGATGG   120
GTGATGACAG  GGTTGGTAGG  TCGTAAATCC  CGGTCACCTT  GGTAGCCACT  ATAGGTGGGT   180
CTTAAGAGAA  GGTTAAGATT  CCTCTTGTGC  CTGCGGCGAG  ACCGCGCACG  GTCCACAGGT   240
GTTGGCCCTA  CCGGTGGGAA  TAAGGGCCCG  ACGTCAGGCT  CGTCGTTAAA  CCGAGCCCGT   300
TACCCACCTG  GGCAAACGAC  GCCCACGTAC  GGTCCACGTC  GCCCTTCAAT  GTCTCTCTTG   360
ACCAATAGGC  GTAGCCGGCG  AGTTGACAAG  GACCAGTGGG  GGCCGGGGGC  TTGGAGAGGG   420
ACTCCAAGTC  CCGCCCTTCC  CGGTGGGCCG  GGAAATGCAT  GGGGCCACCC  AGCTCCGCGG   480
CGGCCTGCAG  CCGGGGTAGC  CCAAGAATCC  TTCGGGTGAG  GGCGGGTGGC  ATTTCCTTTT   540
TCTATACCAT  CATGGCAGTC  CTTCTGCTCC  TTCTCGTGGT  TGAGGCCGGG  GCCATTCTGG   600
CCCCGGCCAC  CCACGCTTGT  CGAGCGAATG  GGCAATATTT  CCTCACAAAT  TGTTGTGCCC   660
CGGAGGACAT  CGGGTTCTGC  CTGGAGGGTG  GATGCCTGGT  GGCCCTGGGG  TGCACGATTT   720
GCACTGACCA  ATGCTG                                                      736
```

( 2 ) INFORMATION FOR SEQ ID NO:176:

( i ) SEQUENCE CHARACTERISTICS:
        ( A ) LENGTH: 688 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO -continued ( i v ) ANTI-SENSE: NO ( v i ) ORIGINAL SOURCE:
( C ) INDIVIDUAL ISOLATE: HGV Variant BG34

( i x ) FEATURE:
( A ) NAME/KEY: CDS
( B ) LOCATION: 272..688

( x i ) SEQUENCE DESCRIPTION: SEQ ID NO:176:

```
GACTCGGCGC CGACTCGGCG ACCGGCCAAA AGGTGGTGGA TGGGTGATGA CAGGGTTGGT        60

AGGTCGTAAA TCCCGGTCAC CTTGGTAGCC ACTATAGGTG GGTCTTAAGA GAAGGTTAAG       120

ATTCCTCTTG TGCCTGCGGC GAGACCGCGC ACGGTCCACA GGTGTTGGCC CTACCGGTGT       180

GAATAAGGGC CCGACGTCAG GCTCGTCGTT AAACCGAGCC CGTCACCCAC CTGGGCAAAC       240

GACGCCCACG TACGGTCCAC GTCGCCCTTC A ATG CCT CTC TTG GCC AAT AGG          292
                                   Met Pro Leu Leu Ala Asn Arg
                                     1               5

AGT ATC CGG CGA GTT GAC AAG GAC CAG TGG GGG CCG GGA GTC ACG GGG         340
Ser Ile Arg Arg Val Asp Lys Asp Gln Trp Gly Pro Gly Val Thr Gly
         10                  15                  20

ATG GAC CCC GGG CTC TGC CCT TCC CGG TGG AAC GGG AAA CGC ATG GGG         388
Met Asp Pro Gly Leu Cys Pro Ser Arg Trp Asn Gly Lys Arg Met Gly
     25                  30                  35

CCA CCC AGC TCC GCG GCG GCC TGC AGC CGG GGT AGC CCA AGA ACC CTT         436
Pro Pro Ser Ser Ala Ala Ala Cys Ser Arg Gly Ser Pro Arg Thr Leu
 40                  45                  50                  55

CGG GTG AGG GCG GGT GGC ATT TCT CTT TTC TGT ATC ATC ATG GCA GTC         484
Arg Val Arg Ala Gly Gly Ile Ser Leu Phe Cys Ile Ile Met Ala Val
                 60                  65                  70

CTC CTG CTC CTT CTC GTG GTT GAG GCC GGG GCC ATT CTG GCC CCG GCC         532
Leu Leu Leu Leu Leu Val Val Glu Ala Gly Ala Ile Leu Ala Pro Ala
             75                  80                  85

ACC CAC GCT TGT CGA GCG AAT GGA CAA TAT TTC CTC ACA AAC TGT TGC         580
Thr His Ala Cys Arg Ala Asn Gly Gln Tyr Phe Leu Thr Asn Cys Cys
         90                  95                 100

GCC CTC GAG GAC ATC GGG TTC TGC CTG GAA GGC GGG TGC CTG GTG GCC         628
Ala Leu Glu Asp Ile Gly Phe Cys Leu Glu Gly Gly Cys Leu Val Ala
     105                 110                 115

TTA GGG TGC ACC ATT TGC ACT GAC CGT TGC TGG CCA CTG TAT CAG GCG         676
Leu Gly Cys Thr Ile Cys Thr Asp Arg Cys Trp Pro Leu Tyr Gln Ala
120                 125                 130                 135

GGT TTG GCT GTG                                                          688
Gly Leu Ala Val
```

( 2 ) INFORMATION FOR SEQ ID NO:177:

( i ) SEQUENCE CHARACTERISTICS:
( A ) LENGTH: 139 amino acids
( B ) TYPE: amino acid
( D ) TOPOLOGY: linear ( i i ) MOLECULE TYPE: protein ( x i ) SEQUENCE DESCRIPTION: SEQ ID NO:177:

```
Met Pro Leu Leu Ala Asn Arg Ser Ile Arg Arg Val Asp Lys Asp Gln
  1               5                  10                  15

Trp Gly Pro Gly Val Thr Gly Met Asp Pro Gly Leu Cys Pro Ser Arg
             20                  25                  30

Trp Asn Gly Lys Arg Met Gly Pro Pro Ser Ser Ala Ala Ala Cys Ser
         35                  40                  45
```

```
Arg  Gly  Ser  Pro  Arg  Thr  Leu  Arg  Val  Arg  Ala  Gly  Gly  Ile  Ser  Leu
     50                      55                           60

Phe  Cys  Ile  Ile  Met  Ala  Val  Leu  Leu  Leu  Leu  Val  Val  Glu  Ala
65                       70                      75                           80

Gly  Ala  Ile  Leu  Ala  Pro  Ala  Thr  His  Ala  Cys  Arg  Ala  Asn  Gly  Gln
                    85                      90                           95

Tyr  Phe  Leu  Thr  Asn  Cys  Cys  Ala  Leu  Glu  Asp  Ile  Gly  Phe  Cys  Leu
               100                     105                      110

Glu  Gly  Gly  Cys  Leu  Val  Ala  Leu  Gly  Cys  Thr  Ile  Cys  Thr  Asp  Arg
          115                     120                     125

Cys  Trp  Pro  Leu  Tyr  Gln  Ala  Gly  Leu  Ala  Val
     130                     135
```

( 2 ) INFORMATION FOR SEQ ID NO:178:

( i ) SEQUENCE CHARACTERISTICS:
        ( A ) LENGTH: 663 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: HGV Variant T55806

( i x ) FEATURE:
        ( A ) NAME/KEY: CDS
        ( B ) LOCATION: 271..663

( x i ) SEQUENCE DESCRIPTION: SEQ ID NO:178:

```
GACTCGGCGC  CGACTCGGCG  ACCGGCCAAA  AGGTGGTGGA  TGGGTGATGC  CAGGGTTGGT      60

AGGTCGTAAA  TCCCGGTCAT  CTTGGTAGCC  ACTATAGGTG  GGTCTTAAGA  GAAGGTTAAG     120

ATTCCTCTTG  TGCCTGCGGC  GAGACCGCGC  ACGGTCCACA  GGTGTTGGCC  CTACCGGTGG     180

AATAAGGGCC  CGACGTCAGG  CTCGTCGTTA  AACCGAGCCC  GTCACCCACC  TGGGCAAACG     240

ACGCTCACGT  ACGGTCCACG  TCGCCCTTCA  ATG  TCT  CTC  TTG  ACC  AAT  AGG  TTT     294
                                    Met  Ser  Leu  Leu  Thr  Asn  Arg  Phe
                                      1                        5

ATC  CGG  CGA  GTT  GAC  AAG  GAC  CAG  TGG  GGG  CCG  GGG  GTT  ACG  GGG  ACG     342
Ile  Arg  Arg  Val  Asp  Lys  Asp  Gln  Trp  Gly  Pro  Gly  Val  Thr  Gly  Thr
          10                      15                           20

GAC  CCC  GAA  CCC  TGC  CCT  TCC  CGG  TGG  GCC  GGG  AAA  TGC  ATG  GGG  CCA     390
Asp  Pro  Glu  Pro  Cys  Pro  Ser  Arg  Trp  Ala  Gly  Lys  Cys  Met  Gly  Pro
25                       30                      35                           40

CCC  AGC  TCC  GCG  GCG  GCC  TGC  AGC  CGG  GGT  AGC  CCA  AGA  ATC  CTT  CGG     438
Pro  Ser  Ser  Ala  Ala  Ala  Cys  Ser  Arg  Gly  Ser  Pro  Arg  Ile  Leu  Arg
                    45                           50                      55

GTG  AGG  GCG  GGT  GGC  ATT  TCT  CTT  TTC  TAT  ACC  ATC  ATG  GCA  GTC  CTT     486
Val  Arg  Ala  Gly  Gly  Ile  Ser  Leu  Phe  Tyr  Thr  Ile  Met  Ala  Val  Leu
                    60                           65                      70

CTG  CTC  TTC  TTC  GTG  GTT  GAG  GCC  GGG  GCG  ATT  CTC  GCC  CCG  GCC  ACC     534
Leu  Leu  Phe  Phe  Val  Val  Glu  Ala  Gly  Ala  Ile  Leu  Ala  Pro  Ala  Thr
               75                           80                      85

CAC  GCT  TGT  CGG  GCG  AAT  GGG  CAA  TAT  TTC  CTC  ACA  AAT  TGT  TGC  GCC     582
His  Ala  Cys  Arg  Ala  Asn  Gly  Gln  Tyr  Phe  Leu  Thr  Asn  Cys  Cys  Ala
          90                           95                      100

CCA  GAG  GAT  GTT  GGG  TTC  TGC  CTG  GAG  GGC  GGA  TGC  CTG  GTG  GCT  CTG     630
Pro  Glu  Asp  Val  Gly  Phe  Cys  Leu  Glu  Gly  Gly  Cys  Leu  Val  Ala  Leu
```

|     |     |     |     | 105 |     |     |     | 110 |     |     |     | 115 |     |     |     | 120 |     |     |
| --- | --- | --- | --- | --- | --- | --- | --- | --- | --- | --- | --- | --- | --- | --- | --- | --- | --- | --- |
| GGG | TGT | ACG | ATT | TGC | ACT | GAC | CGT | TGC | TGG | CCA | | | | | | | | 663 |
| Gly | Cys | Thr | Ile | Cys | Thr | Asp | Arg | Cys | Trp | Pro | | | | | | | | |
|     |     |     |     | 125 |     |     |     | 130 |     |     |     |     |     |     |     |     |     |     |

( 2 ) INFORMATION FOR SEQ ID NO:179:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:179:

| Met | Ser | Leu | Leu | Thr | Asn | Arg | Phe | Ile | Arg | Arg | Val | Asp | Lys | Asp | Gln |
| --- | --- | --- | --- | --- | --- | --- | --- | --- | --- | --- | --- | --- | --- | --- | --- |
| 1 | | | | 5 | | | | | 10 | | | | | 15 | |

| Trp | Gly | Pro | Gly | Val | Thr | Gly | Thr | Asp | Pro | Glu | Pro | Cys | Pro | Ser | Arg |
| --- | --- | --- | --- | --- | --- | --- | --- | --- | --- | --- | --- | --- | --- | --- | --- |
| | | | 20 | | | | 25 | | | | | 30 | | | |

| Trp | Ala | Gly | Lys | Cys | Met | Gly | Pro | Pro | Ser | Ser | Ala | Ala | Ala | Cys | Ser |
| --- | --- | --- | --- | --- | --- | --- | --- | --- | --- | --- | --- | --- | --- | --- | --- |
| | | 35 | | | | | 40 | | | | | 45 | | | |

| Arg | Gly | Ser | Pro | Arg | Ile | Leu | Arg | Val | Arg | Ala | Gly | Gly | Ile | Ser | Leu |
| --- | --- | --- | --- | --- | --- | --- | --- | --- | --- | --- | --- | --- | --- | --- | --- |
| | 50 | | | | | 55 | | | | | 60 | | | | |

| Phe | Tyr | Thr | Ile | Met | Ala | Val | Leu | Leu | Leu | Phe | Phe | Val | Val | Glu | Ala |
| --- | --- | --- | --- | --- | --- | --- | --- | --- | --- | --- | --- | --- | --- | --- | --- |
| 65 | | | | | 70 | | | | | 75 | | | | | 80 |

| Gly | Ala | Ile | Leu | Ala | Pro | Ala | Thr | His | Ala | Cys | Arg | Ala | Asn | Gly | Gln |
| --- | --- | --- | --- | --- | --- | --- | --- | --- | --- | --- | --- | --- | --- | --- | --- |
| | | | | 85 | | | | | 90 | | | | | 95 | |

| Tyr | Phe | Leu | Thr | Asn | Cys | Cys | Ala | Pro | Glu | Asp | Val | Gly | Phe | Cys | Leu |
| --- | --- | --- | --- | --- | --- | --- | --- | --- | --- | --- | --- | --- | --- | --- | --- |
| | | | 100 | | | | | 105 | | | | | 110 | | |

| Glu | Gly | Gly | Cys | Leu | Val | Ala | Leu | Gly | Cys | Thr | Ile | Cys | Thr | Asp | Arg |
| --- | --- | --- | --- | --- | --- | --- | --- | --- | --- | --- | --- | --- | --- | --- | --- |
| | | 115 | | | | | 120 | | | | | 125 | | | |

| Cys | Trp | Pro |
| --- | --- | --- |
| | | 130 |

( 2 ) INFORMATION FOR SEQ ID NO:180:

( i ) SEQUENCE CHARACTERISTICS:
        ( A ) LENGTH: 632 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: HGV Variant EB20-2

( i x ) FEATURE:
        ( A ) NAME/KEY: CDS
        ( B ) LOCATION: 271..632

( x i ) SEQUENCE DESCRIPTION: SEQ ID NO:180:

| GACTCGGCGC | CGACTCGGCG | ACCGGCCAAA | AGGTGGTGGA | TGGGTGATGC | CAGGGTTGGT | 60 |
| --- | --- | --- | --- | --- | --- | --- |
| AGGTCGTAAA | TCCCGGTCAT | CTTGGTAGCC | ACTATAGGTG | GGTCTTAAGA | GAAGGTTAAG | 120 |
| ATTCCTCTTG | TGCCTGCGGC | GAGACCGCGC | ACGGTCCACA | GGTGTTGGCC | CTACCGGTGT | 180 |
| AATAAGGGCC | CGACGTCAGG | CTCGTCGTTA | AACCGAGCCC | GTCACCCACC | TGGGCAAACG | 240 |

|     |     |     |     |     |     |     |     |     | ACGCCCACGT | ACGGTCCACG | TCGCCCTTCA | ATG | CCT | CTC | TTG | GCC | AAT | AGG | AGT | 294 |
| --- | --- | --- | --- | --- | --- | --- | --- | --- | --- | --- | --- | --- | --- | --- | --- | --- | --- | --- | --- | --- |
|     |     |     |     |     |     |     |     |     |     |     |     | Met | Pro | Leu | Leu | Ala | Asn | Arg | Ser | |
|     |     |     |     |     |     |     |     |     |     |     |     | 1   |     |     |     | 5   |     |     |     | |

-continued

```
TAT CTC CGG CGA GTT GGC AAG GAC CAG TGG GGG CCG GGG GTT ACG GGG        342
Tyr Leu Arg Arg Val Gly Lys Asp Gln Trp Gly Pro Gly Val Thr Gly
    10              15                  20

AAG GAC CCC GAA CCC TGC CCT TCC CGG TGG GCC GGG AAA TGC ATG GGG        390
Lys Asp Pro Glu Pro Cys Pro Ser Arg Trp Ala Gly Lys Cys Met Gly
25              30                  35                  40

CCA CCC AGC TCC GCG GCG GCC TGC AGC CGG GGT AGC CCA AAA AAC CTT        438
Pro Pro Ser Ser Ala Ala Ala Cys Ser Arg Gly Ser Pro Lys Asn Leu
                45              50                  55

CGG GTG AGG GCG GGT GGC ATT TTC TTT TCC TAT ACC ATC ATG GCA GTC        486
Arg Val Arg Ala Gly Gly Ile Phe Phe Ser Tyr Thr Ile Met Ala Val
            60              65                  70

CTT CTG CTC CTT CTC GTG GTT GAG GCC GGG GCC ATT TTG GCC CCG GCC        534
Leu Leu Leu Leu Leu Val Val Glu Ala Gly Ala Ile Leu Ala Pro Ala
        75              80                  85

ACC CAC GCT TGC AGA GCT AAT GGG CAA TAT TTC CTC ACA AAC TGT TGT        582
Thr His Ala Cys Arg Ala Asn Gly Gln Tyr Phe Leu Thr Asn Cys Cys
        90              95                  100

GCC TTG GAG GAC ATC GGG TTC TGC CTG GAA GGC GGA TGC TTG GTG GCG CT     632
Ala Leu Glu Asp Ile Gly Phe Cys Leu Glu Gly Gly Cys Leu Val Ala
105             110                 115                 120
```

( 2 ) INFORMATION FOR SEQ ID NO:181:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:181:

```
Met Pro Leu Leu Ala Asn Arg Ser Tyr Leu Arg Arg Val Gly Lys Asp
1               5                   10                  15

Gln Trp Gly Pro Gly Val Thr Gly Lys Asp Pro Glu Pro Cys Pro Ser
            20                  25                  30

Arg Trp Ala Gly Lys Cys Met Gly Pro Pro Ser Ser Ala Ala Ala Cys
        35                  40                  45

Ser Arg Gly Ser Pro Lys Asn Leu Arg Val Arg Ala Gly Gly Ile Phe
    50                  55                  60

Phe Ser Tyr Thr Ile Met Ala Val Leu Leu Leu Leu Leu Val Val Glu
65                  70                  75                  80

Ala Gly Ala Ile Leu Ala Pro Ala Thr His Ala Cys Arg Ala Asn Gly
                85                  90                  95

Gln Tyr Phe Leu Thr Asn Cys Cys Ala Leu Glu Asp Ile Gly Phe Cys
            100                 105                 110

Leu Glu Gly Gly Cys Leu Val Ala
        115                 120
```

( 2 ) INFORMATION FOR SEQ ID NO:182:

( i ) SEQUENCE CHARACTERISTICS:
        ( A ) LENGTH: 9103 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO (vi) ORIGINAL SOURCE:
    (C) INDIVIDUAL ISOLATE: HGV-JC Variant (ix) FEATURE:
    (A) NAME/KEY: CDS
    (B) LOCATION: 276..9005

(xi) SEQUENCE DESCRIPTION: SEQ ID NO:182:

```
CAATGACTCG GCGCCGACTC GGCGACCGGC CAAAAGGTGG TGGATGGGTG ATGACAGGGT      60

TGGTAGGTCG TAAATCCCGG TCACCTTGGT AGCCACTATA GGTGGGTCTT AAGAGAAGGT     120

TAAGATTCCT CTTGTGCCTG CGGCGAGACC GCGCACGGTC CACAGGTGTT GGCCCTACCG     180

GTGGGAATAA GGGCCCGACG TCAGGCTCGT CGTTAAACCG AGCCCGTAAC CCGCCTGGGC     240

AAACGACGCC CACGTACGGT CCACGTCGCC CTTCA ATG TCG CTC TTG ACC AAT        293
                                       Met Ser Leu Leu Thr Asn
                                        1               5
```

```
AGG CTT AGC CGG CGA GTT GAC AAG GAC CAG TGG GGG CCG GGG TTT ATG       341
Arg Leu Ser Arg Arg Val Asp Lys Asp Gln Trp Gly Pro Gly Phe Met
           10              15                  20

GGG AAG GAC CCC AAA CCC TGC CCT TCC CGG CGG ACC GGG AAA TGC ATG       389
Gly Lys Asp Pro Lys Pro Cys Pro Ser Arg Arg Thr Gly Lys Cys Met
        25              30                  35

GGG CCA CCC AGC TCC GCG GCG GCC TGC AGC CGG GGT AGC CCA AGA ATC       437
Gly Pro Pro Ser Ser Ala Ala Ala Cys Ser Arg Gly Ser Pro Arg Ile
    40              45                  50

CTT CGG GTG AGG GCG GGT GGC ATT TCT CTT CCT TAT ACC ATC ATG GAA       485
Leu Arg Val Arg Ala Gly Gly Ile Ser Leu Pro Tyr Thr Ile Met Glu
55              60                  65                  70

GCC CTC CTG TTC CTC CTC GGG GTG GAG GCC GGG GCC ATT CTG GCC CCG       533
Ala Leu Leu Phe Leu Leu Gly Val Glu Ala Gly Ala Ile Leu Ala Pro
                75                  80                  85

GCC ACC CAC GCT TGT CGA GCG AAT GGG CAA TAT TTC CTC ACA AAC TGT       581
Ala Thr His Ala Cys Arg Ala Asn Gly Gln Tyr Phe Leu Thr Asn Cys
            90                  95                  100

TGT GCT CCA GAG GAC ATT GGG TTC TGC CTC GAA GGC GGT TGC CTT GTG       629
Cys Ala Pro Glu Asp Ile Gly Phe Cys Leu Glu Gly Gly Cys Leu Val
        105                 110                 115

GCC CTG GGG TGC ACA GTT TGC ACT GAC CGA TGC TGG CCG CTG TAT CAG       677
Ala Leu Gly Cys Thr Val Cys Thr Asp Arg Cys Trp Pro Leu Tyr Gln
    120                 125                 130

GCG GGC TTG GCT GTG CGG CCT GGC AAG TCC GCA GCC CAG CTG GTG GGG       725
Ala Gly Leu Ala Val Arg Pro Gly Lys Ser Ala Ala Gln Leu Val Gly
135                 140                 145                 150

CAA CTG GGT GGC CTC TAC GGG CCC TTG TCG GTG TCG GCC TAC GTG GCC       773
Gln Leu Gly Gly Leu Tyr Gly Pro Leu Ser Val Ser Ala Tyr Val Ala
                155                 160                 165

GGC ATC CTG GGC CTG GGT GAG GTG TAC TCG GGT GTC CTA ACA GTT GGT       821
Gly Ile Leu Gly Leu Gly Glu Val Tyr Ser Gly Val Leu Thr Val Gly
            170                 175                 180

GTT GCG TTG ACG CGC CGG GTC TAC CCG ATG CCC AAC CTG ACG TGT GCA       869
Val Ala Leu Thr Arg Arg Val Tyr Pro Met Pro Asn Leu Thr Cys Ala
        185                 190                 195

GTA GAG TGT GAG CTT AAG TGG GAA AGT GAG TTT TGG AGA TGG ACT GAG       917
Val Glu Cys Glu Leu Lys Trp Glu Ser Glu Phe Trp Arg Trp Thr Glu
    200                 205                 210

CAG CTG GCC TCC AAT TAC TGG ATT CTG GAA TAC CTT TGG AAG GTC CCG       965
Gln Leu Ala Ser Asn Tyr Trp Ile Leu Glu Tyr Leu Trp Lys Val Pro
215                 220                 225                 230

TTT GAC TTC TGG AGA GGC GTG CTA AGC CTG ACT CCC TTG CTG GTT TGC      1013
Phe Asp Phe Trp Arg Gly Val Leu Ser Leu Thr Pro Leu Leu Val Cys
                235                 240                 245
```

```
GTG GCC GCG TTG CTG CTG CTG GAG CAA CGG ATT GTC ATG GTC TTC CTG      1061
Val Ala Ala Leu Leu Leu Leu Glu Gln Arg Ile Val Met Val Phe Leu
            250             255             260

TTG GTG ACG ATG GCC GGG ATG TCG CAA GGC GCT CCG GCC TCC GTT TTG      1109
Leu Val Thr Met Ala Gly Met Ser Gln Gly Ala Pro Ala Ser Val Leu
        265             270             275

GGG TCT CGC CCC TTT GAC TAC GGG TTG ACA TGG CAG TCT TGT TCC TGC      1157
Gly Ser Arg Pro Phe Asp Tyr Gly Leu Thr Trp Gln Ser Cys Ser Cys
    280             285             290

AGG GCT AAT GGG TCG CGC TAT ACT ACT GGG GAG AAG GTG TGG GAC CGT      1205
Arg Ala Asn Gly Ser Arg Tyr Thr Thr Gly Glu Lys Val Trp Asp Arg
295             300             305             310

GGG AAC GTC ACG CTC CTG TGT GAC TGC CCC AAC GGC CCC TGG GTG TGG      1253
Gly Asn Val Thr Leu Leu Cys Asp Cys Pro Asn Gly Pro Trp Val Trp
            315             320             325

TTG CCG GCC TTT TGC CAA GCA ATC GGC TGG GGC GAT CCC ATC ACT CAT      1301
Leu Pro Ala Phe Cys Gln Ala Ile Gly Trp Gly Asp Pro Ile Thr His
            330             335             340

TGG AGC CAC GGC CAA AAT CGG TGG CCC CTC TCA TGC CCC CAG TAT GTC      1349
Trp Ser His Gly Gln Asn Arg Trp Pro Leu Ser Cys Pro Gln Tyr Val
        345             350             355

TAT GGG TCT GTT TCA GTC ACT TGC GTG TGG GGT TCC GTC TCT TGG TTT      1397
Tyr Gly Ser Val Ser Val Thr Cys Val Trp Gly Ser Val Ser Trp Phe
    360             365             370

GCC TCG ACT GGC GGT CGC GAC TCG AAG ATC GAT GTG TGG AGT CTG GTG      1445
Ala Ser Thr Gly Gly Arg Asp Ser Lys Ile Asp Val Trp Ser Leu Val
375             380             385             390

CCG GTT GGT TCC GCC AGC TGC ACC ATA GCC GCT CTT GGA TCG TCG GAT      1493
Pro Val Gly Ser Ala Ser Cys Thr Ile Ala Ala Leu Gly Ser Ser Asp
            395             400             405

CGG GAC ACG GTA GTT GAG CTC TCC GAG TGG GGA GTC CCG TGC GCA ACG      1541
Arg Asp Thr Val Val Glu Leu Ser Glu Trp Gly Val Pro Cys Ala Thr
            410             415             420

TGC ATT CTG GAT CGT CGG CCG GCC TCG TGC GGC ACC TGT GTG AGA GAC      1589
Cys Ile Leu Asp Arg Arg Pro Ala Ser Cys Gly Thr Cys Val Arg Asp
        425             430             435

TGC TGG CCC GAA ACC GGG TCG GTT AGG TTT CCA TTC CAT CGG TGC GGC      1637
Cys Trp Pro Glu Thr Gly Ser Val Arg Phe Pro Phe His Arg Cys Gly
    440             445             450

GCG GGG CCT AAG CTG ACA AAG GAC TTG GAA GCT GTG CCC TTC GTC AAT      1685
Ala Gly Pro Lys Leu Thr Lys Asp Leu Glu Ala Val Pro Phe Val Asn
455             460             465             470

AGG ACA ACT CCC TTC ACC ATA AGG GGC CCC CTG GGC AAC CAG GGG AGA      1733
Arg Thr Thr Pro Phe Thr Ile Arg Gly Pro Leu Gly Asn Gln Gly Arg
            475             480             485

GGC AAC CCG GTG CGG TCG CCC TTG GGT TTT GGG TCC TAC GCC ATG ACC      1781
Gly Asn Pro Val Arg Ser Pro Leu Gly Phe Gly Ser Tyr Ala Met Thr
            490             495             500

AAG ATC CGA GAC TCC TTA CAT TTG GTG AAA TGT CCC ACA CCA GCC ATT      1829
Lys Ile Arg Asp Ser Leu His Leu Val Lys Cys Pro Thr Pro Ala Ile
        505             510             515

GAG CCT CCC ACC GGG ACG TTT GGG TTC TTC CCC GGA GTG CCG CCT CTT      1877
Glu Pro Pro Thr Gly Thr Phe Gly Phe Phe Pro Gly Val Pro Pro Leu
    520             525             530

AAC AAC TGC CTG CTG TTG GGC ACG GAA GTG TCC GAA GCG CTG GGC GGG      1925
Asn Asn Cys Leu Leu Leu Gly Thr Glu Val Ser Glu Ala Leu Gly Gly
535             540             545             550

GCC GGC CTC ACG GGG GGG TTC TAT GAA CCC CTG GTG CGC AGG CGT TCG      1973
Ala Gly Leu Thr Gly Gly Phe Tyr Glu Pro Leu Val Arg Arg Arg Ser
            555             560             565
```

| | | | | | | | | | | | | | | | | |
|---|---|---|---|---|---|---|---|---|---|---|---|---|---|---|---|---|
| GAG | CTG | ATG | GGG | CGC | CGA | AAT | CCG | GTT | TGC | CCG | GGG | TTT | GCA | TGG | CTG | 2021 |
| Glu | Leu | Met | Gly 570 | Arg | Arg | Asn | Pro 575 | Val | Cys | Pro | Gly | Phe 580 | Ala | Trp | Leu | |
| TCG | TCG | GGT | CGA | CCT | GAC | GGG | TTT | ATA | CAC | GTC | CAG | GGC | CAC | TTG | CAG | 2069 |
| Ser | Ser | Gly 585 | Arg | Pro | Asp | Gly | Phe 590 | Ile | His | Val | Gln | Gly 595 | His | Leu | Gln | |
| GAG | GTC | GAT | GCT | GGC | AAC | TTC | ATC | CCT | CCA | CCT | CGC | TGG | TTG | CTC | TTG | 2117 |
| Glu | Val 600 | Asp | Ala | Gly | Asn | Phe 605 | Ile | Pro | Pro | Pro | Arg 610 | Trp | Leu | Leu | Leu | |
| GAC | TTT | GTG | TTT | GTC | CTG | TTA | TAC | CTG | ATG | AAG | CTG | GCT | GAG | GCA | CGG | 2165 |
| Asp 615 | Phe | Val | Phe | Val | Leu 620 | Leu | Tyr | Leu | Met | Lys 625 | Leu | Ala | Glu | Ala | Arg 630 | |
| CTG | GTC | CCG | TTG | ATC | TTG | CTT | CTG | CTG | TGG | TGG | TGG | GTG | AAC | CAG | TTG | 2213 |
| Leu | Val | Pro | Leu | Ile 635 | Leu | Leu | Leu | Leu | Trp 640 | Trp | Trp | Val | Asn | Gln 645 | Leu | |
| GCA | GTC | CTT | GGA | CTG | CCG | GCT | GTG | GAC | GCC | GCC | GTG | GCT | GGT | GAG | GTC | 2261 |
| Ala | Val | Leu | Gly 650 | Leu | Pro | Ala | Val | Asp 655 | Ala | Ala | Val | Ala | Gly 660 | Glu | Val | |
| TTC | GCG | GGC | CCG | GCC | CTG | TCG | TGG | TGT | CTG | GGC | CTC | CCC | ACC | GTT | AGT | 2309 |
| Phe | Ala | Gly 665 | Pro | Ala | Leu | Ser | Trp 670 | Cys | Leu | Gly | Leu | Pro 675 | Thr | Val | Ser | |
| ATG | ATC | CTG | GGC | TTA | GCA | AAC | CTG | GTG | TTG | TAT | TTC | CGG | TGG | ATG | GGT | 2357 |
| Met | Ile | Leu | Gly 680 | Leu | Ala | Asn | Leu | Val 685 | Leu | Tyr | Phe | Arg | Trp 690 | Met | Gly | |
| CCC | CAA | CGC | CTC | ATG | TTC | CTC | GTG | TTG | TGG | AAG | CTC | GCT | CGG | GGA | GCC | 2405 |
| Pro 695 | Gln | Arg | Leu | Met | Phe 700 | Leu | Val | Leu | Trp | Lys 705 | Leu | Ala | Arg | Gly | Ala 710 | |
| TTC | CCG | CTG | GCA | CTT | CTG | ATG | GGG | ATC | TCG | GCA | ACC | CGC | GGG | CGC | ACC | 2453 |
| Phe | Pro | Leu | Ala | Leu 715 | Leu | Met | Gly | Ile | Ser 720 | Ala | Thr | Arg | Gly | Arg 725 | Thr | |
| TCG | GTG | CTC | GGG | GCC | GAG | TTC | TGC | TTC | GAT | GTC | ACA | TTC | GAG | GTG | GAC | 2501 |
| Ser | Val | Leu | Gly 730 | Ala | Glu | Phe | Cys | Phe 735 | Asp | Val | Thr | Phe | Glu 740 | Val | Asp | |
| ACG | TCG | GTT | TTG | GGC | TGG | GTG | GTG | GCC | AGT | GTG | GTA | GCC | TGG | GCC | ATT | 2549 |
| Thr | Ser | Val 745 | Leu | Gly | Trp | Val | Val 750 | Ala | Ser | Val | Val | Ala 755 | Trp | Ala | Ile | |
| GCG | CTC | CTG | AGC | TCG | ATG | AGC | GCG | GGA | GGG | TGG | AGG | CAC | AAG | GCC | GTG | 2597 |
| Ala | Leu | Leu 760 | Ser | Ser | Met | Ser | Ala 765 | Gly | Gly | Trp | Arg | His 770 | Lys | Ala | Val | |
| ATC | TAT | AGG | ACG | TGG | TGT | AAG | GGG | TAC | CAG | GCA | ATA | CGC | CAA | CGG | GTG | 2645 |
| Ile 775 | Tyr | Arg | Thr | Trp | Cys 780 | Lys | Gly | Tyr | Gln | Ala 785 | Ile | Arg | Gln | Arg | Val 790 | |
| GTG | CGG | AGC | CCC | CTC | GGG | GAG | GGG | CGG | CCC | ACC | AAA | CCC | TTG | ACG | TTT | 2693 |
| Val | Arg | Ser | Pro | Leu 795 | Gly | Glu | Gly | Arg | Pro 800 | Thr | Lys | Pro | Leu | Thr 805 | Phe | |
| GCT | TGG | TGC | TTG | GCC | TCA | TAC | ATC | TGG | CCG | GAT | GCT | GTG | ATG | ATG | GTG | 2741 |
| Ala | Trp | Cys | Leu | Ala 810 | Ser | Tyr | Ile | Trp | Pro 815 | Asp | Ala | Val | Met | Met 820 | Val | |
| GTG | GTA | GCC | TTG | GTG | CTC | CTC | TTT | GGC | CTG | TTC | GAC | GCG | TTG | GAC | TGG | 2789 |
| Val | Val | Ala 825 | Leu | Val | Leu | Leu | Phe 830 | Gly | Leu | Phe | Asp | Ala 835 | Leu | Asp | Trp | |
| GCT | TTG | GAG | GAG | CTC | TTG | GTG | TCC | CGG | CCC | TCG | TTA | CGG | CGT | CTG | GCC | 2837 |
| Ala | Leu | Glu 840 | Glu | Leu | Leu | Val | Ser 845 | Arg | Pro | Ser | Leu | Arg 850 | Arg | Leu | Ala | |
| CGG | GTG | GTT | GAG | TGC | TGT | GTG | ATG | GCG | GGA | GAG | AAG | GCC | ACA | ACC | GTC | 2885 |
| Arg 855 | Val | Val | Glu | Cys | Cys 860 | Val | Met | Ala | Gly | Glu 865 | Lys | Ala | Thr | Thr | Val 870 | |
| CGG | CTG | GTC | TCC | AAG | ATG | TGC | GCG | AGA | GGG | GCC | TAT | TTG | TTT | GAC | CAT | 2933 |
| Arg | Leu | Val | Ser | Lys 875 | Met | Cys | Ala | Arg | Gly 880 | Ala | Tyr | Leu | Phe | Asp 885 | His | |

```
ATG GGC TCT TTT TCG CGC GCT GTC AAG GAG CGC CTG CTG GAG TGG GAC    2981
Met Gly Ser Phe Ser Arg Ala Val Lys Glu Arg Leu Leu Glu Trp Asp
        890             895                 900

GCG GCT TTG GAA CCC CTG TCA TTC ACT AGG ACG GAC TGT CGC ATC ATT    3029
Ala Ala Leu Glu Pro Leu Ser Phe Thr Arg Thr Asp Cys Arg Ile Ile
        905             910                 915

AGA GAT GCT GCG AGG ACC TTG GCC TGC GGG CAG TGC GTC ATG GGC TTG    3077
Arg Asp Ala Ala Arg Thr Leu Ala Cys Gly Gln Cys Val Met Gly Leu
        920             925                 930

CCT GTG GTA GCG CGC CGT GGT GAC GAG GTT CTT ATC GGT GTC TTT CAG    3125
Pro Val Val Ala Arg Arg Gly Asp Glu Val Leu Ile Gly Val Phe Gln
935             940             945                 950

GAT GTG AAC CAT TTG CCT CCC GGA TTC GTC CCG ACC GCA CCC GTT GTC    3173
Asp Val Asn His Leu Pro Pro Gly Phe Val Pro Thr Ala Pro Val Val
                955             960                 965

ATC CGG CGG TGC GGG AAG GGG TTT CTG GGG GTC ACT AAG GCT GCC TTG    3221
Ile Arg Arg Cys Gly Lys Gly Phe Leu Gly Val Thr Lys Ala Ala Leu
        970             975                 980

ACT GGT CGG GAT CCT GAC TTA CAT CCA GGG AAC GTC ATG GTG TTG GGG    3269
Thr Gly Arg Asp Pro Asp Leu His Pro Gly Asn Val Met Val Leu Gly
        985             990                 995

ACG GCT ACG TCG CGA AGC ATG GGG ACA TGC CTG AAC GGC CTG CTG TTC    3317
Thr Ala Thr Ser Arg Ser Met Gly Thr Cys Leu Asn Gly Leu Leu Phe
1000            1005                1010

ACG ACT TTC CAT GGG GCT TCA TCC CGA ACC ATC GCC ACG CCC GTG GGG    3365
Thr Thr Phe His Gly Ala Ser Ser Arg Thr Ile Ala Thr Pro Val Gly
1015            1020            1025                1030

GCC CTT AAT CCC AGG TGG TGG TCC GCC AGT GAT GAC GTC ACG GTG TAC    3413
Ala Leu Asn Pro Arg Trp Trp Ser Ala Ser Asp Asp Val Thr Val Tyr
                1035            1040                1045

CCG CTC CCG GAT GGG GCA ACC TCG TTG ACG CCC TGC ACT TGC CAG GCT    3461
Pro Leu Pro Asp Gly Ala Thr Ser Leu Thr Pro Cys Thr Cys Gln Ala
            1050            1055                1060

GAG TCC TGT TGG GTC ATA CGG TCC GAC GGG GCT TTG TGC CAT GGC TTG    3509
Glu Ser Cys Trp Val Ile Arg Ser Asp Gly Ala Leu Cys His Gly Leu
            1065            1070                1075

AGT AAG GGA GAC AAG GTG GAG CTA GAT GTG GCC ATG GAG GTC TCA GAT    3557
Ser Lys Gly Asp Lys Val Glu Leu Asp Val Ala Met Glu Val Ser Asp
1080            1085                1090

TTC CGT GGC TCG TCC GGC TCA CCT GTC CTG TGC GAC GAG GGG CAC GCA    3605
Phe Arg Gly Ser Ser Gly Ser Pro Val Leu Cys Asp Glu Gly His Ala
1095            1100            1105                1110

GTA GGA ATG CTC GTG TCG GTG CTC CAC TCG GGT GGT CGG GTC ACC GCG    3653
Val Gly Met Leu Val Ser Val Leu His Ser Gly Gly Arg Val Thr Ala
            1115            1120                1125

GCT CGA TTC ACC AGG CCG TGG ACC CAG GTC CCA ACA GAT GCT AAG ACC    3701
Ala Arg Phe Thr Arg Pro Trp Thr Gln Val Pro Thr Asp Ala Lys Thr
        1130            1135                1140

ACC ACT GAA CCC CCT CCG GTG CCG GCA AAG GGA GTT TTC AAG GAA GCC    3749
Thr Thr Glu Pro Pro Pro Val Pro Ala Lys Gly Val Phe Lys Glu Ala
        1145            1150            1155

CCA CTG TTT ATG CCC ACG GGC GCA GGA AAG AGC ACG CGC GTC CCG TTG    3797
Pro Leu Phe Met Pro Thr Gly Ala Gly Lys Ser Thr Arg Val Pro Leu
        1160            1165            1170

GAG TAT GGC AAC ATG GGG CAC AAG GTC CTG ATT TTG AAC CCC TCG GTG    3845
Glu Tyr Gly Asn Met Gly His Lys Val Leu Ile Leu Asn Pro Ser Val
1175            1180            1185                1190

GCG ACA GTG AGG GCC ATG GGC CCT TAC ATG GAG CGA CTG GCG GGA AAA    3893
Ala Thr Val Arg Ala Met Gly Pro Tyr Met Glu Arg Leu Ala Gly Lys
                1195            1200            1205
```

```
CAT CCA AGT ATC TAC TGT GGC CAT GAC ACC ACT GCC TTC ACA AGG ATC            3941
His Pro Ser Ile Tyr Cys Gly His Asp Thr Thr Ala Phe Thr Arg Ile
        1210                    1215                    1220

ACT GAT TCC CCC TTA ACG TAC TCT ACC TAT GGG AGG TTT CTG GCC AAC            3989
Thr Asp Ser Pro Leu Thr Tyr Ser Thr Tyr Gly Arg Phe Leu Ala Asn
        1225                    1230                    1235

CCT AGG CAG ATG CTG CGA GGT GTG TCG GTG GTC ATT TGC GAT GAA TGC            4037
Pro Arg Gln Met Leu Arg Gly Val Ser Val Val Ile Cys Asp Glu Cys
        1240                    1245                    1250

CAC AGT CAT GAT TCC ACT GTG TTG TTG GGG ATT GGA CGG GTC CGG GAG            4085
His Ser His Asp Ser Thr Val Leu Leu Gly Ile Gly Arg Val Arg Glu
1255                    1260                    1265                1270

CTG GCA CGA GAG TGT GGG GTG CAG CTT GTG CTC TAC GCC ACT GCC ACG            4133
Leu Ala Arg Glu Cys Gly Val Gln Leu Val Leu Tyr Ala Thr Ala Thr
                1275                    1280                    1285

CCT CCT GGG TCC CCC ATG ACT CAG CAT CCG TCA ATC ATT GAG ACC AAA            4181
Pro Pro Gly Ser Pro Met Thr Gln His Pro Ser Ile Ile Glu Thr Lys
            1290                    1295                    1300

TTG GAT GTG GGT GAG ATT CCC TTC TAT GGG CAT GGC ATA CCC CTC GAG            4229
Leu Asp Val Gly Glu Ile Pro Phe Tyr Gly His Gly Ile Pro Leu Glu
        1305                    1310                    1315

CGG ATG CGG ACC GGT AGG CAC CTC GTA TTC TGC TAC TCT AAG GCA GAG            4277
Arg Met Arg Thr Gly Arg His Leu Val Phe Cys Tyr Ser Lys Ala Glu
        1320                    1325                    1330

TGT GAG CGG CTA GCC GGT CAG TTT TCT GCT AGG GGA GTT AAC GCC ATA            4325
Cys Glu Arg Leu Ala Gly Gln Phe Ser Ala Arg Gly Val Asn Ala Ile
1335                    1340                    1345                1350

GCC TAT TAC AGG GGA AAA GAC AGT TCT ATC ATC AAG GAC GGA GAT CTG            4373
Ala Tyr Tyr Arg Gly Lys Asp Ser Ser Ile Ile Lys Asp Gly Asp Leu
                1355                    1360                    1365

GTG GTG TGC GCG ACC GAC GCG CTA TCC ACT GGA TAC ACT GGG AAC TTC            4421
Val Val Cys Ala Thr Asp Ala Leu Ser Thr Gly Tyr Thr Gly Asn Phe
            1370                    1375                    1380

GAT TCT GTC ACC GAC TGT GGG TTA GTG GTG GAG GAG GTC GTC GAG GTG            4469
Asp Ser Val Thr Asp Cys Gly Leu Val Val Glu Glu Val Val Glu Val
        1385                    1390                    1395

ACC CTT GAT CCC ACC ATT ACC ATC TCC CTG CGG ACA GTG CCC GCG TCG            4517
Thr Leu Asp Pro Thr Ile Thr Ile Ser Leu Arg Thr Val Pro Ala Ser
        1400                    1405                    1410

GCA GAA CTG TCG ATG CAG AGA CGA GGA CGC ACG GGT AGA GGC AGG TCT            4565
Ala Glu Leu Ser Met Gln Arg Arg Gly Arg Thr Gly Arg Gly Arg Ser
1415                    1420                    1425                1430

GGG CGC TAC TAC TAC GCC GGG GTC GGA AAG GCC CCC GCG GGT GTG GTG            4613
Gly Arg Tyr Tyr Tyr Ala Gly Val Gly Lys Ala Pro Ala Gly Val Val
                1435                    1440                    1445

CGC TCG GGT CCT GTC TGG TCG GCG GTG GAG GCC GGA GTG ACC TGG TAT            4661
Arg Ser Gly Pro Val Trp Ser Ala Val Glu Ala Gly Val Thr Trp Tyr
            1450                    1455                    1460

GGA ATG GAA CCT GAC TTG ACA GCT AAC CTA TTG AGA CTT TAC GAC GAC            4709
Gly Met Glu Pro Asp Leu Thr Ala Asn Leu Leu Arg Leu Tyr Asp Asp
        1465                    1470                    1475

TGC CCT TAC ACC GCA GCC GTC GCA GCT GAC ATC GGT GAA GCC GCG GTG            4757
Cys Pro Tyr Thr Ala Ala Val Ala Ala Asp Ile Gly Glu Ala Ala Val
        1480                    1485                    1490

TTT TTC TCC GGG CTA GCC CCG TTG AGG ATG CAT CCC GAT GTT AGC TGG            4805
Phe Phe Ser Gly Leu Ala Pro Leu Arg Met His Pro Asp Val Ser Trp
1495                    1500                    1505                1510

GCA AAA GTG CGC GGC GTC AAC TGG CCC CTC TTG GTG GGT GTT CAG CGG            4853
Ala Lys Val Arg Gly Val Asn Trp Pro Leu Leu Val Gly Val Gln Arg
        1515                    1520                    1525
```

```
ACC ATG TGC CGG GAA ACA CTG TCT CCC GGA CCA TCG GAC GAC CCC CAA    4901
Thr Met Cys Arg Glu Thr Leu Ser Pro Gly Pro Ser Asp Asp Pro Gln
        1530                1535                1540

TGG GCA GGT CTG AAG GGC CCG AAT CCT GTT CCA CTA CTG CTG AGG TGG    4949
Trp Ala Gly Leu Lys Gly Pro Asn Pro Val Pro Leu Leu Leu Arg Trp
        1545                1550                1555

GGC AAT GAT TTA CCA TCA AAA GTG GCC GGC CAC CAC ATT GTT GAC GAC    4997
Gly Asn Asp Leu Pro Ser Lys Val Ala Gly His His Ile Val Asp Asp
        1560                1565                1570

CTG GTT CGT AGG CTT GGT GTG GCG GAG GGT TAT GTC CGC TGC GAT GCG    5045
Leu Val Arg Arg Leu Gly Val Ala Glu Gly Tyr Val Arg Cys Asp Ala
1575            1580                1585                1590

GGG CCG ATC TTA ATG GTC GGC CTC GCT ATC GCG GGG GGG ATG ATC TAC    5093
Gly Pro Ile Leu Met Val Gly Leu Ala Ile Ala Gly Gly Met Ile Tyr
                1595                1600                1605

GCA TCT TAC ACC GGG TCT TTA GTG GTG GTG ACA GAC TGG GAT GTA AAG    5141
Ala Ser Tyr Thr Gly Ser Leu Val Val Val Thr Asp Trp Asp Val Lys
                    1610                1615                1620

GGG GGT GGC AGC CCT CTT TAT CGG CAT GGA GAC CAG GCC ACG CCA CAG    5189
Gly Gly Gly Ser Pro Leu Tyr Arg His Gly Asp Gln Ala Thr Pro Gln
                    1625                1630                1635

CCG GTT GTG CAG GTC CCC CCG GTA GAC CAT CGG CCG GGG GGG GAG TCT    5237
Pro Val Val Gln Val Pro Pro Val Asp His Arg Pro Gly Gly Glu Ser
1640                1645                1650

GCG CCT TCG GAT GCC AAG ACA GTG ACA GAT GCG GTG GCG GCC ATC CAG    5285
Ala Pro Ser Asp Ala Lys Thr Val Thr Asp Ala Val Ala Ala Ile Gln
1655                1660                1665                1670

GTG GAT TGC GAT TGG TCA GTC ATG ACC CTG TCG ATC GGG GAA GTG CTG    5333
Val Asp Cys Asp Trp Ser Val Met Thr Leu Ser Ile Gly Glu Val Leu
                    1675                1680                1685

TCC TTG GCT CAG GCT AAA ACA GCT GAG GCC TAC ACG GCA ACC GCC AAG    5381
Ser Leu Ala Gln Ala Lys Thr Ala Glu Ala Tyr Thr Ala Thr Ala Lys
                        1690                1695                1700

TGG CTC GCT GGC TGC TAC ACG GGG ACG CGG GCC GTT CCC ACT GTT TCA    5429
Trp Leu Ala Gly Cys Tyr Thr Gly Thr Arg Ala Val Pro Thr Val Ser
                        1705                1710                1715

ATT GTT GAC AAG CTC TTT GCC GGA GGG TGG GCG GCT GTG GTT GGC CAC    5477
Ile Val Asp Lys Leu Phe Ala Gly Gly Trp Ala Ala Val Val Gly His
        1720                1725                1730

TGT CAC AGC GTC ATA GCT GCG GCG GTG GCT GCC TAC GGG GCT TCC AGG    5525
Cys His Ser Val Ile Ala Ala Ala Val Ala Ala Tyr Gly Ala Ser Arg
1735                1740                1745                1750

AGT CCG CCG TTG GCA GCC GCG GCT TCC TAC CTG ATG GGA CTG GGC GTC    5573
Ser Pro Pro Leu Ala Ala Ala Ala Ser Tyr Leu Met Gly Leu Gly Val
                1755                1760                1765

GGA GGC AAC GCT CAG ACG CGT TTG GCG TCT GCC CTC CTG TTG GGG GCC    5621
Gly Gly Asn Ala Gln Thr Arg Leu Ala Ser Ala Leu Leu Leu Gly Ala
                    1770                1775                1780

GCT GGC ACC GCC CTG GGC ACT CCC GTC GTG GGT TTA ACC ATG GCG GGG    5669
Ala Gly Thr Ala Leu Gly Thr Pro Val Val Gly Leu Thr Met Ala Gly
            1785                1790                1795

GCG TTC ATG GGG GGT GCT AGC GTC TCT CCC TCC TTG GTC ACC ATC TTG    5717
Ala Phe Met Gly Gly Ala Ser Val Ser Pro Ser Leu Val Thr Ile Leu
1800                1805                1810

TTG GGG GCC GTG GGA GGC TGG GAG GGC GTC GTC AAC GCT GCT AGC CTT    5765
Leu Gly Ala Val Gly Gly Trp Glu Gly Val Val Asn Ala Ala Ser Leu
1815                1820                1825                1830

GTC TTT GAC TTC ATG GCG GGG AAA CTA TCG TCA GAA GAT CTG TGG TAC    5813
Val Phe Asp Phe Met Ala Gly Lys Leu Ser Ser Glu Asp Leu Trp Tyr
            1835                1840                1845
```

```
GCC ATC CCA GTG CTC ACC AGC CCG GGG GCG GGC CTT GCG GGG ATC GCC    5861
Ala Ile Pro Val Leu Thr Ser Pro Gly Ala Gly Leu Ala Gly Ile Ala
        1850            1855            1860

CTT GGG TTG GTG CTG TAC TCA GCT AAC AAC TCT GGT ACT ACC ACT TGG    5909
Leu Gly Leu Val Leu Tyr Ser Ala Asn Asn Ser Gly Thr Thr Thr Trp
        1865            1870            1875

TTG AAC CGT CTG CTG ACT ACG TTA CCT AGG TCT TCT TGC ATC CCT GAC    5957
Leu Asn Arg Leu Leu Thr Thr Leu Pro Arg Ser Ser Cys Ile Pro Asp
        1880            1885            1890

AGC TAT TTC CAA CAG GCC GAT TAC TGT GAC AAG GTC TCG GCC GTG CTT    6005
Ser Tyr Phe Gln Gln Ala Asp Tyr Cys Asp Lys Val Ser Ala Val Leu
1895            1900            1905            1910

CGC CGA CTG AGC CTC ACC CGC ACT GTG GTG GCC CTA GTC AAT AGG GAA    6053
Arg Arg Leu Ser Leu Thr Arg Thr Val Val Ala Leu Val Asn Arg Glu
        1915            1920            1925

CCC AAG GTG GAC GAG GTA CAG GTG GGG TAC GTC TGG GAT CTC TGG GAG    6101
Pro Lys Val Asp Glu Val Gln Val Gly Tyr Val Trp Asp Leu Trp Glu
        1930            1935            1940

TGG ATC ATG CGT CAA GTG CGC ATG GTC ATG GCC AGG CTC CGG GCT CTC    6149
Trp Ile Met Arg Gln Val Arg Met Val Met Ala Arg Leu Arg Ala Leu
        1945            1950            1955

TGC CCC GTG GTG TCA CTG CCT TTG TGG CAC TGC GGG GAG GGG TGG TCC    6197
Cys Pro Val Val Ser Leu Pro Leu Trp His Cys Gly Glu Gly Trp Ser
        1960            1965            1970

GGA GAG TGG TTG TTG GAC GGC CAT GTG GAG AGT CGC TGT CTT TGC GGG    6245
Gly Glu Trp Leu Leu Asp Gly His Val Glu Ser Arg Cys Leu Cys Gly
1975            1980            1985            1990

TGC GTG ATC ACC GGC GAT GTT TTC AAT GGG CAA CTC AAA GAG CCA GTT    6293
Cys Val Ile Thr Gly Asp Val Phe Asn Gly Gln Leu Lys Glu Pro Val
        1995            2000            2005

TAC TCT ACA AAG TTG TGC CGG CAC TAT TGG ATG GGG ACC GTT CCT GTG    6341
Tyr Ser Thr Lys Leu Cys Arg His Tyr Trp Met Gly Thr Val Pro Val
        2010            2015            2020

AAC ATG CTG GGT TAC GGC GAA ACA TCA CCC CTC TTG GCC TCT GAC ACC    6389
Asn Met Leu Gly Tyr Gly Glu Thr Ser Pro Leu Leu Ala Ser Asp Thr
        2025            2030            2035

CCG AAG GTG GTG CCT TTT GGG ACG TCG GGC TGG GCT GAG GTG GTG GTG    6437
Pro Lys Val Val Pro Phe Gly Thr Ser Gly Trp Ala Glu Val Val Val
        2040            2045            2050

ACC CCT ACC CAC GTG GTG ATC AGG AGA ACC TCT CCC TAC GAG TTG CTG    6485
Thr Pro Thr His Val Val Ile Arg Arg Thr Ser Pro Tyr Glu Leu Leu
2055            2060            2065            2070

CGC CAA CAA ATC CTA TCA GCT GCA GTT GCT GAG CCC TAT TAT GTC GAC    6533
Arg Gln Gln Ile Leu Ser Ala Ala Val Ala Glu Pro Tyr Tyr Val Asp
        2075            2080            2085

GGC ATA CCG GTC TCA TGG GAC GCG GAC GCT CGT GCG CCT GCT ATG GTT    6581
Gly Ile Pro Val Ser Trp Asp Ala Asp Ala Arg Ala Pro Ala Met Val
        2090            2095            2100

TAT GGC CCT GGG CAA AGT GTT ACC ATT GAC GGG GAG CGC TAC ACC CTG    6629
Tyr Gly Pro Gly Gln Ser Val Thr Ile Asp Gly Glu Arg Tyr Thr Leu
        2105            2110            2115

CCG CAT CAA CTG CGG CTC AGG AAT GTA GCG CCC TCT GAG GTT TCA TCC    6677
Pro His Gln Leu Arg Leu Arg Asn Val Ala Pro Ser Glu Val Ser Ser
        2120            2125            2130

GAG GTG TCC ATA GAC ATT GGG ACG GAG ACT GAA GAC TCA GAA CTG ACT    6725
Glu Val Ser Ile Asp Ile Gly Thr Glu Thr Glu Asp Ser Glu Leu Thr
2135            2140            2145            2150

GAG GCC GAC CTG CCG CCG GCA GCT GCA GCC CTC CAG GCT ATC GAG AAT    6773
Glu Ala Asp Leu Pro Pro Ala Ala Ala Ala Leu Gln Ala Ile Glu Asn
        2155            2160            2165
```

```
GCT GCG AGG ATT CTT GAG CCT CAT ATT GAT GTC ATC ATG GAG GAT TGC       6821
Ala Ala Arg Ile Leu Glu Pro His Ile Asp Val Ile Met Glu Asp Cys
        2170                2175                2180

AGT ACA CCC TCT CTT TGT GGT AGT AGC CGA GAG ATG CCT GTG TGG GGA       6869
Ser Thr Pro Ser Leu Cys Gly Ser Ser Arg Glu Met Pro Val Trp Gly
        2185                2190                2195

GAA GAC ATC CCC CGC ACT CCA TCG CCA GCA CTT ATC TCG GTT ACC GAG       6917
Glu Asp Ile Pro Arg Thr Pro Ser Pro Ala Leu Ile Ser Val Thr Glu
        2200                2205                2210

AGC AGC TCA GAT GAG AAG ACC CCG TCG GTG TCC TCC TCG CAG GAG GAT       6965
Ser Ser Ser Asp Glu Lys Thr Pro Ser Val Ser Ser Ser Gln Glu Asp
2215                2220                2225                2230

ACC CCG TCC TCT GAC TCA TTC GAA GTC ATC CAA GAG TCT GAG ACA GCT       7013
Thr Pro Ser Ser Asp Ser Phe Glu Val Ile Gln Glu Ser Glu Thr Ala
                2235                2240                2245

GAA GGA GAG GAA AGT GTC TTC AAC GTG GCT CTT TCC GTA CTA GAA GCC       7061
Glu Gly Glu Glu Ser Val Phe Asn Val Ala Leu Ser Val Leu Glu Ala
        2250                2255                2260

TTG TTT CCA CAG AGT GAT GCC ACT AGA AAG CTT ACC GTC AGG ATG AAT       7109
Leu Phe Pro Gln Ser Asp Ala Thr Arg Lys Leu Thr Val Arg Met Asn
        2265                2270                2275

TGC TGC GTT GAG AAG AGC GTC ACG CGC TTC TTT TCT TTG GGG CTG ACG       7157
Cys Cys Val Glu Lys Ser Val Thr Arg Phe Phe Ser Leu Gly Leu Thr
        2280                2285                2290

GTG GCT GAT GTG GCC AGT CTG TGT GAG ATG GAG ATC CAG AAC CAT ACA       7205
Val Ala Asp Val Ala Ser Leu Cys Glu Met Glu Ile Gln Asn His Thr
2295                2300                2305                2310

GCC TAT TGT GAC AAG GTG CGC ACT CCG CTC GAA TTG CAA GTT GGG TGC       7253
Ala Tyr Cys Asp Lys Val Arg Thr Pro Leu Glu Leu Gln Val Gly Cys
                2315                2320                2325

TTG GTG GGC AAT GAA CTT ACC TTT GAA TGT GAT AAG TGT GAG GCT AGG       7301
Leu Val Gly Asn Glu Leu Thr Phe Glu Cys Asp Lys Cys Glu Ala Arg
        2330                2335                2340

CAA GAG ACT TTG GCC TCC TTC TCC TAT ATT TGG TCT GGG GTG CCA TTG       7349
Gln Glu Thr Leu Ala Ser Phe Ser Tyr Ile Trp Ser Gly Val Pro Leu
        2345                2350                2355

ACT AGG GCC ACA CCG GCT AAA CCA CCT GTG GTG AGG CCG GTG GGG TCC       7397
Thr Arg Ala Thr Pro Ala Lys Pro Pro Val Val Arg Pro Val Gly Ser
        2360                2365                2370

TTG TTG GTG GCT GAC ACC ACG AAA GTG TAT GTC ACA AAC CCG GAC AAT       7445
Leu Leu Val Ala Asp Thr Thr Lys Val Tyr Val Thr Asn Pro Asp Asn
2375                2380                2385                2390

GTT GGG AGA AGA GTG GAC AAG GTG ACC TTC TGG CGC GCC CCC AGG GTC       7493
Val Gly Arg Arg Val Asp Lys Val Thr Phe Trp Arg Ala Pro Arg Val
                2395                2400                2405

CAT GAC AAA TAT CTC GTG GAC TCC ATC GAG CGT GCC AGG AGG GCG GCT       7541
His Asp Lys Tyr Leu Val Asp Ser Ile Glu Arg Ala Arg Arg Ala Ala
        2410                2415                2420

CAA GCC TGC CAA AGC ATG GGT TAC ACT TAT GAG GAA GCA ATA AGG ACT       7589
Gln Ala Cys Gln Ser Met Gly Tyr Thr Tyr Glu Glu Ala Ile Arg Thr
        2425                2430                2435

GTT AGG CCA CAT GCT GCC ATG GGC TGG GGA TCT AAG GTG TCG GTC AAG       7637
Val Arg Pro His Ala Ala Met Gly Trp Gly Ser Lys Val Ser Val Lys
        2440                2445                2450

GAC TTG GCC ACC CCT GCG GGG AAG ATG GCC GTC CAC GAC CGA CTT CAG       7685
Asp Leu Ala Thr Pro Ala Gly Lys Met Ala Val His Asp Arg Leu Gln
2455                2460                2465                2470

GAG ATA CTT GAG GGG ACT CCG GTC CCT TTT ACT CTT ACT GTG AAA AAG       7733
Glu Ile Leu Glu Gly Thr Pro Val Pro Phe Thr Leu Thr Val Lys Lys
                2475                2480                2485
```

-continued

```
GAG GTG TTC TTC AAA GAC CGT AAG GAG GAG AAG GCC CCC CGC CTC ATT      7781
Glu Val Phe Phe Lys Asp Arg Lys Glu Glu Lys Ala Pro Arg Leu Ile
            2490                2495                2500

GTG TTC CCC CCC CTG GAC TTC CGG ATA GCT GAG AAG CTT ATC CTG GGA      7829
Val Phe Pro Pro Leu Asp Phe Arg Ile Ala Glu Lys Leu Ile Leu Gly
        2505                2510                2515

GAC CCG GGG CGG GTG GCC AAG GCG GTG TTG GGG GGG GCT TAC GCC TTC      7877
Asp Pro Gly Arg Val Ala Lys Ala Val Leu Gly Gly Ala Tyr Ala Phe
    2520                2525                2530

CAG TAC ACC CCA AAT CAG CGA GTT AAG GAG ATG CTC AAA CTG TGG GAG      7925
Gln Tyr Thr Pro Asn Gln Arg Val Lys Glu Met Leu Lys Leu Trp Glu
2535                2540                2545                2550

TCA AAG AAA ACA CCT TGC GCC ATC TGT GTG GAC GCC ACT TGC TTC GAC      7973
Ser Lys Lys Thr Pro Cys Ala Ile Cys Val Asp Ala Thr Cys Phe Asp
                2555                2560                2565

AGT AGC ATT ACT GAA GAG GAC GTG GCG CTG GAG ACA GAG CTG TAC GCT      8021
Ser Ser Ile Thr Glu Glu Asp Val Ala Leu Glu Thr Glu Leu Tyr Ala
            2570                2575                2580

CTG GCC TCT GAC CAT CCA GAG TGG GTG CGA GCT TTG GGG AAG TAC TAT      8069
Leu Ala Ser Asp His Pro Glu Trp Val Arg Ala Leu Gly Lys Tyr Tyr
        2585                2590                2595

GCC TCA GGA ACC ATG GTC ACC CCT GAG GGG GTT CCC GTA GGT GAG AGG      8117
Ala Ser Gly Thr Met Val Thr Pro Glu Gly Val Pro Val Gly Glu Arg
    2600                2605                2610

TAT TGT AGA TCC TCA GGC GTT TTG ACT ACC AGC GCG AGT AAC TGC CTG      8165
Tyr Cys Arg Ser Ser Gly Val Leu Thr Thr Ser Ala Ser Asn Cys Leu
2615                2620                2625                2630

ACC TGC TAC ATC AAG GTG AAA GCC GCT TGT GAG AGA GTG GGG CTG AAA      8213
Thr Cys Tyr Ile Lys Val Lys Ala Ala Cys Glu Arg Val Gly Leu Lys
                2635                2640                2645

AAT GTC TCG CTT CTC ATA GCC GGC GAT GAC TGT TTG ATC ATA TGC GAA      8261
Asn Val Ser Leu Leu Ile Ala Gly Asp Asp Cys Leu Ile Ile Cys Glu
            2650                2655                2660

CGG CCA GTG TGC GAC CCT TGT GAC GCC TTG GGC AGA GCC CTG GCG AGC      8309
Arg Pro Val Cys Asp Pro Cys Asp Ala Leu Gly Arg Ala Leu Ala Ser
        2665                2670                2675

TAT GGG TAT GCT TGC GAG CCT TCG TAT CAT GCA TCA CTG GAC ACG GCC      8357
Tyr Gly Tyr Ala Cys Glu Pro Ser Tyr His Ala Ser Leu Asp Thr Ala
    2680                2685                2690

CCC TTC TGC TCC ACT TGG CTC GCT GAG TGC AAC GCA GAT GGG AAA CGC      8405
Pro Phe Cys Ser Thr Trp Leu Ala Glu Cys Asn Ala Asp Gly Lys Arg
2695                2700                2705                2710

CAT TTC TTC CTG ACC ACG GAC TTT CGG AGG CCG CTT GCT CGC ATG TCG      8453
His Phe Phe Leu Thr Thr Asp Phe Arg Arg Pro Leu Ala Arg Met Ser
                2715                2720                2725

AGC GAG TAT AGT GAC CCA ATG GCT TCG GCC ATA GGT TAC ATC CTC CTG      8501
Ser Glu Tyr Ser Asp Pro Met Ala Ser Ala Ile Gly Tyr Ile Leu Leu
            2730                2735                2740

TAT CCC TGG CAT CCC ATC ACA CGG TGG GTC ATC ATC CCT CAT GTG CTA      8549
Tyr Pro Trp His Pro Ile Thr Arg Trp Val Ile Ile Pro His Val Leu
        2745                2750                2755

ACG TGC GCA TTC AGG GGT GGT GGT ACA CCG TCT GAT CCG GTT TGG TGT      8597
Thr Cys Ala Phe Arg Gly Gly Gly Thr Pro Ser Asp Pro Val Trp Cys
    2760                2765                2770

CAG GTG CAT GGT AAC TAC TAC AAG TTT CCA CTG GAC AAA CTG CCT AAC      8645
Gln Val His Gly Asn Tyr Tyr Lys Phe Pro Leu Asp Lys Leu Pro Asn
2775                2780                2785                2790

ATC ATC GTG GCC CTC CAC GGA CCA GCA GCG TTG AGG GTT ACC GCA GAC      8693
Ile Ile Val Ala Leu His Gly Pro Ala Ala Leu Arg Val Thr Ala Asp
                2795                2800                2805
```

|  |  |  |  |  |  |  |  |  |  |  |  |  |  |  |  |
|---|---|---|---|---|---|---|---|---|---|---|---|---|---|---|---|
| ACA | ACT | AAG | ACA | AAA | ATG | GAA | GCT | GGG | AAG | GTG | CTG | AGT | GAC | CTC | AAG |
| Thr | Thr | Lys | Thr 2810 | Lys | Met | Glu | Ala | Gly 2815 | Lys | Val | Leu | Ser | Asp 2820 | Leu | Lys |

8741

|  |  |  |  |  |  |  |  |  |  |  |  |  |  |  |  |
|---|---|---|---|---|---|---|---|---|---|---|---|---|---|---|---|
| CTC | CCT | GGC | CTA | GCG | GTC | CAC | CGA | AAG | AAG | GCC | GGA | GCA | CTG | CGA | ACA |
| Leu | Pro | Gly 2825 | Leu | Ala | Val | His | Arg | Lys 2830 | Lys | Ala | Gly | Ala | Leu 2835 | Arg | Thr |

8789

|  |  |  |  |  |  |  |  |  |  |  |  |  |  |  |  |
|---|---|---|---|---|---|---|---|---|---|---|---|---|---|---|---|
| CGC | ATG | CTT | CGG | TCG | CGC | GGT | TGG | GCC | GAG | TTG | GCG | AGG | GGC | CTG | TTG |
| Arg | Met 2840 | Leu | Arg | Ser | Arg | Gly | Trp | Ala 2845 | Glu | Leu | Ala | Arg | Gly 2850 | Leu | Leu |

8837

|  |  |  |  |  |  |  |  |  |  |  |  |  |  |  |  |
|---|---|---|---|---|---|---|---|---|---|---|---|---|---|---|---|
| TGG | CAT | CCA | GGC | CTC | CGG | CTC | CCT | CCC | CCT | GAG | ATT | GCT | GGT | ATC | CCG |
| Trp 2855 | His | Pro | Gly | Leu | Arg 2860 | Leu | Pro | Pro | Pro | Glu 2865 | Ile | Ala | Gly | Ile | Pro 2870 |

8885

|  |  |  |  |  |  |  |  |  |  |  |  |  |  |  |  |
|---|---|---|---|---|---|---|---|---|---|---|---|---|---|---|---|
| GGG | GGT | TTC | CCC | CTC | TCC | CCC | CCC | TAC | ATG | GGG | GTG | GTG | CAT | CAA | TTG |
| Gly | Gly | Phe | Pro | Leu 2875 | Ser | Pro | Pro | Tyr | Met 2880 | Gly | Val | Val | His | Gln 2885 | Leu |

8933

|  |  |  |  |  |  |  |  |  |  |  |  |  |  |  |  |
|---|---|---|---|---|---|---|---|---|---|---|---|---|---|---|---|
| GAT | TTT | ACA | AGC | CAG | AGG | AGT | CGC | TGG | CGG | TGG | CTG | GGG | TTC | TTA | GCC |
| Asp | Phe | Thr | Ser 2890 | Gln | Arg | Ser | Arg | Trp 2895 | Arg | Trp | Leu | Gly | Phe 2900 | Leu | Ala |

8981

|  |  |  |  |  |  |  |  |  |  |
|---|---|---|---|---|---|---|---|---|---|
| CTG | CTC | ATC | GTA | GCC | CTC | TTC | GGG | TGAACTAAAT | TCATCTGTTG CGGCAAGGTC |
| Leu | Leu | Ile | Val 2905 | Ala | Leu | Phe | Gly 2910 |  |  |

9035

CAGTGACTGA TCATCACTGG AGGAGGTTCC CGCCCTCCCC GCCCCAGGGG TCTCCCCGCT 9095

GGGTAAAA 9103

( 2 ) INFORMATION FOR SEQ ID NO:183:

( i ) SEQUENCE CHARACTERISTICS:
        ( A ) LENGTH: 2910 amino acids
        ( B ) TYPE: amino acid
        ( D ) TOPOLOGY: linear ( i i ) MOLECULE TYPE: protein ( x i ) SEQUENCE DESCRIPTION: SEQ ID NO:183:

| Met 1 | Ser | Leu | Leu | Thr 5 | Asn | Arg | Leu | Ser | Arg 10 | Arg | Val | Asp | Lys | Asp 15 | Gln |
|---|---|---|---|---|---|---|---|---|---|---|---|---|---|---|---|
| Trp | Gly | Pro | Gly 20 | Phe | Met | Gly | Lys | Asp 25 | Pro | Lys | Pro | Cys | Pro 30 | Ser | Arg |
| Arg | Thr | Gly 35 | Lys | Cys | Met | Gly | Pro 40 | Ser | Ser | Ala | Ala | Ala 45 | Cys | Ser |  |
| Arg | Gly 50 | Ser | Pro | Arg | Ile | Leu 55 | Arg | Val | Arg | Ala | Gly 60 | Gly | Ile | Ser | Leu |
| Pro 65 | Tyr | Thr | Ile | Met | Glu 70 | Ala | Leu | Leu | Phe | Leu 75 | Leu | Gly | Val | Glu | Ala 80 |
| Gly | Ala | Ile | Leu | Ala 85 | Pro | Ala | Thr | His | Ala 90 | Cys | Arg | Ala | Asn | Gly 95 | Gln |
| Tyr | Phe | Leu | Thr 100 | Asn | Cys | Cys | Ala | Pro 105 | Glu | Asp | Ile | Gly | Phe 110 | Cys | Leu |
| Glu | Gly | Gly 115 | Cys | Leu | Val | Ala | Leu 120 | Gly | Cys | Thr | Val | Cys 125 | Thr | Asp | Arg |
| Cys | Trp 130 | Pro | Leu | Tyr | Gln | Ala 135 | Gly | Leu | Ala | Val | Arg 140 | Pro | Gly | Lys | Ser |
| Ala 145 | Ala | Gln | Leu | Val | Gly 150 | Gln | Leu | Gly | Gly | Leu 155 | Tyr | Gly | Pro | Leu | Ser 160 |
| Val | Ser | Ala | Tyr | Val 165 | Ala | Gly | Ile | Leu | Gly 170 | Leu | Gly | Glu | Val | Tyr 175 | Ser |
| Gly | Val | Leu | Thr 180 | Val | Gly | Val | Ala | Leu 185 | Thr | Arg | Arg | Val | Tyr 190 | Pro | Met |

| | | | | | | | | | | | | | | |
|---|---|---|---|---|---|---|---|---|---|---|---|---|---|---|
|Pro|Asn|Leu 195|Thr|Cys|Ala|Val|Glu 200|Cys|Glu|Leu|Lys|Trp 205|Glu|Ser|Glu|
|Phe|Trp 210|Arg|Trp|Thr|Glu|Gln 215|Leu|Ala|Ser|Asn|Tyr 220|Trp|Ile|Leu|Glu|
|Tyr 225|Leu|Trp|Lys|Val|Pro 230|Phe|Asp|Phe|Trp|Arg 235|Gly|Val|Leu|Ser|Leu 240|
|Thr|Pro|Leu|Leu|Val 245|Cys|Val|Ala|Ala|Leu 250|Leu|Leu|Leu|Glu|Gln 255|Arg|
|Ile|Val|Met|Val 260|Phe|Leu|Leu|Val|Thr 265|Met|Ala|Gly|Met|Ser 270|Gln|Gly|
|Ala|Pro|Ala 275|Ser|Val|Leu|Gly|Ser 280|Arg|Pro|Phe|Asp|Tyr 285|Gly|Leu|Thr|
|Trp|Gln 290|Ser|Cys|Ser|Cys|Arg 295|Ala|Asn|Gly|Ser|Arg 300|Tyr|Thr|Thr|Gly|
|Glu 305|Lys|Val|Trp|Asp|Arg 310|Gly|Asn|Val|Thr|Leu 315|Leu|Cys|Asp|Cys|Pro 320|
|Asn|Gly|Pro|Trp|Val 325|Trp|Leu|Pro|Ala|Phe 330|Cys|Gln|Ala|Ile|Gly 335|Trp|
|Gly|Asp|Pro|Ile 340|Thr|His|Trp|Ser|His 345|Gly|Gln|Asn|Arg|Trp 350|Pro|Leu|
|Ser|Cys|Pro 355|Gln|Tyr|Val|Tyr|Gly 360|Ser|Val|Ser|Val|Thr 365|Cys|Val|Trp|
|Gly|Ser 370|Val|Ser|Trp|Phe|Ala 375|Ser|Thr|Gly|Gly|Arg 380|Asp|Ser|Lys|Ile|
|Asp 385|Val|Trp|Ser|Leu|Val 390|Pro|Val|Gly|Ser|Ala 395|Ser|Cys|Thr|Ile|Ala 400|
|Ala|Leu|Gly|Ser|Ser 405|Asp|Arg|Asp|Thr|Val 410|Val|Glu|Leu|Ser|Glu 415|Trp|
|Gly|Val|Pro|Cys 420|Ala|Thr|Cys|Ile|Leu 425|Asp|Arg|Arg|Pro|Ala 430|Ser|Cys|
|Gly|Thr|Cys 435|Val|Arg|Asp|Cys|Trp 440|Pro|Glu|Thr|Gly|Ser 445|Val|Arg|Phe|
|Pro|Phe 450|His|Arg|Cys|Gly|Ala 455|Gly|Pro|Lys|Leu|Thr 460|Lys|Asp|Leu|Glu|
|Ala 465|Val|Pro|Phe|Val|Asn 470|Arg|Thr|Thr|Pro|Phe 475|Thr|Ile|Arg|Gly|Pro 480|
|Leu|Gly|Asn|Gln|Gly 485|Arg|Gly|Asn|Pro|Val 490|Arg|Ser|Pro|Leu|Gly 495|Phe|
|Gly|Ser|Tyr|Ala 500|Met|Thr|Lys|Ile|Arg 505|Asp|Ser|Leu|His|Leu 510|Val|Lys|
|Cys|Pro|Thr 515|Pro|Ala|Ile|Glu|Pro 520|Pro|Thr|Gly|Thr|Phe 525|Gly|Phe|Phe|
|Pro|Gly 530|Val|Pro|Pro|Leu|Asn 535|Asn|Cys|Leu|Leu|Leu 540|Gly|Thr|Glu|Val|
|Ser 545|Glu|Ala|Leu|Gly|Gly 550|Ala|Gly|Leu|Thr|Gly 555|Gly|Phe|Tyr|Glu|Pro 560|
|Leu|Val|Arg|Arg|Arg 565|Ser|Glu|Leu|Met|Gly 570|Arg|Arg|Asn|Pro|Val 575|Cys|
|Pro|Gly|Phe|Ala 580|Trp|Leu|Ser|Ser|Gly 585|Arg|Pro|Asp|Gly|Phe 590|Ile|His|
|Val|Gln|Gly 595|His|Leu|Gln|Glu|Val 600|Asp|Ala|Gly|Asn|Phe 605|Ile|Pro|Pro|
|Pro|Arg|Trp|Leu|Leu|Leu|Asp|Phe|Val|Phe|Val|Leu|Leu|Tyr|Leu|Met|

-continued

|     |     |     | 610 |     |     |     |     | 615 |     |     |     | 620 |     |     |     |
|-----|-----|-----|-----|-----|-----|-----|-----|-----|-----|-----|-----|-----|-----|-----|-----|
| Lys 625 | Leu | Ala | Glu | Ala | Arg 630 | Leu | Val | Pro | Leu 635 | Ile | Leu | Leu | Leu | Trp 640 |
| Trp | Trp | Val | Asn | Gln 645 | Leu | Ala | Val | Leu | Gly 650 | Leu | Pro | Ala | Val | Asp 655 | Ala |
| Ala | Val | Ala | Gly 660 | Glu | Val | Phe | Ala | Gly 665 | Pro | Ala | Leu | Ser | Trp 670 | Cys | Leu |
| Gly | Leu | Pro | Thr 675 | Val | Ser | Met | Ile 680 | Leu | Gly | Leu | Ala | Asn 685 | Leu | Val | Leu |
| Tyr | Phe 690 | Arg | Trp | Met | Gly | Pro 695 | Gln | Arg | Leu | Met | Phe 700 | Leu | Val | Leu | Trp |
| Lys 705 | Leu | Ala | Arg | Gly | Ala 710 | Phe | Pro | Leu | Ala | Leu 715 | Leu | Met | Gly | Ile | Ser 720 |
| Ala | Thr | Arg | Gly | Arg 725 | Thr | Ser | Val | Leu | Gly 730 | Ala | Glu | Phe | Cys | Phe 735 | Asp |
| Val | Thr | Phe | Glu 740 | Val | Asp | Thr | Ser | Val 745 | Leu | Gly | Trp | Val | Val 750 | Ala | Ser |
| Val | Val | Ala 755 | Trp | Ala | Ile | Ala | Leu 760 | Leu | Ser | Ser | Met | Ser 765 | Ala | Gly | Gly |
| Trp | Arg 770 | His | Lys | Ala | Val | Ile 775 | Tyr | Arg | Thr | Trp | Cys 780 | Lys | Gly | Tyr | Gln |
| Ala 785 | Ile | Arg | Gln | Arg | Val 790 | Val | Arg | Ser | Pro | Leu 795 | Gly | Glu | Gly | Arg | Pro 800 |
| Thr | Lys | Pro | Leu | Thr 805 | Phe | Ala | Trp | Cys | Leu 810 | Ala | Ser | Tyr | Ile | Trp 815 | Pro |
| Asp | Ala | Val | Met 820 | Met | Val | Val | Val | Ala 825 | Leu | Val | Leu | Leu | Phe 830 | Gly | Leu |
| Phe | Asp | Ala 835 | Leu | Asp | Trp | Ala | Leu 840 | Glu | Glu | Leu | Leu | Val 845 | Ser | Arg | Pro |
| Ser | Leu | Arg 850 | Arg | Leu | Ala | Arg 855 | Val | Val | Glu | Cys | Cys 860 | Val | Met | Ala | Gly |
| Glu 865 | Lys | Ala | Thr | Thr | Val 870 | Arg | Leu | Val | Ser | Lys 875 | Met | Cys | Ala | Arg | Gly 880 |
| Ala | Tyr | Leu | Phe | Asp 885 | His | Met | Gly | Ser | Phe 890 | Ser | Arg | Ala | Val | Lys 895 | Glu |
| Arg | Leu | Leu | Glu 900 | Trp | Asp | Ala | Ala | Leu 905 | Glu | Pro | Leu | Ser | Phe 910 | Thr | Arg |
| Thr | Asp | Cys 915 | Arg | Ile | Ile | Arg | Asp 920 | Ala | Ala | Arg | Thr | Leu 925 | Ala | Cys | Gly |
| Gln | Cys 930 | Val | Met | Gly | Leu | Pro 935 | Val | Val | Ala | Arg | Arg 940 | Gly | Asp | Glu | Val |
| Leu 945 | Ile | Gly | Val | Phe | Gln 950 | Asp | Val | Asn | His | Leu 955 | Pro | Pro | Gly | Phe | Val 960 |
| Pro | Thr | Ala | Pro | Val 965 | Val | Ile | Arg | Arg | Cys 970 | Gly | Lys | Gly | Phe | Leu 975 | Gly |
| Val | Thr | Lys | Ala 980 | Ala | Leu | Thr | Gly | Arg 985 | Asp | Pro | Asp | Leu | His 990 | Pro | Gly |
| Asn | Val | Met 995 | Val | Leu | Gly | Thr | Ala 1000 | Thr | Ser | Arg | Ser | Met 1005 | Gly | Thr | Cys |
| Leu | Asn | Gly 1010 | Leu | Leu | Phe | Thr 1015 | Thr | Phe | His | Gly | Ala 1020 | Ser | Ser | Arg | Thr |
| Ile 1025 | Ala | Thr | Pro | Val | Gly 1030 | Ala | Leu | Asn | Pro | Arg 1035 | Trp | Trp | Ser | Ala | Ser 1040 |

| | | | | | | | | | | | | | | |
|---|---|---|---|---|---|---|---|---|---|---|---|---|---|---|
|Asp|Asp|Val|Thr|Val|Tyr|Pro|Leu|Pro|Asp|Gly|Ala|Thr|Ser|Leu|Thr|
| | | | |1045| | | |1050| | | |1055| | |
|Pro|Cys|Thr|Cys|Gln|Ala|Glu|Ser|Cys|Trp|Val|Ile|Arg|Ser|Asp|Gly|
| | | |1060| | | |1065| | | |1070| | | | |
|Ala|Leu|Cys|His|Gly|Leu|Ser|Lys|Gly|Asp|Lys|Val|Glu|Leu|Asp|Val|
| | |1075| | | |1080| | | |1085| | | | | |
|Ala|Met|Glu|Val|Ser|Asp|Phe|Arg|Gly|Ser|Ser|Gly|Ser|Pro|Val|Leu|
| |1090| | | |1095| | | |1100| | | | | | |
|Cys|Asp|Glu|Gly|His|Ala|Val|Gly|Met|Leu|Val|Ser|Val|Leu|His|Ser|
|1105| | | |1110| | | |1115| | | |1120| | | |
|Gly|Gly|Arg|Val|Thr|Ala|Ala|Arg|Phe|Thr|Arg|Pro|Trp|Thr|Gln|Val|
| | | |1125| | | |1130| | | |1135| | | | |
|Pro|Thr|Asp|Ala|Lys|Thr|Thr|Thr|Glu|Pro|Pro|Val|Pro|Ala|Lys|
| | |1140| | | |1145| | | |1150| | | | | |
|Gly|Val|Phe|Lys|Glu|Ala|Pro|Leu|Phe|Met|Pro|Thr|Gly|Ala|Gly|Lys|
| | |1155| | | |1160| | | |1165| | | | | |
|Ser|Thr|Arg|Val|Pro|Leu|Glu|Tyr|Gly|Asn|Met|Gly|His|Lys|Val|Leu|
| |1170| | | |1175| | | |1180| | | | | | |
|Ile|Leu|Asn|Pro|Ser|Val|Ala|Thr|Val|Arg|Ala|Met|Gly|Pro|Tyr|Met|
|1185| | | |1190| | | |1195| | | |1200| | | |
|Glu|Arg|Leu|Ala|Gly|Lys|His|Pro|Ser|Ile|Tyr|Cys|Gly|His|Asp|Thr|
| | | |1205| | | |1210| | | |1215| | | | |
|Thr|Ala|Phe|Thr|Arg|Ile|Thr|Asp|Ser|Pro|Leu|Thr|Tyr|Ser|Thr|Tyr|
| |1220| | | |1225| | | |1230| | | | | | |
|Gly|Arg|Phe|Leu|Ala|Asn|Pro|Arg|Gln|Met|Leu|Arg|Gly|Val|Ser|Val|
| |1235| | | |1240| | | |1245| | | | | | |
|Val|Ile|Cys|Asp|Glu|Cys|His|Ser|His|Asp|Ser|Thr|Val|Leu|Leu|Gly|
| |1250| | | |1255| | | |1260| | | | | | |
|Ile|Gly|Arg|Val|Arg|Glu|Leu|Ala|Arg|Glu|Cys|Gly|Val|Gln|Leu|Val|
|1265| | | |1270| | | |1275| | | |1280| | | |
|Leu|Tyr|Ala|Thr|Ala|Thr|Pro|Pro|Gly|Ser|Pro|Met|Thr|Gln|His|Pro|
| | |1285| | | |1290| | | |1295| | | | | |
|Ser|Ile|Ile|Glu|Thr|Lys|Leu|Asp|Val|Gly|Glu|Ile|Pro|Phe|Tyr|Gly|
| |1300| | | |1305| | | |1310| | | | | | |
|His|Gly|Ile|Pro|Leu|Glu|Arg|Met|Arg|Thr|Gly|Arg|His|Leu|Val|Phe|
| |1315| | | |1320| | | |1325| | | | | | |
|Cys|Tyr|Ser|Lys|Ala|Glu|Cys|Glu|Arg|Leu|Ala|Gly|Gln|Phe|Ser|Ala|
| |1330| | | |1335| | | |1340| | | | | | |
|Arg|Gly|Val|Asn|Ala|Ile|Ala|Tyr|Tyr|Arg|Gly|Lys|Asp|Ser|Ser|Ile|
|1345| | | |1350| | | |1355| | | |1360| | | |
|Ile|Lys|Asp|Gly|Asp|Leu|Val|Val|Cys|Ala|Thr|Asp|Ala|Leu|Ser|Thr|
| | | |1365| | | |1370| | | |1375| | | | |
|Gly|Tyr|Thr|Gly|Asn|Phe|Asp|Ser|Val|Thr|Asp|Cys|Gly|Leu|Val|Val|
| | |1380| | | |1385| | | |1390| | | | | |
|Glu|Glu|Val|Val|Glu|Val|Thr|Leu|Asp|Pro|Thr|Ile|Thr|Ile|Ser|Leu|
| | |1395| | | |1400| | | |1405| | | | | |
|Arg|Thr|Val|Pro|Ala|Ser|Ala|Glu|Leu|Ser|Met|Gln|Arg|Arg|Gly|Arg|
| |1410| | | |1415| | | |1420| | | | | | |
|Thr|Gly|Arg|Gly|Arg|Ser|Gly|Arg|Tyr|Tyr|Tyr|Ala|Gly|Val|Gly|Lys|
|1425| | | |1430| | | |1435| | | |1440| | | |
|Ala|Pro|Ala|Gly|Val|Val|Arg|Ser|Gly|Pro|Val|Trp|Ser|Ala|Val|Glu|
| | | |1445| | | |1450| | | |1455| | | | |
|Ala|Gly|Val|Thr|Trp|Tyr|Gly|Met|Glu|Pro|Asp|Leu|Thr|Ala|Asn|Leu|
| | |1460| | | |1465| | | |1470| | | | | |

-continued

Leu Arg Leu Tyr Asp Asp Cys Pro Tyr Thr Ala Ala Val Ala Ala Asp
   1475              1480                1485

Ile Gly Glu Ala Ala Val Phe Phe Ser Gly Leu Ala Pro Leu Arg Met
   1490              1495                1500

His Pro Asp Val Ser Trp Ala Lys Val Arg Gly Val Asn Trp Pro Leu
1505              1510                1515                1520

Leu Val Gly Val Gln Arg Thr Met Cys Arg Glu Thr Leu Ser Pro Gly
                 1525              1530              1535

Pro Ser Asp Asp Pro Gln Trp Ala Gly Leu Lys Gly Pro Asn Pro Val
             1540              1545              1550

Pro Leu Leu Leu Arg Trp Gly Asn Asp Leu Pro Ser Lys Val Ala Gly
             1555              1560              1565

His His Ile Val Asp Asp Leu Val Arg Arg Leu Gly Val Ala Glu Gly
         1570              1575              1580

Tyr Val Arg Cys Asp Ala Gly Pro Ile Leu Met Val Gly Leu Ala Ile
1585              1590              1595              1600

Ala Gly Gly Met Ile Tyr Ala Ser Tyr Thr Gly Ser Leu Val Val Val
             1605              1610              1615

Thr Asp Trp Asp Val Lys Gly Gly Gly Ser Pro Leu Tyr Arg His Gly
             1620              1625              1630

Asp Gln Ala Thr Pro Gln Pro Val Val Gln Val Pro Pro Val Asp His
             1635              1640              1645

Arg Pro Gly Gly Glu Ser Ala Pro Ser Asp Ala Lys Thr Val Thr Asp
1650              1655              1660

Ala Val Ala Ala Ile Gln Val Asp Cys Asp Trp Ser Val Met Thr Leu
1665              1670              1675              1680

Ser Ile Gly Glu Val Leu Ser Leu Ala Gln Ala Lys Thr Ala Glu Ala
             1685              1690              1695

Tyr Thr Ala Thr Ala Lys Trp Leu Ala Gly Cys Tyr Thr Gly Thr Arg
             1700              1705              1710

Ala Val Pro Thr Val Ser Ile Val Asp Lys Leu Phe Ala Gly Gly Trp
         1715              1720              1725

Ala Ala Val Val Gly His Cys His Ser Val Ile Ala Ala Ala Val Ala
     1730              1735              1740

Ala Tyr Gly Ala Ser Arg Ser Pro Pro Leu Ala Ala Ala Ala Ser Tyr
1745              1750              1755              1760

Leu Met Gly Leu Gly Val Gly Gly Asn Ala Gln Thr Arg Leu Ala Ser
             1765              1770              1775

Ala Leu Leu Leu Gly Ala Ala Gly Thr Ala Leu Gly Thr Pro Val Val
             1780              1785              1790

Gly Leu Thr Met Ala Gly Ala Phe Met Gly Gly Ala Ser Val Ser Pro
         1795              1800              1805

Ser Leu Val Thr Ile Leu Leu Gly Ala Val Gly Gly Trp Glu Gly Val
     1810              1815              1820

Val Asn Ala Ala Ser Leu Val Phe Asp Phe Met Ala Gly Lys Leu Ser
1825              1830              1835              1840

Ser Glu Asp Leu Trp Tyr Ala Ile Pro Val Leu Thr Ser Pro Gly Ala
             1845              1850              1855

Gly Leu Ala Gly Ile Ala Leu Gly Leu Val Leu Tyr Ser Ala Asn Asn
             1860              1865              1870

Ser Gly Thr Thr Thr Trp Leu Asn Arg Leu Leu Thr Thr Leu Pro Arg
     1875              1880              1885

Ser Ser Cys Ile Pro Asp Ser Tyr Phe Gln Gln Ala Asp Tyr Cys Asp

```
                1890                    1895                   1900
Lys  Val  Ser  Ala  Val  Leu  Arg  Arg  Leu  Ser  Leu  Thr  Arg  Thr  Val  Val
1905                     1910                   1915                     1920

Ala  Leu  Val  Asn  Arg  Glu  Pro  Lys  Val  Asp  Glu  Val  Gln  Val  Gly  Tyr
                    1925                   1930                    1935

Val  Trp  Asp  Leu  Trp  Glu  Trp  Ile  Met  Arg  Gln  Val  Arg  Met  Val  Met
                    1940                   1945                    1950

Ala  Arg  Leu  Arg  Ala  Leu  Cys  Pro  Val  Val  Ser  Leu  Pro  Leu  Trp  His
                    1955                   1960                    1965

Cys  Gly  Glu  Gly  Trp  Ser  Gly  Glu  Trp  Leu  Leu  Asp  Gly  His  Val  Glu
                    1970                   1975                    1980

Ser  Arg  Cys  Leu  Cys  Gly  Cys  Val  Ile  Thr  Gly  Asp  Val  Phe  Asn  Gly
1985                     1990                   1995                     2000

Gln  Leu  Lys  Glu  Pro  Val  Tyr  Ser  Thr  Lys  Leu  Cys  Arg  His  Tyr  Trp
                    2005                   2010                    2015

Met  Gly  Thr  Val  Pro  Val  Asn  Met  Leu  Gly  Tyr  Gly  Glu  Thr  Ser  Pro
                    2020                   2025                    2030

Leu  Leu  Ala  Ser  Asp  Thr  Pro  Lys  Val  Val  Pro  Phe  Gly  Thr  Ser  Gly
                    2035                   2040                    2045

Trp  Ala  Glu  Val  Val  Val  Thr  Pro  Thr  His  Val  Val  Ile  Arg  Arg  Thr
                    2050                   2055                    2060

Ser  Pro  Tyr  Glu  Leu  Leu  Arg  Gln  Gln  Ile  Leu  Ser  Ala  Ala  Val  Ala
2065                     2070                   2075                     2080

Glu  Pro  Tyr  Tyr  Val  Asp  Gly  Ile  Pro  Val  Ser  Trp  Asp  Ala  Asp  Ala
                    2085                   2090                    2095

Arg  Ala  Pro  Ala  Met  Val  Tyr  Gly  Pro  Gly  Gln  Ser  Val  Thr  Ile  Asp
                    2100                   2105                    2110

Gly  Glu  Arg  Tyr  Thr  Leu  Pro  His  Gln  Leu  Arg  Leu  Arg  Asn  Val  Ala
                    2115                   2120                    2125

Pro  Ser  Glu  Val  Ser  Ser  Glu  Val  Ser  Ile  Asp  Ile  Gly  Thr  Glu  Thr
                    2130                   2135                    2140

Glu  Asp  Ser  Glu  Leu  Thr  Glu  Ala  Asp  Leu  Pro  Pro  Ala  Ala  Ala  Ala
2145                     2150                   2155                     2160

Leu  Gln  Ala  Ile  Glu  Asn  Ala  Ala  Arg  Ile  Leu  Glu  Pro  His  Ile  Asp
                    2165                   2170                    2175

Val  Ile  Met  Glu  Asp  Cys  Ser  Thr  Pro  Ser  Leu  Cys  Gly  Ser  Ser  Arg
                    2180                   2185                    2190

Glu  Met  Pro  Val  Trp  Gly  Glu  Asp  Ile  Pro  Arg  Thr  Pro  Ser  Pro  Ala
                    2195                   2200                    2205

Leu  Ile  Ser  Val  Thr  Glu  Ser  Ser  Ser  Asp  Glu  Lys  Thr  Pro  Ser  Val
                    2210                   2215                    2220

Ser  Ser  Ser  Gln  Glu  Asp  Thr  Pro  Ser  Ser  Asp  Ser  Phe  Glu  Val  Ile
2225                     2230                   2235                     2240

Gln  Glu  Ser  Glu  Thr  Ala  Glu  Gly  Glu  Glu  Ser  Val  Phe  Asn  Val  Ala
                    2245                   2250                    2255

Leu  Ser  Val  Leu  Glu  Ala  Leu  Phe  Pro  Gln  Ser  Asp  Ala  Thr  Arg  Lys
                    2260                   2265                    2270

Leu  Thr  Val  Arg  Met  Asn  Cys  Cys  Val  Glu  Lys  Ser  Val  Thr  Arg  Phe
                    2275                   2280                    2285

Phe  Ser  Leu  Gly  Leu  Thr  Val  Ala  Asp  Val  Ala  Ser  Leu  Cys  Glu  Met
                    2290                   2295                    2300

Glu  Ile  Gln  Asn  His  Thr  Ala  Tyr  Cys  Asp  Lys  Val  Arg  Thr  Pro  Leu
2305                     2310                   2315                     2320
```

-continued

```
Glu Leu Gln Val Gly Cys Leu Val Gly Asn Glu Leu Thr Phe Glu Cys
            2325                2330                2335
Asp Lys Cys Glu Ala Arg Gln Glu Thr Leu Ala Ser Phe Ser Tyr Ile
            2340                2345                2350
Trp Ser Gly Val Pro Leu Thr Arg Ala Thr Pro Ala Lys Pro Pro Val
            2355                2360                2365
Val Arg Pro Val Gly Ser Leu Leu Val Ala Asp Thr Thr Lys Val Tyr
            2370                2375                2380
Val Thr Asn Pro Asp Asn Val Gly Arg Arg Val Asp Lys Val Thr Phe
2385                2390                2395                2400
Trp Arg Ala Pro Arg Val His Asp Lys Tyr Leu Val Asp Ser Ile Glu
            2405                2410                2415
Arg Ala Arg Arg Ala Ala Gln Ala Cys Gln Ser Met Gly Tyr Thr Tyr
            2420                2425                2430
Glu Glu Ala Ile Arg Thr Val Arg Pro His Ala Ala Met Gly Trp Gly
            2435                2440                2445
Ser Lys Val Ser Val Lys Asp Leu Ala Thr Pro Ala Gly Lys Met Ala
            2450                2455                2460
Val His Asp Arg Leu Gln Glu Ile Leu Glu Gly Thr Pro Val Pro Phe
2465                2470                2475                2480
Thr Leu Thr Val Lys Lys Glu Val Phe Phe Lys Asp Arg Lys Glu Glu
            2485                2490                2495
Lys Ala Pro Arg Leu Ile Val Phe Pro Pro Leu Asp Phe Arg Ile Ala
            2500                2505                2510
Glu Lys Leu Ile Leu Gly Asp Pro Gly Arg Val Ala Lys Ala Val Leu
            2515                2520                2525
Gly Gly Ala Tyr Ala Phe Gln Tyr Thr Pro Asn Gln Arg Val Lys Glu
            2530                2535                2540
Met Leu Lys Leu Trp Glu Ser Lys Lys Thr Pro Cys Ala Ile Cys Val
2545                2550                2555                2560
Asp Ala Thr Cys Phe Asp Ser Ser Ile Thr Glu Glu Asp Val Ala Leu
            2565                2570                2575
Glu Thr Glu Leu Tyr Ala Leu Ala Ser Asp His Pro Glu Trp Val Arg
            2580                2585                2590
Ala Leu Gly Lys Tyr Tyr Ala Ser Gly Thr Met Val Thr Pro Glu Gly
            2595                2600                2605
Val Pro Val Gly Glu Arg Tyr Cys Arg Ser Ser Gly Val Leu Thr Thr
            2610                2615                2620
Ser Ala Ser Asn Cys Leu Thr Cys Tyr Ile Lys Val Lys Ala Ala Cys
2625                2630                2635                2640
Glu Arg Val Gly Leu Lys Asn Val Ser Leu Leu Ile Ala Gly Asp Asp
            2645                2650                2655
Cys Leu Ile Ile Cys Glu Arg Pro Val Cys Asp Pro Cys Asp Ala Leu
            2660                2665                2670
Gly Arg Ala Leu Ala Ser Tyr Gly Tyr Ala Cys Glu Pro Ser Tyr His
            2675                2680                2685
Ala Ser Leu Asp Thr Ala Pro Phe Cys Ser Thr Trp Leu Ala Glu Cys
            2690                2695                2700
Asn Ala Asp Gly Lys Arg His Phe Phe Leu Thr Thr Asp Phe Arg Arg
2705                2710                2715                2720
Pro Leu Ala Arg Met Ser Ser Glu Tyr Ser Asp Pro Met Ala Ser Ala
            2725                2730                2735
Ile Gly Tyr Ile Leu Leu Tyr Pro Trp His Pro Ile Thr Arg Trp Val
            2740                2745                2750
```

Ile Ile Pro His Val Leu Thr Cys Ala Phe Arg Gly Gly Thr Pro
        2755                2760                2765

Ser Asp Pro Val Trp Cys Gln Val His Gly Asn Tyr Tyr Lys Phe Pro
        2770                2775                2780

Leu Asp Lys Leu Pro Asn Ile Ile Val Ala Leu His Gly Pro Ala Ala
2785                2790                2795                2800

Leu Arg Val Thr Ala Asp Thr Thr Lys Thr Lys Met Glu Ala Gly Lys
                2805                2810                2815

Val Leu Ser Asp Leu Lys Leu Pro Gly Leu Ala Val His Arg Lys Lys
            2820                2825                2830

Ala Gly Ala Leu Arg Thr Arg Met Leu Arg Ser Arg Gly Trp Ala Glu
            2835                2840                2845

Leu Ala Arg Gly Leu Leu Trp His Pro Gly Leu Arg Leu Pro Pro Pro
2850                2855                2860

Glu Ile Ala Gly Ile Pro Gly Gly Phe Pro Leu Ser Pro Pro Tyr Met
2865                2870                2875                2880

Gly Val Val His Gln Leu Asp Phe Thr Ser Gln Arg Ser Arg Trp Arg
                2885                2890                2895

Trp Leu Gly Phe Leu Ala Leu Leu Ile Val Ala Leu Phe Gly
            2900                2905                2910

( 2 ) INFORMATION FOR SEQ ID NO:184:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GV5446IRT ( x i ) SEQUENCE DESCRIPTION: SEQ ID NO:184:

CGGTCCCTCG AACTCCAGCG AGTCTTTTTT TTTTTTTT        39

( 2 ) INFORMATION FOR SEQ ID NO:185:

( i ) SEQUENCE CHARACTERISTICS:
        ( A ) LENGTH: 70 amino acids
        ( B ) TYPE: amino acid
        ( C ) STRANDEDNESS: double
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: GE-CAP from T55806

( x i ) SEQUENCE DESCRIPTION: SEQ ID NO:185:

Met Ser Leu Leu Thr Asn Arg Phe Ile Arg Arg Val Asp Lys Asp Gln
1               5                   10                  15

Trp Gly Pro Gly Val Thr Gly Thr Asp Pro Glu Pro Cys Pro Ser Arg
            20                  25                  30

Trp Ala Gly Lys Cys Met Gly Pro Pro Ser Ser Ala Ala Ala Cys Ser

```
                    3 5                     4 0                          4 5
      Arg   Gly   Ser   Pro   Arg   Ile   Leu   Arg   Val   Arg   Ala   Gly   Gly   Ile   Ser   Leu
            5 0                            5 5                     6 0

Phe   Tyr   Thr   Ile   Met   Ala
      6 5                     7 0
```

( 2 ) INFORMATION FOR SEQ ID NO:186:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-S59 Variant ( x i ) SEQUENCE DESCRIPTION: SEQ ID NO:186:

```
AGACGCAATG  ACTCGGCGCC  GACTCGGCGA  CCGGCCAAAA  GGTGGTGGAT  GGGTGATGAC    60
AGGGTTGGTA  GGTCGTAAAT  CCCGGTCACC  TTGGTAGCCA  CTATAGGTGG  GTCTTAAGAG   120
AAGGTTAAGA  TTCCTCTTGT  GCCTGCGGCG  AGACCGCGCA  CGGTCCACAG  GTGTTGGCCC   180
TACCGGTGTG  AATAAGGGCC  CGACGTCAGG  CTCGTCGTTA  AACCGAGCCC  GTTACCCACC   240
TGGGCAAACG  ACGCCACGT   ACGGTCCACG  TCGCCCTTCA  ATGCCTCTCT  TGGCCAATAG   300
GTTTATCCGG  CGAGTTGACA  AGGACCAGTG  GGGGCCGGGG  GCTTGGGGAA  GGACCTCAAG   360
CCCTGCCCTT  CCCGGTGGGG  CGGGAAATGC  ATGGGCCAC   C                       401
```

( 2 ) INFORMATION FOR SEQ ID NO:187:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-S368 Variant ( x i ) SEQUENCE DESCRIPTION: SEQ ID NO:187:

```
AGACGCAATG  ACTCGGCGCC  AACTCGGCGA  CCGGCCAAAA  GGTGGTGGAT  GGGTGATGAC    60
AGGGTTGGTA  GGTCGTAAAT  CCCGGTCACC  TTGGTAGCCA  CTATAGGTGG  GTCTTAAGAG   120
AAGGTTAAGA  TTCCTCTTGT  GCCTGCGGCG  AGACCGCGCA  CGGTCCACAG  GTGTTGGCCC   180
TACCGGTGTG  AATAAGGGCC  CGACGTCAGG  CTCGTCGTTA  AACCGAGCCC  GTTACCCACC   240
CGGGCAAACG  ACGCCACGT   ACGGTCCACG  TCGCCCTTCA  ATGTCTCTCT  TGACCAATAG   300
GCTTAGCCGG  CGAGTTGACA  AGGACCAGTG  GGGGCCGGGG  GCTTGGAGAG  GGACTCCAAG   360
TCCTGCCCTT  CCCGGTGGGC  CGGGAAATGC  ATGGGCCAC   C                       401
```

( 2 ) INFORMATION FOR SEQ ID NO:188:

( i ) SEQUENCE CHARACTERISTICS:

(A) LENGTH: 402 base pairs
            (B) TYPE: nucleic acid
            (C) STRANDEDNESS: double
            (D) TOPOLOGY: unknown (i i) MOLECULE TYPE: DNA (i i i) HYPOTHETICAL: NO (i v) ANTI-SENSE: NO (v i) ORIGINAL SOURCE:
            (C) INDIVIDUAL ISOLATE: HGV-S309 VARIANT (x i) SEQUENCE DESCRIPTION: SEQ ID NO:188:

```
AGACGCAATG ACTCGGCGCC GACTCGGCGA CCGGCCAAAA GGTGGTGGAT GGGTGATGAC        60
AGGGTTGGTA GGTCGTAAAT CCCGGTCATC CTGGTAGCCA CTATAGGTGG GTCTTAAGAG       120
AAGGTTAAGA TTCCTCTTGT GCATGCGGCG AGAACGCGCA CGGTCCACAG GTGTTGGCCC       180
TACCGGTGTG AATAAGGGCC CGACGTCAGG CTCGTCGTTA AACCGAGCCC GTTACCCACC       240
TGGGCAAACG ACGCCCACGT ACGGTCCACG TCGCCCTTCA ATGTCTCTCT TGACCAATAG       300
GTTTATCCGG CGAGTTGACA AGGACCAGTG GGGGCCGGGG GTCACGGGGA AGGACCCCGG       360
ATCCTGCCCT TCCCGGTGGG CCGGGAAATG CATGGGGCCA CC                          402
```

(2) INFORMATION FOR SEQ ID NO:189:

(i) SEQUENCE CHARACTERISTICS:
            (A) LENGTH: 402 base pairs
            (B) TYPE: nucleic acid
            (C) STRANDEDNESS: double
            (D) TOPOLOGY: unknown (i i) MOLECULE TYPE: DNA (i i i) HYPOTHETICAL: NO (i v) ANTI-SENSE: NO (v i) ORIGINAL SOURCE:
            (C) INDIVIDUAL ISOLATE: HGV-FZ VARIANT (x i) SEQUENCE DESCRIPTION: SEQ ID NO:189:

```
AGACGCAATG ACTCGGCGCC GACTCGGCGA CCGGCCAAAA GGTGGTGGAT GGGTGATGAC        60
AGGGTTGGTA GGTCGTAAAT CCCGGTCACC TTGGTAGCCA CTATAGGTGG GTCTTAAGAG       120
AAGGTTAAGA TTCCTCTTGT GCCTGCGGCG AGACCGCGCA CGGTCCACAG GTGTTGGCCC       180
TACCGGTGTG AATAAGGGCC CGACGTCAGG CTCGTCGTTA AACCGAGCCC GCTACCCACC       240
TGGGCAAACG ACGCCCATGT ACGGTCCACG TCGCCCTTCA ATGTCTCTCT TGACCAATAG       300
GATTCGTCCG GCGAGTTGAC AAGGACCAGT GGGGCCGGG GGCCTGGGA AGGACCCCAG         360
ACCCTGCCCT TCCCGGTGGG ACGGGAAATG CATGGGGCCA CC                          402
```

(2) INFORMATION FOR SEQ ID NO:190:

(i) SEQUENCE CHARACTERISTICS:
            (A) LENGTH: 401 base pairs
            (B) TYPE: nucleic acid
            (C) STRANDEDNESS: double
            (D) TOPOLOGY: unknown (i i) MOLECULE TYPE: DNA (i i i) HYPOTHETICAL: NO (i v) ANTI-SENSE: NO (v i) ORIGINAL SOURCE:

( C ) INDIVIDUAL ISOLATE: HGV-G21 VARIANT ( x i ) SEQUENCE DESCRIPTION: SEQ ID NO:190:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGTCC | 180 |
| TACCGGTGTG | AATAAGGACC | CGACGTCAGG | CTCGTCGTTA | AACCGAGCCC | GTTACCCACC | 240 |
| TGGGCAAACG | ACGCCCACGT | ACGGTCCACG | TCGCCCTTCA | ATGTCTCTCT | TGACCAATAG | 300 |
| GCTTAGCCGG | CGAGTTGACA | AGGACCAGTG | GGGGCCGGGG | GCTTGGGGAA | GGACCCCAAG | 360 |
| CCCTGCCCTT | CCCGGTGGGC | CGGGAAATGC | ATGGGGCCAC | C | | 401 |

( 2 ) INFORMATION FOR SEQ ID NO:191:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G23 VARIANT ( x i ) SEQUENCE DESCRIPTION: SEQ ID NO:191:

| | | | | | | |
|---|---|---|---|---|---|---|
| AGACGCAATG | ACTCGGCGCC | AACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCGCAG | GTGTTGGCCC | 180 |
| TACCGGTGTG | AATAAGGGCC | CGACATCAGG | CATGTCGTTA | AACCGAGCCC | GTTACCCGCC | 240 |
| TGGGCTAACG | ACGCCCACGT | ACGGTCCACG | TCGCCCTTCA | ATGTCTCTCT | TGACCAATAG | 300 |
| GTTTATCCGG | CGAGTTGACA | AGGACCAGTG | GGGGCCGGGG | GTTACGGGGA | AGGACCCCGA | 360 |
| ACCCTGCCCT | TCCCGGCGGA | CCGGGAAATG | CATGGGCCA | CC | | 402 |

( 2 ) INFORMATION FOR SEQ ID NO:192:

( i ) SEQUENCE CHARACTERISTICS:
        ( A ) LENGTH: 405 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G59 VARIANT ( x i ) SEQUENCE DESCRIPTION: SEQ ID NO:192:

| | | | | | | |
|---|---|---|---|---|---|---|
| AGACGCAATG | ACTCGGCGCC | GACTCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGGG | AATAAGGGCC | CGACGTCAGG | CTCGTCGTTA | AACTGAGCCC | GTAACCCACC | 240 |

```
TGGGCAAACG ACGCCCACGT ACGGTCCACG TCGCCCTTCA ATGCCTCTCT TGGCCAATAG    300

GGATTATTCC CGGCGAGTTG GCAAGGACCA GTGGGGGCCG GGAGCTACAG AGAAGGACTC    360

TGAGCTCTGC CCTTCCGGT  GGAACGGGAA ATGCATGGGG CCACC                    405
```

( 2 ) INFORMATION FOR SEQ ID NO:193:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-E36 VARIANT ( x i ) SEQUENCE DESCRIPTION: SEQ ID NO:193:

```
AGACGCAATG ACTCGGCGCC GACTCGGCGA CCGGCCAAAA GGTGGTGGAT GGGTGATGAC    60

AGGGTTGGTA GGTCGTAAAT CCCGGTCACC TTGGTAGCCA CTATAGGTGG GTCTTAAGAG   120

AAGGTTAAGA TTCCTCTTGT GCCTGCGGCG AGACCGCGCA CGGCCCACAG GTGTTGGCCC   180

TACCGGTGTG AATAAGGGCC CGACGTCAGG CTCGTCGTTA AACCGAGCCC ACTACCCACC   240

TGGGCAAACG ACGCCCACGT ACGGTCTACG TCGCCCTTCA ATGTCTCTCT TGACCAATAG   300

GCTAAGCCGG CGAGTTGACA AAGACCAGTG GGGCCGGGG  GTCACAGGGA TGGACCCTGG   360

ACCCTGCCCT TCCGGTGGA  GTGGGAAATG CATGGGGCCA CC                      402
```

( 2 ) INFORMATION FOR SEQ ID NO:194:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-R38730 VARIANT ( x i ) SEQUENCE DESCRIPTION: SEQ ID NO:194:

```
AGACGCAATG ACTCGGCGCC GACTCGGCGA CCGGCCAAAA GGTGGTGGAT GGGTGATGAC    60

AGGGTTGGTA GGTCGTAAAT CCCGGTCACC TTGGTAGCCA CTATAGGTGG GTCTTAAGAG   120

AAGGTTAAGG ATCCTCTTGT GCCTGCGGCG AGACCGCGCA CGGTCCACAG GTGTTGGCCC   180

TACCGGTGTG AATAAGGGCC CGACGTCAGG CTCGTCGTTA AACCGAGCCC GTATCCCACC   240

TGGGCAAACG ACGCCCACGT ACGGTCCACG TCGCCCTTCA ATGTCTCTCT TGACCAATAG   300

GTTCGTCCGG CGAGTTGACA AGGACCAGTG GGGCCGGGG  GTTGCGGGGA AGGACCCCGA   360

ACTCTGCCCT TCCGGTGGG  CCGGGAAATG CATGGGGCCA CC                      402
```

( 2 ) INFORMATION FOR SEQ ID NO:195:

( i ) SEQUENCE CHARACTERISTICS:
        ( A ) LENGTH: 401 base pairs
        ( B ) TYPE: nucleic acid ( C ) STRANDEDNESS: double
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: HGV-G281 VARIANT ( x i ) SEQUENCE DESCRIPTION: SEQ ID NO:195:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGTCC | 180 |
| TACCGGTGTG | AATAAGGACC | CGACGTCAGG | CTCGTCGTTA | AACCGAGCCC | GTTACCCACC | 240 |
| TGGGCAAACG | ACGCCCACGT | ACGGTCCACG | TCGCCCTTCA | ATGTCTCTCT | TGACCAATAG | 300 |
| GCTTAGCCGG | CGAGTTGACA | AGGACCAGTG | GGGGCCGGGG | GCTTGGGGAA | GGACCCCAAG | 360 |
| CCCTGCCCTT | CCCGGTGGGC | CGGGAAATGC | ATGGGCCAC | C | | 401 |

( 2 ) INFORMATION FOR SEQ ID NO:196:

( i ) SEQUENCE CHARACTERISTICS:
( A ) LENGTH: 402 base pairs
( B ) TYPE: nucleic acid
( C ) STRANDEDNESS: double
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: HGV-G157 VARIANT ( x i ) SEQUENCE DESCRIPTION: SEQ ID NO:196:

| | | | | | | |
|---|---|---|---|---|---|---|
| AGACGCAATG | ACTCGGCGCC | GACCCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGGG | 120 |
| AAGGTTAAGA | TTCCTCTTGT | GCCTGTGGCG | AGACAGCGCA | CGGTCCACAG | GTGTTGGCCC | 180 |
| TACCGGTGTG | AATAAGGGCC | CGACGTCAGG | CTCGTCGTTA | AACCGAGACC | GACACCCACC | 240 |
| TGGGCAAACG | ACGCCCACGT | ACGGTCCACG | TCGCCCTTCA | ATGTCTCTCT | TGACCAATAG | 300 |
| GCTTTGCCGG | CGAGTTGACA | AGGACCAGTG | GGGCCGGGT | GCTGGGGAA | GGACCCCCTT | 360 |
| GCACCGCCCT | TCCCGGTGGG | ACGGGAAATG | CATGGGCCA | CC | | 402 |

( 2 ) INFORMATION FOR SEQ ID NO:197:

( i ) SEQUENCE CHARACTERISTICS:
( A ) LENGTH: 401 base pairs
( B ) TYPE: nucleic acid
( C ) STRANDEDNESS: double
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: HGV-G154 VARIANT ( x i ) SEQUENCE DESCRIPTION: SEQ ID NO:197:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCATC | CTGGTAGCCA | CTATAGGTGG | GTCTTAAGAG | 120 |
| AAGGTTAAGA | TTCCTCTTAC | GCCTGCGGCG | AGACCGCGCA | CGGTCCACAG | GTGCTGGCCT | 180 |
| TACCGGTGTG | AATAAAGGCC | CGACGTCAGG | CTCGTCGTTA | AACCGAGCCC | GTCACCCACC | 240 |
| TGGGCAAACG | ACGCCCACGT | ACGGTCCACG | TCGCCCTTCA | ATGTCTCTCT | TGACCAGTAG | 300 |
| GTTAACCGG | CGAGTTGACA | AGGACCAGTG | GGGGCCGGGG | CCTTGGAGAT | GGACTCCAAG | 360 |
| TCCTGCCCTT | CCCGGTGGGC | CGGGAAATGC | ATGGGCCAC | C | | 401 |

( 2 ) INFORMATION FOR SEQ ID NO:198:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G213 VARIANT ( x i ) SEQUENCE DESCRIPTION: SEQ ID NO:198:

| | | | | | | |
|---|---|---|---|---|---|---|
| AGACGCAATG | ACTCGGCGCC | AACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGTCC | 180 |
| TACCGGTGGG | AATAAGGGCC | CGACGTCAGG | CTCGTCGTTA | AACCGAGCCC | GTCACCCACC | 240 |
| TGGGCAAACG | ACGCCCACGT | ATGGTCCACG | TCGCCCTTCA | ATGCCTCTCT | TGGCCAATAG | 300 |
| GTTTATCCGG | CGAGTTGACA | AGGACCAGTG | GGGGCCGGGG | GTTCGGGGAA | GGACCCCGTA | 360 |
| CCCTGCCCTT | CCCGGTGGAA | CGGGAAATGC | ATGGGCCAC | C | | 401 |

( 2 ) INFORMATION FOR SEQ ID NO:199:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-G204 VARIANT ( x i ) SEQUENCE DESCRIPTION: SEQ ID NO:199:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGTT | AATAAGGGCC | CGACGTCAGG | CTCGTCGTTA | AACCGAGCCC | GTCACCCACC | 240 |
| TGGGCAAACG | ACGCCCACGT | ACGGTCCACG | TCGCCCTTCA | ATGTCTCTCT | TGACCAATAG | 300 |

```
GCTTAGCCGG CGAGTTGACA AGGACCAGTG GGGGCCGGGG GCCTGGAGAG GGACTCCAGG    360

TCCTGCCCTT CCCGGTGGGC CGGGAAATGC ATGGGGCCAC C                        401
```

(2) INFORMATION FOR SEQ ID NO:200:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HGV-G191 VARIANT (xi) SEQUENCE DESCRIPTION: SEQ ID NO:200:

```
AGACGCAATG ACTCGGCGCC GACTCGGCGA CCGGCCAAAA GGTGGTGGAT GGGTGATGAC     60

AGGGTTGGTA GGTCGTAAAT CCCGGTCATC CTGGTAGCCA CTATAGGTGG GTCTTAAGAG    120

AAGGTTAAGG ATCCTCTTGT GCCTGCGGCG AGACCGCGCA CGGTCCACAG GTGTTGGCCC    180

TACCGGTGTG AATAAGGGCC CGACGTCAGG CTCGTCGCTA AACCGAGCCC GTATCCCACC    240

TGGGCAAACG ACGCCACGT ACGGTCCACG TCGCCCTTCA ATGTCTCTCT TGACCAATAG     300

GTTTATCCGG CGAGTTGACA AGGACCAGTG GGGGCCGGAG GTTACGGGGA AGGACCCCGA    360

GCCTCGCCCT TCCCGGTGGG CCGGGAAATG CATGGGCCA CC                       402
```

(2) INFORMATION FOR SEQ ID NO:201:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HGV-G299 VARIANT (xi) SEQUENCE DESCRIPTION: SEQ ID NO:201:

```
AGACGCAATG ACTCGGCGCC GACTCGGCGA CCGGCCAAAA GGTGGTGGAT GGGTGATGAC     60

AGGGTTGGTA GGTCGTAAAT CCCGGTCACC TTGGTAGCCA CTATAGGTGG GTCTTAAGAG    120

AAGGTTAAGA TTCCTCTTGT GCCTGCGGCG AGACCGCGCA CGGTCCACAG GTGTTGGCCC    180

TACCGGTGTG AATAAGGGCC CGACGTCAGG CTCGTCGTTA AACCGAGCCC GTCACCCACC    240

TGGGCAAACG ACGCCACGC ACGGTCCACG TCGCCCTTCA ATGCCTCTCT TGGCCAATAG     300

GAGTATCCGG CGAGTTGACA AGGACCAGTG GGGGCCGGGA GTCACGGGGA TGGACCCCGG    360

GCTCTGCCCT TCCCGGTGGA ACGGGAAATG CATGGGCCA CC                       402
```

(2) INFORMATION FOR SEQ ID NO:202:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-T56957 VARIANT ( x i ) SEQUENCE DESCRIPTION: SEQ ID NO:202:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCACC TTGGTAGCCA CTATAGGTGG GTCTTAAGAG     120
AAGGTTAAGA TTCCTCTTGT GCCTGCGGCG AGACCGCGCA CGGTCCACAG GTGTTGGCCC     180
TACCGGTGTG AATAAGGGCC CGACGTCAGG CTCGTCGTTA AACCGAGCCC ATCACCCACC     240
TGGGCAAACG ACGCCCACGT ACGGTCCACG TCGCCCTACA ATGTCTCTCT TGACCAATAG     300
GCTTAGCCGG CGAGTTGACA AGGACCAGTG GGGGCCGGGG GTCACAGGGA TGGACCCTGG     360
GCCCTGCCCT TCCCGGTGGG GTGGGAAATG CATGGGCCA CC                        402
```

( 2 ) INFORMATION FOR SEQ ID NO:203:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-C01698 VARIANT ( x i ) SEQUENCE DESCRIPTION: SEQ ID NO:203:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCACC TTGGTAGCCA CTATAGGTGG GTCTTAAGAG     120
AAGGTTAAGA TTCCTCTTGT GCCTGCGGCG AGACCGCGCA CGGTCCACAG GTGTTGGCCC     180
TACCGGTGTG AATAAGGGCC CGACGTCAGG CTCGTCGTTA AACCGAGCCC GTCACCCACC     240
TGGGCAAACG ACGCCCACGT ACGGTCCACG TCGCCCTTCA ATGTCTCTCT TGACCAATAG     300
GCTTAGCCGG CGAGTTGACA AGGACCAGTG GGGGCCGGGG GCTTGGAGAT GGACTCCAAG     360
TCCTGCCCTT CCCGGTGGGC CGGGAAATGC ATGGGCCAC C                         401
```

( 2 ) INFORMATION FOR SEQ ID NO:204:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-T27034 VARIANT ( x i ) SEQUENCE DESCRIPTION: SEQ ID NO:204:

```
AGACGCAATG  ACTCGGCGCC  GACTCGGCGA  CCGGCCAAAA  GGTGGTGGAT  GGGTGATGAC    60

AGGGTTGGTA  GGTCGTAAAT  CCCGGTCACC  TTGGTAGCCA  CTATAGGTGG  GTCTTAAGAG   120

AAGGTTAAGA  TTCCTCTTGT  GCCTGCGGCG  AGACCGCGCA  CGGTCCACAG  GTGTTGGCCC   180

TACCGGTGTG  AATAAGGGCC  CGACGTCAGG  CTCGTCGTTA  AACCGAGCCC  ATTTCCGCC    240

TGGGCTAACG  ACGCCCACGT  ACGGTCCACG  TCGCCCTTCA  ATGTCTCTCT  TGACCAATAG   300

GTTTATCCGG  CGAGTTGACA  AGGACCAGTG  GGGGCCGGGA  GTCACTGGGA  TGGACCCAGG   360

GCTCTGCCCT  TCCCGGCGGG  GTGGGAAAAG  CATGGGGCCA  CC                      402
```

( 2 ) INFORMATION FOR SEQ ID NO:205:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-E57963 VARIANT ( x i ) SEQUENCE DESCRIPTION: SEQ ID NO:205:

```
AGACGCAATG  ACTCGGCGCC  GACTCGGCGA  CCGGCCAAAA  GGTGGTGGAT  GGGTGATGAC    60

AGGGTTGGTA  GGTCGTAAAT  CCCGGTCACC  TTGGTAGCCA  CTATAGGTGG  GTCTTAAGAG   120

AAGGTTAAGA  TTCCTCTTGT  GCCTGCGGCG  AGACCGCGCA  CGGTCCGCAG  GTGTTGGCCC   180

TACCGGTGTG  AATAAGGGCC  CGACGTCAGG  CTCGTCGTTA  AACCGAGCCC  GTCACCCACC   240

TGGGCAAACG  ACGCCCACGT  ACGGTCCACG  TCGCCCTTCA  ATGTCTCTCT  TGACCAATAG   300

GCTTAGCCGG  CGAGTTGACA  AGGACCAGTG  GGGGCCGGGG  GCTTGGAGAA  GGACTCCAAG   360

TCCTGCCCTT  CCCGGTGGGC  CGGGAAATGC  ATGGGCCAC   C                       401
```

( 2 ) INFORMATION FOR SEQ ID NO:206:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-R37166 VARIANT ( x i ) SEQUENCE DESCRIPTION: SEQ ID NO:206:

```
AGACGCAATG  ACTCGGCGCC  GACTCGGCGA  CCGGCCAAAA  GGTGGTGGAT  GGGTGATGAC    60

AGGGTTGGTA  GGTCGTAAAT  CCCGGTCACC  TTGGTAGCCA  CTATAGGTGG  GTCTTAAGAG   120

AAGGTTAAGA  TTCCTCTTGT  GCCTGCGGCG  AGACCGCGCA  CGGTCCACAG  GTGTTGGCCC   180

TACCGGTGTG  AATAAGGGCC  CGACGTCAGG  CTCGTCGTTA  AACCGAGCCC  GTAACCCGCC   240

TGGGCAAACG  ACGCCCACGT  ACGGTCCACG  TCGCCCTTCA  ATGTCTCTCT  TGACCAATAG   300

GTTAACCGG   CGAGTTGACA  AGGACCAGTG  GGGGCCGGGG  CCTTGGAGAT  GGACTCCAAG   360
```

```
TCCTGCCCTT CCCGGCGGGC CGGGAAATGC ATGGGGCCAC C                              401
```

( 2 ) INFORMATION FOR SEQ ID NO:207:

( i ) SEQUENCE CHARACTERISTICS:
        ( A ) LENGTH: 404 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-B5 VARIANT ( x i ) SEQUENCE DESCRIPTION: SEQ ID NO:207:

```
AGACGCAATG ACTCGGCGCC GACTCGGCGA CCGGCCAAAA GGTGGTGGAT GGGTGATGAC    60
AGGGTTGGTA GGTCGTAAAT CCCGGTCATC CTGGTAGCCA CTATAGGTGG GTCTTAAGGG   120
AAGGTTAAGA TTCCTCTTGT GCCTGCGGCG AGACCGCGCA CGGTCCACAG GTGTTGGCCC   180
TACCGGTGTG AATAAGGGCC CGACGTCAGG CTCGTCGTTA AACCGAGCCC GTCACCCACC   240
TGGGCTAACG ACGCCCACGT ACGGTCCACG TCGCCCTTCA ATGTCTCTCT TGACCAATAG   300
GCTTTTTGCC GGCGAGTTGA CAAGGACCAG TGGGGCCGG  GGGTTATGGG GAAGGACCCC   360
AAACCCTGCC CTTCCCGGTG GGCCGGGAAA TGCATGGGGC CACC                    404
```

( 2 ) INFORMATION FOR SEQ ID NO:208:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-B33 VARIANT ( x i ) SEQUENCE DESCRIPTION: SEQ ID NO:208:

```
AGACGCAATG ACTCGGCGCC GACTCGGCGA CCGGCCAAAA GGTGGTGGAT GGGTGATGAC    60
AGGGTTGGTA GGTCGTAAAT CCCGGTCATC CTGGTAGCCA CTATAGGTGG GTCTTAAGAG   120
AAGGTTAAGA TTCCTCTTGT GCCTGCGGCG AGACCGCGCA CGGTCCACAG GTGTTGGCCC   180
TACCGGTGTG AATAAGGGCC CGACGTCAGG CTCGTCGTTA AACCGAGCCC GTTCCCGCC    240
TGGGCAAACG ACGCCCACGT ACGGTCCACG TCGCCCTTCA ATGTCTCTCT TGACCAATAG   300
GTTTATCCGG CGAGTTGACA AGGACCAGTG GGGCCGGGG  ATCATGGGGA AGGACCCCAG   360
ATCCTGCCCT TCCCGGCGGG CCGGGAAATG CATGGGCCA  CC                      402
```

( 2 ) INFORMATION FOR SEQ ID NO:209:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-FH010 VARIANT ( x i ) SEQUENCE DESCRIPTION: SEQ ID NO:209:

| | | | | | | |
|---|---|---|---|---|---|---|
| AGACGCAATG | ACTCGGCGCC | GACCCGGCGA | CCGGCCAAAA | GGTGGTGGAT | GGGTGATGCC | 60 |
| AGGGTTGGTA | GGTCGTAAAT | CCCGGTCATC | TTGGTAGCCA | CTATAGGTGG | GTCTTAAGGG | 120 |
| AAGGTTAAGA | TTCCTCTTGT | GCCTGTGGCG | AGACAGCGCA | CGGTCCACAG | GTGTTGGCCC | 180 |
| TACCGGTGTG | AATAAGGGCC | CGACGTCAGG | CTCGTCGTTA | AACTGAGACC | GACACCCACC | 240 |
| TGGGCAAACG | ACGCCCACGT | ACGGTCCACG | TCGCCCTTCA | ATGTCTCTCT | TGACCAATAG | 300 |
| GCTTTGCCGG | CGAGTTGACA | AGGACCAGTG | GGGGCCGGGG | GCTGGGGAA | GGACCCCAG | 360 |
| TCCTGCCCTT | CCCGGTGGGA | CGGGAAATGC | ATGGGCCAC | C | | 401 |

( 2 ) INFORMATION FOR SEQ ID NO:210:

( i ) SEQUENCE CHARACTERISTICS:
    ( A ) LENGTH: 401 base pairs
    ( B ) TYPE: nucleic acid
    ( C ) STRANDEDNESS: double
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-PNF2161 VARIANT ( x i ) SEQUENCE DESCRIPTION: SEQ ID NO:210:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCACAG | GTGTTGGCCC | 180 |
| TACCGGTGGG | AATAAGGGCC | CGACGTCAGG | CTCGTCGTTA | AACCGAGCCC | GTTACCCACC | 240 |
| TGGGCAAACG | ACGCCCACGT | ACGGTCCACG | TCGCCCTTCA | ATGTCTCTCT | TGACCAATAG | 300 |
| GCGTAGCCGG | CGAGTTGACA | AGGACCAGTG | GGGGCCGGGG | GCTTGGAGAG | GACTCCAAG | 360 |
| TCCCGCCCTT | CCCGGTGGGC | CGGGAAATGC | ATGGGCCAC | C | | 401 |

( 2 ) INFORMATION FOR SEQ ID NO:211:

( i ) SEQUENCE CHARACTERISTICS:
    ( A ) LENGTH: 402 base pairs
    ( B ) TYPE: nucleic acid
    ( C ) STRANDEDNESS: double
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-JC VARIANT ( x i ) SEQUENCE DESCRIPTION: SEQ ID NO:211:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |

```
AGGGTTGGTA GGTCGTAAAT CCCGGTCACC TTGGTAGCCA CTATAGGTGG GTCTTAAGAG      120

AAGGTTAAGA TTCCTCTTGT GCCTGCGGCG AGACCGCGCA CGGTCCACAG GTGTTGGCCC      180

TACCGGTGGG AATAAGGGCC CGACGTCAGG CTCGTCGTTA AACCGAGCCC GTAACCGCC       240

TGGGCAAACG ACGCCCACGT ACGGTCCACG TCGCCCTTCA ATGTCGCTCT TGACCAATAG      300

GCTTAGCCGG CGAGTTGACA AGGACCAGTG GGGGCCGGGG TTTATGGGGA AGGACCCCAA      360

ACCCTGCCCT TCCCGGCGGA CCGGGAAATG CATGGGGCCA CC                        402
```

( 2 ) INFORMATION FOR SEQ ID NO:212:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-7155 VARIANT ( x i ) SEQUENCE DESCRIPTION: SEQ ID NO:212:

```
AGACGTTATG AACCGGCGCC GCCCGGCGA  CCGGCAAAA  GGTGGTGGAT GGGTGATGCC      60

AGGGTTGGTA GGTCGTAAAT CCCGGTCATC TTGGTAGCCA CTATAGGTGG GTCTTAAGGG     120

GTGGTCAAGG TCCCTCTAGC GCTTGTGGCG AGAAAGCGCA CGGTCCACAG GTGTTGGCCC     180

TACCGGTGTG AATAAGGGCC CGACGTCAGG CTCGTCGTTA AACCGAGCCC ATTATCCTCC     240

TGGGCAAACG ACGCCCACGT ACGGTCCACG TCGCCCTTCA ATGTCTCTCT TGACCAATAG     300

GCTTTGCCGG CGAGTTGACA AGGACCAGTG GGGGCCGGGT GCCGGGGAA  GGACCCCCGG     360

TACTGCCCCT CCCGGAGGAG TGGGAAATGC ATGGGCCAC  C                        401
```

( 2 ) INFORMATION FOR SEQ ID NO:213:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-7244 VARIANT ( x i ) SEQUENCE DESCRIPTION: SEQ ID NO:213:

```
AGACGTTAAG AACCGGCGCC GCCCGGCGA  CCGGCAAAA  GGTGGTGGAT GGGTGATGCC      60

AGGGTTGGTA GGTCGTAAAT CCCGGTCATC TTGGTAGCCA CTATAGGTGG GTCTTAAGGG     120

GTGGTCAAGG TCCCTCTGGC GCTTGTGGCG AGAAAGCGCA CGGTCCACAG GTGTTGGCCC     180

TACCGGTGTG AATAAGGGCC CGACGTCAGG CTCGTCGTTA AACCGAGCCC ATTACCCTCC     240

TGGGCAAACG ACGCCCATGT ACGGTCCACG TCGCCCTTCA ATGTCTCTCT TGACCAATAG     300

GCTTTGCCGG CGAGTTGACA AGGACCAGTG GGGGCCGGGT GGCGGGGAA  GGACCCCCGT     360

CACTGCCCTT CCCGGAGGGG TGGGAAATGC ATGGGGCCAC C                        401
```

( 2 ) INFORMATION FOR SEQ ID NO:214:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-K27 VARIANT ( x i ) SEQUENCE DESCRIPTION: SEQ ID NO:214:

```
AGACGTTAAG TACCGGCGCC GACCCGGCGA CCGGCCAAAA GGTGGTGGAT GGGTGATGCC      60
AGGGTTGGTA GGTCGTAAAT CCCGGTCATC TTGGTAGCCA CTATAGGTGG GTCTTAAGGG     120
TTGGTCAAGG TCCCTCTGGC GCTTGTGGCG AGAAAGCGCA CGGTCCACAG GTGTTGGCCC     180
TACCGGTGTG AATAAGGGCC CGACGTCAGG CTCGTCGTTA AACCGAGCCC ATTACCCACC     240
TGGGCAAACA ACGCCACGT  ACGGTCCACG TCGCCCTACA ATGTCTCTCT TGACCAATAG     300
GCTTTGCCGG CGAGTTGACA AGGACCAGTG GGGGCTGGGC GGCGAGGGAA GGACCCTCGT     360
CGCTGCCCTT CCCGGCGGGG TGGGGAATGC ATGGGCCAC C                         401
```

( 2 ) INFORMATION FOR SEQ ID NO:215:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-K30 VARIANT ( x i ) SEQUENCE DESCRIPTION: SEQ ID NO:215:

```
AGACGTTAAG AACCGGCGCC TTCCCGGCGA CCGGCCAAAA GGTGGTGGAT GGGTGATGCC      60
AGGGTTGGTA GGTCGTAAGT CCCGGTCATC TTGGTAGCCA CTATAGGTGG GTCTTAAGGG     120
AGGGTTAAGG TCCCTCTGGC GCTTGTGGCG AGAAAGCGCA CGGTCCACAG GTGTTGGCCC     180
TACCGGTGTG AATAAGGGCC CGACGTCAGG CTCGTCGTTA AACCGAGCCC ATTACCCACC     240
TGGGCAAACA ACGCCACGT  ACGGTCCACG TCGCCCTTCA ATGTCTCTCT TGACCAATAG     300
GCTTTGCCGG CGAGTTGACA AGGACCAGTG GGGGCTGGGC GGTAGGGAA  GGACCCTTGC     360
CGCTGCCCTT CCCGGTGGGG TGGGAAATGC ATGGGCCAC C                         401
```

( 2 ) INFORMATION FOR SEQ ID NO:216:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: HGV-T55875 VARIANT ( x i ) SEQUENCE DESCRIPTION: SEQ ID NO:216:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCACC TTGGTAGCCA CTATAGGTGG GTCTTAAGAG     120
AAGGTTAAGA TTCCTCTTGT GCCTGCGACG AGACCGCGCA CGGTCCGCAG GTGTTGGCCC     180
TACCGGTGTG AATAAGGGCC CGACGTCAGG CTCGTCGTTA AACCGAGCCC GTCACCCACC     240
TGGGCAAACG ACGCCCACGT ACGGTCCACG TCGCCCTTCA ATGCCTCTCT TGGCCAATAG     300
GTTTAACCGG CGAGTTGGCA AGGACCAGTG GGGGCCGGGG GCTTGGAGAG GGACTCCAAG     360
TCCTGCCCTT CCCGGTGGGC CGGGAAATGC ATGGGCCAC C                          401
```

( 2 ) INFORMATION FOR SEQ ID NO:217:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-T56633 VARIANT ( x i ) SEQUENCE DESCRIPTION: SEQ ID NO:217:

```
AGACGCAATG ACTCGGCGCC GACTCGGCGA CCGGCCAAAA GGTGGTGGAT GGGTGATGAC      60
AGGGTTGGTA GGTCGTAAAT CCCGGTCACC TTGGTAGCCA CTATAGGTGG GTCTTAAGAG     120
AAGGTTAAGA TTCCTCTTGT GCCTGCGGCG AGACCGCGCA CGGTCCACAG GTGTTGGCCC     180
TACCGGTGTG AATAAGGGCC CGACGTCAGG CTCGTCGTTA AACCGAGCCC ACTACCCACC     240
TGGGCTAACG ACGCCCACGT ACGGTCCACG TCGCCCTTCA ATGTCTCTCT TGACCAATAG     300
GCTAGTCCGG CGAGTTGACA AGGACCAGTG GGGGCCGGAG GTCACAGGGA TGGACCCTGG     360
GCCTTGCCCT TCCCGGTGGA GTGGGAAAAG CATGGGGCCA CC                        402
```

( 2 ) INFORMATION FOR SEQ ID NO:218:

( i ) SEQUENCE CHARACTERISTICS:
        ( A ) LENGTH: 404 base pairs
        ( B ) TYPE: nucleic acid
        ( C ) STRANDEDNESS: double
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: HGV-EB20 VARIANT ( x i ) SEQUENCE DESCRIPTION: SEQ ID NO:218:

```
AGACGCAATG ACTCGGCGCC GACTCGGCGA CCGGCCAAAA GGTGGTGGAT GGGTGATGCC      60
AGGGTTGGTA GGTCGTAAAT CCCGGTCATC TTGGTAGCCA CTATAGGTGG GTCTTAAGAG     120
```

```
AAGGTTAAGA  TTCCTCTTGT  GCCTGCGGCG  AGACCGCGCA  CGGTCCACAG  GTGTTGGCCC    180

TACCGGTGTA  ATAAGGGCCC  GACGTCAGGC  TCGTCGTTAA  ACCGAGCCCG  TCACCCACCT    240

GGGCAAACGA  CGCCCACGTA  CGGTCCACGT  CGCCCTTCAA  TGCCTCTCTT  GGCCAATAGG    300

AGTTATCTCC  GGCGAGTTGG  CAAGGACCAG  TGGGGGCCGG  GGGTTACGGG  GAAGGACCCC    360

GAACCCTGCC  CTTCCGGTG  GGCCGGGAAA  TGCATGGGGC  CACC                      404
```

(2) INFORMATION FOR SEQ ID NO:219:

(i) SEQUENCE CHARACTERISTICS:
        (A) LENGTH: 401 base pairs
        (B) TYPE: nucleic acid
        (C) STRANDEDNESS: double
        (D) TOPOLOGY: unknown (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HGV-T55806 VARIANT (xi) SEQUENCE DESCRIPTION: SEQ ID NO:219:

```
AGACGCAATG  ACTCGGCGCC  GACTCGGCGA  CCGGCCAAAA  GGTGGTGGAT  GGGTGATGCC    60

AGGGTTGGTA  GGTCGTAAAT  CCCGGTCATC  TTGGTAGCCA  CTATAGGTGG  GTCTTAAGAG    120

AAGGTTAAGA  TTCCTCTTGT  GCCTGCGGCG  AGACCGCGCA  CGGTCCACAG  GTGTTGGCCC    180

TACCGGTGGA  ATAAGGGCCC  GACGTCAGGC  TCGTCGTTAA  ACCGAGCCCG  TCACCCACCT    240

GGGCAAACGA  CGCTCACGTA  CGGTCCACGT  CGCCCTTCAA  TGTCTCTCTT  GACCAATAGG    300

TTTATCCGGC  GAGTTGACAA  GGACCAGTGG  GGGCCGGGG  TTACGGGAC  GGACCCCGAA      360

CCCTGCCCTT  CCCGGTGGGC  CGGGAAATGC  ATGGGCCAC  C                         401
```

(2) INFORMATION FOR SEQ ID NO:220:

(i) SEQUENCE CHARACTERISTICS:
        (A) LENGTH: 402 base pairs
        (B) TYPE: nucleic acid
        (C) STRANDEDNESS: double
        (D) TOPOLOGY: unknown (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HGV-BG34 VARIANT (xi) SEQUENCE DESCRIPTION: SEQ ID NO:220:

```
AGACGCAATG  ACTCGGCGCC  GACTCGGCGA  CCGGCCAAAA  GGTGGTGGAT  GGGTGATGAC    60

AGGGTTGGTA  GGTCGTAAAT  CCCGGTCACC  TTGGTAGCCA  CTATAGGTGG  GTCTTAAGAG    120

AAGGTTAAGA  TTCCTCTTGT  GCCTGCGGCG  AGACCGCGCA  CGGTCCACAG  GTGTTGGCCC    180

TACCGGTGTG  AATAAGGGCC  CGACGTCAGG  CTCGTCGTTA  AACCGAGCCC  GTCACCCACC    240

TGGGCAAACG  ACGCCCACGT  ACGGTCCACG  TCGCCCTTCA  ATGCCTCTCT  TGGCCAATAG    300

GAGTATCCGG  CGAGTTGACA  AGGACCAGTG  GGGGCCGGGA  GTCACGGGGA  TGGACCCCGG    360

GCTCTGCCCT  TCCCGGTGGA  ACGGGAAACG  CATGGGCCA  CC                        402
```

(2) INFORMATION FOR SEQ ID NO:221:

(i) SEQUENCE CHARACTERISTICS:
 (A) LENGTH: 402 base pairs
 (B) TYPE: nucleic acid
 (C) STRANDEDNESS: double
 (D) TOPOLOGY: unknown (ii) MOLECULE TYPE: DNA (iii) HYPOTHETICAL: NO (iv) ANTI-SENSE: NO (vi) ORIGINAL SOURCE:
 (C) INDIVIDUAL ISOLATE: HGV-BE12 VARIANT (xi) SEQUENCE DESCRIPTION: SEQ ID NO:221:

| | | | | | | |
|---|---|---|---|---|---|---|
| AGACGCAATG | ACTCGGCGCC | GACTCGGCGA | CCGGCCAAAA | GGTGGTGGAT | GGGTGATGAC | 60 |
| AGGGTTGGTA | GGTCGTAAAT | CCCGGTCACC | TTGGTAGCCA | CTATAGGTGG | GTCTTAAGAG | 120 |
| AAGGTTAAGA | TTCCTCTTGT | GCCTGCGGCG | AGACCGCGCA | CGGTCCGCAG | GTGTTGGTCC | 180 |
| TACCGGTGTG | AATAAGGACC | CGACGTCAGG | CTCGTCGTTA | AACCGAGCCC | GCCACCCACC | 240 |
| TGGGCAAACG | ACGCCCACGT | ACGGTCCACG | TCGCCCTTCA | ATGCCTCTCT | TGGCCAATAG | 300 |
| GTTTATCCGG | CGAGTTGACA | AGGACCAGTG | GGGGCCGGGG | GCTCCGGGGA | AGAACCCCGA | 360 |
| GCCCCGCCCT | TCCCGGTGGG | ACGGGAAATG | CATGGGCCA | CC | | 402 |

(2) INFORMATION FOR SEQ ID NO:222:

(i) SEQUENCE CHARACTERISTICS:
  (A) LENGTH: 24 base pairs
  (B) TYPE: nucleic acid
  (C) STRANDEDNESS: single
  (D) TOPOLOGY: unknown (ii) MOLECULE TYPE: DNA (iii) HYPOTHETICAL: NO (iv) ANTI-SENSE: NO (vi) ORIGINAL SOURCE:
  (C) INDIVIDUAL ISOLATE: HGV-FORWARD PRIMER (xi) SEQUENCE DESCRIPTION: SEQ ID NO:222:

CCAAAAGGTG GTGGATGGGT GATG    24

(2) INFORMATION FOR SEQ ID NO:223:

(i) SEQUENCE CHARACTERISTICS:
  (A) LENGTH: 24 base pairs
  (B) TYPE: nucleic acid
  (C) STRANDEDNESS: single
  (D) TOPOLOGY: unknown (ii) MOLECULE TYPE: DNA (iii) HYPOTHETICAL: NO (iv) ANTI-SENSE: NO (vi) ORIGINAL SOURCE:
  (C) INDIVIDUAL ISOLATE: HGV-FORWARD PRIMER (xi) SEQUENCE DESCRIPTION: SEQ ID NO:223:

GTGATGMCAG GGTTGGTAGG TCGT    24

(2) INFORMATION FOR SEQ ID NO:224:

(i) SEQUENCE CHARACTERISTICS:

(A) LENGTH: 26 base pairs
(B) TYPE: nucleic acid
(C) STRANDEDNESS: single
(D) TOPOLOGY: unknown (ii) MOLECULE TYPE: DNA (iii) HYPOTHETICAL: NO (iv) ANTI-SENSE: NO (vi) ORIGINAL SOURCE:
(C) INDIVIDUAL ISOLATE: HGV-FORWARD PRIMER (xi) SEQUENCE DESCRIPTION: SEQ ID NO:224:

GGTAGCCACT ATAGGTGGGT CTTAAG 26

(2) INFORMATION FOR SEQ ID NO:225:

(i) SEQUENCE CHARACTERISTICS:
(A) LENGTH: 25 base pairs
(B) TYPE: nucleic acid
(C) STRANDEDNESS: single
(D) TOPOLOGY: unknown (ii) MOLECULE TYPE: DNA (iii) HYPOTHETICAL: NO (iv) ANTI-SENSE: NO (vi) ORIGINAL SOURCE:
(C) INDIVIDUAL ISOLATE: HGV-REVERSE PRIMER (xi) SEQUENCE DESCRIPTION: SEQ ID NO:225:

GAGMGRCATT GWAGGGCGAC GTRGA 25

(2) INFORMATION FOR SEQ ID NO:226:

(i) SEQUENCE CHARACTERISTICS:
(A) LENGTH: 21 base pairs
(B) TYPE: nucleic acid
(C) STRANDEDNESS: single
(D) TOPOLOGY: unknown (ii) MOLECULE TYPE: DNA (iii) HYPOTHETICAL: NO (iv) ANTI-SENSE: NO (vi) ORIGINAL SOURCE:
(C) INDIVIDUAL ISOLATE: HGV-REVERSE PRIMER (xi) SEQUENCE DESCRIPTION: SEQ ID NO:226:

GRCATTGWAG GGCGACGTRG A 21

(2) INFORMATION FOR SEQ ID NO:227:

(i) SEQUENCE CHARACTERISTICS:
(A) LENGTH: 22 base pairs
(B) TYPE: nucleic acid
(C) STRANDEDNESS: single
(D) TOPOLOGY: unknown (ii) MOLECULE TYPE: DNA (iii) HYPOTHETICAL: NO (iv) ANTI-SENSE: NO (vi) ORIGINAL SOURCE:
(C) INDIVIDUAL ISOLATE: HGV-REVERSE PRIMER ( x i ) SEQUENCE DESCRIPTION: SEQ ID NO:227:

CCCCACTGGT CYTTGYCAAC TC 22

( 2 ) INFORMATION FOR SEQ ID NO:228:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PRIMER GV75- 36FE ( x i ) SEQUENCE DESCRIPTION: SEQ ID NO:228:

GCGAGATCTA AAATGCAGGC CTGATGGGT 29

( 2 ) INFORMATION FOR SEQ ID NO:229:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PRIMER GV75- 7064RLE ( x i ) SEQUENCE DESCRIPTION: SEQ ID NO:229:

GCGAGATCTA AAATGTGGAC TGCTAAGCC 29

( 2 ) INFORMATION FOR SEQ ID NO:230:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: PRIMER FV94- 28F ( x i ) SEQUENCE DESCRIPTION: SEQ ID NO:230:

GCGAGATCTA AAATGGCAAG CCCCAGAAAC CGACGCCTAT CTAAGT 46

( 2 ) INFORMATION FOR SEQ ID NO:231:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: unknown ( i i ) MOLECULE TYPE: DNA (iii) HYPOTHETICAL: NO (iv) ANTI-SENSE: NO (vi) ORIGINAL SOURCE:
   (C) INDIVIDUAL ISOLATE: PRIMER FV94- 2864R (xi) SEQUENCE DESCRIPTION: SEQ ID NO:231:

GGCATGATGA ATTCGCAACG AGGGCCGGGA CACCAAGAT                              39

(2) INFORMATION FOR SEQ ID NO:232:

(i) SEQUENCE CHARACTERISTICS:
       (A) LENGTH: 39 base pairs
       (B) TYPE: nucleic acid
       (C) STRANDEDNESS: single
       (D) TOPOLOGY: unknown (ii) MOLECULE TYPE: DNA (iii) HYPOTHETICAL: NO (iv) ANTI-SENSE: NO (vi) ORIGINAL SOURCE:
       (C) INDIVIDUAL ISOLATE: PRIMER FV94- 6439F (xi) SEQUENCE DESCRIPTION: SEQ ID NO:232:

GCGAGATCTA AAATGGGCCT CCGACACCCC GAAGGTTGT                              39

(2) INFORMATION FOR SEQ ID NO:233:

(i) SEQUENCE CHARACTERISTICS:
       (A) LENGTH: 39 base pairs
       (B) TYPE: nucleic acid
       (C) STRANDEDNESS: single
       (D) TOPOLOGY: unknown (ii) MOLECULE TYPE: DNA (iii) HYPOTHETICAL: NO (iv) ANTI-SENSE: NO (vi) ORIGINAL SOURCE:
       (C) INDIVIDUAL ISOLATE: PRIMER FV94- 9331R (xi) SEQUENCE DESCRIPTION: SEQ ID NO:233:

GCGAGATCTG AATTCTTCCC GGGGTGCACC CCTTCAGAT                              39

(2) INFORMATION FOR SEQ ID NO:234:

(i) SEQUENCE CHARACTERISTICS:
       (A) LENGTH: 9327 base pairs
       (B) TYPE: nucleic acid
       (C) STRANDEDNESS: double
       (D) TOPOLOGY: unknown (ii) MOLECULE TYPE: cDNA (iii) HYPOTHETICAL: NO (iv) ANTI-SENSE: NO (vi) ORIGINAL SOURCE:
       (C) INDIVIDUAL ISOLATE: 3ZHGV-6, HGV FROM PNF2161

(xi) SEQUENCE DESCRIPTION: SEQ ID NO:234:

GCAAGCCCCA GAAACCGACG CCTATCTAAG TAGACGCAAT GACTCGGCGC CGACTCGGCG       60
ACCGGCCAAA AGGTGGTGGA TGGGTGATGA CAGGGTTGGT AGGTCGTAAA TCCCGGTCAC      120

-continued

| | | | | | |
|---|---|---|---|---|---|
| CTTGGTAGCC | ACTATAGGTG | GGTCTTAAGA | GAAGGTTAAG | ATTCCTCTTG | TGCCTGCGGC | 180
| GAGACCGCGC | ACGGTCCACA | GGTGTTGGCC | CTACCGGTGG | GAATAAGGGC | CCGACGTCAG | 240
| GCTCGTCGTT | AAACCGAGCC | CGTTACCCAC | CTGGGCAAAC | GACGCCCACG | TACGGTCCAC | 300
| GTCGCCCTTC | AATGTCTCTC | TTGACCAATA | GGCGTAGCCG | GCGAGTTGAC | AAGGACCAGT | 360
| GGGGCCGGG | GGCTTGGAGA | GGGACTCCAA | GTCCGCCCT | TCCCGGTGGG | CCGGGAAATG | 420
| CATGGGGCCA | CCCAGCTCCG | CGGCGGCCTG | CAGCCGGGGT | AGCCCAAGAA | TCCTTCGGGT | 480
| GAGGGCGGGT | GGCATTTCCT | TTTCTATAC | CATCATGGCA | GTCCTTCTGC | TCCTTCTCGT | 540
| GGTTGAGGCC | GGGGCCATTC | TGGCCCCGGC | CACCCACGCT | TGTCGAGCGA | ATGGGCAATA | 600
| TTTCCTCACA | AATTGTTGTG | CCCCGGAGGA | CATCGGGTTC | TGCCTGGAGG | GTGGATGCCT | 660
| GGTGGCCCTG | GGGTGCACGA | TTTGCACTGA | CCAATGCTGG | CCACTGTATC | AGGCGGGTTT | 720
| GGCTGTGCGG | CCTGGCAAGT | CCGCGGCCCA | ACTGGTGGGG | GAGCTGGGTA | GCCTATACGG | 780
| GCCCCTGTCG | GTCTCGGCCT | ATGTGGCTGG | GATCCTGGGC | CTGGGTGAGG | TGTACTCGGG | 840
| TGTCCTAACG | GTGGGAGTCG | CGTTGACGCG | CCGGATCTAC | CCGGTGCCTA | ACCTGACGTG | 900
| TGCAGTCGCG | TGTGAGTTAA | AGTGGGAAAG | TGAGTTTTGG | AGATGGACTG | AACAGCTGGC | 960
| CTCCAACTAC | TGGATTCTGG | AATACCTCTG | GAAGGTCCCA | TTTGATTTCT | GGAGAGGCGT | 1020
| GATAAGCCTG | ACCCCCTTGT | TGGTTTGCGT | GGCCGCATTG | CTGCTGCTTG | AGCAACGGGT | 1080
| TGTCATGGTC | TTCCTGTTGG | TGACGATGGC | CGGGATGTCG | CAAGGCGCCC | CTGCCTCCGT | 1140
| TTTGGGGTCA | CGCCCCTTTG | ACTACGGGTT | GACTTGGCAG | ACCTGCTCTT | GCAGGGCCAA | 1200
| CGGTTCGCGT | TTTTCGACTG | GGGAGAAGGT | GTGGGACCGT | GGGAACGTTA | CGCTTCAGTG | 1260
| TGACTGCCCT | AACGGCCCCT | GGGTGTGGTT | GCCAGCCTTT | TGCCAAGCAA | TCGGCTGGGG | 1320
| TGACCCCATC | ACTTATTGGA | GCCACGGGCA | AAATCAGTGG | CCCCTTTCAT | GCCCCAGTA | 1380
| TGTCTATGGG | TCTGCTACAG | TCACTTGCGT | GTGGGGTTCC | GCTTCTTGGT | ATGCCTCCAC | 1440
| CAGTGGTCGC | GACTCGAAGA | TAGATGTGTG | GAGTTTAGTG | CCAGTGGCT | CTGCCACCTG | 1500
| CACCATAGCC | GCACTTGGAT | CATCGGATCG | CGACACGGTG | CCTGGGCTCT | CCGAGTGGGG | 1560
| AATCCCGTGC | GTGACGTGTG | TTCTGGACCG | TCGGCCTGCT | TCATGCGGCA | CCTGTGTGAG | 1620
| GGACTGCTGG | CCCGAGACCG | GGTCGGTTAG | GTTCCCATTC | CATCGGTGCG | GCGTGGGGCC | 1680
| TCGGCTGACA | AAGGACTTGG | AAGCTGTGCC | CTTCGTCAAT | AGGACAACTC | CCTTCACCAT | 1740
| TAGGGGGCCC | CTGGGCAACC | AGGGCCGAGG | CAACCCGGTG | CGGTCGCCCT | TGGGTTTTGG | 1800
| GTCCTACGCC | ATGACCAGGA | TCCGAGATAC | CCTACATCTG | GTGGAGTGTC | CCACACCAGC | 1860
| CATCGAGCCT | CCCACCGGGA | CGTTTGGGTT | CTTCCCCGGG | ACGCCGCCTC | TCAACAACTG | 1920
| CATGCTCTTG | GGCACGGAAG | TGTCCGAGGC | ACTTGGGGGG | GCTGGCCTCA | CGGGGGGGTT | 1980
| CTATGAACCC | CTGGTGCGCA | GGTGTTCGGA | GCTGATGGGA | AGCCGAAATC | CGGTTTGTCC | 2040
| GGGGTTTGCA | TGGCTCTCTT | CGGGCAGGCC | TGATGGGTTT | ATACATGTCC | AGGGTCACTT | 2100
| GCAGGAGGTG | GATGCAGGCA | ACTTCATCCC | GCCCCGCGC | TGGTTGCTCT | TGGACTTTGT | 2160
| ATTTGTCCTG | TTATACCTGA | TGAAGCTGGC | TGAGGCACGG | TTGGTCCCGC | TGATCTTGCT | 2220
| GCTGCTATGG | TGGTGGGTGA | ACCAGCTGGC | AGTCCTAGGG | CTGCCGGCTG | TGGAAGCCGC | 2280
| CGTGGCAGGT | GAGGTCTTCG | CGGGCCCTGC | CCTGTCCTGG | TGTCTGGGAC | TCCGGTCGT | 2340
| CAGTATGATA | TTGGGTTTGG | CAAACCTGGT | GCTGTACTTT | AGATGGTTGG | GACCCCAACG | 2400
| CCTGATGTTC | CTCGTGTTGT | GGAAGCTTGC | TCGGGGAGCT | TTCCCGCTGG | CCCTCTTGAT | 2460
| GGGGATTTCG | GCGACCCGCG | GGCGCACCTC | AGTGCTCGGG | GCCGAGTTCT | GCTTCGATGC | 2520

-continued

```
TACATTCGAG GTGGACACTT CGGTGTTGGG CTGGGTGGTG GCCAATGTGG TAGCTTGGGC      2580
CATTGCGCTC CTGAGCTCGA TGAGCGCAGG GGGGTGGAGG CACAAAGCCG TGATCTATAG      2640
GACGTGGTGT AAGGGGTACC AGGCAATCCG TCAAAGGGTG GTGAGGAGCC CCCTCGGGGA      2700
GGGGCGGCCT GCCAAACCCC TGACCTTTGC CTGGTGCTTG GCCTCGTACA TCTGGCCAGA      2760
TGCTGTGATG ATGGTGGTGG TTGCCTTGGT TCTTCTCTTT GGCCTGTTCG ACGCGTTGGA      2820
TTGGGCCTTG GAGGAGATCT TGGTGTCCCG GCCCTCGCTG CGGCGTTTGG CTCGGGTGGT      2880
TGAGTGCTGT GTGATGGCGG GTGAGAAGGC CACAACCGTC CGGCTGGTCT CCAAGATGTG      2940
TGCGAGAGGA GCTTATTTGT TCGATCATAT GGGCTCATTT TCGCGTGCTG TCAAGGAGCG      3000
CCTGTTGGAA TGGACGCGG CTCTTGAACC TCTGTCATTC ACTAGGACGG ACTGTCGCAT      3060
CATACGGGAT GCCGCGAGGA CTTTGTCCTG CGGGCAATGC GTCATGGGTT TACCCGTGGT      3120
TGCGCGCCGT GGTGATGAGG TTCTCATCGG CGTCTTCCAG GATGTGAATC ATTTGCCTCC      3180
CGGGTTTGTT CCGACCGCGC CTGTTGTCAT CCGACGGTGC GGAAAGGGCT TCTTGGGGGT      3240
CACAAAGGCT GCCTTGACAG GTCGGGATCC TGACTTACAT CCAGGGAACG TCATGGTGTT      3300
GGGGACGGCT ACGTCGCGAA GCATGGGAAC ATGCTTGAAC GGCCTGCTGT TCACGACCTT      3360
CCATGGGGCT TCATCCCGAA CCATCGCCAC ACCCGTGGGG GCCCTTAATC CAGATGGTG      3420
GTCAGCCAGT GATGATGTCA CGGTGTATCC ACTCCCGGAT GGGGCTACTT CGTTAACGCC      3480
TTGTACTTGC CAGGCTGAGT CCTGTTGGGT CATCAGATCC GACGGGGCCC TATGCCATGG      3540
CTTGAGCAAG GGGGACAAGG TGGAGCTGGA TGTGGCCATG GAGGTCCCTG ATTTCCGTGG      3600
CTCGTCTGGC TCACCGGTCC TATGTGACGA GGGGCACGCA GTAGGAATGC TCGTGTCTGT      3660
GCTTCACTCC GGTGGTAGGG TCACCGCGGC ACGGTTCACT AGGCCGTGGA CCCAAGTGCC      3720
AACAGATGCC AAAACCACCA CTGAACCCCC TCCGGTGCCG GCCAAGGAG TTTTCAAAGA      3780
GGCCCCGTTG TTTATGCCTA CGGGAGCGGG AAAGAGCACT CGCGTCCCGT TGGAGTACGG      3840
CAACATGGGG CACAAGGTCT TAGTCTTGAA CCCCTCAGTG GCCACTGTGC GGGCCATGGG      3900
CCCGTACATG GAGCGGCTGG CGGGTAAACA TCCAAGTATA TACTGTGGGC ATGATACAAC      3960
TGCTTTCACA AGGATCACTG ACTCCCCCCT GACGTATTCA ACCTATGGGA GGTTTTTGGC      4020
CAACCCTAGG CAGATGCTAC GGGGCGTTTC GGTGGTCATT TGTGATGAGT GCCACAGTTA      4080
TGACTCAACC GTGCTGTTAG GCATTGGGAG GGTTCGGGAG CTGGCGCGTG GGTGCGGAGT      4140
GCAACTAGTG CTCTACGCCA CCGCTACGCC TCCCGGATCC CCTATGACGC AGCACCCTTC      4200
CATAATTGAG ACAAAATTGG ACGTGGGCGA GATTCCCTTT TATGGGCACG GAATACCCCT      4260
CGAGCGGATG CGAACCGGAA GGCACCTCGT GTTCTGCCAT TCTAAGGCTG AGTGCGAGCG      4320
CCTTGCTGGC CAGTTCTCCG CTAGGGGGT CAATGCCATT GCCTATTATA GGGGTAAAGA      4380
CAGTTCTATC ATCAAGGATG GGACCTGGT GGTCTGTGCC ACAGACGCGC TTTCCACTGG      4440
GTACACTGGA AATTTCGACT CCGTCACCGA CTGTGGATTA GTGGTGGAGG AGGTCGTTGA      4500
GGTGACCCTT GATCCTACCA TTACCATCTC CCTGCGGACA GTGCCTGCGT CGGCTGAACT      4560
GTCGATGCAA AGACGAGGAC GCACGGGTAG GGGCAGGTCT GGACGCTACT ACTACGCGGG      4620
GGTGGGCAAA GCCCCTGCGG GTGTGGTGCG CTCAGGTCCT GTCTGGTCGG CGGTGGAAGC      4680
TGGAGTGACC TGGTACGGAA TGGAACCTGA CTTGACAGCT AACCTACTGA GACTTTACGA      4740
CGACTGCCCT TACACCGCAG CCGTCGCGGC TGATATCGGA GAAGCCGCGG TGTTCTTCTC      4800
TGGGCTCGCC CCATTGAGGA TGCACCCTGA TGTCAGCTGG GCAAAAGTTC GCGGCGTCAA      4860
CTGGCCCCTC TTGGTGGGTG TTCAGCGGAC CATGTGTCGG GAAACACTGT CTCCCGGCCC      4920
```

```
ATCGGATGAC CCCCAATGGG CAGGTCTGAA GGGCCCAAAT CCTGTCCCAC TCCTGCTGAG   4980
GTGGGGCAAT GATTTACCAT CTAAAGTGGC CGGCCACCAC ATAGTGGACG ACCTGGTCCG   5040
GAGACTCGGT GTGGCGGAGG GTTACGCCCG CTGCGACGCT GGGCCGATCT TGATGATCGG   5100
TCTAGCTATC GCGGGGGGAA TGATCTACGC GTCGTACACC GGGTCGCTAG TGGTGGTGAC   5160
AGACTGGGAT GTGAAGGGGG GTGGCGCCCC CCTTTATCGG CATGGAGACC AGGCCACGCC   5220
TCAGCCGGTG GTGCAGGTTC CTCCGGTAGA CCATCGGCCG GGGGTGAAT CAGCACCATC    5280
GGATGCCAAG ACAGTGACAG ATGCGGTGGC AGCGATCCAG GTGGACTGCG ATTGGACTAT   5340
CATGACTCTG TCGATCGGAG AAGTGTTGTC CTTGGCTCAG GCTAAGACGG CCGAGGCCTA   5400
CACAGCAGCC ACCAAGTGGC TCGCTGGCTG CTATACGGGG ACGCGGGCCG TTCCCACTGT   5460
ATCCATTGTT GACAAGCTCT TCGCCGGAGG GTGGGCGGCT GTGGTGGGCC ATTGCCACAA   5520
CGTGATTGCT GCGGCGGTGG CGGCCTACGG GGCTTCAAAG AGCCCGCCGT TGGCAGCCGC   5580
GGCTTCCTAC CTGATGGGGT TGGGCGTTGG AGGCAACGCT CAGACGCGTC TGGCATCTGC   5640
CCTCCTATTG GGGGCTGCTG GAACCGCCTT GGGCACTCCT GTCGTGGGCT TGACCATGGC   5700
AGGTGCGTTC ATGGGGGGCG CCAGTGTCTC CCCCTCCTTG GTCACCATTT TATTGGGGGC   5760
CGTCGGAGGT TGGGAGGGTG TTGTCAACGC GGCGAGCCTA GTCTTTGACT TCATGGCGGG   5820
GAAACTTTCA TCAGAAGATC TGTGGTATGC CATCCCGGTA CTGACCAGCC CGGGGGCGGG   5880
CCTTGCGGGG ATCGCTCTCG GGTTGGTTTT GTATTCAGCT AACAACTCTG GCACTACCAC   5940
TTGGTTGAAC CGTCTGCTCA CTACGTTACC AAGGTCTTCA TGTATCCCGG ACAGTTACTT   6000
TCAGCAAGTT GACTATTGCG ACAAGGTCTC AGCCGTGCTC CGGCGCCTGA GCCTCACCCG   6060
CACAGTGGTT GCCCTGGTCA ACAGGGAGCC TAAGGTGGAT GAGGTACAGG TGGGGTATGT   6120
CTGGGACCTG TGGGAGTGGA TCATGCGCCA AGTGCGCGTG GTCATGGCCA GACTCAGGGC   6180
CCTCTGCCCC GTGGTGTCAT TACCCTTGTG GCACTGCGGG GAGGGGTGGT CCGGGGAATG   6240
GTTGCTTGAC GGTCATGTTG AGAGTCGCTG CCTCTGTGGC TGCGCGATCA CTGGTGACGT   6300
TCTGAATGGG CAACTCAAAG AACCAGTTTA CTCTACCAAG CTGTGCCGGC ACTATTGGAT   6360
GGGGACTGTC CCTGTGAACA TGCTGGGTTA CGGTGAAACG TCGCCTCTCC TGGCCTCCGA   6420
CACCCCGAAG GTTGTGCCCT TCGGGACGTC TGGCTGGGCT GAGGTGGTGG TGACCACTAC   6480
CCACGTGGTA ATCAGGAGAA CCTCCGCCTA TAAGCTGCTG CGCCAGCAAA TCCTATCGGC   6540
TGCTGTAGCT GAGCCCTACT ACGTCGACGG CATTCCGGTC TCATGGACG CGGACGCTCG    6600
TGCGCCCGCC ATGGTCTATG GCCCTGGGCA AAGTGTTACC ATTGACGGGG AGCGCTACAC   6660
CCTGCCTCAT CAACTGAGGC TCAGGAATGT GGCGCCCTCT GAGGTTTCAT CCGAGGTGTC   6720
CATTGACATT GGGACGGAGA CTGGAGACTC AGAACTGACT GAGGCCGATC TGCCGCCGGC   6780
GGCTGCTGCT CTCCAAGCGA TCGAGAATGC TGCGAGGATT CTTGAACCGC ACATTGATGC   6840
CATCATGGAG GACTGCAGTA CACCCTCTCT TTGTGGTAGT AGCCGAGAGA TGCCTGTATG   6900
GGGAGAAGAC ATCCCCCGTA CTCCATCGCC AGCACTTATC TCGGTTACTG AGAGCAGCTC   6960
AGATGAGAAG ACCCCGTCGG TGTCCTCCTC GCAGGAGGAT ACCCCGTCCT CTGACTCATT   7020
CGAGGTCATC CAAGAGTCCG AGACAGCCGA AGGGGAGGAA AGCGTCTTCA ACGTGGCTCT   7080
TTCCGTATTA GAAGCCTCAT TCCACAGAG CGACGCGACC AGGAAGCTTA CCGTCAAGAT    7140
GTCGTGCTGC GTTGAAAAGA GCGTCACGCG CTTTTTCTCA TTGGGGTTGA CGGTGGCTGA   7200
TGTTGCTAGC CTGTGTGAGA TGGAAATCCA GAACCATACA GCCTATTGTG ACAAGGTGCG   7260
CACTCCGCTT GAATTGCAGG TTGGGTGCTT GGTGGGCAAT GAACTTACCT TTGAATGTGA   7320
```

-continued

```
CAAGTGTGAG GCTAGGCAAG AAACCTTGGC CTCCTTCTCT TACATTTGGT CTGGAGTGCC    7380
GCTGACTAGG GCCACGCCGG CCAAGCCTCC CGTGGTGAGG CCGGTTGGCT CTTTATTAGT    7440
GGCCGACACT ACTAAGGTGT ATGTTACCAA TCCAGACAAT GTGGGACGGA GGGTGGACAA    7500
GGTGACCTTC TGGCGTGCTC CTAGGGTTCA TGATAAGTAC CTCGTGGACT CTATTGAGCG    7560
CGCTAAGAGG GCCGCTCAAG CCTGCCTAAG CATGGGTTAC ACTTATGAGG AAGCAATAAG    7620
GACTGTAAGG CCACATGCTG CCATGGGCTG GGGATCTAAG GTGTCGGTTA AGGACTTAGC    7680
CACCCCCGCG GGGAAGATGG CCGTCCATGA CCGGCTCCAG GAGATACTTG AAGGGACTCC    7740
GGTCCCCTTT ACTCTTACTG TGAAAAGGA GGTGTTCTTC AAAGACCGGA AGGAGGAGGA    7800
GGCCCCCCGC CTCATTGTGT TCCCCCCCCT GGACTTCCGG ATAGCTGAAA AGCTCATCTT    7860
GGGAGACCCA GACCGGGTAG CCAAGGCGGT GTTGGGGGGG GCCTACGCCT TCCAGTACAC    7920
CCCAAATCAG CGAGTTAAGG AGATGCTCAA GCTATGGGAG TCTAAGAAGA CCCCTTGCGC    7980
CATCTGTGTG GACGCCACCT GCTTCGACAG TAGCATAACT GAAGAGGACG TGGCTTTGGA    8040
GACAGAGCTG TACGCTCTGG CCTCTGACCA TCCAGAATGG GTGCGGGCAC TTGGGAAATA    8100
CTATGCCTCA GGCACCATGG TCACCCCGGA AGGGGTGCCC GTCGGTGAGA GGTATTGCAG    8160
ATCCTCGGGT GTCCTAACAA CTAGCGCGAG CAACTGCTTG ACCTGCTACA TCAAGGTGAA    8220
AGCCGCCTGT GAGAGGGTGG GGCTGAAGAA TGTCTCTCTT CTCATAGCCG GCGATGACTG    8280
CTTGATCATA TGTGAGCGGC CAGTGTGCGA CCCAAGCGAC GCTTTGGGCA GAGCCCTAGC    8340
GAGCTATGGG TACGCGTGCG AGCCCTCATA TCATGCATCC TTGGACACGG CCCCCTTCTG    8400
CTCCACTTGG CTTGCTGAGT GCAATGCAGA TGGGAAGCGC CATTTCTTCC TGACCACGGA    8460
CTTCCGGAGG CCGCTCGCTC GCATGTCGAG TGAGTATAGT GACCCGATGG CTTCGGCGAT    8520
CGGTTACATC CTCCTTTATC CTTGGCACCC CATCACACGG TGGGTCATCA TCCCTCATGT    8580
GCTAACGTGC GCATTCAGGG GTGGAGGCAC ACCGTCTGAT CCGGTTTGGT GCCAGGTACA    8640
TGGTAACTAC TACAAGTTTC CACTGGACAA ACTGCCTAAC ATCATCGTGG CCCTCCACGG    8700
ACCAGCAGCG TTGAGGGTTA CCGCAGACAC AACTAAAACA AAGATGGAGG CTGGTAAGGT    8760
TCTGAGCGAC CTCAAGCTCC CTGGCTTAGC AGTCCACCGA AAGAAGGCCG GGGCGTTGCG    8820
AACACGCATG CTCCGCTCGC GCGGTTGGGC TGAGTTGGCT AGGGGCTTGT TGTGGCATCC    8880
AGGCCTACGG CTTCCTCCCC CTGAGATTGC TGGTATCCCG GGGGTTTCC CTCTCTCCCC    8940
CCCCTATATG GGGGTGGTAC ACCAATTGGA TTTTACAAGC CAGAGGAGTC GCTGGCGGTG    9000
GTTGGGGTTC TTAGCCCTGC TCATCGTAGC CCTCTTCGGG TGAACTAAAT TCATCTGTTG    9060
CGGCGAGGTC TGGTGACTGA TCGTCACCGG AGGAGGTTCC CGCCCTCCCC GCCCCAGGGG    9120
TCTCCCCGCT GGGTAAAAAG GGCCCGGCCT TGGGAGGCAT GGTGGTTACT AACCCCCTGG    9180
CAGGGTTAAA GCCTGATGGT GCTAATGCAC TGCCACTTCG GTGGCGGGTC GCTACCTTAT    9240
AGCGTAATCC GTGACTACGG GCTGCTCGCA GAGCCCTCCC CGGATGGGGC ACAGTGCACT    9300
GAGATCTGAA GGGGTGCACC CCGGGAA                                         9327
```

( 2 ) INFORMATION FOR SEQ ID NO:235:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO (iv) ANTI-SENSE: NO (vi) ORIGINAL SOURCE:
            (C) INDIVIDUAL ISOLATE: Primer GLI- F (xi) SEQUENCE DESCRIPTION: SEQ ID NO:235:

TAGCATGGCC TTTGCAGGGC TG 22

(2) INFORMATION FOR SEQ ID NO:236:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer GLI- R (xi) SEQUENCE DESCRIPTION: SEQ ID NO:236:

AAGCTGTGAC CGTCTCCG 18

(2) INFORMATION FOR SEQ ID NO:237:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer GE1- NF (xi) SEQUENCE DESCRIPTION: SEQ ID NO:237:

GCCGCCATGG CGGGGAAACT TTCATCAGAA G 31

(2) INFORMATION FOR SEQ ID NO:238:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer GE1- NR (xi) SEQUENCE DESCRIPTION: SEQ ID NO:238:

GCGCGGATCC TAGTGACACC ACGGGGCAGA GG 32

(2) INFORMATION FOR SEQ ID NO:239:

(i) SEQUENCE CHARACTERISTICS:

(A) LENGTH: 33 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: NO (vi) ORIGINAL SOURCE:
                (C) INDIVIDUAL ISOLATE: Primer GE57F (xi) SEQUENCE DESCRIPTION: SEQ ID NO:239:

GCCGCCATGG CTCTCTTGAC CAATAGGTTT ATC                33

(2) INFORMATION FOR SEQ ID NO:240:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: NO (vi) ORIGINAL SOURCE:
                (C) INDIVIDUAL ISOLATE: Primer GE57R (xi) SEQUENCE DESCRIPTION: SEQ ID NO:240:

GCGCGGATCC AGAAATGCCA CCCGCCCTCA C                  31

(2) INFORMATION FOR SEQ ID NO:241:

(i) SEQUENCE CHARACTERISTICS:
                (A) LENGTH: 61 amino acids
                (B) TYPE: amino acid
                (D) TOPOLOGY: linear (ii) MOLECULE TYPE: protein (iii) HYPOTHETICAL: NO (iv) ANTI-SENSE: NO (vi) ORIGINAL SOURCE:
                (C) INDIVIDUAL ISOLATE: GE57 amino acid sequence (xi) SEQUENCE DESCRIPTION: SEQ ID NO:241:

```
Met Ser Leu Leu Thr Asn Arg Phe Ile Arg Arg Val Asp Lys Asp Gln
 1           5                  10                 15

Trp Gly Pro Gly Val Thr Gly Thr Asp Pro Glu Pro Cys Pro Ser Arg
            20                 25                 30

Trp Ala Gly Lys Cys Met Gly Pro Pro Ser Ser Ala Ala Ala Cys Ser
            35                 40                 45

Arg Gly Ser Pro Arg Ile Leu Arg Val Arg Ala Gly Gly
            50                 55                 60
```

(2) INFORMATION FOR SEQ ID NO:242:

(i) SEQUENCE CHARACTERISTICS:
                (A) LENGTH: 52 base pairs
                (B) TYPE: nucleic acid
                (C) STRANDEDNESS: single
                (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Forward Primer for E1

(x i) SEQUENCE DESCRIPTION: SEQ ID NO:242:

GCGCAGATCT AAAATGAGCC GTGGTGGCAT TTCCTTTTTC TATACCATCA TG    52

(2) INFORMATION FOR SEQ ID NO:243:

(i) SEQUENCE CHARACTERISTICS:
 (A) LENGTH: 38 base pairs
 (B) TYPE: nucleic acid
 (C) STRANDEDNESS: single
 (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Reverse Primer for E1

(x i) SEQUENCE DESCRIPTION: SEQ ID NO:243:

GCGCAGATCT CCAGAAATCA AATGGGACCT TCCAGAGG    38

(2) INFORMATION FOR SEQ ID NO:244:

(i) SEQUENCE CHARACTERISTICS:
 (A) LENGTH: 26 base pairs
 (B) TYPE: nucleic acid
 (C) STRANDEDNESS: single
 (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Forward Primer for E2 with insect
  signal sequence (x i) SEQUENCE DESCRIPTION: SEQ ID NO:244:

CGCGAGATCT GTCGCAAGGC GCCCCT    26

(2) INFORMATION FOR SEQ ID NO:245:

(i) SEQUENCE CHARACTERISTICS:
 (A) LENGTH: 28 base pairs
 (B) TYPE: nucleic acid
 (C) STRANDEDNESS: single
 (D) TOPOLOGY: linear (i i) MOLECULE TYPE: DNA (i i i) HYPOTHETICAL: NO (i v) ANTI-SENSE: NO (v i) ORIGINAL SOURCE:
 (C) INDIVIDUAL ISOLATE: Reverse Primer for E2 with insect
  signal sequence (x i) SEQUENCE DESCRIPTION: SEQ ID NO:245:

GCGCAGATCT AGTTGCCTGC ATCCACCT    28

( 2 ) INFORMATION FOR SEQ ID NO:246:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Forward Primer for E2 with HGV
            signal sequence ( x i ) SEQUENCE DESCRIPTION: SEQ ID NO:246:

CGCGAGATCT AAAATGAAAC TGCTTGTCAT GGTCTTCCTG TT         42

( 2 ) INFORMATION FOR SEQ ID NO:247:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Reverse Primer for E2 with HGV
            signal sequence ( x i ) SEQUENCE DESCRIPTION: SEQ ID NO:247:

GCGCAGATCT AGTTGCCTGC ATCCACCT         28

( 2 ) INFORMATION FOR SEQ ID NO:248:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Forward Primer for NS2a ( x i ) SEQUENCE DESCRIPTION: SEQ ID NO:248:

GCGCAGATCT GGCCGTGGCA GGTGAGGTCT TCGC         34

( 2 ) INFORMATION FOR SEQ ID NO:249:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (iii) HYPOTHETICAL: NO (iv) ANTI-SENSE: NO (vi) ORIGINAL SOURCE:
(C) INDIVIDUAL ISOLATE: Reverse Primer for NS2a (xi) SEQUENCE DESCRIPTION: SEQ ID NO:249:

GCGCAGATCT TAACGCCGCA ACGAGGGCCG G　　　　　　　　　　　　　　　　31

(2) INFORMATION FOR SEQ ID NO:250:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Forward Primer for NS2b (xi) SEQUENCE DESCRIPTION: SEQ ID NO:250:

GCGCGGATCC AAAATGATCG CTCGGGTGGT TGAGTGCTGT GTGATG　　　　　　　46

(2) INFORMATION FOR SEQ ID NO:251:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Reverse Primer for NS2b (xi) SEQUENCE DESCRIPTION: SEQ ID NO:251:

GCGCGGATCC AGGCGCGGTC GGAACAAACC CG　　　　　　　　　　　　　　32

(2) INFORMATION FOR SEQ ID NO:252:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Forward Primer NS3

(xi) SEQUENCE DESCRIPTION: SEQ ID NO:252:

GCGAGATCTA AAATGTGCGG AAAGGGCTTC TTGGGGGTC　　　　　　　　　　39

(2) INFORMATION FOR SEQ ID NO:253:

( i ) SEQUENCE CHARACTERISTICS:
   ( A ) LENGTH: 39 base pairs
   ( B ) TYPE: nucleic acid
   ( C ) STRANDEDNESS: single
   ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
   ( C ) INDIVIDUAL ISOLATE: Reverse Primer NS3

( x i ) SEQUENCE DESCRIPTION: SEQ ID NO:253:

GCGAGATCTC ATCTCCGGAC CAGGTCGTCC ACTATGTGG    39

( 2 ) INFORMATION FOR SEQ ID NO:254:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Forward Primer NS4a ( x i ) SEQUENCE DESCRIPTION: SEQ ID NO:254:

GGCGGATCCA AAATGATCGG TGTGGCGGAG G    31

( 2 ) INFORMATION FOR SEQ ID NO:255:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Reverse Primer NS4a ( x i ) SEQUENCE DESCRIPTION: SEQ ID NO:255:

GGCGGGATCC ATGCGCCGGA GCACGG    26

( 2 ) INFORMATION FOR SEQ ID NO:256:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: Forward Primer NS4b ( x i ) SEQUENCE DESCRIPTION: SEQ ID NO:256:

GCGGGATCCA AAATGATCAG CCTCACCCGC ACAG 34

( 2 ) INFORMATION FOR SEQ ID NO:257:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Reverse Primer NS5a ( x i ) SEQUENCE DESCRIPTION: SEQ ID NO:257:

GGCGGGATCC TACCTCCTGA TTACCACGT 29

( 2 ) INFORMATION FOR SEQ ID NO:258:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Forward Primer NS5a ( x i ) SEQUENCE DESCRIPTION: SEQ ID NO:258:

GCGAGATCTA AAATGACCTC CGCCTATAAG CTGCTGCGCC AG 42

( 2 ) INFORMATION FOR SEQ ID NO:259:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Reverse Primer NS5a ( x i ) SEQUENCE DESCRIPTION: SEQ ID NO:259:

GGCAGATCTA CCTCCGTCCC ACATTGTCTG GATTGGTAAC 40

( 2 ) INFORMATION FOR SEQ ID NO:260:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear (  i  i  ) MOLECULE TYPE: DNA (  i  i  i  ) HYPOTHETICAL: NO (  i  v  ) ANTI-SENSE: NO (  v  i  ) ORIGINAL SOURCE:
 ( C ) INDIVIDUAL ISOLATE: Forward Primer NS5b (  x  i  ) SEQUENCE DESCRIPTION: SEQ ID NO:260:

GCGAGATCTA AAATGGTGGA CAAGGTGACC TTCTGGCGTG CTC 43

( 2 ) INFORMATION FOR SEQ ID NO:261:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear (  i  i  ) MOLECULE TYPE: DNA (  i  i  i  ) HYPOTHETICAL: NO (  i  v  ) ANTI-SENSE: NO (  v  i  ) ORIGINAL SOURCE:
 ( C ) INDIVIDUAL ISOLATE: Reverse Primer NS5b (  x  i  ) SEQUENCE DESCRIPTION: SEQ ID NO:261:

GCGAGATCTC ACCCGAAGAG GGCTACGATG AGCAGG 36

( 2 ) INFORMATION FOR SEQ ID NO:262:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear (  i  i  ) MOLECULE TYPE: DNA (  i  i  i  ) HYPOTHETICAL: NO (  i  v  ) ANTI-SENSE: NO (  v  i  ) ORIGINAL SOURCE:
 ( C ) INDIVIDUAL ISOLATE: Forward Primer E1-E2-NS2a (  x  i  ) SEQUENCE DESCRIPTION: SEQ ID NO:262:

GCGCAGATCT AAAATGAGCC GTGGTGGCAT TTCCTTTTTC TATACCATCA TG 52

( 2 ) INFORMATION FOR SEQ ID NO:263:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear (  i  i  ) MOLECULE TYPE: DNA (  i  i  i  ) HYPOTHETICAL: NO (  i  v  ) ANTI-SENSE: NO (  v  i  ) ORIGINAL SOURCE:
 ( C ) INDIVIDUAL ISOLATE: Reverse Primer E1-E2-NS2a (  x  i  ) SEQUENCE DESCRIPTION: SEQ ID NO:263:

GCGCAGATCT TAACGCCGCA ACGAGGGCCG G 31

( 2 ) INFORMATION FOR SEQ ID NO:264:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer 9E3- REV ( x i ) SEQUENCE DESCRIPTION: SEQ ID NO:264:

GCTGGCTGAG GCACGGTTGG TC        22

( 2 ) INFORMATION FOR SEQ ID NO:265:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer E39- 94PR ( x i ) SEQUENCE DESCRIPTION: SEQ ID NO:265:

CACCATCATC ACAGCATCTG GC        22

( 2 ) INFORMATION FOR SEQ ID NO:266:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GEP- F12

( x i ) SEQUENCE DESCRIPTION: SEQ ID NO:266:

GCAACCATGG AACCTGCCAA ACCCCTGACC TT        32

( 2 ) INFORMATION FOR SEQ ID NO:267:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GEP- R12

( x i ) SEQUENCE DESCRIPTION: SEQ ID NO:267:

AGCCCCATGG AAGGTCGTGA A                                     21

( 2 ) INFORMATION FOR SEQ ID NO:268:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GEP- F14

( x i ) SEQUENCE DESCRIPTION: SEQ ID NO:268:

TTGGGATCCC TCGTGTTCCG CCATTCTAAG                             30

( 2 ) INFORMATION FOR SEQ ID NO:269:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer GEP- R13

( x i ) SEQUENCE DESCRIPTION: SEQ ID NO:269:

TATGGATCCT GGTAAATCAT TGCCCCACCT                             30

( 2 ) INFORMATION FOR SEQ ID NO:270:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer 470EP- F8

( x i ) SEQUENCE DESCRIPTION: SEQ ID NO:270:

GCTGAATTCG CCATGGCGAC GTGCGCATTC AGGGGTGGA                   39

( 2 ) INFORMATION FOR SEQ ID NO:271:

( i ) SEQUENCE CHARACTERISTICS:
( A ) LENGTH: 27 base pairs
( B ) TYPE: nucleic acid
( C ) STRANDEDNESS: single ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer GEP- R14

( x i ) SEQUENCE DESCRIPTION: SEQ ID NO:271:

GGAGGATCCG CGACCCGCCA CCGAAGT 27

( 2 ) INFORMATION FOR SEQ ID NO:272:

( i ) SEQUENCE CHARACTERISTICS:
    ( A ) LENGTH: 48 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( C ) INDIVIDUAL ISOLATE: Y5 epitope ( x i ) SEQUENCE DESCRIPTION: SEQ ID NO:272:

```
Ile  Asp  Gly  Glu  Arg  Tyr  Thr  Leu  Pro  His  Gln  Leu  Arg  Leu  Arg  Asn
1                   5                        10                       15

Val  Ala  Pro  Ser  Glu  Val  Ser  Ser  Glu  Val  Ser  Ile  Asp  Ile  Gly  Thr
                20                       25                       30

Glu  Ala  Glu  Asn  Ser  Glu  Leu  Thr  Glu  Ala  Asp  Leu  Pro  Pro  Ala  Ala
           35                       40                       45
```

( 2 ) INFORMATION FOR SEQ ID NO:273:

( i ) SEQUENCE CHARACTERISTICS:
    ( A ) LENGTH: 55 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( C ) INDIVIDUAL ISOLATE: Q9 Epitope ( x i ) SEQUENCE DESCRIPTION: SEQ ID NO:273:

```
Cys  Gly  Leu  Leu  Thr  Arg  His  His  Thr  Ala  Leu  Asn  His  Pro  Ser  Gln
1                   5                        10                       15

Thr  Pro  Gln  Arg  Gly  Pro  Gly  His  Gln  Asp  Leu  Leu  Gln  Gly  Pro  Ile
                20                       25                       30

Gln  Arg  Val  Glu  Gln  Ala  Lys  Glu  Lys  Asp  Gln  Gly  Asn  His  His  His
           35                       40                       45

His  His  Ser  Ile  Trp  Pro  Asp
     50                   55
```

( 2 ) INFORMATION FOR SEQ ID NO:274:

( i ) SEQUENCE CHARACTERISTICS:
    ( A ) LENGTH: 35 amino acids
    ( B ) TYPE: amino acid ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
    ( C ) INDIVIDUAL ISOLATE: Q11 Epitope ( x i ) SEQUENCE DESCRIPTION: SEQ ID NO:274:

```
Ala  Ala  Val  Ala  Glu  Pro  Tyr  Tyr  Val  Asp  Gly  Ile  Pro  Val  Ser  Trp
 1             5                        10                       15
Asp  Ala  Asp  Ala  Arg  Ala  Pro  Ala  Met  Val  Tyr  Gly  Pro  Gly  Gln  Ser
              20                        25                       30
Val  Thr  Ile
           35
```

( 2 ) INFORMATION FOR SEQ ID NO:275:

( i ) SEQUENCE CHARACTERISTICS:
        ( A ) LENGTH: 225 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Q7-12-1 env clone ( x i ) SEQUENCE DESCRIPTION: SEQ ID NO:275:

```
GTGCCCTTCG  TCAACAGGAC  AACTCTCTTC  ACCATTAGGG  GGCCCCTGGG  CAACCAGGGC     60
CGAGGCAACC  CGGTGCGGTC  GCCCTTGGGT  TTTGGGTCCT  ACGCCATGAC  CAGGATCCGA    120
GATACCCTAC  ATCTGGTGGA  GTGTCCCACA  CCAGCCATCG  AGCCTCCCAC  CGGGACGTCT    180
GGGTTCTTCC  CCGGGACGCC  GCCTCTCAAC  AACTGCATGC  ATATG                    225
```

( 2 ) INFORMATION FOR SEQ ID NO:276:

( i ) SEQUENCE CHARACTERISTICS:
        ( A ) LENGTH: 192 base pairs
        ( B ) TYPE: nucleic acid
        ( C ) STRANDEDNESS: both
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Y12-15-1 NS3 clone DNA ( x i ) SEQUENCE DESCRIPTION: SEQ ID NO:276:

```
AACATGGGGC  ACAAGGTCTT  AATCTTGAAC  CCCTCAGTGG  CCACTGTGCG  GGCCATGGGC     60
CCGTACATGG  AGCGGCTGGC  GGGTAAACAT  CCAAGTATAT  ACTGTGGGCA  TGATACAACT    120
GCTTTCACAA  GGATCACTGA  CTCCCCCCTG  ACGTATTCAA  CCTATGGGAG  GTTTTTGGCC    180
AACCCTAGGC  AA                                                             192
```

( 2 ) INFORMATION FOR SEQ ID NO:277:

(i) SEQUENCE CHARACTERISTICS:
  (A) LENGTH: 264 base pairs
  (B) TYPE: nucleic acid
  (C) STRANDEDNESS: both
  (D) TOPOLOGY: linear (ii) MOLECULE TYPE: DNA (iii) HYPOTHETICAL: NO (iv) ANTI-SENSE: NO (vi) ORIGINAL SOURCE:
  (C) INDIVIDUAL ISOLATE: Y12-10-2 NS3 clone (xi) SEQUENCE DESCRIPTION: SEQ ID NO:277:

```
CCCCTCGAGC GGATGCGAAC CGGAAGGCAC CTCGTGTTCT GCCATTCTAA GGCTGAGTGC      60

GAGCGCCTTG CTGGCCAGTT CTCCGCTAGG GGGGTCAATG CCATTGCCTA TTATAGGGGT     120

AAAGACAGCT CTATCATCAA GGATGGGGAC CTGGTGGTCT GTGCTACAGA CGCGCTTTCC     180

ACTGGGTACA CTGGAAATTT CGACTCCGTC ACCGACTGTG GATTAGTGGT GGAGGAGGTC     240

GTTGAGGTGA CCCTTGATCC CACC                                           264
```

HEPATITIS G VIRUS AND MOLECULAR CLONING THEREOF

This application is a divisional of U.S. application Ser. No. 08/444,733, filed May 19, 1995, which is a continuation-in-part of U.S. application Ser. No. 08/344,271, filed Nov. 23, 1994, abandoned, which is a continuation-in-part of U.S. application Ser. No. 08/285,561, filed on Aug. 3, 1994, abandoned, which is a continuation-in-part of U.S. application Ser. No. 08/264,985 filed on May 20, 1994, abandoned, and is a continuation-in-part of U.S. patent application Ser. No. 08/389,886, filed Feb. 15, 1995 abandoned, herein incorporated by reference, which is a continuation-in-part of 08/357,509, filed Dec. 16, 1994 abandoned, herein incorporated by reference, which is a continuation-in-part of U.S. patent application Ser. No. 08/329,729, filed Oct. 26, 1994 abandoned, herein incorporated by reference, which is a continuation-in-part of U.S. patent application Ser. No. 08/285,558, filed Aug. 3, 1994 abandoned, and U.S. patent application Ser. No. 08/285,543 abandoned, filed Aug. 3, 1994, herein incorporated by reference, which are continuations-in-part of U.S. patent application Ser. No. 08/246,985, filed May 20, 1994 abandoned, herein incorporated by reference.

FIELD OF INVENTION

This invention relates to nucleic acid, polypeptide, antigen, epitope, vaccine and antibody compositions related to a NonA/NonB/NonC/NonD/NonE (N-(ABCDE)) hepatitis-associated viral agent (HGV). The invention also relates to diagnostic and therapeutic methods.

REFERENCES

Abstracts, The 1992 San Diego Conf.: Genetic Recognition, Clin. Chem. 39(4):705 (1993).

Alexander, W. A., et al., *J. Virol.* 66:2934–2942 (1992).

Alter, H. J., et al., *New Eng. J. Med.* 321:1494–1500 (1989a).

Alter, M. J., et al., *N. Engl. J. Med.* 327:1899 (1989b).

Alter, H. J., *Abstracts of Tnt. Symp. on Viral Hepatitis and Liver Dis.*, p. 47 (1993).

Altschul, S., et al., *J. Mol. Biol.* 215:403–10 (1990).

Ascadi, G., et al., *Nature* 352:815 (1991).

Ausubel, F. M., et al., *CURRENT PROTOCOLS IN MOLECULAR BIOLOGY*, John Wiley and Sons, Inc., Media Pa.

Barany, F., PCR Methods Appl. 1:5 (1991).

Barham, W. B., et al., *J. Med. Virol.* 42:129–132 (1994).

Baron, S., et al., *JAMA* 266:1375 (1991).

Bazan, J. F., et al., *Virology* 171:637–639 (1989).

Beames, et al., *Biotechniques* 11:378 (1991).

Belyavsky, A., et al., *Nuc. Acids Res.* 17:2919–2932 (1989).

Blackburn, G. F., et al., *Clin. Chem.* 37:1534–1539 (1991).

Bradley, D. W., et al., *J. Infec. Dis.*, 148:2 (1983).

Bradley, D. W., et al., *J. Gen. Virol.*, 69:1 (1988).

Bradley, D. W. et al., *Proc. Nat. Acad. Sci., USA*, 84:6277 (1987).

Briand, J. P., et al., *J. Immunol. Meth.* 156:255 (1992).

Cahill, P., et al., *Clin. Chem.* 37:1482 (1991).

Carter, J. M., et al., *Methods Mol. Biol.* 36:207–223 (1994).

Chambers, T. J., et al., *Ann. Rev. Microbiol.* 44:649 (1990a).

Chambers, T. J., et al., *PNAS* 87:8898 (1990b).

Chomczynski et al, *Anal. Biochem.* 162:159 (1987).

Christian, R. B., et al., *J. Mol. Biol.* 227:771 (1992).

Commandaeur, et al., *Virology* 198:282–287 (1994).

Crea, R., U.S. Pat. No. 4,888,286, issued Dec. 19, 1989.

DeGraaf, M. E., et al., *Gene* 128:13 (1993).

DiBisceglie, A. M., et al., *Hepatology* 16:649 (1992).

DiBisceglie, A. M., et al., *NEJM* 321:1506 (1989).

DiCesare, J., et al., Biotechniques 15:152–157 (1993).

Dienstag, J. L., et al, *Sem Liver Disease* 6:67 (1986).

Earl, P. L., et al., "Expression of proteins in mammalian cells using vaccinia" *In Current Protocols in Molecular Biology* (F. M. Ausubel, et al. Eds.), Greene Publishing Associates & Wiley Interscience, New York (1991).

Eaton, M. A. W., et al., U.S. Pat. No. 4,719,180, issued Jan. 12, 1988.

Egholm, et al., *Nature* 365:566 (1993).

Elroy-Stein, O., et al., *Proc. Natl. Acad. Sci. USA.* 86:6126–6130 (1989).

EPO patent application 88310922.5, filed 11/18/88.

Falkner, F. G., et al., *J. Virol.* 62:1849–1854 (1988).

Farci, P., et al., *NEJM* 330:88 (1994).

Felgner and Rhodes, *Nature* 349:251 (1991).

Fickett, J. W., *Nuc. Acids Res.* 10:5303–5318 (1982).

Fling, S. P., et al., *Analytical Biochem.* 155:83–88 (1986).

Folgori, A., et al., *EMBO J.* 13:2236 (1994).

Francki, R. I. B., et al., *Arch. Virol. Suppl.* 12:223 (1991).

Frank, R., and Doring, R., *Tetrahedron* 44:6031–6040 (1988).

Frohman, M. A., et al., *Proc. Natl. Acad. Sci. USA* 85:8998–9002 (1988).

Fuerst, T. R., et al., *Proc. Natl. Acad. Sci. USA* 83:8122–8126 (1986).

Gellissen, G., et al., *Antonie Van Leeuwenhoek*, 62(1–2):79–93 (1992).

Geysen, M., et al., *Proc. Natl. Acad. Sci. USA* 81:3998–4002 (1984).

Gingeras, T. R., et al., *Ann. Biol. Clin.* 48:498 (1990).

Gingeras, T. R., et al., *J. Inf. Dis.* 164:1066–(1991).

Goeddel, D. V., *Methods in Enzymology* 185 (1990).

Grakoui, A., et al., *J. Virol.* 67:2832 (1993).

Grakoui, A., et al., *J. Virol.* 67:1385–1395 (1993).

Guatelli, J. C., et al., *Proc. Natl. Acad. Sci. USA* 87:1874 (1990).

Gubler, U., et al, *Gene*, 25:263 (1983).

Guthrie, C., and G. R. Fink, *Methods in Enzymology* 194 (1991).

Gutterman, J. U., *PNAS* 91:1198 (1994).

Harlow, E., et al., *ANTIBODIES: A LABORATORY MANUAL*, Cold Spring Harbor Laboratory Press (1988).

Haynes, J., et al., *Nuc. Acid. Res.* 11:687–706 (1983).

Hieter, P. A., et al., *Cell* 22:197–207 (1980).

Hijikata, M., et al., *PNAS* 88:5547 (1991).

Hochuli, E., in *GENETIC ENGINEERING. PRINCIPALS AND PRACTICE*, VOL. 12 (J. Stelow Ed.) Plenum, N.Y., pp. 87–98 (1990).

Holodniy, M., et al., *Biotechniques* 12:36 (1992).

Hopp, T. P., et al., *Proc. Natl. Acad. Sci. USA* 78:3824–3828 (1981).

Horn, T., and Urdea, M. S., *Nuc. Acids. Res.* 17:6959 (1989).

Houghten, R. A., *Proc. Natl. Acad. Sci. USA* 82:5131 (1985).

Hudson, D., J. Org. Chem. 53:617 (1988).

Irwin, M. J., et al., *J. Virol.* 58:5036 (1994).

Jacob, J. R., et al., in *THE MOLECULAR BIOLOGY OF HCV*, Section 4, pages 387–392 (1991).

Jacob, J. R., et al., *Hepatology* 10:921–927 (1989).

Jacob, J. R., et al., *J. Infect. Dis.* 161:1121–1127 (1990).

Janknecht, R., et al., *Proc. Natl. Acad. Sci. USA* 88:8972–8976 (1991).

Kaufman, R. J., "Selection and coamplification of heterologous genes in mammalian cells," in *Methods in Enzymology*, vol. 185, pp537–566. Academic Press, Inc., San Diego Calif. (1991).

Kakumu, S., et al., *Gastroenterol.* 105:507 (1993).

Katz, E. D., and Dong, M., *Biotechniques* 8:546 (1990).

Kawasaki, E. S., et al., in *PCR TECHNOLOGY: PRINCIPLES AND APPLICATIONS OF DNA AMPLIFICATION* (H. A. Erlich, ed.) Stockton Press (1989).

King, L. A., et al., *The baculovirus expression system. A laboratory guide*, Chapman & Hall, London, New York, Tokyo, Melbourne, Madras, 1992.

Kyte, J., & Doolittle, R. F., *J. Mol. Biol.* 157:105–132 (1982).

Koonin, E. V., and Dolja, V. V., *Critical Reviews in Biochem. & Mol. Biol.* 28:375–430 (1993).

Krausslich, H. G., et al., *VIRAL PROTEINASES AS TARGETS FOR CHEMOTHERAPY* (Cold Spring Harbor Press, Plainville, N.Y.) (1989).

Kumar, R., et al., *AIDS Res. Human Retroviruses* 5(3):345–354 (1989).

Lanford, R. E., et al., *In Vitro Cell. Dev. Biol.* 25:174–182 (1989).

Larder, B. A., and Kemp, S. D., *Science* 246:1155 (1989).

Lau, Y. F., et al., *Mol. Cell. Biol.* 4:1469–1475 (1984).

Lomell, H., et al., *Clin. Chem.* 48:492 (1990).

Maniatis, T., et al., *MOLECULAR CLONING: A LABORATORY MANUAL*, Cold Spring Harbor Laboratory (1982).

Marshall, W. S., and Caruthers, M. H., *Science* 259:1564 (1993).

Messing, J., *Methods in Enzymol.* 101:20 (1983).

Michelle, et al., *International Symposium on Viral Hepatitis*.

Miller, J. H., *EXPERIMENTS IN MOLECULAR GENETICS*, Cold Spring Harbor Laboratories, Cold Spring Harbor, N.Y. (1972).

Morrissey, D. V., et al., *Anal. Biochem.* 181:345 (1989).

Moss, B., et al., *CURRENT PROTOCOLS IN MOLECULAR BIOLOGY* (Section IV, Unit 16) (1991).

Moss, B., et al., U.S. Pat. No. 5,135,855, issued Aug. 4, 1992.

Mullis, K. B., U.S. Pat. No. 4,683,202, issued Jul. 28, 1987.

Mullis, K. B., et al., U.S. Pat. No. 4,683,195, issued Jul 28, 1987.

Obeid, O. E., et al., *Virus Research* 32:69–84 (1994).

Osikowicz, G., et al., *Clin. Chem.* 36:1586 (1990).

Patterson, J. L., and Fernandez-Larsson, R., *Rev. Infect. Dis.* 12:1139 (1990).

Pearson, W. R. and Lipman, D. J., PNAS 85:2444–2448 (1988).

Pearson, W. R., *Methods in Enzymology* 183:63–98 (1990).

Pitha, *Biochem Biophys Acta*, 204:39 (1970a).

Pitha, *Biopolymers*, 9:965 (1970b).

Porath, J., *Protein Exp. and Purif.* 3:263 (1992).

Pritchard, C. G., and Stefano, J. E., *Ann. Biol. Chem.* 48:492 (1990).

Reichard, O., et al., *Lancet* 337:1058 (1991).

Reilly, P. R., et al., *BACULOVIRUs EXPRESSION VECTORS: A LABORATORY MANUAL* (1992).

Reyes, G., et al., *Science*, 247:1335 (1990).

Reyes, G., et al., *Molecular and Cellular Probes* 5:473–481 (1991).

Rice, C. M., et al., *New Biol.* 1:285–296 (1989).

Roberts, N. A., et al., *Science* 248:358 (1990).

Romanos, M. A., et al., *Yeast* 8(6):423–488 (1992).

Sanger, et al., *Proc. Natl. Acad. Sci.* 74:5463 (1977).

Sambrook, J., et al., In *MOLECULAR CLONING: A LABORATORY MANUAL*, Cold Spring Harbor Laboratory Press, Vol. 2 (1989).

Saiki, R. K., et al., *Science* 239:487–491 (1988).

Schagger, H., et al., *Anal. Biochem.* 166:368–379 (1987).

Scharf, S. J., et al., *Science* 233:1076 (1986).

Schuler, G. D., et al., *Proteins: Struc., Func. and Genet.* 9:180 (1989).

Scott, J. K., and Smith, G. P., *Science* 249:386 (1990).

Scott, J. K., et al., *Proc. Natl. Acad. Sci. USA* 89:5398 (1992).

Smith, D. B., et al., *Gene* 67:31 (1988).

Smith, J. P., *Curr. Opin. Biotechnol.* 2:668 (1991).

Sreenivasan, M. A., et al., *J. Gen. Virol.* 65:1005 (1984).

Sumiyoshi, H., et al., *J. Virol.* 66:5425–5431 (1992).

Summerton, J., et al., U.S. Pat. No. 5,142,047, issued 08/25/92.

Summerton, J., et al., U.S. Pat. No. 5,185,444 issued 02/09/93.

Tam, A., et al., *Virology* 185:120 (1991).

Tam, J. P., *Proc. Natl. Acad. Sci. USA* 85:5409 (1988).

Tessier, D. C., *Gene* 98:177–183 (1991).

Tonkinson, J. L., and Stein, C. A., *Antiviral Chem. and Chemother.* 4(4):193–200 (1993).

Ulmer, et al., *Science* 259:1745 (1993).

Urdea, M., *Clin. Chem.* 39:725 (1993).

Urdea, M., et al., *AIDS* 7:S11 (1993).

Wages, J. M., et al., *Amplifications* 10:1–6 (1993).

Walker, G. T., *PCR Methods Appl.* 3:1–6 (1993).

Wang, A. M., et al. in *PCR PROTOCOLS: A GUIDE TO METHODS AN APPLICATIONS* (M.A. Innis, et al., eds.) Academic Press (1990).

Wang, B., et al., *Proc. Natl. Acad. Sci. USA* 90:4156 (1993).

Whetsell, A. J., et al., *J. Clin. Micro.* 30:845 (1992).

Wolf, J. A., et al., *Nature* 247:1465 (1990).

Vacca, J. P., et al., *PNAS* 91:4096 (1994).

VanGemen, B., et al., *J. Virol. Methods* 43:177 (1993).

Valenzuela, P., et al., *Nature* 298:344 (1982).

Valenzuela, P., et al., in *HEPATITIS B*, eds. I. Millman, et al., Plenum Press, pages 225–236 (1984).

Yarbrough, et al., *J. Virol.* 65:5790 (1991).

Yoo, B. J., et al., *J. Virol.* 69:32–38 (1995).

Yoshio, T., et al., U.S. Pat. No. 4,849,350, issued Jul. 18, 1989.

Zhang, Y., et al., *J. Virol.* 65:6101–6110 (1991).

BACKGROUND OF THE INVENTION

Viral hepatitis resulting from a virus other than hepatitis A virus (HAV) and hepatitis B virus (HBV) has been referred to as non-A, non-B hepatitis (NANBH). NANBH can be further defined based on the mode of transmission of an individual type, for example, enteric versus parenteral.

One form of NANBH, known as enterically transmitted NANBH or ET-NANBH, is contracted predominantly in poor-sanitation areas where food and drinking water have been contaminated by fecal matter. The molecular cloning of the causative agent, referred to as the hepatitis E virus (HEV), has recently been described (Reyes et al., 1990; Tam et al.).

A second form of NANB, known as parenterally transmitted NANBH, or PT-NANBH, is transmitted by parenteral routes, typically by exposure to blood or blood products. The rate of this hepatitis varied by (i) locale, (ii) whether ALT testing was done in blood banks, and (iii) elimination of high-risk patients for AIDS. Appoximately 10% of transfusions caused PT-NANBH infection and about half of those went on to a chronic disease state (Dienstag). After implementation of anti-HCV testing, HCV seroconversion per unit transfused was decreased to less than 1% among heart surgery patients (Alter).

Human plasma samples documented as having produced post-transfusion NANBH in human recipients have been used successfully to produce PT-NANBH infection in chimpanzees (Bradley). RNA isolated from infected chimpanzee plasma has been used to construct cDNA libraries in an expression vector for immunoscreening with serum from human subjects with chronic PT-NANBH infection. This procedure identified a PT-NANBH specific cDNA clone and the viral sequence was then used as a probe to identify a set of overlapping fragments making up 7,300 contiguous basepairs of a PT-NANBH viral agent. The sequenced viral agent has been named the hepatitis C virus (HCV) (for example, the sequence of HCV is presented in EPO patent application 88310922.5, filed 11/18/88). The full-length sequence (~9,500 nt) of HCV is now available.

Primate transmission studies conducted at the Centers for Disease Control (CDC; Phoenix, Ariz., 1973–1975; 1978–1983) originally provided substantial evidence for the existence of multiple agents of non-A, non-B hepatitis (NANBH): the primary agents associated with the majority of cases of NANBH are now recognized to be HCV and HEV (see above), for PT-NANBH and ET-NANBH, respectively. Later epidemiologic studies conducted at the CDC (Atlanta, Ga., 1989-present) using both research (prototype) and commercial tests for anti-HCV antibody showed that approximately 20% of all community-acquired NANBH was also non-C. Further testing of these samples for the presence of HEV (Reyes, et al., WO A 9115603 (Genelabs Inc.) Oct. 17, 1991) have indicated that these cases of community-acquired non-A, non-B, non-C hepatitis were also non-E.

Liver biopsy specimens, sera and plasma of Sentinel County patients (study of Drs. Miriam Alter and Kris Krawczynski) also showed that many bona fide cases of NANBH were also non-C hepatitis (serologically and by Reverse Transcriptase-Polymerase Chain Reaction (RT-PCR; Kawasaki, et al.; Wang, et al., 1990) negative for all markers of HCV infection) developed subsequently into chronic hepatitis with presentation of chronic persistent hepatitis (CPH) or chronic active hepatitis (CAH) consistent with a viral infection.

SUMMARY OF THE INVENTION

The invention pertains to the characterization and isolation of a newly discovered NonA/NonB/NonC/NonD/—NonE (N—(ABCDE)) hepatitis-associated viral agent, herein designated Hepatitis G Virus (HGV). Disclosed here is a family of CDNA replicas of portions of HGV genome. Also disclosed are methods for the isolation and characterization of further HGV sequences and sequences of HGV variants.

The present invention includes HGV genomic polynucleotides, cDNAs thereto and complements thereof. With respect to polynucleotides, some aspects of the invention include: a purified Hepatitis G Virus genomic polynucleotide; HGV derived RNA and DNA polynucleotides; recombinant HGV polynucleotides; a recombinant polynucleotide making up a sequence derived from HGV or HGV variant cDNA or complementary sequences thereof; a recombinant polynucleotide encoding an epitope of HGV; a recombinant vector including any of the above recombinant polynucleotides, and a host cell transformed with any of these vectors. Another aspect of the invention is a polynucleotide probe for HGV and/or its variants.

Current studies on the nature of the genome of HGV, utilizing sequence information to compare HGV to other viral sequences, suggest that HGV is a member of the Flaviviridae family of viruses.

Portions of the HGV-derived CDNA sequences are effective as probes to isolate variants of the virus which occur naturally, or to determine the presence of virus in samples. These cDNAs also make available HGV-encoded polypeptide sequences, including HGV-specific polypeptide antigens. These coding sequences allow the production of polypeptides which are useful as reagents in diagnostic tests and/or as components of vaccines, or as standards. Further, it is possible to isolate and sequence other portions of the HGV genome by utilizing probes derived from these cDNAs, therefore giving rise to additional probes and polypeptides useful in the prophylactic, therapeutic and diagnosis applications.

Other aspects of the invention include: a recombinant expression system which incorporates an open reading frame (ORF) derived from HGV cDNA or complements thereof, wherein the ORF is linked operably to a control sequence which is compatible with a desired host, a cell transformed with the recombinant expression system, and a polypeptide produced by the transformed cell.

Yet another aspect of the invention are purified HGV particles; a preparation of polypeptides from the purified HGV; a purified HGV polypeptide; a purified HGV peptide; and a purified polypeptide which comprises an epitope immunologically identifiable with an epitope contained in HGV or an HGV variant.

Included aspects of the invention are an HGV polypeptide; a recombinant polypeptide consisting of a sequence derived from a HGV genome, HGV cDNA or complements thereof; a recombinant polypeptide made of an HGV epitope; and a fusion polypeptide comprised of an HGV polypeptide.

Both polyclonal and monoclonal antibodies directed against HGV epitopes contained within the polypeptide sequences are also useful as therapeutic agents, for diagnostic tests, for the isolation of the HGV agent from which these cDNAs derive, and for screening of antiviral agents.

Also included in the invention are a purified preparation of polyclonal antibodies directed against an HGV epitope; and monoclonal antibodies directed against HGV epitopes.

Some aspects of the invention pertaining to kits are those for: investigating samples for the presence of polynucleotides derived from HGV which comprise a polynucleotide probe including a nucleotide sequence from HGV of approximately 8 or more nucleotides, in an appropriate container; analyzing samples for the presence of antibodies directed against an HGV antigen made up of a polypeptide which contains an HGV epitope present in the HGV antigen, in a suitable container; and analyzing samples for the presence of HGV antigens made up of an anti-HGV antibody, in a suitable container.

Still other aspects of the invention include a polypeptide comprised of an HGV epitope, which is attached to a solid substrate; and an antibody to an HGV epitope, which is attached to a solid substrate.

Other aspects of the invention are: a technique for the production of an HGV polypeptide, which includes incubating host cells which are transformed with an expression vector, containing a sequence encoding an HGV polypeptide, under conditions which allow expression of said polypeptide; and a polypeptide which has been produced by this method (containing, for example, an HGV epitope).

Also included in the invention are a method for the detection of HGV nucleic acids in samples comprising reacting nucleic acids of the sample with a probe for an HGV polynucleotide, under conditions allowing the creation of a polynucleotide duplex between the probe and the HGV nucleic acid from the sample; as well as detecting a polynucleotide duplex containing the probe. The invention includes the following hybridization based detection methods: reporter labeling; polymerase chain reaction; self-sustained sequence replication; ligase chain reaction; and strand displacement amplification. Further, detection methods include signal amplification (e.g., branch-chained DNA probes and the Q-beta replicase method).

The invention also includes immunoassays, including an immunoassay for detecting HGV, comprising the incubation of a sample (which is suspected of being infected with HGV) with a probe antibody directed against an antigen/epitope of HGV, to be detected under conditions allowing the formation of an antigen-antibody complex; and detecting the antigen-antibody complex which contains the probe antibody. An immunoassay for the detection of antibodies which are directed against an HGV antigen comprising the incubation of a sample suspected of containing HGV with a probe polypeptide including an epitope of HGV, under conditions that allow the formation of an antibody-antigen complex; and distinguishing the antibody-antigen complex which contains the probe antigen.

Also forming part of the invention are HGV vaccines, for the treatment and/or prevention of HGV infection, comprising an immunogenic peptide containing an HGV epitope, or an inactivated preparation of HGV, or a reduced preparation of HGV.

In still another aspect, the invention includes a tissue culture grown cell, infected with HGV. In one embodiment, the tissue culture grown cells are primate liver cells.

Another aspect of the invention is a method for producing antibodies to HGV, comprising administering to a test subject an immunogenic polypeptide containing HGV epitopes in an adequate amount to elicit an immune response.

The present invention also includes an HGV mosaic polypeptide, where the mosaic polypeptide contains at least two epitopes of HGV, and, where the polypeptide substantially lacks amino acids normally intervening between the epitopes in the native HGV coding sequence. Such mosaic polypeptides are useful in the applications and methods discussed above.

The present invention further includes a random peptide epitope (mimitope) that mimics a natural HGV antigenic epitope during epitope presentation. Such mimitopes are useful in the applications and methods discussed above. Also included in the present invention is a method of identifying a random peptide HGV epitope. In the method, a library of random peptide epitopes is generated or selected. The library is contacted with an anti-HGV antibody. Mimitopes are identified that are specifically immunoreactive with the antibody. Sera (containing anti-HGV antibodies) or antibodies generated by the methods of the present invention can be used. Random peptide libraries can, for example, be displayed on phage or generated as combinatorial libraries.

In another aspect, the present invention includes therapeutic compounds and methods for the prevention and/or treatment of HGV infection.

These and other objects and features of the invention will be more fully appreciated when the following detailed description of the invention is read in conjunction with the accompanying drawings.

BRIEF DESCRIPTION OF THE FIGURES

FIGS. 5A and 5B: amino acid alignments of HGV with two other members of Flaviviridae family—Hog Cholera Virus and Hepatitis C Virus.

FIG. 6 shows a map of a portion of the vector pGEX-Hisb-GE3-2, a bacterial expression plasmid carrying an HGV epitope.

FIGS. 10A to 11F show the results of Western blot analysis of antigens GE-NS2b and GE-NS5a.

FIG. 11 presents a Kyte-Doolittle hydrophobicity plot of the coding sequence of HGV.

FIGS. 14A to 14C show the results of Western blot analysis of HGV pET clone GE-E2. FIG. 14D shows a corresponding coomassie stained gel.

FIGS. 15A to 15C show the results of Western blot analysis of HGV pET clone GE-NS5b. FIG. 15D shows a corresponding coomassie stained gel.

DETAILED DESCRIPTION OF THE INVENTION

I. DEFINITIONS

Figure 1:
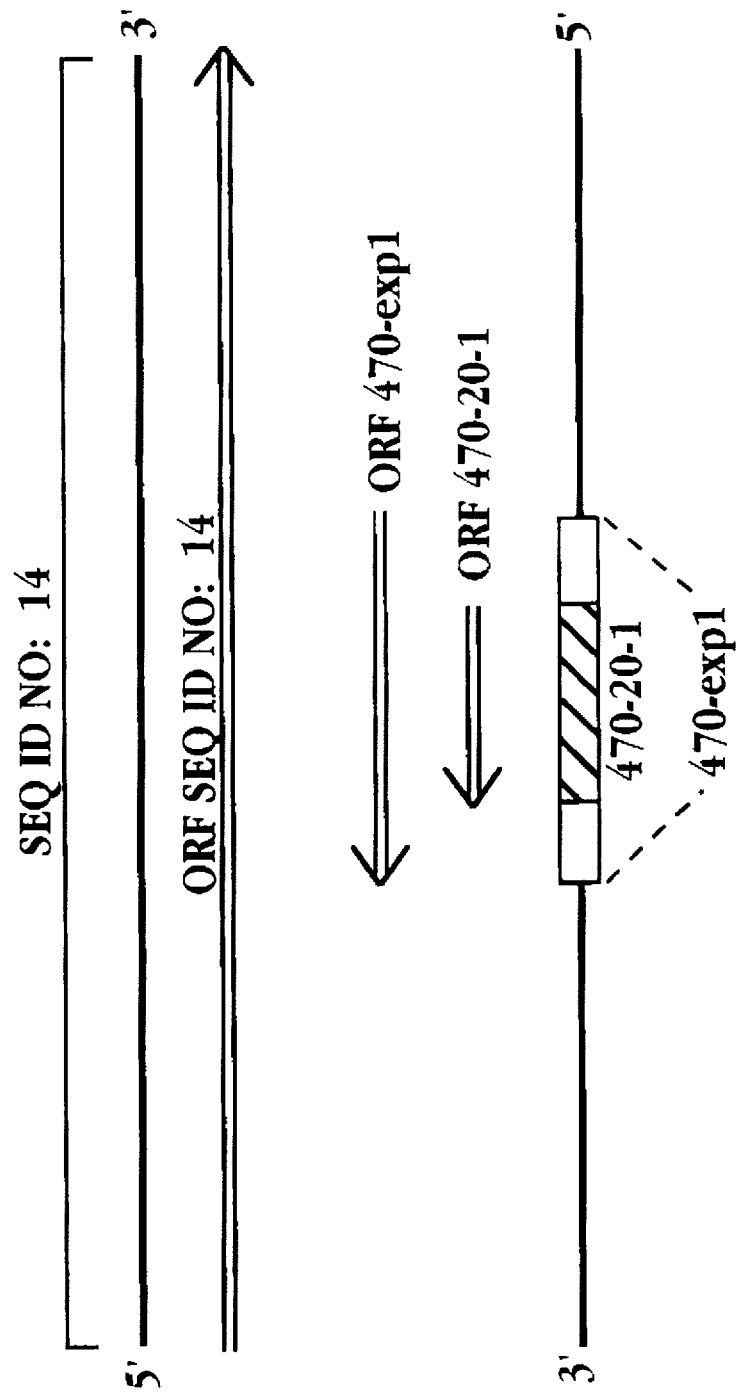
FIG. 1: the relationship of the SEQ ID NO:14 open reading frame to the 470-20-1 clone.

The terms defined below have the following meaning herein:

1. "nonA/nonB/nonC/nonD/nonE hepatitis viral agent {N-(ABCDE)}", herein provisionally designated HGV, means a virus, virus type, or virus class which (i) is transmissible in some primates, including, mystax, chimpanzees or humans as characterized by elevated serum alanine amino-transferase levels in an infected primate (ii) is serologically distinct from hepatitis A virus (HAV), hepatitis B virus (HBV), hepatitis C virus (HCV), hepatitis D virus, and hepatitis E (HEV) (although HGV may co-infect a subject with these viruses), and (iii) is a member of the virus family Flaviviridae.

2. "HGV variants" are defined as viral isolates that have at least about 40%, preferably 55% or 65%, or more preferably 80% global sequence homology, that is, sequence identity over a length of the viral genome polynucleotide sequence, to the HGV polynucleotide sequences disclosed herein (e.g., SEQ ID NO:14).

"Sequence homology" is determined essentially as follows. Two polynucleotide sequences of similar length (preferably, the entire viral genome) are considered to be homologous to one another, if, when they are aligned using the ALIGN program, over 40%, preferably 55% or 65%, or more preferably 80% of the nucleic acids in the highest scoring alignment are identically aligned using a ktup of 1, the default parameters and the default PAM matrix.

The ALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

In determining whether two viruses are "highly homologous" to each other, the complete sequence of all the viral proteins (or the polyprotein) for one virus are optimally, globally aligned with the viral proteins or polyprotein of the other virus using the ALIGN program of the above suite using a ktup of 1, the default parameters and the default PAM matrix. Regions of dissimilarity or similarity are not excluded from the analysis. Differences in lengths between the two sequences are considered as mismatches. Alternatively, viral structural protein regions are typically used to determine relatedness between viral isolates. Highly homologous viruses have over 40%, or preferably 55% or 65%, or more preferably 80% global polypeptide sequence identity.

3. Two nucleic acid fragments are considered to be "selectively hybridizable" to an HGV polynucleotide, if they are capable of specifically hybridizing to HGV or a variant thereof (e.g., a probe that hybridizes to HGV nucleic acid but not to polynucleotides from other members of the virus family Flaviviridae) or specifically priming a polymerase chain reaction: (i) under typical hybridization and wash conditions, as described, for example, in Maniatis, et al., pages 320–328, and 382–389, (ii) using reduced stringency wash conditions that allow at most about 25–30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (for example, in Saiki, R. K. et al.), which result in specific amplification of sequences of HGV or its variants.

Preferably, highly homologous nucleic acid strands contain less than 20–30% basepair mismatches, even more preferably less than 5–20% basepair mismatches. These degrees of homology can be selected by using wash conditions of appropriate stringency for identification of clones from gene libraries (or other sources of genetic material), as is well known in the art.

4. An "HGV polynucleotide," as used herein, is defined as follows. For polynucleotides greater than about 100 nucleotides, HGV polynucleotides encompass polynucleotide sequences encoded by HGV variants and homologous sequences as defined in "2" above. For polynucleotides less than about 100 nucleotides in length, HGV polynucleotide encompasses sequences that selectively hybridizes to sequences of HGV or its variants. Further, HGV polynucleotides include polynucleotides encoding HGV polypeptides (see below).

The term "polynucleotide" as used herein refers to a polymeric molecule having a backbone that supports bases capable of hydrogen bonding to typical nucleic acids, where the polymer backbone presents the bases in a manner to permit such hydrogen bonding in a sequence specific fashion between the polymeric molecule and a typically nucleic acid (e.g., single-stranded DNA). Such bases are typically inosine, adenosine, guanosine, cytosine, uracil and thymidine. Numerous polynucleotide modifications are known in the art, for example, labels, methylation, and substitution of one or more of the naturally occurring nucleotides with an analog.

Polymeric molecules include double and single stranded RNA and DNA, and backbone modifications thereof, for example, methylphosphonate linkages. Further, such polymeric molecules include alternative polymer backbone structures such as, but not limited to, polyvinyl backbones (Pitha, 1970a/b), morpholino backbones (Summerton, et al., 1992, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates). In addition linkages may contain the following exemplary modifications: pendant moieties, such as, proteins (including, for example, nucleases, toxins, antibodies, signal peptides and poly-L-lysine); intercalators (e.g., acridine and psoralen), chelators (e.g., metals, radioactive metals, boron and oxidative metals), alkylators, and other modified linkages (e.g., alpha anomeric nucleic acids).

5. An "HGV polypeptide" is defined herein as any polypeptide homologous to an HGV polypeptide. "Homology," as used herein, is defined as follows. In one embodiment, a polypeptide is homologous to an HGV polypeptide if it is encoded by nucleic acid that selectively hybridizes to sequences of HGV or its variants.

In another embodiment, a polypeptide is homologous to an HGV polypeptide if it is encoded by HGV or its variants, as defined above, polypeptides of this group are typically larger than 15, preferable 25, or more preferable 35, contiguous amino acids. Further, for polypeptides longer than about 60 amino acids, sequence comparisons for the purpose of determining "polypeptide homology" are performed using the local alignment program LALIGN. The polypeptide sequence, is compared against the HGV amino acid sequence or any of its variants, as defined above, using the LALIGN program with a ktup of 1, default parameters and the default PAM.

Any polypeptide (typically a polypeptide not specifically immunoreactive with HGV antibodies) with an optimal alignment longer than 60 amino acids and greater than 60%, preferably 70%, or more preferably 80% of identically aligned amino acids is considered to be a "homologous polypeptide." The LALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

6. A polynucleotide is "derived from" HGV if it has the same or substantially the same basepair sequence as a region of an HGV genome, CDNA of HGV or complements thereof, or if it displays homology as noted under "2", "3" or "4" above.

A polypeptide or polypeptide "fragment" is "derived from" HGV if it is (i) encoded by an open reading frame of an HGV polynucleotide, or (ii) displays homology to HGV polypeptides as noted under "2" and "5" above, or (iii) is specifically immunoreactive with HGV positive sera.

7. "Substantially isolated" and "purified" are used in several contexts and typically refer to at least partial purification of an HGV virus particle, component (e.g., polynucleotide or polypeptide), or related compound (e.g., anti-HGV antibodies) away from unrelated or contaminating components (e.g., serum cells, proteins, non-HGV polynucleotides and non-anti-HGV antibodies). Methods and procedures for the isolation or purification of compounds or components of interest are described below (e.g., affinity purification of fusion proteins and recombinant production of HGV polypeptides).

8. In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

9. An "epitope" is the antigenic determinant defined as the specific portion of an antigen with which the antigen binding portion of a specific antibody interacts.

10. An antigen or epitope is "specifically immunoreactive" with HGV positive sera when the epitope/antigen binds to antibodies present in the HGV infected sera but does not bind to antibodies present in the majority (greater than about 90%, preferably greater than 95%) of sera from individuals who are not or have not been infected with HGV. "Specifically immunoreactive" antigens or epitopes may also be immunoreactive with monoclonal or polyclonal antibodies generated against specific HGV epitopes or antigens.

An antibody or antibody composition (e.g., polyclonal antibodies) is "specifically immunoreactive" with HGV when the antibody or antibody composition is immunoreactive with an HGV antigen but not with HAV, HBV, HCV, HDV or HEV antigens. Further, "specifically immunoreactive antibodies" are not immunoreactive with antigens typically present in normal sera obtained from subjects not infected with or exposed to HGV, HAV, HBV, HCV, HDV or HEV.

II. N- (ABCDE) SERA.

Availability of a serologic test for anti-HCV and the development of an RT-PCR assay for HCV-RNA (Kawasaki, et al.; Wang, et al., 1990) allowed the identification of several cases of both post-transfusion and community acquired non-HCV hepatitis. The human hepatitis case, PNF 2161, was originally identified as having NANB hepatitis (NANBH) through the Sentinel Counties Study of community acquired hepatitis, sponsored by the Centers for Disease Control and Prevention (Alter, et al., 1989b). PNF 2161 was a sample obtained from an elderly Caucasian male patient who developed acute hepatitis approximately 8 weeks following a blood transfusion, with a peak serum ALT level of 1141 IU (normal, <45 IU). Following resolution of the episode of acute hepatitis, he had fluctuating, but persistently elevated ALT levels over the next seven years, consistent with chronic hepatitis, although histopathologic confirmation of this diagnosis was not obtained.

The plasma specimen used to clone HGV (as described herein) was obtained in June 1989, approximately $4^{1/2}$ years following the episode of acute hepatitis, and cryo-preserved. Patient PNF 2161 was initially believed not to be infected with HCV, based on consistently negative results with a first generation immunoassay test (Ortho HCV ELISA Test System; Ortho Diagnostics, Raritan, N.J.). However, subsequent testing using a second generation HCV immunoassay (Ortho) and PCR with HCV 5'-non-coding region primers demonstrated that the patient was infected with HCV.

III. ISOLATION OF HGV ASSOCIATED SEQUENCES.

As one approach toward identifying clones containing HGV sequences, a CDNA library was prepared from infected-HGV sera in the expression vector lambda gt11 (Example 1). Polynucleotide sequences were then selected for the expression of peptides which are immunoreactive with serum PNF 2161. First round screening was typically performed using the PNF 2161 serum (used to generate the phage library). It is also possible to screen with other suspected N—(ABCDE) sera.

Recombinant proteins identified by this approach provide candidates for peptides which can serve as substrates in diagnostic tests. Further, the nucleic acid coding sequences identified by this approach serve as useful hybridization probes for the identification of additional HGV coding sequences.

The sera described above were used to generate cDNA libraries in lambda gt11 (Example 1). In the method illustrated in Example 1, infected serum was precipitated in 8% PEG without dilution, and the libraries were generated from the resulting pelleted virus. Sera from infected human sources were treated in the same fashion.

As an advantageous alternative to PEG precipitation, ultracentrifugation can be used to pellet particulate agents from infected sera or other biological specimens. To isolate viral particles from which nucleic acids could be extracted, serum, ranging up to 2 ml, is diluted to approximately 10 ml with PBS, spun at 3K for 10 minutes, and the supernatant is centrifuged for a minimum of 2 hours at 40,000 rpm (approximately 110,000×g) in a Ti70.1 rotor (Beckman Instruments, Fullerton, Calif.) at 40° C. The supernatant is then aspirated and the pellet extracted by standard nucleic acid extraction techniques.

CDNA libraries were generated using random primers in reverse transcription reactions with RNA extracted from pelleted sera as starting material. The resulting molecules were ligated to *Sequence Independent Single Primer Amplification* (SISPA; Reyes, et al., 1991) linker primers and expanded in a non-selective manner, and then cloned into a suitable vector, for example, lambda gt11, for expression and screening of peptide antigens. Alternatively, the lambda gt1o vector may also be used.

Lambda gt11 is a particularly useful expression vector which contains a unique EcoRI insertion site 53 base pairs upstream of the translation termination codon of the β-galactosidase gene. Thus, an inserted sequence is expressed as a β-galactosidase fusion protein which contains the N-terminal portion of the β-galactosidase gene product, the heterologous peptide, and optionally the C-terminal region of the β-galactosidase peptide (the C-terminal portion being expressed when the heterologous peptide coding sequence does not contain a translation termination codon).

This vector also produces a temperature-sensitive repressor (cI857) which causes viral lysogeny at permissive temperatures, e.g., 32° C., and leads to viral lysis at elevated temperatures, e.g., 42° C. Advantages of this vector include: (1) highly efficient recombinant clone generation, (2) ability to select lysogenized host cells on the basis of host-cell growth at permissive, but not non-permissive, temperatures, and (3) production of recombinant fusion protein. Further, since phage containing a heterologous insert produces an inactive β-galactosidase enzyme, phage with inserts are typically identified using a colorimetric substrate conversion reaction employing β-galactosidase.

Example 1 describes the preparation of a CDNA library for the N-(ABCDE) hepatitis sera PNF 2161. The library was immunoscreened using PNF 2161 (Example 3). A number of lambda gt11 clones were identified which were immunoreactive. Immunopositive clones were plaque-purified and their immunoreactivity retested. Also, the immunoreactivity of the clones with normal human sera was also tested.

These clones were also examined for the "exogenous" nature of the cloned insert sequence. This basic test establishes that the cloned fragment does not represent a portion of human or other potentially contaminating nucleic acids (e.g., *E. coli*, *S. cerevisiea* and mitochondrial). The clone inserts were isolated by EcoRI digestion following polymerase chain reaction amplification. The inserts were purified then radiolabelled and used as hybridization probes against membrane bound normal human DNA, normal mystax DNA and bacterial DNA (control DNAs) (Example 4A).

Clone 470-20-1 (PNF2161 cDNA source) was one of the clones isolated by immunoscreening with the PNF 2161 serum. The clone was not reactive with normal human sera. The clone has a large open reading frame (203 base pairs; SEQ ID NO:3), in-frame with the β-galactosidase gene of the lambda gt11 vector. The clone is exogenous by genomic DNA hybridization analysis and genomic PCR analysis, using human, yeast and *E. coli* genomic DNAs (Example 4B).

The sequence was present in PNF2161 serum as determined by RT-PCR (Example 4C). RT-PCR of serially diluted PNF 2161 RNA suggested at least about $10^5$ copies of 470-20-1 specific sequence per ml. The sequence was also detected in sucrose density gradient fractions at densities consistent with the sequence banding in association with a virus-like particle (Example 5).

Bacterial lysates of *E. coli* expressing a second clone, clone 470-exp1, (SEQ ID NO:37) were also shown to be specifically immunoreactive with PNF 2161 serum at comparable levels to clone 470-20-1. The coding sequence of 470-exp1 was flanked by termination codons (based on sequence comparisons to SEQ ID NO:14, also see FIG. 1) and had an internal methionine.

Further sequences contained in SEQ ID NO:14, adjacent to clone 470-20-1, were obtained by anchor polymerase chain reaction (Anchor PCR) using primers from clone 470-20-1 (Example 6). In this case a PNF 2161 2-cDNA source library was used as template, where the cDNA/ complement double-stranded DNA products were ligated to lambda arms, but the mixture was not packaged. 470-20-1 specific primers were used in amplification reactions with SISPA-amplified PNF 2161 cDNA as a template (Example 4). The identity of the amplified DNA fragments were confirmed by (i) size and (ii) hybridization with a 470-20-1 specific oligonucleotide probe (SEQ ID NO:16). The 470-20-1 specific signal was detected in cDNA amplified by PCR from SISPA-amplified PNF 2161, demonstrating the presence of the 470-20-1 sequences in the source material.

The 470-20-1 specific primers were also used in amplification reactions with the following RNA sources as substrate: normal mystax liver RNA, normal tamarin (*Sanguins laboriatis*) liver RNA, and MY131 liver RNA (Example 4). The results from these experiments demonstrate the 470-20-1 sequences are present in the parent serum sample (PNF 2161) and in an RNA liver sample from an animal challenged with the PNF 2161 sample (MY131). Both normal control RNAs were negative for the presence of 470-20-1 sequences.

Further, PNF 2161 serum and other cloning source or related source materials were directly tested by PCR using primers from selected cloned sequences. Specific amplification products were detected by hybridization to a specific oligonucleotide probe 470-20-1-152F (SEQ ID NO:16). A specific signal was reproducibly detected in multiple extracts of PNF 2161, with the 470-20-1 specific primers.

The disease association between HGV and liver disease is further supported by the data presented in Example 4F. Sera from hepatitis patients and from blood donors with abnormal liver function were assessed for the presence of HGV by RT-PCR screening, using HGV specific primers. HGV specific sequence were detected in 6/152 of these sera samples. No HGV positives were detected among the control samples (n=11).

The results presented above indicate the isolation of a viral agent associated with N-(ABCDE) viral infection of liver (i.e., hepatitis) and/or infection, and resulting disease, of other tissue and cell types.

IV. FURTHER CHARACTERIZATION OF HGV RECOMBINANT ANTIGENS.

A. Screening Recombinant Libraries.

Further candidate HGV antigens can be obtained from the libraries of the present invention using the screening methods described above. The CDNA library described above has been deposited with the American Type Culture Collection, 12301 Parklawn Dr., Rockville, Md., 20852, and has been assigned the following designation: PNF 2161 cDNA source, ATCC 75268. The deposit was accepted by the International Depository Authority on Jul. 16, 1992.

A second PNF 2161 DNA library has been generated essentially as described for the first PNF 2161 cDNA library, except that second PNF 2161 cDNA source library was ligated to lambda gt11 arms but was not packaged. This non-packaged library was used to obtain the extension clones described below. A packaged version of this second library (PNF 2161 2-cDNA source library) has been deposited with the American Type Culture Collection, 12301 Parklawn Drive, Rockville, Md., 20852, and has been assigned the following designation: PNF 2161 2-cDNA source, ATCC 75837. c4

In addition to the recombinant libraries generated above, other recombinant libraries from N-(ABCDE) hepatitis sera can likewise be generated and screened as described herein.

B. Epitope Mapping, Cross Hybridization and Isolation of Genomic Sequences.

Antigen encoding DNA fragments can be identified by (i) immunoscreening, as described above, or (ii) computer analysis of coding sequences (e.g., SEQ ID NO:14) using an algorithm (such as, "ANTIGEN," Intelligenetics, Mountain View, Calif.) to identify potential antigenic regions. An antigen-encoding DNA fragment can be subcloned. The subcloned insert can then be fragmented by partial DNase I digestion to generate random fragments or by specific restriction endonuclease digestion to produce specific subfragments. The resulting DNA fragments can be inserted into the lambda gt11 vector and subjected to immunoscreening in order to provide an epitope map of the cloned insert.

In addition, the DNA fragments can be employed as probes in hybridization experiments to identify overlapping HGV sequences, and these in turn can be further used as probes to identify a set of contiguous clones. The generation of sets of contiguous clones allows the elucidation of the sequence of the HGV's genome.

Any of the above-described clone sequences (e.g., derived from SEQ ID NO:14 or clone 470-20-1) can be used to probe the cDNA and DNA libraries, generated in a vector such as lambda gt10 or "LAMBDA ZAP II" (Stratagene, San Diego, Calif.). Specific subfragments of known sequence may be isolated by polymerase chain reaction or after restriction endonuclease cleavage of vectors carrying such sequences. The resulting DNA fragments can be used as radiolabelled probes against any selected library. In particular, the 5' and 3' terminal sequences of the clone inserts are useful as probes to identify additional clones.

Further, the sequences provided by the 5' end of cloned inserts are useful as sequence specific primers in first-strand CDNA or DNA synthesis reactions (Maniatis et al.; Scharf et al.). For example, specifically primed PNF 2161 cDNA and DNA libraries can be prepared by using specific primers derived from SEQ ID NO:14 on PNF 2161 nucleic acids as a template. The second-strand of the new cDNA is synthesized using RNase H and DNA polymerase I. The above procedures identify or produce DNA/cDNA molecules corresponding to nucleic acid regions that are 5' adjacent to the known clone insert sequences. These newly isolated sequences can in turn be used to identify further flanking sequences, and so on, to identify the sequences composing the entire genome of HGV. As described above, after new HGV sequences are isolated, the polynucleotides can be cloned and immunoscreened to identify specific sequences encoding HGV antigens.

Extension clone sequences (SEQ ID NO:14), containing further sequences of interest, have been obtained for clone PNF 470-20-1 (SEQ ID NO:3) using the "Anchor PCR" method described in Example 6. Briefly, the strategy consists of ligating PNF 2161 SISPA cDNA to lambda gt11 arms and amplifying the ligation reaction with a gt11-specific primer and one of two 470-20-1 specific primers.

The amplification products are electrophoretically separated, transferred to filters and the DNA bound to the filters is probed with a 470-20-1 specific probe. Bands corresponding to hybridization positive band signals were gel purified, cloned and sequenced.

C. Preparation of Antigenic Polypeptides and Antibodies.

The recombinant peptides of the present invention can be purified by standard protein purification procedures which may include differential precipitation, molecular sieve chromatography, ion-exchange chromatography, isoelectric focusing, gel electrophoresis and affinity chromatography.

In one embodiment of the present invention, the polynucleotide sequences of the antigens of the present invention have been cloned in the plasmid p-GEX (Example 7A) or various derivatives thereof (pGEX-GLI). The plasmid pGEX (Smith, et al., 1988) and its derivatives express the polypeptide sequences of a cloned insert fused in-frame to the protein glutathione-S-transferase (sj26). In one vector construction, plasmid pGEX-hisB, an amino acid sequence of 6 histidines is introduced at the carboxy terminus of the fusion protein.

The various recombinant PGEX plasmids can be transformed into appropriate strains of E. coli and fusion protein production can be induced by the addition of IPTG (isopropyl-thio galactopyranoside) as described in Example 7A. Solubilized recombinant fusion protein can then be purified from cell lysates of the induced cultures using glutathione agarose affinity chromatography (Example 7A).

Insoluble fusion protein expressed by the plasmid pGEX-hisB can be purified by means of immobilized metal ion affinity chromatography (Porath) in buffers containing 6M Urea or 6M guanidinium isothiocyanate, both of which are useful for the solubilization of proteins. Alternatively insoluble proteins expressed in pGEX-GLI or derivatives thereof can be purified using combinations of centrifugation to remove soluble proteins followed by solubilization of insoluble proteins and standard chromatographic methodologies, such as ion exchange or size exclusion chromatography, and other such methods are known in the art.

In the case of β-galactosidase fusion proteins (such as those produced by lambda gt11 clones) the fused protein can be isolated readily by affinity chromatography, by passing cell lysis material over a solid support having surface-bound anti-β-galactosidase antibody. For example, purification of a β-galactosidase/fusion protein, derived from 470-20-1 coding sequences, by affinity chromatography is described in Example 7B.

Also included in the invention is an expression vector, such as the lambda gt11 or pGEX vectors described above, containing HGV coding sequences and expression control elements which allow expression of the coding regions in a suitable host. The control elements generally include a promoter, translation initiation codon, and translation and transcription termination sequences, and an insertion site for introducing the insert into the vector.

The DNA encoding the desired antigenic polypeptide can be cloned into any number of commercially available vectors to generate expression of the polypeptide in the appropriate host system. These systems include, but are not limited to, the following: baculovirus expression (Reilly, et al.; Beames, et al.; Pharmingen; Clontech, Palo Alto, Calif.), vaccinia expression (Earl, 1991; Moss, et al.), expression in bacteria (Ausubel, et al.; Clontech), expression in yeast (Gellissen, 1992; Romanos, 1992; Goeddel; Guthrie and Fink), expression in mammalian cells (Clontech; Gibco-BRL, Ground Island, N.Y.), e.g., Chinese hamster ovary (CHO) cell lines (Haynes, 1983, Lau, 1984, Kaufman, 1990). These recombinant polypeptide antigens can be expressed directly or as fusion proteins. A number of features can be engineered into the expression vectors, such as leader sequences which promote the secretion of the expressed sequences into culture medium.

Expression of large HGV polypeptides using several of these systems is described in Example 16.

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinant expressed polypeptide produced HGV polypeptide antigens are typically isolated from lysed cells or culture media. Purification can be carried out by methods known in the art including salt fractionation, ion exchange chromatography, and affinity chromatography. Immunoaffinity chromatography can be employed using antibodies generated based on the HGV antigens identified by the methods of the present invention.

HGV polypeptide antigens may also be isolated from HGV particles (see below).

Continuous antigenic determinants of polypeptides are generally relatively small, typically 6 to 10 amino acids in length. Smaller fragments have been identified as antigenic regions, for example, in conformational epitopes. HGV polypeptide antigens are identified as described above. The resulting DNA coding regions of either strand can be expressed recombinantly either as fusion proteins or isolated polypeptides. In addition, amino acid sequences can be conveniently chemically synthesized using commercially available synthesizer (Applied Biosystems, Foster City, Calif.) or "PIN" technology (Applied Biosytems).

In another embodiment, the present invention includes mosaic proteins that are composed of multiple epitopes. An HGV mosaic polypeptide typically contains at least two epitopes of HGV, where the polypeptide substantially lacks amino acids normally intervening between the epitopes in the native HGV coding sequence. Synthetic genes (Crea; Yoshio et al.; Eaton et al.) encoding multiple, tandem epitopes can be constructed that will produce mosaic proteins using standard recombinant DNA technology using polypeptide expression vector/host system described above.

Further, multiple antigen peptides can be synthesized chemically by methods described previously (Tam, J. P., 1988; Briand et al.). For example, a small immunologically inert core matrix of lysine residues with α- and ε- amino groups can be used to anchor multiple copies of the same or different synthetic peptides (typically 6–15 residues long) representing epitopes of interest. Mosaic proteins or multiple antigen peptide antigens give higher sensitivity and specificity in immunoassays due to the signal amplification resulting from distribution of multiple epitopes.

Antigens obtained by any of these methods can be used for antibody generation, diagnostic tests and vaccine development.

In another aspect, the invention includes specific antibodies directed against the polypeptide antigens of the present invention. Antigens obtained by any of these methods may be directly used for the generation of antibodies or they may be coupled to appropriate carrier molecules. Many such carriers are known in the art and are commercially available (e.g., Pierce, Rockford Ill.). Typically, to prepare antibodies, a host animal, such as a rabbit, is immunized with the purified antigen or fused protein antigen. Hybrid, or fused, proteins may be generated using a variety of coding sequence derived from other proteins, such as glutathione-S-transferase or β-galactosidase. The host serum or plasma is collected following an appropriate time interval, and this serum is tested for antibodies specific against the antigen. Example 8 describes the production of rabbit serum antibodies which are specific against the 470-20-1 antigen in the Sj26/470-20-1 hybrid protein. These techniques are equally applicable to all immunogenic sequences derived from HGV, including, but not limited to, those derived from the coding sequence presented as SEQ ID NO:14.

The gamma globulin fraction or the IgG antibodies of immunized animals can be obtained, for example, by use of saturated ammonium sulfate precipitation or DEAE Sephadex chromatography, affinity chromatography, or other techniques known to those skilled in the art for producing polyclonal antibodies.

Alternatively, purified antigen or fused antigen protein may be used for producing monoclonal antibodies. Here the spleen or lymphocytes from an immunized animal are removed and immortalized or used to prepare hybridomas by methods known to those skilled in the art. To produce a human-derived hybridoma, a human lymphocyte donor is selected. A donor known to be infected with a HGV may serve as a suitable lymphocyte donor. Lymphocytes can be isolated from a peripheral blood sample. Epstein-Barr virus (EBV) can be used to immortalize human lymphocytes or a suitable fusion partner can be used to produce human-derived hybridomas. Primary in vitro sensitization with viral specific polypeptides can also be used in the generation of human monoclonal antibodies.

Antibodies secreted by the immortalized cells are screened to determine the clones that secrete anti-bodies of the desired specificity, for example, by using the ELISA or Western blot method (Example 10; Ausubel et al.).

Using HGV-positive serum or plasma, or the antibodies of the present invention, other antigenic peptides and epitopes can be isolated. For example, a number of different techniques have been developed for the simultaneous synthesis of many peptides (Geysen, et al.; Houghten; Frank and Doring; Hudson). The method developed by Geysen, et al., is especially useful because of the relative simplicity with which large numbers of different peptide sequences can be generated and tested for antigenicity. In the Geysen method (also referred to as MULTI-PIN peptide synthesis), the peptides are synthesized on polyacrylamide acid grafted polyethylene rods attached to a micro-titer plate. The MULTI-PIN strategy allows large numbers of syntheses (96 peptides per plate) to be immunologically screened using the polyclonal or monoclonal antibodies of the present invention and commercially available reagents and instrumentation. Immunoreactive peptides are identified and characterized.

It has been reported that up to 6,000 oligopeptides can be synthesized in a two week period, thus making it practical (by synthesizing all of the possible overlapping amino acid sequences of a particular antigen) to screen viral antigen sequences for epitopes to the resolution of a single amino acid (Geysen, et al.).

An alternative method of scanning for immunodominate peptides is to synthesize longer peptides (e.g., 10 to 30 amino acids) corresponding to HGV coding sequences using conventional automated peptide synthesis (Carter, et al., 1994; Obeid, et al., 1994; Commandaeur, et al., 1994). This method has the advantage that the longer peptides can fold into shapes that mimic conformational epitopes.

Also, HGV antibodies, in particular, monoclonals, can be used to identify random polypeptides that mimic their virus-encoded target polypeptides (Scott and Smith, 1990; Smith, 1991). For example, random peptide libraries displayed on phage (RPL) (Scott and Smith, 1990) can be used as a source of peptide ligands for antibody generation or for vaccine development. RPL approach allows the expression of peptide-ligand containing fusion proteins on the phage surface and enrichment of these ligand encoding phages by affinity selection using antibodies (Smith, J.P., 1991; Christian, et al.; Scott, et al., 1992; Folgori, et al.). These random peptide epitopes detected by specific antibodies mimic the natural antigenic epitopes (mimotopes) during epitope presentation. HGV antigenic mimics (mimotopes) can be isolated from RPL. Hexa- to decapeptide phagotope (mimotope displayed on phage) expressing RPL can be made by published methods (Scott and Smith; Smith, J.P. 1991; Christian, et al.; Scott, et al.; DeGraaf, et al.; Folgori, et al.) and screened by HGV-associated human sera or the antibodies of the present invention.

One example of the use of RPL for isolation of 470-20-1 mimotopes is as follows. The random decapeptide-pIII fusion phage display library is constructed according to the methods described previously (DeGraaf, et al., 1993). Briefly, a chemically synthesized single-stranded degenerate insert is annealed to shorter oligonucleotides which generate SfiI restriction overhangs. Annealed DNA is ligated into SfiI-cut fUSE-5 vector DNA.

E. coli MC1061 is transformed with the ligated DNA. The library is amplified through approximately ten population doublings in LB medium with 20 mg/ml tetracycline. This library is affinity selected using one or more of 470-20-1 immunoreactive sera (or antibodies of the present invention). Polystyrene beads (Precision Plastic Ball Company, Chicago, Ill.) are coated with ammonium sulfate fractionated positive serum (e.g., PNF 2161) in 50 mM NaHCO3, pH 9.6 overnight at 4° C. Antibody coated beads are thoroughly washed with PBS and blocked with BSA.

These serum coated, blocked beads are pre-incubated with an excess of M13K07-UV killed phage for 4 hours at 40° C. Library phage are then added to the above pre-incubation mixture and incubated for 12 hours at 4° C. Unbound phage are removed and the beads are washed extensively with TTB (50 mM Tris, pH 7.5, 150 mM NaCl, 0.5% "TWEEN 20" (v/v), 1 mg/ml BSA) buffer. Bound phage are eluted with elution buffer (0.1M HCl adjusted to pH 2.2 with 2M Tris-HCl, pH 9.0). Eluted, enriched phage are screened with a second positive serum (e.g., Mys 136 sera) by plaque immunoscreening.

Further screening of the selected phagotopes can be carried out using large panels of positive and negative sera or specific HGV monoclonal antibodies. Selected phagotopes can be used directly in ELISA assay or antibody generation. Alternatively, the sequences of the phagotope encoding nucleotides can be determined and expressed in conventional vector/host system and used as antigen.

Mimic polypeptides identified as described above can in turn can serve as antigens in detection assays or can be used for the generation of antigen-specific antibodies.

D. Elisa and Protein Blot Screening.

When HGV antigens are identified, typically through plaque immunoscreening as described above, the antigens can be expressed and purified. The antigens can then be screened rapidly against a large number of suspected HGV hepatitis sera using alternative immunoassays, such as, ELISAs or Protein Blot Assays (Western blots) employing the isolated antigen peptide. The antigen polypeptides fusion can be isolated as described above, usually by affinity chromatography to the fusion partner such as β-galactosidase or glutathione-S-transferase. Alternatively, the antigen itself can be purified using antibodies generated against it (see below).

A general ELISA assay format is presented in Example 10. Harlow, et al., describe a number of useful techniques for immunoassays and antibody/antigen screening.

The purified antigen polypeptide or fusion polypeptide containing the antigen of interest, is attached to a solid support, for example, a multiwell polystyrene plate. Sera to be tested are diluted and added to the wells. After a period of time sufficient for the binding of antibodies to the bound antigens, the sera are washed out of the wells. A labelled reporter antibody is added to each well along with an appropriate substrate: wells containing antibodies bound to the purified antigen polypeptide or fusion polypeptide containing the antigen are detected by a positive signal.

A typical format for protein blot analysis using the polypeptide antigens of the present invention is presented in Example 10. General protein blotting methods are described by Ausubel, et al. In Example 10, the 470-20-1/sj26 fusion protein was used to screen a number of sera samples. The results presented in Example 10 demonstrate that several different source N-(ABCDE) hepatitis sera are immunoreactive with the polypeptide antigen.

The results presented above demonstrate that the polypeptide antigens of the present invention can, by these methods, be rapidly screened against panels of suspected HGV infected serum samples for the detection of HGV.

E. Cell Culture Systems, Animal Models and Isolation of HGV.

HGV infectivity studies have been carried out in chimpanzees, cynomolgus monkey and-four mystax subjects (Example 4H). These studies have yielded further information about HGV infectivity in these animal models. The HGV described in the present specification have the advantage of being capable of infecting tamarins, cynomologous monkeys and chimpanzees.

Alternatively, primary hepatocytes obtained from infected animals (chimpanzees, baboons, monkeys, or humans) can be cultured in vitro. A serum-free medium, supplemented with growth factors and hormones, has been described which permits the long-term maintenance of differentiated primate hepatocytes (Lanford, et al.; Jacob, et al., 1989, 1990, 1991). In addition to primary hepatocyte cultures, immortalized cultures of infected cells may also be generated. For example, primary liver cultures may be fused to a variety of cells (like HepG2) to provide stable immortalized cell lines. Primary hepatocyte cell cultures may also be immortalized by introduction of oncogenes or genes causing a transformed phenotype. Such oncogenes or genes can be derived from a number of sources known in the art including SV40, human cellular oncogenes and Epstein Barr Virus.

Further, the un-infected hepatocytes (e.g., primary or continuous hepatoma cell lines) may be infected by exposing the cells in culture to the HGV either as partially purified particle preparations (prepared, for example, from infected sera by differential centrifugation and/or molecular sieving) or in infectious sera. These infected cells can then be propagated and the virus passaged by methods known in the art. In addition, other cell types, such as lymphoid cell lines, may be useful for the propagation of HGV.

Protein similarity studies of HGV have detected amino acid regions similar to other viruses in the family Flaviviridae. It is known that members of this family of viruses can be propagated in a variety of tissue culture systems (ATCC-Viruses catalogue, 1990). By analogy it is likely that HGV can be propagated in one or more of the following tissue culture systems: Hela cells, primary hamster kidney cells, monkey kidney cells, vero cells, LLC-MK2 (rhesus monkey kidney cells), KB cells(human oral epidermoid carcinoma cells), duck embryo cells, primary sheep leptomeningeal cells, primary sheep choroid plexus cells, pig kidney cells, bovine embryonic kidney cells, bovine turbinate cells, chick embryo cells, primary rabbit kidney cells, BHD-21 cells, or PK-13 cells.

In addition to expression of HGV, regions of HGV polynucleotide sequences, cDNA or in vitro transcribed RNA can be introduced by recombinant means into tissue culture cells. Such recombinant manipulations allow the individual expression of individual components of the HGV.

RNA samples can be prepared from infected tissue or, in particular, from infected cell cultures. The RNA samples can be fractionated on gels and transferred to membranes for hybridization analysis using probes derived from the cloned HGV sequences.

HGV particles may be isolated from infected sera, infected tissue, the above-described cell culture media, or the cultured infected cells by methods known in the art. Such methods include techniques based on size fractionation (i.e., ultrafiltration, precipitation, sedimentation), using anionic and/or cationic exchange materials, separation on the basis of density, hydrophilic properties, and affinity chromatography. During the isolation procedure the HGV can be identified (i) using the anti-HGV hepatitis associated agent antibodies of the present invention, (ii) by using hybridization probes based on identified HGV nucleic acid sequences (e.g., Example 5) or (iii) by RT-PCR.

Antibodies directed against HGV can be used in purification of HGV particles through immunoaffinity chromatography (Harlow, et al.; Pierce). Antibodies directed against HGV polypeptides or fusion polypeptides (such as 470-20-1) are fixed to solid supports in such a manner that the antibodies maintain their immunoselectivity. To accomplish such attachment of antibodies to solid support bifunctional coupling agents (Pierce; Pharmacia, Piscataway, N.J.) containing spacer groups are frequently used to retain accessibility of the antigen binding site of the antibody.

HGV particles can be further characterized by standard procedures including, but not limited to, immunofluorescence microscopy, electron microscopy, Western blot analysis of proteins composing the particles, infection studies in animal and/or cell systems utilizing the partially purified particles, and sedimentation characteristics. The results presented in Example 5 suggest that the viral particle of the present invention is more similar to an enveloped viral particle than to a non-enveloped viral particle.

HGV particles can be disrupted to obtain HGV genomes. Disruption of the particles can be achieved by, for example, treatment with detergents in the presence of chelating agents. The genomic nucleic acid can then be further characterized. Characterization may include analysis of DNase and RNase sensitivity. The strandedness (Example 4I) and conformation (e.g., circular) of the genome can be determined by techniques known in the art, including visualization by electron microscopy and sedimentation characteristics.

The isolated genomes also make it possible to sequence the entire genome whether it is segmented or not, and whether it is an RNA or DNA genome (using, for example RT-PCR, chromosome walking techniques, or PCR which utilizes primers from adjacent cloned sequences). Determination of the entire sequence of HGV allows genomic organization studies and the comparison of the HGV sequences to the coding and regulatory sequences of known viral agents.

F. Screening for Agents having Anti-HGV Hepatitis Activity.

The use of cell culture and animal model systems for propagation of HGV provides the ability to screen for anti-hepatitis agents which inhibit the production of infectious HGV: in particular, drugs that inhibit the replication of HGV. Cell culture and animal models allow the evaluation of the effect of such anti-hepatitis drugs on normal cellular functions and viability. Potential anti-viral agents (including natural products or synthetic compounds; for example, small molecules, complex mixtures such as fungal extracts, and anti-sense oligonucleotides) are typically screened for anti-viral activity over a range of concentrations. The effect on HGV replication and/or antigen production is then evaluated, typically by monitering viral macromolecular synthesis or accumulation of macromolecules (e.g., DNA, RNA or protein). This evaluation is often made relative to the effect of the anti-viral agent on normal cellular function (DNA replication, RNA transcription, general protein translation, etc.).

The detection of the HGV can be accomplished by many methods including those described in the present specification. For example, antibodies can be generated against the antigens of the present invention and these antibodies used in antibody-based assays (Harlow, et al.) to identify and quantitate HGV antigens in cell culture. HGV antigens can be quantitated in culture using competition assays: polypeptides encoded by the cloned HGV sequences can be used in such assays. Typically, a recombinantly produced HGV antigenic polypeptide is produced and used to generate a monoclonal or polyclonal antibody. The recombinant HGV polypeptide is labelled using a reporter molecule. The inhibition of binding of this labelled polypeptide to its cognate antibody is then evaluated in the presence of samples (e.g., cell culture media or sera) that contain HGV antigens. The level of HGV antigens in the sample is determined by comparison of levels of inhibition to a standard curve generated using unlabelled recombinant proteins at known concentrations.

The HGV sequences of the present invention are particularly useful for the generation of polynucleotide probes/primers that may be used to quantitate the amount of HGV nucleic acid sequences produced in a cell culture system. Such quantification can be accomplished in a number of ways. For example, probes labelled with reporter molecules can be used in standard dot-blot hybridizations or competition assays of labelled probes with infected cell nucleic acids. Further, there are a number of methods using the polymerase chain reaction to quantitate target nucleic acid levels in a sample (Osikowicz, et al.).

Protective antibodies can also be identified using the cell culture and animal model systems described above. For example, polyclonal or monoclonal antibodies are generated against the antigens of the present invention. These antibodies are then used to pre-treat an infectious HGV-containing inoculum (e.g., serum) before infection of cell cultures or animals. The ability of a single antibody or mixtures of antibodies to protect the cell culture or animal from infection is evaluated. For example, in cell culture and animals the absence of viral antigen and/or nucleic acid production serves as a screen. Further in animals, the absence of HGV hepatitis disease symptoms, e.g., elevated ALT values, is also indicative of the presence of protective antibodies.

Alternatively, convalescent sera can be screened for the presence of protective antibodies and then these sera used to identify HGV hepatitis associated agent antigens that bind with the antibodies. The identified HGV antigen is then recombinantly or synthetically produced. The ability of the antigen to generate protective antibodies is tested as above.

After initial screening, the antigen or antigens identified as capable of generating protective antibodies, either singly or in combination, can be used as a vaccine to inoculate test animals. The animals are then challenged with infectious HGV. Protection from infection indicates the ability of the animals to generate antibodies that protect them from infection. Further, use of the animal models allows identification of antigens that activate cellular immunity.

In animal model studies, a protective immune response in response to challenge by a viral preparation (e.g., infected serum) (i) protects the animal from infection or (ii) prevents manifestation of disease.

G. Vaccines and the Generation of Protective Immunity.

Vaccines can be prepared from one or more of the immunogenic polypeptides identified by the method of the present invention. Genomic organization similarities between the isolated sequences from HGV and other known viral proteins may provide information concerning the polypeptides that are likely to be candidates for effective vaccines. In addition, a number of computer programs can be used for to identify likely regions of isolated sequences that encode protein antigenic determinant regions (for example, Hopp, et al.; "ANTIGEN," Intelligenetics, Mountain View Calif.).

Vaccines containing immunogenic polypeptides as active ingredients are typically prepared as injectables either as solutions or suspensions. Further, the immunogenic polypeptides may be prepared in a solid or lyophilized state that is suitable for resuspension, prior to injection, in an aqueous form. The immunogenic polypeptides may also be emulsified or encapsulated in liposomes. The polypeptides are frequently mixed with pharmaceutically acceptable excipients that are compatible with the polypeptides. Such excipients include, but are not limited to, the following and combinations of the following: saline, water, sugars (such as dextrose and sorbitol), glycerol, alcohols (such as ethanol [EtOH]), and others known in the art. Further, vaccine preparations may contain minor amounts of other auxiliary substances such as wetting agents, emulsifying agents (e.g., detergents), and pH buffering agents. In addition, a number of adjuvants are available which may enhance the effectiveness of vaccine preparations. Examples of such adjuvants include, but are not limited to, the following: the group of related compounds including N-acetyl-muranyl-L-threonyl-D-isoglutamine and N-acetyl-nor-muranyl-L-alanyl-D-isoglutamine, and aluminum hydroxide.

The immunogenic polypeptides used in the vaccines of the present invention may be recombinant, synthetic or isolated from, for example, attenuated HGV particles. The polypeptides are commonly formulated into vaccines in neutral or salt forms. Pharmaceutically acceptable organic and inorganic salts are well known in the art.

HGV hepatitis associated agent vaccines are parenterally administered, typically by subcutaneous or intramuscular injection. Other possible formulations include oral and suppository formulations. Oral formulations commonly employ excipients (e.g., pharmaceutical grade sugars, saccharine, cellulose, and the like) and usually contain within 10–98% immunogenic polypeptide. Oral compositions take the form of pills, capsules, tablets, solutions, suspensions, powders, etc., and may be formulated to allow sustained or long-term release. Suppository formulations use traditional binders and carriers and typically contain between 0.1% and 10% of the immunogenic polypeptide.

In view of the above information, multivalent vaccines against HGV hepatitis associated agents can be generated which are composed of one or more structural or non-structural viral-agent polypeptide(s). These vaccines can contain, for example, recombinant expressed HGV polypeptides, polypeptides isolated from HGV virions, synthetic polypeptides or assembled epitopes in the form of mosaic polypeptides. In addition, it may be possible to prepare vaccines, which confer protection against HGV hepatitis infection through the use of inactivated HGV. Such inactivation might be achieved by preparation of viral lysates followed by treatment of the lysates with appropriate organic solvents, detergents or formalin.

Vaccines may also be prepared from attenuated HGV strains. Such attenuated HGV may be obtained utilizing the above described cell culture and/or animal model systems. Typically, attenuated strains are isolated after multiple passages in vitro or in vivo. Detection of attenuated strains is accomplished by methods known in the art. One method for detecting attenuated HGV is the use of antibody probes against HGV antigens, sequence-specific hybridization probes, or amplification with sequence-specific primers for infected animals or assay of HGV-infected in vitro cultures.

Alternatively, or in addition to the above methods, attenuated HGV strains may be constructed based on the genomic information that can be obtained from the information presented in the present specification. Typically, a region of the infectious agent genome that encodes, for example, a polypeptide that is related to viral pathogenesis can be deleted. The deletion should not interfere with viral replication. Further, the recombinant attenuated HGV construct allows the expression of an epitope or epitopes that are capable of giving rise to protective immune responses against the HGV. The desired immune response may include both humeral and cellular immunity. The genome of the attenuated HGV is then used to transform cells and the cells grown under conditions that allow viral replication. Such attenuated strains are useful not only as vaccines, but also as production sources of viral antigens and/or HGV particles.

Hybrid particle immunogens that contain HGV epitopes can also be generated. The immunogenicity of HGV epitopes may be enhanced by expressing the epitope in eucaryotic systems (e.g., mammalian or yeast systems) where the epitope is fused or assembled with known particle forming proteins. One such protein is the hepatitis B surface antigen. Recombinant constructs where the HGV epitope is directly linked to coding sequence for the particle forming protein will produce hybrid proteins that are immunogenic with respect to the HGV epitope and the particle forming protein. Alternatively, selected portions of the particle-forming protein coding sequence, which are not involved in particle formation, may be replaced with coding sequences corresponding to HGV epitopes. For example, regions of specific immunoreactivity to the particle-forming protein can be replaced by HGV epitope sequences.

The hepatitis B surface antigen has been shown to be expressed and assembled into particles in the yeast Saccharomyces cerevisiea and in mammalian cells (Valenzuela, et al., 1982 and 1984; Michelle, et al.). These particles have been shown to have enhanced immunoreactivity. Formation of these particles using hybrid proteins, i.e., recombinant constructs with heterologous viral sequences, has been previously disclosed (EPO 175,261, published Mar. 26, 1986). Such hybrid particles containing HGV epitopes may also be useful in vaccine applications.

The vaccines of the present invention are administered in dosages compatible with the method of formulation, and in such amounts that will be pharmacologically effective for prophylactic or therapeutic treatments. The quantity of immunogen administered depends on the subject being treated, the capacity of the treatment subject's immune system for generation of protective immune response, and the desired level of protection.

HGV vaccines of the present invention can be administered in single or multiple doses. Dosage regimens are also determined relative to the treatment subject's needs and tolerances. In addition to the HGV immunogenic polypeptides, vaccine formulations may be administered in conjunction with other immunoregulatory agents.

In an additional approach to HGV vaccination, DNA constructs encoding HGV proteins under appropriate regulatory control are introduced directly into mammalian tissue, in vivo. Introduction of such constructs produces "genetic immunization". Similar DNA constructs have been shown to be taken up by cells and the encoded proteins expressed (Wolf, et al.; Ascadi, et al.). Injected DNA does not appear to integrate into host cells chromatin or replicate. This expression gives rise to substantial humoral and cellular immune responses, including protection from in vivo viral challenge in animal systems (Wang, et al., 1993; Ulmer, et al.). In one embodiment, the DNA construct is injected into skeletal muscle following pre-treatment with local anesthetics, such as, bupivicaine hydrochloride with methylparaben in isotonic saline, to facilitate cellular DNA uptake. The injected DNA constructs are taken up by muscle cells and the encoded proteins expressed.

Compared to vaccination with soluble viral subunit proteins, genetic immunization has the advantage of authentic in vivo expression of the viral proteins. These viral proteins are expressed in association with host cell histocompatibility antigens, and other proteins, as would occur with natural viral infection. This type of immunization is capable of inducing both humoral and cellular immune responses, in contrast to many soluble subunit protein vaccines. Accordingly, this type of immunization retains many of the beneficial features of live attenuated vaccines, without the use of infectious agents for vaccination and attendant safety concerns.

Direct injection of plasmid or other DNA constructs encoding the desired vaccine antigens into in vivo tissues is one delivery means. Other means of delivery of the DNA constructs can be employed as well. These include a variety of lipid-based approaches in which the DNA is packaged using liposomes, cationic lipid reagents or cytofectins (such as, lipofectin). These approaches facilitate in vivo uptake and expression, as summarized by Felgner and Rhodes (1991). Various modifications to these basic approaches include the following: incorporation of peptides, or other moieties, to facilitate (i) targeting to particular cells, (ii) the intracellular disposition of the DNA construct following uptake, or (iii) to facilitate expression. Alternatively, the sequences encoding the desired vaccine antigens may be inserted into a suitable retroviral vector. The resulting recombinant retroviral vector inoculated into the subject for in vivo expression of the vaccine antigen. The antigen then induces the immune responses. As noted above, this approach has been shown to induce both humoral and cellular immunity to viral antigens (Irwin, et al.).

Further, the HGV vaccines of the present invention may be administered in combination with other vaccine agents, for example, with other hepatitis vaccines.

H. Synthetic Peptides.

Using the coding sequences of HGV polypeptide, synthetic peptides can be generated which correspond to these polypeptides. Synthetic peptides can be commercially synthesized or prepared using standard methods and apparatus in the art (Applied Biosystems, Foster City Calif.).

Alternatively, oligonucleotide sequences encoding peptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio et al.; Eaton et al.). Oligonucleotide coding sequences can be expressed by standard recombinant procedures (Maniatis et al.; Ausubel et al.).

V. CHARACTERIZATION OF THE VIRAL GENOME.

As shown in Example 4, the HGV genome appears to be an RNA molecule and has the closest sequence similarity to viral sequences that are categorized in the Flaviviridae family of viruses. This family includes the Flaviviruses, Pestiviruses and an unclassified Genus made up of one member, Hepatitis C virus. The HGV virus does not have significant global (i.e., over the length of the virus) sequence identity with other recognized members of the Flaviviridae— with the exception of the protein motifs discussed below.

In general members of the Flaviviridae are enveloped viruses that have densities in sucrose gradients between 1.1 and 1.23 g/ml and are sensitive to heat, organic solvents and detergents. As shown in Example 5, HGV has density characteristics similar to an enveloped Flaviviridae virus (HCV). The integrity of the HGV virion also appears to be sensitive to organic solvents (Example 5).

Flaviviridae virions contain a single molecule of linear single-stranded (ss) RNA which also serves as the only mRNA that codes for the viral proteins. The ssRNA molecule is typically between the size of 9 and 12 kilobases long.

Viral proteins are derived from one polyprotein precursor that is subsequently processed to the mature viral proteins. Most members of the Flaviviridae do not contain poly(A) tails at their 3' ends. Virions are about 15–20% lipid by weight.

Members in the Flaviviridae family have a core protein and two or three membrane-associated proteins. The analogous structural proteins of members in the three genera Flavivirus family show little similarity to one another at the sequence level. The nonstructural proteins contain conserved motifs for RNA dependent RNA polymerase (RDRP), helicase, and a serine protease. These short blocks of conserved amino acids or motifs can be detected using computer algorithms known in the art such as "MACAW" (Schuler, et al.). These motifs are presumably related to constraints imposed by substrates processed by these proteins (Koonin and Dolja). The order of these motifs is conserved in all members of the Flaviviridae family. The genome of HGV contains protein motifs found in members of the Flaviviridae family, for example, (i) the helicase gene, (ii) the serine-like protease domain, and (iii) the RNA dependent RNA polymerase (RDRP) of (see FIG. 5. "GDD" sequence);

Sequence information is disclosed herein on several different strains/isolates of HGV. This information can be used by one skilled in the art to isolate new stains/isolates using the techniques of hybridization, primer extension, and RT-PCR as described herein (e.g., using degenerate primers based on the disclosed HGV variant sequences).

In the present case, HGV is an new isolate believed to be a member of the family Flaviviridae. Within this virus family, examination of the structural proteins encoded by a virus allows the most definitive determination of whether a viral isolate is a member of a distinct species of virus. Non-structural proteins are most conserved between different species of viruses within a family of virus species. This is believed to be the result of the necessity for preserving enzymatic functions, such as, the following: the proteolytic cleavage of a viral polyprotein, and replication of the RNA genome by viral helicase and RNA dependent RNA polymerase of the virus.

Examination of several species within any genus of the Flaviviridae family, e.g., the flavivirus genus, demonstrates that the genes for these conserved functions are more highly conserved between species than the structural proteins. Accordingly, one of the major determining factors of whether a virus isolate represents a new species, versus a "variant isolate" of a known species, is a determination of global homology of the structural proteins between known viral species and the new virus isolate.

Local homologies found within regions about 200 amino acids or less which are found in non-structural proteins are indeterminant indicators of whether an isolate is a variant or a new species. Typically, virus isolates having global structural protein homologies of less than or about 40% are classified as either different species (viruses) or different genuses. The structural regions of HGV each have homologies lower than 40% compared with any virus described in "GENBANK" (comparisons carried out by methods standard in the art). Accordingly, HGV is considered to be a new species and possibly a new genus of positive strand RNA virus.

Another important region that is examined in determining the phylogenetic placement of a viral isolate is the 5' and 3' untranslated regions (UTRs). These regions are compared between viral isolates. For example, all the members HCV, an unclassified genus of Flaviviridae, have 5' untranslated regions that are greater than about 90% conserved with all other members in the genus. Further, the members of the HCV share 3' untranslated regions between about 24 and about 50 nucleotides long.

No significant alignments are found with any virus in "GENBANK" (Ver. 86) when the 5'-untranslated region is used as a query sequence with FASTA on BLASTN. Further, HGV contains a 3' untranslated region that is at least about 250 nucleotides long that also contains little homology to any other known virus.

Members of the Flaviviridae family are known to replicate in a wide variety of animals ranging from (i) hematophagous arthropod vectors (ticks and mosquitoes), where they do not cause disease, to (ii) a large range of vertebrate hosts (humans, primates, other mammals, marsupials, and birds). Over 30 members of the Flaviviridae family cause diseases in man, ranging from febrile illness, or rash, to potentially fatal diseases such as hemorrhagic fever, encephalitis, or hepatitis. At least 10 members of the Flaviviridae family cause severe and economically important diseases in domestic animals.

VI. Utility

A. The Invention.

In one aspect, the invention pertains to polynucleotides derived from a Hepatitis G Virus (HGV) polynucleotide in substantially isolated form. In one embodiment the HGV polynucleotide is characterized by (i) transmission in primates, (ii) serologically distinguishable from hepatitis A virus (HAV), hepatitis B virus (HBV), hepatitis C virus (HCV), hepatitis D virus, and hepatitis E virus (HEV), and (iii) membership of the virus family Flaviviridae. Polynucleotides of the invention may be comprised of DNA or RNA (or analogs or variants thereof) and may be produced recombinantly, isolated, or synthesized according to methods known in the art.

Generally, HGV polynucleotides of the invention will be at least 10 nucleotides in length. In an alternative embodiment, the HGV polynucleotide will be at least 15 nucleotides in length. In still a further alternative embodiment, the HGV polynucleotide will be at least 20 nucleotides in length.

In a more specific embodiment, polynucleotides of the invention include cDNA or cDNA complements of the HGV genome. In a more specific embodiment, such a CDNA or cDNA complement will have at least a 40% sequence homology to a polynucleotide selected from the group consisting of SEQ ID NO:14, SEQ ID NO:37, and SEQ ID NO:19, or complements thereof. In yet another embodiment such cDNA's will exhibit at least 55% sequence homology to a polynucleotide selected from the group consisting of SEQ ID NO:14, SEQ ID NO:37, and SEQ ID NO:19, or complements thereof. In more specific embodiments, cDNA or cDNA complement polynucleotides of the invention will have sequences derived from sequences selected from the group consisting of SEQ ID NO:14, SEQ ID NO:37, and SEQ ID NO:9, or complements thereof.

In another general embodiment, polynucleotides of the invention are polynucleotide probes that specifically hybridize with HGV. In yet another general embodiment, polynucleotides of the invention will encode an epitope of HGV. More specifically, such epitope encoding polynucleotides may include sequences derived from SEQ ID NO:14, SEQ ID NO:19 or SEQ ID NO:37.

In another general embodiment, the polynucleotide of the invention includes a contiguous sequence of nucleotides that is capable of selectively hybridizing to an HGV polynucleotide. In this regard, HGV is characterized as a genome comprising an open reading frame (ORF) encoding an amino acid sequence having at least 40% sequence homology to one of the following amino acid sequences: the 2873 amino acid sequence of SEQ ID NO:15, the 190 amino acid sequence of SEQ ID NO:38, or the 67 amino acid sequence of SEQ ID NO:20. More particularly, the polynucleotide probe will specifically hybridize with HGV. Such a polynucleotide probe may carry detection labels or other modifications or be fixed to a solid support.

DNA polynucleotides as described above may also encode an HGV specifically immunoreactive antigenic determinants. In this regard, HGV is characterized as having a genome, cDNA or complements thereof comprising an open reading frame (ORF) encoding an amino acid sequence. Such, an amino acid sequence having at least 40% sequence homology to one of the following amino acid sequences: the 2873 amino acid sequence of SEQ ID NO:15, the 190 amino acid sequence of SEQ ID NO:38, or the 67 amino acid sequence of SEQ ID NO:20.

In another specific embodiment, an HGV-encoding DNA polynucleotide that is specifically reactive with an HGV antigenic determinant will, in accordance with the invention, include an amino acid sequence having at least 55% sequence homology to the 2873 amino acid sequence of SEQ ID NO:15 or to the 190 amino acid sequence of SEQ ID NO:38 or to the 67 amino acid sequence of SEQ ID NO:20.

In yet another specific embodiment, the DNA polynucleotide may exhibit at least 40% sequence homology to a polynucleotide selected from the group consisting of SEQ ID NO:14, SEQ ID NO:37, and SEQ ID NO:19, or complements thereof.

In still a further embodiment, the invention includes a DNA polynucleotide that encodes an HGV-derived polypeptide. More particularly, the polypeptide encoded by the polynucleotide will include a contiguous sequence of at least 15–60 amino acids having 55% sequence homology to a contiguous sequence of at least 15–60 amino acids encoded by an HGV genome, cDNA or complements thereof.

In a specific embodiment, HGV-polypeptide encoding polynucleotides may be encoded within the PNF 2161 cDNA source lambda gt11 library. In yet another specific embodiment, the DNA polynucleotide may encode an epitope of HGV. In still a further embodiment, the polynucleotide may be a probe that specifically hybridizes with HGV.

In a related aspect, the invention includes a recombinant vector that contains a DNA polynucleotide that encodes an HGV polypeptide. In another related aspect, the invention includes a cell transformed with such a vector.

In still another related aspect, the invention includes a polynucleotide probe that specifically hybridizes with an HGV hepatitis virus genome, CDNA or complements thereof. In a more specific embodiment, the polynucleotide probe sequence has at least 40% homology to a sequence derived from SEQ ID NO:19, SEQ ID NO:37, or SEQ ID NO:14, or complements thereof. In another specific embodiment, the polynucleotide probe is derived from SEQ ID NO:19, SEQ ID NO:37, or SEQ ID NO:14, or complements thereof.

In another related aspect, the invention includes a method of detecting an HGV hepatitis virus nucleic acid in a test subject. According to the method a nucleic acid-containing sample is obtained from the subject. The sample is then combined with and at least one polynucleotide probe that specifically hybridizes with the HGV hepatitis viral genome. HGV nucleic acid/probe complexes, formed by hybridization of the HGV nucleic acid with probe, are then detected. Such detecting may be accomplished by hybridization of a probe containing at least one reporter moiety to the HGV nucleic acid.

In a more specific embodiment, the above-described method includes the use of HGV nucleic acid specific probes where the two probes (primers) define an internal region of the HGV nucleic acid. In this embodiment, each probe has one strand containing a 3'-end internal to the HGV nucleic acid internal region. The nucleic acid/probe hybridization complexes are then converted to double-strand probe containing fragments by primer extension reactions. Probe-containing fragments are amplified by successively repeating the steps of (i) denaturing the double-strand fragments to produce single-strand fragments, (ii) hybridizing the single strands with the probes to form strand/probe complexes, (iii) generating double-strand fragments from the strand/probe complexes in the presence of DNA polymerase and all four deoxyribonucleotides, and (iv) repeating steps (i) to (iii) until a desired degree of amplification has been achieved. Amplification products are then identified according to established procedures. The method of the invention may further include a third polynucleotide probe capable of selectively hybridizing to the internal region described above but not to the specific probe/primer sequences used for amplification.

In another specific embodiment, detection of HGV nucleic acid/probe complexes is accomplished by a target amplification method, such as by self-sustained sequence replication, ligase chain reaction, or strand displacement amplification. In a further specific embodiment detection is accomplished employing a signal amplification technique such as branch-chained DNA probes or the Q-beta replicase method.

In still another related aspect, the invention includes a kit for analyzing samples for the presence of polynucleotides derived HGV hepatitis virus. In a general embodiment, the kit includes at least one polynucleotide probe containing a nucleotide sequence that will specifically hybridize with an HGV polynucleotide and a suitable container. In a specific embodiment, the kit includes two polynucleotide probes defining an internal region of the HGV polynucleotide, where each probe has one strand containing a 3'-end internal to the region. In a further embodiment, the probes may be useful as primers for polymerase chain reaction amplification.

In still a further related aspect, the invention includes the HGV hepatitis virus particle in substantially isolated form. The invention also includes a polypeptide or a preparation of polypeptides from the HGV hepatitis virus in substantially isolated form. In this regard, the HGV virus is characterized as follows: (i) it is transmissible in primates; (ii) it is serologically distinct from hepatitis A virus (HAV), hepatitis B virus (HBV), hepatitis C virus (HCV), hepatitis D virus, and hepatitis E virus (HEV); and (iii) it is a member of the virus family Flaviviridae. HGV polypeptides, as defined above, may be prepared by conventional means, including chemical synthesis and recombinant DNA expression. Such polypeptides may also be fixed to a solid phase.

In a specific embodiment the polypeptide is specifically immunoreactive with at least one anti-HGV antibody. In still a further specific embodiment, the polypeptide comprises an antigenic determinant specifically immunoreactive with HGV. In this context, HGV is characterized by having a genome comprising an open reading frame (ORF) encoding an amino acid sequence having at least 40% sequence homology to the 2873 amino acid sequence of SEQ ID NO:15 or to the 190 amino acid sequence of SEQ ID NO:38 or to the 67 amino acid sequence of SEQ ID NO:20. In a more specific embodiment, the ORF encodes amino acid sequence has at least 55% sequence homology to one of the aforementioned amino acid sequences. In still a further embodiment, the polypeptide sequence is derived from the 2873 amino acid sequence of SEQ ID NO:15, or fragments thereof, the 190 amino acid sequence of SEQ ID NO:38, or fragments thereof, or the 67 amino acid sequence of SEQ ID NO:20, or fragments thereof.

In another specific embodiment, the polypeptide from the HGV hepatitis virus includes a contiguous sequence of at least about 60 amino acids encoded by an HGV genome, cDNA or complements thereof. More specifically, such peptide sequence may be encoded by the PNF 2161 cDNA source lambda gt11 library.

Recombinantly expressed HGV polypeptides may, in a more specific embodiment, include a polypeptide sequence derived from SEQ ID NO:20, SEQ ID NO:38, or SEQ ID NO:15. In another embodiment such a polypeptide may be encoded by a sequence derived from SEQ ID NO:14, or from the complement of SEQ ID NO:14.

In a further related embodiment, in accordance with the invention, an HGV hepatitis virus polypeptide may be a fusion polypeptide comprising an HGV polypeptide and a second polypeptide. More specifically, such a fusion polypeptide may include, as a second polypeptide signal sequences, β-galactosidase or glutathione-S-transferase protein sequences. Alternatively, the second polypeptide may comprise a particle forming protein.

The above-described polypeptides may be derived from structural or non-structural viral proteins.

In still a further related aspect, the invention includes a cloning vector capable of expressing, under suitable conditions, an open reading frame (ORF) of cDNA derived from HGV hepatitis virus genome, cDNA or complements thereof. In this aspect of the invention, the ORF is operably linked to a control sequence compatible with a desired host. In a related aspect, the invention includes a cell transformed with such a vector. In a more specific embodiment of the vector, the ORF may be derived from SEQ ID NO:14 or its complement. In yet further specific embodiments, the ORF may be derived from SEQ ID NO:37 or SEQ ID NO:19.

In a related aspect, the invention includes a method of producing an HGV hepatitis virus polypeptide. The method includes culturing cells containing the above-described vectors under conditions suitable to achieve expression of the open reading frame (ORF) sequence. In a more specific embodiment, the ORF sequence encodes a polypeptide sequence selected from the group of polypeptide sequences, or fragments thereof, consisting of SEQ ID NO:15, SEQ ID NO:38 and SEQ ID NO:20. Further, the ORF sequences may be derived from an HGV cDNA, or complement thereof. In yet another specific embodiment, the vector is a lambda gt11 phage vector expressed in Escherichia coli cells.

In a further related aspect, the invention includes a diagnostic kit for use in screening serum containing antibodies specific against HGV hepatitis virus infection. Such a kit may include a substantially isolated HGV polypeptide antigen comprising an epitope which is specifically immunoreactive with at least one anti-HGV antibody. Such a kit also includes means for detecting the binding of said antibody to the antigen. In regard to such a kit, HGV is characterized by having a genome, cDNA or complements thereof comprising an open reading frame (ORF) encoding an amino acid sequence. Such an amino acid sequence typically having at least 40% sequence homology to the 2873 amino acid sequence of SEQ ID NO:15 or to the 190 amino acid sequence of SEQ ID NO:38 or to the 67 amino acid sequence of SEQ ID NO:20. In specific embodiments, the kit may include a recombinantly produced or chemically synthesized polypeptide antigen. The polypeptide antigen of the kit may also be attached to a solid support.

In a more specific embodiment, the detecting means of the above-described kit includes a solid support to which said polypeptide antigen is attached. Such a kit may also include a non-attached reporter-labelled anti-human antibody. In this embodiment, binding of the antibody to the HGV polypeptide antigen can be detected by binding of the reporter-labelled antibody the antibody.

In a related aspect, the invention includes a method of detecting HGV hepatitis virus infection in a test subject. This detection method includes reacting serum from an HGV test subject with a substantially isolated HGV polypeptide antigen, and examining the antigen for the presence of bound antibody. In a specific embodiment, the method includes a polypeptide antigen attached to a solid support, and the serum is reacted with the support. Subsequently, the support is reacted with a reporter-labelled anti-human antibody. The solid support is then examined for the presence of reporter-labelled antibody.

In a further aspect, the invention includes an HGV hepatitis virus vaccine composition. The composition includes a substantially isolated HGV polypeptide antigen, where the antigen includes an epitope which is specifically immunoreactive with at least one anti-HGV antibody. The peptide antigen may be produced according to methods known in the art, including recombinant expression or chemical synthesis. The peptide antigen is preferably present in a pharmacologically effective dose in a pharmaceutically acceptable carrier.

In still a further related aspect, the invention includes a monoclonal antibody that is specifically immunoreactive with the HGV hepatitis virus epitope. In another related aspect, the invention includes a substantially isolated preparation of polyclonal antibodies specifically immunoreactive with HGV. In a more specific embodiment, such polyclonal antibodies are prepared by affinity chromatography.

In a related aspect, the invention includes a method for producing antibodies to HGV. The method includes administering to a test subject a substantially isolated HGV polypeptide antigen, where the antigen includes an epitope which is specifically immunoreactive with at least one anti-HGV antibody. The antigen is administered in an amount sufficient to produce an immune response in the subject.

In yet another related aspect, the invention includes a diagnostic kit for use in screening serum containing HGV antigens. The diagnostic kit includes a substantially isolated antibody specifically immunoreactive with an HGV polypeptide antigen, and means for detecting the binding of the polypeptide antigen to the antibody. In one embodiment, the antibody is attached to a solid support. In a specific embodiment, the antibody may be a monoclonal antibody. The detecting means of the kit may include a second, labelled monoclonal antibody. Alternatively, or in addition, the detecting means may include a labelled, competing antigen.

In another, related aspect, the invention includes a method of detecting HGV infection in a test subject. According to this aspect of the invention, serum from a test subject is reacted with a substantially isolated HGV specific antibody of the kit described above. The HGV specific antibody is then examined for the presence of bound antigen.

In still a further related aspect, the invention includes an in vitro grown cell infected with HGV. In a specific embodiment, the cell is a hepatocyte grown in tissue culture. More specifically, the tissue culture cell may be an immortalized hepatocyte, or it may be a from a cell line derived from liver of an HGV infected primate.

In a related aspect, the invention includes a method of propagating HGV. The method includes culturing in vitro grown, HGV-infected cells, as described above, under conditions effective to promote the propagation of HGV. In another related aspect, the invention includes HGV particles produced by such a propagation method.

In still a further aspect, the invention includes a mosaic polypeptide. Such a polypeptide may include at least two epitopes of HGV, where the polypeptide substantially lacks amino acids normally intervening between the epitopes in the native HGV coding sequence. In a more specific embodiment, the mosaic polypeptide is attached to a solid support. In still a further related aspect, the invention includes a nucleic acid that encodes the above-described mosaic polypeptide.

In another related aspect, the invention includes a method of detecting HGV infection in a test subject. The method includes contacting an antibody-containing sample from the subject with a mosaic polypeptide, as described above, and examining the antigen for the presence of bound antibody.

In still a further related aspect, the invention includes an HGV vaccine composition. The vaccine composition includes mosaic polypeptide that includes more than one HGV epitope. The mosaic polypeptide is present in a pharmacologically effective dose in a pharmaceutically acceptable carrier.

B. Immunoassays for HGV.

One utility for the antigens obtained by the methods of the present invention is their use as diagnostic reagents for the detection of antibodies present in the sera of test subjects infected with HGV hepatitis virus, thereby indicating infection in the subject; for example, 470-20-1 antigen, antigens encoded by SEQ ID NO:14 or its complement, and antigens encoded by portions of either strand of the complete viral sequence. The antigens of the present invention can be used singly, or in combination with each other, in order to detect HGV. The antigens of the present invention may also be coupled with diagnostic assays for other hepatitis agents such as HAV, HBV, HCV, and HEV.

In one diagnostic configuration, test serum is reacted with a solid phase reagent having a surface-bound antigen obtained by the methods of the present invention, e.g., the 470-20-1 antigen. After binding with anti-HGV antibody to the reagent and removing unbound serum components by washing, the reagent is reacted with reporter-labelled anti-human antibody to bind reporter to the reagent in proportion to the amount of bound anti-HGV antibody on the solid support. The reagent is again washed to remove unbound labelled antibody, and the amount of reporter associated with the reagent is determined. Typically, the reporter is an enzyme which is detected by incubating the solid phase in the presence of a suitable fluorometric or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Also forming part of the invention is an assay system or kit for carrying out this diagnostic method. The kit generally includes a support with surface-bound recombinant HGV antigen (e.g., the 470-20-1 antigen, as above), and a reporter-labelled anti-human antibody for detecting surface-bound anti-HGV antigen antibody.

In a second diagnostic configuration, known as a homogeneous assay, antibody binding to a solid support produces some change in the reaction medium which can be directly detected in the medium. Known general types of homogeneous assays proposed heretofore include (a) spin-labelled reporters, where antibody binding to the antigen is detected by a change in reported mobility (broadening of the spin splitting peaks), (b) fluorescent reporters, where binding is detected by a change in fluorescence efficiency or polarization, (c) enzyme reporters, where antibody binding causes enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labelled anti-human antibody to the antibody being examined (for example from acute, chronic or convalescent phase) and measuring the amount of reporter bound to the solid support, as in the first method, or may involve observing the effect of antibody binding on a homogeneous assay reagent, as in the second method.

A third diagnostic configuration involves use of HGV antibodies capable of detecting HGV-specific antigens. The HGV antigens may be detected, for example, using an antigen capture assay where HGV antigens present in candidate serum samples are reacted with a HGV specific monoclonal or polyclonal antibody. The antibody is bound to a solid substrate and the antigen is then detected by a second, different labelled anti-HGV antibody. Antibodies can be prepared, utilizing the peptides of the present invention, by standard methods. Further, substantially isolated antibodies (essentially free of serum proteins which may affect reactivity) can be generated (e.g., affinity purification (Harlow et al.)).

C. Hybridization Assays for HGV.

One utility for the nucleic acid sequences obtained by the methods of the present invention is their use as diagnostic agents for HGV sequences present in sera, thereby indicating infection in the individual. Primers and/or probes derived from the coding sequences of the present invention, in particular, Clone 470-20-1 and SEQ ID NO:14, can be used singly, or in combination with each other, in order to detect HGV.

In one diagnostic configuration, test serum is reacted under PCR or RT-PCR conditions using primers derived from, for example, 470-20-1 sequences. The presence of HGV, in the serum used in the amplification reaction, can be detected by specific amplification of the sequences targeted by the primers. Example 4 describes the use of polymerase chain amplification reactions, employing primers derived from the clones of the present invention, to screen different source material. The results of these amplification reactions demonstrate the ability of primers derived from the clones of the present invention (for example, 470-20-1), to detect homologous sequences by amplification reactions employing a variety of different source templates. The amplification reactions in Example 4 included use of nucleic acids obtained directly from sera as template material.

Alternatively, probes can be derived from the HGV sequences of the present invention. These probes can then be labelled and used as hybridization probes against nucleic acids obtained from test serum or tissue samples. The probes can be labelled using a variety of reporter molecules and detected accordingly: for example, radioactive isotopic labelling and chemiluminescent detection reporter systems (Tropix, Bedford, Mass.).

Target amplification methods, embodied by the polymerase chain reaction, the self-sustained sequence replication technique ["3SR," (Guatelli, et al.; Gingeras, et al., 1990) also known as "NASBA" (VanGemen, et al.)], the ligase chain reaction (Barany), strand-displacement amplification ["SDA," (Walker)], and other techniques, multiply the number of copies of the target sequence. Signal amplification techniques, exemplified by branched-chain DNA probes (Horn and Urdea; Urdea; Urdea, et al.) and the Q-beta replicase method (Cahill, et al.; Lomell, et al.), first bind a specific molecular probe, then replicate all of or part of this probe or in some other manner amplify the probe signal.

For the detection of the specific nucleic acid sequences disclosed in the present invention or contiguous sequences in the same or a similar (related) viral genome, amplification and detection methodologies may be employed, as alternatives to amplification by the PCR. A number of such techniques are known to the field of nucleic acid diagnostics (The 1992 San Diego Conference: Genetic Recognition, *Clin. Chem.* 39(4):705 (1993)).

1. SELF-SUSTAINED SEQUENCE REPLICATION.

The Self-Sustained Sequence Replication (3SR) technique results in amplification to a similar magnitude as PCR, but isothermally. Rather than thermal cycle-driven PCR, the 3SR operates as a concerted three-enzyme reaction of a) CDNA synthesis by reverse transcriptase, b) RNA strand degradation by RNase H, and c) RNA transcription by T7 RNA polymerase.

As the entire reaction sequence occurs isothermally (typically at 42° C.), expensive temperature-cycling instrumentation is not required. In the absence of duplex denaturation via heating, organic solvents, or other mechanism, only single-stranded templates (i.e., predominantly RNA) are amplified.

Suitable primers for use in 3SR amplification can be selected from the viral sequences of the present invention by those having ordinary skill in the art. For example, for isothermal amplification of viral sequences by the 3SR technique, primer 470-20-1-77F (SEQ ID NO:9) is modified by the addition of the T7 promoter sequence and a preferred T7 transcription initiation site to the 5'-end of the oligonucleotide. This modification results in a suitable 3SR primer T7-470-20-1-77F (SEQ ID NO:9). Primer 470-20-1-211R (SEQ ID NO:10) can be used in these reactions either without modification or T7 promoter.

RNA extracted from PNF 2161 is incubated with AMV reverse transcriptase (30 U), RNase H (3 U), T7 RNA polymerase (100 U), in 100 ul reactions containing 20 mM Tris-HCl, pH 8.1 (at room temperature), 15 mM $MgCl_2$, 10 mM KCl, 2 mM spermidine HCl, 5 mM dithiothreitol (DTT), 1 mM each of dATP, dCTP, dGTP, and TTP, 7 mM each of ATP, CTP, GTP, and UTP, and 0.15 uM each primer. Amplification takes place during incubation at 42° C. for 1-2 h.

Initially, primer T7-470-20-1-77F anneals to the target RNA, and is extended by AMV reverse transcriptase to form CDNA complementary to the starting RNA strand. Following degradation of the RNA strand by RNase H, reverse transcriptase catalyzes the synthesis of the second strand DNA, resulting in a double-stranded template containing the (double-stranded) T7 promoter sequence. RNA transcription results in production of single-stranded RNA. This RNA then serves to re-enter the cycle for additional rounds of amplification, finally resulting in a pool of high-concentration product RNA. The product is predominantly single-stranded RNA of the same strand as the primer containing the T7 promoter (T7-470-20-1-77F), with much smaller amounts of cDNA.

Alternatively, the other primer (470-20-1-211R) may contain the T7 promoter, or both primers may contain the promoter, resulting in production of both strands of RNA as products of the reaction. Products of the 3SR reaction may be detected, characterized, or quantitated by standard techniques for the analysis of RNA (e.g., Northern blots, RNA slot or dot blots, direct gel electrophoresis with RNA-staining dyes). Further, the products may be detected by methods making use of biotin-avidin affinity interactions or specific hybridizations of nucleic acid probes.

In one technique for rapid and specific analysis of 3SR products, solution hybridization of the product to radiolabelled oligonucleotide 470-20-1-152R (SEQ ID NO:21) is followed by non-denaturing polyacrylamide gel electrophoresis. This assay (a gel mobility shift-type assay) results in the detection of specific probe-product hybrid as a slower-moving band than the band corresponding to unhybridized oligonucleotide.

2. LIGASE CHAIN REACTION (LCR)

As another example of a detection system, the HGV sequence may form the basis for design of ligase chain reaction (LCR) primers. LCR makes use of the nick-closing activity of DNA ligase to join two immediately adjacent oligonucleotides possessing adjacent 5'-phosphate ("donor" oligo) and 3'-hydroxyl ("¹acceptor" oligo) terminii. The property of DNA ligase to join only fully complementary ends in a template-dependent way, leads to a high degree of specificity, in that ligation will not occur unless the terminii to be linked are perfectly matched in sequence to the target strand.

As an alternative to PCR, with some advantages in terms of specificity for discrimination of single base mismatches between primer and target nucleic acid, the LCR may be used to detect or "type" strains of virus possessing homology to HGV sequences. These techniques are suitable for assessing the presence of specific mutations when such base changes are known to confer drug resistance (e.g., Larder and Kemp; Gingeras, et al., 1991). In the presence of template-complementary donor and acceptor oligonucleotides and oligonucleotides complementary to the donor and acceptor, exponential amplification by LCR is possible. In this embodiment, each round of ligation generates additional template for subsequent rounds, in a cyclic reaction.

For example, primer 470-20-1-211R (SEQ ID NO:10), an adjacent oligonucleotide (B, SEQ ID NO:22) and cognate oligos (211R', SEQ ID NO:23, and B', SEQ ID NO:24), can be used to perform LCR amplification of the sequence of this invention. Reverse transcription is first performed by standard methods to generate cDNA, which is then amplified in reactions containing 0.1–1 µM each of the four LCR primers, 20 mM Tris-HCl, pH 8.3 (room temperature), 25 mM KCl, 10 mM $MgCl_2$, 10 mM dithiothreitol (DTT), 0.5 mM AND+, 0.01% Triton X-100, and 5 Units of DNA ligase (Ampligase, Epicentre Technologies, Madison, Wis., or other commercial supplier of thermostable DNA ligase), in 25 ul reactions.

Thermal cycling is performed at 94° C. for 1 min. 30 s; 94° C. for 1 min., 65° C. for 2 min., repeated for 25–40 cycles. Specificity of product synthesis depends on primer-template match at the 3'-terminal position. Products are detected by polyacrylamide gel electrophoresis, followed by ethidium bromide staining; alternatively, one of the acceptor oligos (211R' or B) is 5'-radiolabelled for visualization by autoradiography following gel electrophoresis.

Alternatively, a donor oligo is 3'-end-labelled with a specific bindable moiety (e.g., biotin), and the acceptor is 5'-labelled with a specific detectable group (e.g., a fluorescent dye), for solid phase capture and detection.

3. METHODS FOR ANALYSIS OF AMPLIFIED DNA

Numerous techniques have been described for the analysis of amplified DNA. Several such techniques are advantageous for high-throughput applications, where gel electrophoresis is impractical, for example, rapid and high-resolution HPLC techniques (Katz and Dong). However, in general, methods for infectious disease organism screening using nucleic acid probes involve a separate post-amplification hybridization step in order to assure requisite specificity for pathogen detection.

One such detection embodiment is an affinity-based hybrid capture technique (Holodniy, et al.). In this embodiment the PCR is conducted with one biotinylated primer. Following amplification, the double-stranded product is denatured then hybridized to a peroxidase-labelled probe complementary to the strand having incorporated the biotinylated primer. The hybridized product is then incubated in a buffer which is in contact with an avidin (or streptavidin) coated surface (e.g., membrane filter, microwell, latex or paramagnetic beads).

The mass of coated solid phase which contacts the volume of PCR product to be analyzed by this method must contain sufficient biotin-binding sites to capture essentially all of the free biotinylated primer, as well as the much lower concentration of biotinylated PCR product. Following three to four washes of the solid phase, bound hybridized product is detected by incubation with o-phenylenediamine in citrate buffer containing hydrogen peroxide.

Alternatively, capture may be mediated by probe-coated surfaces, followed by affinity-based detection via the biotinylated primer and an avidin-reporter enzyme conjugate (Whetsell, et al.).

4. ADDITIONAL METHODS

Viral sequences of the present invention may also form the basis for a signal amplification approach to detection, using branched-chain DNA probes. Branched-chain probes (Horn and Urdea; Urdea) have been described for detection and quantification of rare RNA and DNA sequences (Urdea, et al.). In this method, an oligonucleotide probe (RNA, DNA, or nucleic acid analogue) is synthesized with a sequence complementary to the target RNA or DNA. The probe also contains a unique branching sequence or sequences not complementary to the target RNA or DNA.

This unique sequence constitutes a target for hybridization of branched secondary detector probes, each of which contains one or more other unique sequences, serving as targets for tertiary probes. At each branch point in the signal amplification pathway, a different unique sequence directs hybridization of secondary, tertiary, etc., detection probes. The last probe in the series typically is linked to an enzyme useful for detection (e.g., alkaline phosphatase). The sequential hybridization of primers eventually results in the buildup of a highly-branched structure, the arms of which terminate in enzyme-linked probes.

Enzymatic turnover provides a final amplification, and the choice of highly sensitive chemiluminescent substrates (e.g., LumiPhos, Lumigen, Detroit, Mich., as a substrate for alkaline phosphatase labels) results in exquisite sensitivity, on the order of 10,000 molecules or less of original target sequence per assay. In such a detection method, amplification depends only on molecular hybridization, rather than enzymatic mechanisms, and is thus far less susceptible to inhibitory substances in clinical specimens than, for example, PCR. Thus, this detection method allows the use of crude techniques for nucleic acid release in test samples, without extensive purification before assay.

Amplification for sensitive detection of the viral sequences of the present invention may also be accomplished by the Q-β replicase technique (Cahill, et al.; Lomell, et al.; Pritchard, et al.). In this method, a specific probe is designed to be complementary to the target sequence. This probe is then inserted by standard molecular cloning techniques into the sequence of the replicatable RNA from Q-β phage. Insertion into a specific region of the replicon does not prevent replication by Q-β replicase.

Following molecular hybridization, and several cycles of washing, the replicase is added and amplification of the probe RNA ensues. "Reversible target capture" is one known technique for reducing the potential background from replication of unhybridized probes (Morrissey, et al.). Amplified replicons are detectable by standard molecular hybridization techniques employing DNA, RNA or nucleic acid analogue probes.

Additional methods for amplification and detection of rare DNA or RNA sequences are known in the literature and preferred to the PCR for some applications in the field of molecular diagnostics. These alternative techniques may form the basis for detection, characterization (e.g., sequence diversity existing as multiple related strains of the sequence described herein, genotypic changes characteristic of drug resistance), or quantification of the sequence disclosed in the present invention.

Also forming part of the invention are assay systems or kits for carrying out the amplification/-hybridization assay methods just described. Such kits generally include either specific primers for use in amplification reactions or hybridization probes.

D. Therapeutic Uses.

As discussed above, the HGV antigens of the present invention can be used in vaccine preparation.

Further, antibodies generated against the polypeptide antigens of the present invention can be used for passive immunotherapy or passive immunoprophylaxis. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with establishment of infection. Thus, antibodies reactive with the HGV antigens can be passively administered alone or in conjunction with another anti-viral agent to a host infected with HGV to enhance the ability of the host to deal with the infection.

The HGV sequences disclosed herein identify HGV as a member of the Flaviviridae family (see above). The Flaviviridae are classified into 3 genera, flaviviruses, petstiviruses, and the hepatitis C virus genera (Francki, et al.). All Flaviviridae possess a positive strand RNA genome of 9.0–12 kb in length which encodes a single long polypeptide of 3000–4000 amino acids. This polypeptide is proteolytically cleaved into approximately 10 proteins, including, a viral capsid protein, viral envelope protein(s), and a minimum of 5 non-structural proteins (NS). The non-structural proteins include a chymotrypsin like serine protease, RNA helicase (NS3), and an RNA-dependent RNA polymerase (NS5). The NS3 protein of Flaviviridae is required for proteolytic cleavage of the viral polypeptide. The NS5 protein is required for replication of the viral genome (Chambers, et al., 1990a).

Additionally, several cellular proteins have been identified as being involved in the replication of the Flaviviridae.

For example, cellular signal peptidase enzyme may be required to cleave the viral polypeptide at several cleavage sites, to allow for expression of the viral protease (Hijikata, et al.).

Inhibitors which prevent these proteins from carrying out their required functions in flavivirus replication may also have therapeutic value at treating infection with HGV. Finally cytokines or other polypeptides which are known to have antiviral activity and/or modulate the human immune system may be efficacious at treating HGV infection.

One compound known to inhibit Flaviviridae RNA dependent RNA polymerases, which by analogy may be expected to inhibit the activity of the NS5 protein of HGV, is the nucleotide analogue 1-B-D-ribofuranosyl-1-2,4-triazole, 3-carboxamide, also known as ribavirin (Patterson, et al.). The method of action of ribavirin is thought to involve depletion of intercellular guanine pools and interference with the capping of viral RNAs (Patterson et al.).

In individuals infected with HCV, significant reductions in viral titer and in serum levels of alanine aminotransferase (ALT—an indicator enzyme for liver dysfunction) were observed while ribavirin was administered (Reichard, et al.; Di Bisceglie, et al., 1992). Ribavirin appears to have broad efficacy for treating Flaviviridae infections, accordingly, beneficial results are expected after administration of ribavirin to individuals suffering from HGV derived liver disease.

Another class of compounds known to be efficacious for treating Flaviviridae infections include the cytokines interferon α, interferon β, and interferon γ (Baron, et al.; Gutterman). Interferons are thought to act as antivirals by both (i) inducing the expression of cellular proteins that interfere with the replication and translation of viral RNAs, and (ii) by the activation of components of the human cellular immune system (Baron, et al.). The interferons have broad applicability to the treatment of viral infections including infection with HBV, HDV, and HCV (Gutterman; Farci, et al.). In particular, multiple studies have indicated that the interferons, either alone or in combination with other antiviral therapies, are effective at treating infection with hepatitis C virus (Di Bisceglie, et al., 1989; Kakumu, et al.). Due to both the apparent hepatotropic nature of HGV and its classification in the family Flaviviridae, HGV infection may be expected to respond to similar interferon therapy.

Still another class of compounds with potent anti-viral activity are inhibitors of viral proteases (Krausslich, et al.). All Flaviviridae encode a chymotrypsin-like serine protease which is required to cleave multiple sites of the genome polypeptide at multiple sites in the non-structural region. The amino acid residues that make up the catalytic site of this protease are well described and include a Histidine, an Aspartic acid, and a Serine residue (Grakoui, et al.). Furthermore studies of the flavivirus, Yellow Fever Virus have indicated that mutation of the Serine residue of the active site inhibits viral replication (Chambers, et al., 1990b).

Inhibitors of the HGV NS3 protein can be designed to mimic the transition state of enzymatic cleavage. Alternatively, such inhibitors may be isolated by mass screening of previously synthesized compounds. The activity of putative HGV NS3 proteinase inhibitors can be determined through the use of in vitro transcription/translation systems, which are widely used in Flaviviridae research (Hijikata, et al.; Grakoui, et al.).

Alternatively, the HGV genome can be cloned into a suitable vector for eukaryotic protein expression, such a bacculovirus or vaccinia, and the efficacy of the compounds can be determined in tissue culture systems (Grakoui, et al.). Similar approaches have been employed successfully to obtain potent inhibitors of the HIV protease (Vacca, et al.; Roberts, et al.).

Another approach to treating disease caused by infection with the HGV relies on the synthesis of antisense oligonucleotides (Tonkinson and Stein) or oligonucleotide analogs which encode portions of the sequences of HGV disclosed in the present invention. As is true for all Flaviviridae, it would be expected that the genome of HGV is a positive strand RNA molecule of 9–12 kb in size. The single stranded nature of the viral genome should make HGV exquisitely sensitive to antisense oligonucleotides. Possible target sequences which might be employed to inhibit viral replication include the 5' untranslated region of HGV, the ribosome binding site of HGV or other sequences which would interfere with the translation of the HGV genome.

Antisense oligonucleotides can be synthesized using commercially available synthesizers. Preferably the oligonucleotides are synthesized using phosphorodithioate backbones which have the advantage of being resistant to nuclease cleavage (Marshall & Caruthers). Additionally other oligonucleotide analogues, such as those having a uncharged or amide type backbone (Egholm, et al.) may be employed. These oligonucleotides are commercially available (Biosearch, Millipore, Bedford, Mass.) and advantageous in that their lack of charge allows them to cross biological membranes, which are typically resist the passage of charged macromolecules.

Oligonucleotides (or analogs thereof) for antisense applications are typically greater than 8 nucleotides in length to facilitate hybridization to a target sequence within the HGV genome. Upon hybridization of, for example, DNA oligomers to viral RNA target sequences, the hybridization complex can be degraded by a cellular enzyme such as RNAse H. The reduction in HGV templates then lessens the severity of HGV associated disease.

The usefulness and efficacy of the above described therapeutic methods can be evaluated in vitro, using the cell systems described above, and in vivo, using the animal model systems described above.

The following examples illustrate, but in no way are intended to limit the present invention.

MATERIALS AND METHODS

Synthetic oligonucleotide linkers and primers were prepared using commercially available automated oligonucleotide synthesizers. Alternatively, custom designed synthetic oligonucleotides may be purchased from commercial suppliers.

Standard molecular biology and cloning techniques were performed essentially as previously described in Ausubel, et al., Sambrook, et al., and Maniatis, et al.

Common manipulations relevant to employing antisera and/or antibodies for screening and detection of immunoreactive protein antigens were performed essentially as described (Harlow, et al.). Similarly ELISA and Western blot assays for the detection of anti viral antibodies were performed either as described by their manufacturer (Abbott, N. Chicago, Ill., Genelabs Diagnostics, Singapore) or using standard techniques known in the art (Harlow, et al).

EXAMPLES

EXAMPLE 1

Construction of PNF2161 cDNA Libraries

A. Isolation of RNA from Sera.

One milliliter of undiluted PNF 2161 serum was precipitated by the addition of PEG (MW 6,000) to 8% and centrifugation at 12K, for 15 minutes in a microfuge, at 4° C. RNA was extracted from the resulting serum pellet essentially as described by Chomczynski.

The pellet was treated with a solution containing 4M guanidinium isothiocyanate, 0.18% 2-mercaptoethanol, and 0.5% sarcosyl. The treated pellet was extracted several times with acidic phenol-chloroform, and the RNA was precipitated with ethanol. This solution was held at $-70°$ C. for approximately 10 minutes and then spun in a microfuge at 4° C. for 10 minutes. The resulting pellet was resuspended in 100 µl of DEPC-treated (diethyl pyrocarbonate) water, and 10 µl of 3M NaOAc, pH=5.2, two volumes of 100% ethanol and one volume of 100% isopropanol were added to the solution. The solution was held at $-70°$ C. for at least 10 minutes. The RNA pellet was recovered by centrifugation in a microfuge at 12,000 ×g for 15 minutes at 5° C. The pellet was washed in 70% ethanol and dried under vacuum.

B. SYNTHESIS OF cNA (i) FIRST STRAND SYNTHESIS

The synthesis of cDNA molecules was accomplished as follows. The above described RNA preparations were transcribed into cDNA, according to the method of Gubler et al. using random nucleotide hexamer primers (CDNA Synthesis Kit, BMB, Indianapolis, Ill. or GIBCO/BRL).

After the second-strand cDNA synthesis, T4 DNA polymerase was added to the mixture to maximize the number of blunt-ends of cDNA molecules. The reaction mixture was incubated at room temperature for 10 minutes. The reaction mixture was extracted with phenol/chloroform and chloroform isoamyl alcohol.

The cDNA was precipitated by the addition of two volumes of 100% ethanol and chilling at $-70°$ C. for 15 minutes. The cDNA was collected by centrifugation, the pellet washed with 70% ethanol and dried under vacuum.

C. Amplification of the Double Stranded cDNA Molecules.

The cDNA pellet was resuspended in 12 µl distilled water. To the resuspended cDNA molecules the following components were added: 5 µl phosphorylated linkers (Linker AB, a double strand linker comprised of SEQ ID NO:1 and SEQ ID NO:2, where SEQ ID NO:2 is in a 3' to 5' orientation relative to SEQ ID NO:1—as a partially complementary sequence to SEQ ID NO:1), 2 µl 10× ligation buffer (0.66M Tris.Cl pH=7.6, 50 MM $MgCl_2$, 50 mM DTT, 10 mM ATP) and 1 µl T4 DNA ligase (0.3 to 0.6 Weiss Units). Typically, the cDNA and linker were mixed at a 1:100 ratio. The reaction was incubated at 14° C. overnight. The following morning the reaction was incubated at 70° C. for three minutes to inactivate the ligase.

To 100 µl of 10 mM Tris-Cl buffer, pH 8.3, containing 1.5 MM $MgCl_2$ and 50 mM KC1 (Buffer A) was added about 1 µl of the linker-ligated cDNA preparation, 2 µM of a primer having the sequence shown as SEQ ID NO:1, 200 AM each of DATP, dCTP, dGTP, and dTTP, and 2.5 units of Thermus aguaticus DNA polymerase (Taq polymerase). The reaction mixture was heated to 940° C. for 30 sec for denaturation, allowed to cool to 50° C. for 30 sec for primer annealing, and then heated to 72° C. for 0.5–3 minutes to allow for primer extension by Taq polymerase. The amplification reaction, involving successive heating, cooling, and polymerase reaction, was repeated an additional 25–40 times with the aid of a Perkin-Elmer Cetus DNA thermal cycler (Mullis; Mullis, et al.; Reyes, et al., 1991; Perkin-Elmer Cetus, Norwalk, Conn.).

After the amplification reactions, the solution was then phenol/chloroform, chloroform/isoamyl alcohol extracted and precipitated with two volumes of ethanol. The resulting amplified CDNA pellets were resuspended in 20 Al TE (pH=7.5).

D. Cloning of the cDNA into Lambda Vectors.

The linkers used in the construction of the cDNAs contained an EcoRI site which allowed for direct insertion of the amplified cDNAs into lambda gt11 vectors (Promega, Madison Wis. or Stratagene, La Jolla, Calif.). Lambda vectors were purchased from the manufacturer (Promega) which were already digested with EcoRI and treated with alkaline phosphatase, to remove the 5' phosphate and prevent self-ligation of the vector.

The EcoRI-digested cDNA preparations were ligated into lambda gt11 (Promega). The conditions of the ligation reactions were as follows: 1 µl vector DNA (Promega, 0.5 mg/ml); 0.5 or 3 µl of the PCR amplified insert cDNA; 0.5 µl 10×ligation buffer (0.5M Tris-HCl, pH=7.8; 0.1M $MgCl_2$; 0.2 M DTT; 10 mM ATP; 0.5 mg/ml bovine serum albumin (BSA)), 0.5 µl T4 DNA ligase (0.3 to 0.6 Weiss units) and distilled water to a final reaction volume of 5 µl.

The ligation reactions were incubated at 14° C. overnight (12–18 hours). The ligated cDNA was packaged by standard procedures using a lambda DNA packaging system ("GIGAPAK", Stratagene, LaJolla, Calif.), and then plated at various dilutions to determine the titer. A standard X-gal blue/white assay was used to determine recombinant frequency of the libraries (Miller; Maniatis et al.).

Percent recombination in each library was also determined as follows. A number of random clones were selected and corresponding phage DNA isolated. Polymerase chain reaction (Mullis; Mullis, et al.) was then performed using isolated phage DNA as template and lambda DNA sequences, derived from lambda sequences flanking the EcoRI insert site for the cDNA molecules, as primers. The presence or absence of insert was evident from gel analysis of the polymerase chain reaction products.

The cDNA-insert phage libraries generated from serum sample PNF 2161 was deposited with the American Type Culture Collection, 12301 Parklawn Dr., Rockville Md. 20852, and has been assigned the deposit designation ATCC 75268 (PNF 2161 CDNA source).

EXAMPLE 2

Immunoscreening of Recombinant Libraries

The lambda gt11 libraries generated in Example 1 were immunoscreened for the production of antigens recognizable by the PNF 2161 serum from which the libraries were generated. The phage were plated for plaque formation using the Escherichia coli bacterial plating strain *E. coli* KM392. Alternatively, *E. coli* Y1090R (Promega, Madison Wis.) may be used.

The fusion proteins expressed by the lambda gt11 clones were screened with serum antibodies essentially as described by Ausubel, et al.

Each library was plated at approximately 2×10⁴ phages per 150 mm plate. Plates were overlaid with nitrocellulose filters overnight. Filters were washed with TBS (10 mM, Tris pH 7.5; 150 mM NaCl), blocked with AIB (TBS buffer with 1% gelatin) and incubated with a primary antibody diluted 100 times in AIB.

After washing with TBS, filters were incubated with a second antibody, goat-anti-human IgG conjugated to alkaline phosphatase (Promega). Reactive plaques were developed with a substrate (for example, BCIP, 5-bromo-4-chloro-3-indolyl-phosphate), with NBT (nitro blue tetrazolium salt (Sigma)). Positive areas from the primary screening were replated and immunoscreened until pure plaques were obtained.

EXAMPLE 3

Screening of the PNF 2161 Library

The cDNA library of PNF 2161 in lambda gt11 was screened, as described in Example 2, with PNF 2161 sera. The results of the screening are presented in Table 1.

TABLE 1

PNF2161 Libraries

| Library[1] | % Recomb.[2] | Antibody[3] | # Screened | # Clones Plaque-Purified |
|---|---|---|---|---|
| PNF/RNA | 85 | PNF | 5.5 × 10⁵ | 4 |
| PNF/RNA | 90 | PNF | 8 × 10⁴ | 7 |
| TOTALS: | | | | 11 |

[1]cDNA library constructed from the indicated human source.
[2]Percent recombinant clones in the indicated λgt11 library as determined by blue/white plaque assay and confirmed by PCR amplification of randomly selected clones.
[3]Antisera source used for the immunoscreening of each indicated library.

One of the clones isolated by the above screen (PNF 2161 clone 470-20-1, SEQ ID NO:3; β-galactosidase in-frame fusion translated sequence, SEQ ID NO:4), was used to generate extension clones, as described in Example 6. Clone 470-20-1 nucleic acid sequence is presented as SEQ ID NO:3 (protein sequence SEQ ID NO:4). The isolated nucleic acid sequence without the SISPA cloning linkers is presented as SEQ ID NO:19 (protein SEQ ID NO:20).

EXAMPLE 4

Characterization of the Immunoreactive 470-20-1 Clone

A. Southern Blot Analysis of Immunoreactive Clones.

The inserts of immunoreactive clones were screened for their ability to hybridize to the following control DNA sources: normal human peripheral blood lymphocyte (purchased from Stanford University Blood Bank, Stanford, Calif.) DNA, and *Escherichia coli* KM392 genomic DNA (Ausubel, et al.; Maniatis, et al.; Sambrook, et al.). Ten micrograms of human lymphocyte DNA and 2 micrograms of *E. coli* genomic DNA-were digested with EcoRI and HindIII. The restriction digestion products were electrophoretically fractionated on an agarose gel (Ausubel, et al.) and transferred to nylon or nitrocellulose membranes (Schleicher and Schuell, Keene, N.H.) as per the manufacturer's instructions.

Probes from the immunoreactive clones were prepared as follows. Each clone was amplified using primers corresponding to lambda gt11 sequences that flank the EcoRI cloning site of the gt11 vector. Amplification was carried out by polymerase chain reactions utilizing each immunoreactive clone as template. The resulting amplification products were digested with EcoRI, the amplified fragments gel purified and eluted from the gel (Ausubel, et al.). The resulting amplified fragments, derived from the immunoreactive clones, were then random prime labelled using a commercially available kit (BMB) employing ³²p-dNTPs.

The random primed probes were then hybridized to the above-prepared nylon membrane to test for hybridization of the insert sequences to the control DNAs. The 470-20-1 insert did not hybridize with any of the control DNAs.

As positive hybridization controls, a probe derivative from a human C-kappa gene fragment (Hieter) was used as single gene copy control for human DNA and a *E. coli* polymerase gene fragment was similarly used for *E. coli* DNA.

B. Genomic PCR.

PCR detection was developed first to verify exogenicity with respect to several genomic DNAs which could have been inadvertently cloned during library construction, then to test for the presence of the cloned sequence in the cloning source and related specimen materials. Several different types of specimens, including SISPA-amplified nucleic acids and nucleic acids extracted from the primary source, and nucleic acids extracted from related source materials (e.g., from animal passage studies), were tested.

The term "genomic PCR" refers to testing for the presence of specific sequences in genomic DNA from relevant organisms. For example, a genomic PCR for a Mystax-derived clone would include genomic DNAs as follows:

1. human DNA (1 µg/rxn.)
2. Mystax DNA (0.1–1 µg/rxn.)
3. *E. coli* (10–100 ng/rxn.)
4. yeast (10–100 ng/rxn.)

Human and Mystax DNAs are tested, as the immediate and ultimate source for the agent. *E. coli* genomic DNA, as a frequent contaminant of commercial enzyme preparations, is tested. Yeast is also tested, as a ubiquitous organism, whose DNA can contaminate reagents and thus, be cloned.

In addition, a negative control (i.e., buffer or water only), and positive controls to include approximately 10⁵c/rxn., are also amplified.

Amplification conditions vary, as may be determined for individual sequences, but follow closely the following standard PCR protocol: PCR was performed in reactions containing 10 mM Tris, pH 8.3, 50 mM KCl, 1.75 mM MgCl₂, 1.0 µM each primer, 200 µM each DATP, dCTP, and dGTP, and 300 µM dUTP, 2.5 units Taq DNA polymerase, and 0.2 units uracil-N-glycosylase per 100 ul reaction. Cycling was for at least 1 minute at 940° C., followed by 30 to 40 repetitions of denaturation (92°–94° C. for 15 seconds), annealing (55°–56° C. for 30 seconds), and extension (720° C. for 30 seconds). PCR reagents were assembled, and amplification reactions were constituted, in a specially-designated laboratory maintained free of amplified DNA.

As a further barrier to contamination by amplified sequences and thus compromise of the test by "false positives," the PCR was performed with dUTP replacing TTP, in order to render the amplified sequences biochemically distinguishable from native DNA. To enzymatically render unamplifiable any contaminating PCR product, the enzyme uracil-N-glycosylase was included in all genomic PCR reactions. Upon conclusion of thermal cycling, the reactions were held at 72° C. to prevent renaturation of uracil-N-glycosylase and possible degradation of amplified U-containing sequences.

A "HOT START PCR" was performed, using standard techniques ("AMPLIWAX", Perkin-Elmer Biotechnology; alternatively, manual techniques were used), in order to make the above general protocol more robust for amplification of diverse sequences, which ideally require different amplification conditions for maximal sensitivity and specificity.

Detection of amplified DNA was performed by hybridization to specific oligonucleotide probes located internal to the two PCR primer sequences and having no or minimal overlap with the primers. In some cases, direct visualization of electrophoresed PCR products was performed, using ethidium bromide fluorescence, but probe hybridization was in each case also performed, to help ensure discrimination between specific and non-specific amplification products. Hybridization to radiolabelled probes in solution was followed by electrophoresis in 8–15% polyacrylamide gels (as appropriate to the size of the amplified sequence) and autoradiography.

Clone 470-20-1 was tested by genomic PCR, against human, *E. Coli*, and yeast DNAs. No specific sequence was detected in negative control reactions, nor in any genomic DNA which was tested, and $10^5$ copies of DNA/reaction resulted in a readily-detectable signal. This sensitivity (i.e., $10^5$/reaction) is adequate for detection of single-copy human sequences in reactions containing 1 ug total DNA, representing the DNA from approximately $1.5\times10^5$ cells.

C. Direct Serum PCR

Serum or other cloning source or related source materials were directly tested by PCR using primers from selected cloned sequences. In these experiments, HGV viral particles were directly precipitated from sera with polyethylene glycol (PEG), or, in the case of PNF and certain other sera, were pelleted by ultracentrifugation. For purification of RNA, the pelleted materials were dissolved in guanidinium thiocyanate and extracted by the acid guanidinium phenol technique (Chomczynski, et al.).

Alternatively, a modification of this method afforded through and implemented by the use of commercially available reagents, e.g., "TRIREAGENT" (Molecular Research Center, Cincinnati, Ohio) or "TRIZOL" (Life Technologies, Gaithersburg, Md.), and associated protocols was used to isolate RNA. In addition, RNA suitable for PCR analysis was isolated directly from serum or other fluids containing virus, without prior concentration or pelleting of virus particles, through the use of "PURESCRIPT" reagents and protocols (Gentra Systems, Minneapolis, Minn.).

Isolated DNA was used directly as a template for the PCR. RNA was reverse transcribed using reverse transcriptase (Gibco/BRL), and the cDNA product was then used as a template for subsequent PCR amplification.

In the case of 470-20-1, nucleic acid from the equivalent of 20–50 ul of PNF serum was used as the input template into each RT-PCR or PCR reaction. Primers were designed based on the 470-20-1 sequence, as follows: 470-20-1-77F (SEQ ID NO:9) and 470-20-1-211R (SEQ ID NO:10). Reverse performed using MMLV-RT (Gibco/BRL) and random hexamers (Promega) by incubation at room temperature for approximately 10 minutes, 42° C. for 15 minutes, and 99° C. for 5 minutes, with rapid cooling to 4° C. The synthesized cDNA was amplified directly, without purification, by PCR, in reactions containing 1.75 mM $MgCl_2$, 0.2–1 µM each primer, 200 uM each DATP, dCTP, dGTP, and dTTP, and 2.5–5.0 units Taq DNA polymerase ("AMPLITAQ", Perkin-Elmer) per 100 ul reaction. Cycling was for at least one minute at 94° C., followed by 40–45 repetitions of denaturation (94° C. for 15 seconds for 10 cycles; 92° C. or 94° C. for 15 seconds for the succeeding cycles), annealing (55° C. for 30 seconds), and extension (72° C. for 30 seconds), in the "GENEAMP SYSTEM 9600" thermal cycler (Perkin-Elmer) or comparable cycling conditions in other thermal cyclers (Perkin-Elmer; MJ Research, Watertown, Mass.).

Positive controls consisted of (i) previously amplified PCR product whose concentration was estimated using the Hoechst 33258 fluroescence assay, (ii) purified plasmid DNA containing the DNA sequence of interest, or (iii) purified RNA transcripts derived from plasmid clones in which the DNA sequence of interest is disposed under the transcriptional control of phage RNA promoters such as T7, T3, or SP6 and RNA prepared through the use of commercially available in vitro transcription kits. In addition, an aliquot of positive control DNA corresponding to approximately 10–100 copies/rxn, can be spiked into reactions containing nucleic acids extracted from the cloning source specimen, as a control for the presence of inhibitors of DNA amplification reactions. Each separate extract was tested with at least one positive control.

Specific products were detected by hybridization to a specific oligonucleotide probe 470-20-1-152F (SEQ ID NO:16), for confirmation of specificity. Hybridization of 10 ul of PCR product was performed in solution in 20 ul reactions containing approximately $1\times10^6$ cpm of $^{32}$P-labelled 470-20-1-152F. Specific hybrids were detected following electrophoretic separation from unhybridized oligo in polyacrylamide gels, and autoradiography.

In addition to PNF, extracted nucleic acids from normal serum was also reverse transcribed and amplified, using the "serum PCR" protocol sequence. No signal was detected in normal human serum. The specific signal in PNF serum was reproducibly detected in multiple extracts, with the 470-20-1 specific primers.

D. AMPLIFICATION FROM SISPA UNCLONED NUCLEIC ACIDS

SISPA (Sequence-Independent Single Primer Amplification) amplified CDNA was used as templates (Example 1). Sequence-specific primers designed from selected cloned sequences were used to amplify DNA fragments of interest from the templates. Typically, the templates were the SISPA-amplified samples used in the cloning manipulations. For example, amplification primers 470-20-1-77F (SEQ ID NO:9) and 470-20-1-211R (SEQ ID NO:10) were selected from the clone 470-20-1 sequence (SEQ ID NO:3). These primers were used in amplification reactions with the SISPA-amplified PNF2161 cDNA as a template.

The identity of the amplified DNA fragments were confirmed by (i) hybridization with the specific oligonucleotide probe 470-20-1-152F (SEQ ID NO:16), designed based on the 470-20-1 sequence (SEQ ID NC:3) and/or (ii) size. The probe used for DNA blot detection was labelled with digoxygenin using terminal transferase according to the manufacturer's recommendations (BMB). Hybridization to the amplified DNA was then performed using either Southern blot or liquid hybridization (Kumar, et al., 1989) analyses.

Positive control DNA used in the amplification reactions was previously amplified PCR product whose concentration was estimated by the Hoechst 33258 fluorescence assay, or, alternatively, purified plasmid DNA containing the cloned inserts of interest.

The 470-20-1 specific signal was detected in cDNA amplified by PCR from SISPA-amplified PNF2161. Negative control reactions were nonreactive, and positive control DNA templates were detected.

E. Amplification from Liver RNA Samples.

RNA was prepared from liver biopsy material following the methods of Cathal, et al., wherein tissue was extracted in 5M guanidine thiocyanate followed by direct precipitation of RNA by 4M LiCl. After washing of the RNA pellet with 2M LiCl, residual contaminating protein was removed by extraction with phenol:chloroform and the RNA recovered by ethanol precipitation.

The 470-20-1 specific primers were also used in amplification reactions with the following RNA sources as substrate: normal mystax liver RNA, normal tamarin (Sanguinus labiatus) liver RNA, and MY131 liver RNA. MY131 is a mystax that was inoculated intravenously with 1 ml of PNF 2161 plasma. There were obvious elevations of a liver enzyme (SCID) and histological evidence of an apparent viral infection. The histological correlation was most obvious in the liver of MY131, whose liver was obtained at or near the peak of SCID activity. Mystax 131 liver RNA did not give amplified products with the noncoding primers (SEQ ID NO:7 and SEQ ID NO:8) of HCV.

The amplification reactions were carried out in duplicate for two experiments. The results of these amplification reactions are presented in Table 2.

TABLE 2

| PCR with 470-20-1 Primers | | | | |
|---|---|---|---|---|
| | Exp. 1 | | Exp. 2 | |
| | A | B | A | B |
| Normal My liver RNA | – | – | – | – |
| Normal tamarin liver RNA | – | – | – | – |
| My131 liver RNA | + | + | + | + |
| PNF 2161 | ++ | ++ | ++ | ++ |

These results demonstrate the 470-20-1 sequences are present in the parent serum sample (PNF 2161) and in a liver RNA sample from a passage animal of the PNF 2161 sample (MY131). However, both control RNAs were negative for the presence of 470-20-1 sequences.

F. Screening of a Serum Panel for HGV Sequences by Polymerase Chain Reaction Using RNA Templates.

1. HIGH-ALT DONORS

The disease association between HGV and liver disease was assessed by polymerase chain reaction screening, using HGV specific primers, of sera from is hepatitis patients and from blood donors with abnormal liver function. The latter consisted of serum from blood donations with serum ALT levels greater than 45 International Units per ml.

A serum panel consisting of 152 total sera was selected. The following sera were selected for the serum panel: 104 high-ALT sera from screened blood donations at the Stanford University Blood Bank (SUBB); 34 N-(ABCDE) hepatitis sera from northern California, Egypt, and Peru; and 14 sera from other donors suspected of having liver disease and/or hepatitis virus infection. The negative controls for the panel were as follows: 9 highly-screened blood donors (SUBB) notable for the absence of risk factors for viral infections ("supernormal" sera, e.g., O-negative, Rh-negative; negative for HIV, known hepatitis agents, and CMV; whose multiple previous blood donations had been transfused without causing disease); and 2 random blood donors. These sera were assayed for the presence of HGV specific sequences by RT-PCR using the 470-20-1 primers 77F (SEQ ID NO:9) and 211R (SEQ ID NO:10).

RNA extraction and RT-PCR were performed essentially as described in Example 4C, except that the primer 470-20-1-211R was 5'-biotinylated to facilitate rapid screening of amplified products by a method involving hybridization in solution, followed by affinity capture of hybridized probe using streptavidin-coated paramagnetic beads. Methods for the analysis of nucleic acids by hybridization to specific labelled probes with capture of the hybridized sequences through affinity interactions are well known in the art of nucleic acid analysis.

Depending on the amount of serum available for testing, RNA from 30 to 50 µl of serum was used per RT/PCR reaction. Each serum was tested in duplicate, with positive controls corresponding to 10, 100, or 1000 copies of RNA transcript per reaction and with appropriate negative (buffer) controls. No negative controls were reactive, and at least 10 copies per reaction were detectable in each PCR run. Indeterminate results were defined as specific hybridizing signal being present in only one of two duplicate reactions.

Efficient, highly sensitive analysis of the products from the amplification analysis of this serum panel was performed using an instrument specifically designed for affinity-based hybrid capture using electrochemiluminscent oligonucleotide probes (QPCR System 5000™, Perkin-Elmer). Assays utilizing the QPCR 5000™ have been described (DiCesare, et al; Wages, et al).

The products of each reaction were assayed by hybridization to probe 470-20-1-152F (5'-end-labelled with an electrochemiluminescent ruthenium chelate), and measurement using the "QPCR 5000." Based on a cutoff of the sum of the mean and three times the standard deviation of negative controls in a given amplification run, a total of 34 possible positives were selected for confirmatory testing.

The 34 samples were analyzed by solution hybridization and electrophoresis (Example 4C). Out of these 34 samples, 6 sera (i.e., 6/152) were shown to have specific hybridizing sequences in duplicate reactions. Of these six samples, three were strongly reactive by comparison with positive controls: one High-ALT serum from SUBB, and two N-(ABCDE) sera from Egypt.

A second blood sample was obtained from the highly positive SUBB serum donor one year after the initial sample was taken. The second serum sample was confirmed to be HGV positive by the PCR methods described above. This result confirms persistant infection by HGV in a human. The serum was designated "JC." Further, the serum donor was HCV negative (determined by seroreactivity tests and PCR) and antibody negative for HAV and HBV.

In addition, a third N-(ABCDE) serum from Egypt, a northern California blood donor with N-(ABCDE) hepatitis, and a N-(ABCDE) hepatitis serum, were also shown to be weakly positive by this method. Two other sera gave indeterminate results, defined as the presence of specific sequences in one of two amplification reactions.

Subsequent PCR analysis of replicate serum aliquots from these HGV-positive and indeterminate sera resulted in HGV-positive results in 6 of 8 sera tested and indeterminate results in the remaining 2 sera.

A second primer set was used for the confirmation of HGV positive samples. This primer set (GV57-4512MF, SEQ ID NO:121, and GV57-4657MR, SEQ ID NO:122) for diagnostic amplification, was selected from a conserved region of HGV derived from the putative NS5 coding region. An approximately 2.2 kb fragment was amplified from each of 5 separate HGV isolates. The primers used for the amplification reactions were 470EXT4-2189R (SEQ ID NO:119) and 470EXT4-29F (SEQ ID NO:120). The amplified DNA fragments were sequenced and the sequences aligned. Highly conserved regions were identified from the alignment and optimal primer sequences were designed incorporating mixed base synthesis at those positions that remained divergent throughout the five sequences. The resulting NS5 primers were as follows: GV57-4512MF, SEQ ID NO:121, and GV57-4657MR, SEQ ID NO:122. These primers were used to amplify a diagnostic fragment of 165 bp from test samples.

An internal probe sequence, GV22dc-89MF (SEQ ID NO:123) was derived from another highly conserved region for detection of the specifically amplified product. The probe is also of sufficient length to allow for detection of minimally divergent HGV sequences under lowered stringency conditions.

Analysis of specimens for the presence of the diagnostic NS5 sequence followed the same conditions for sample preparation, amplification, and liquid hybridization as described for the 470-20-1 primers (Example 4C). The concordance of results for sera samples analyzed by PCR using both the 470-20-1 and NS5 primer pairs are shown in Table 3.

TABLE 3

|  |  | 470-20-1 Primer Pair | | |
|---|---|---|---|---|
|  |  | + | − | Indeterminant |
| NS5-Region | + | 71 | 0 | 1 |
| Primer | − | 6 | 13 | 2 |
| Pair (GV57) | Indeterminant | 2 | 1 | 0 |

Further PCR analyses of additional aliquots obtained from the 8 sera identified above as being HGV-positive were carried out using the 470-20-1 primer set (SEQ ID NO:9 and SEQ ID NO:10) and the NS5 primer set. In these assays, the HGV PCR analyses gave consistently positive results in 5 of the 8 sera. These results are presented in Table 4.

In contrast, none of the two random donors or nine highly-screened "supernormal" sera was positive in either set of PCR analysis.

These results reinforce the disease association between HGV and liver disease.

TABLE 4

| Specimen Group | Number Tested | Number Positive |
|---|---|---|
| High-ALT Donor | 104 | 1 |
| Non-ABCDE, other | 48 | 4 |
| Normal Donor | 2 | 0 |
| "Supernormal" | 9 | 0 |
| Totals | 163 | 5 |

Further testing of sera from High-ALT donors has yielded the following results. A total of 495 sera have been tested, in addition to the initial panel of 104 sera described above. Of these 495 specimens, 6 were identified as HGV positive using the primer pair 470-20-1-77F (SEQ ID NO:9) and 470-20-1-211R (SEQ ID NO:10). These six sera have the following HCV profiles: R25342, HCV negative; R17749, HCV positive; J53171, HCV positive, HBV positive; J54406, HCV negative; R08074, HCV negative; and X31049, HCV negative. Positive scores are based on repeated reactivity in at least 2 separate reactions. R25342 was tested and confirmed positive by PCR using the NS5 primer pair. Accordingly, a detection rate of approximately 1.2% has been observed (7 of 599 tested).

Freshly-obtained plasma samples from blood donors with elevated ALT were also obtained from SUBB, the Peninsula Blood Bank (Burlingame, Calif.), and the New York Blood Center (New York, N.Y.), for testing for HGV RNA by PCR (470-20-1 primer pair). Of 214 total donations which were tested, a total of 5 (approximately 2.3%) were HGV RNA positive. These five sera have the following HCV profiles: T55806, HCV positive; T55875, HCV negative; T56633, HCV negative; R38730, HCV negative; and 3831781, HCV negative. Subsequent donations from two of these donors, T55806 and T55875, were also HGV RNA positive. T55806, T55875 and T56633 were tested and confirmed positive by PCR using the NS5 primer pair.

2. SCREENING OF ACCEPTED BLOOD DONORS

To assess the prevalence of HGV in the normal blood donor population, serum was collected from screened blood donors for transfusion at SUBB. A total of 968 specimens, representing 769 unique donors, was tested for HGV RNA. The samples were screened by PCR using the 470-20-1 primer pair.

A total of 16 sera were identified as having detectable HGV RNA. Of these, 6 represent duplicates from 3 donors, such that a total of 13 unique donors of 769 tested were HGV positive by RNA PCR. All positive samples were tested and confirmed positive by PCR using the NS5 primer pair. These donors were characterized by normal ALT levels, as well as otherwise normal serology. Accordingly, approximately 1.7% of the sera tested in the normal blood donor population are HGV positive. Therefore, the presence of HGV was detected in both accepted and rejected blood donors.

3. SPECIMENS FROM VARIOUS GEOGRAPHIC LOCALES.

The presence of HGV infection in populations of hepatitis patients from geographically widespread sources was assessed by PCR. The PCR reactions were carried out essentially as described in Example 4C using the 470-20-1 PCR primer pairs. Serum samples from Egypt, Greece, Australia (see Example 4F-4), Peru, England, Italy, Germany, South Korea, United States and Japan were tested. HGV RNA was detectable in subsets of all populations tested.

4. POST-TRANSFUSION ASSOCIATED HGV INFECTION AND PARENTERAL TRANSMISSION.

HGV RNA was detected in several post-transfusion hepatitis cases (those of Japanese and European origin were included in Example 4F-3). For 4 total cases, one from Japan, two from the U.S. and one from Australia, multiple time-points were assayed for the presence of HGV RNA. For 3 of these cases, (i) pre-transfusion samples were available to estabish previous HGV status of the patient, and (ii) samples were available from individual blood donors to those three cases, to establish donor HGV status.

The first case was a Japanese patient transfused on Dec. 2, 1980. Following the transfusion the patient developed Non-B Non-C hepatitis. A total of 5 sera from this patient were tested for HGV RNA by PCR using the 470-20-1 primer pair. HGV RNA was detectable from about 2 weeks to about 8 months following transfusion. A sample taken greater than 1 year post-transfusion was indeterminate (i.e., positive in one duplicate reaction only). No pre-transfusion sample was available for testing.

Cases BIZ and STO (Tables 5 and 6, respectively) were from a prospectively-followed heart surgery study (Alter, et al., 1989) conducted at the NIH. For each of these patients, pre-transfusion sera were available and were determined to be negative for HGV RNA by PCR using the 470-20-1 primer pair. BIZ tested positive for HGV RNA from day one post-transfusion to week 198 post-transfusion. Of 9 total blood donors to BIZ, 2 out of 8 tested were found to be HGV positive. STO tested positive for HGV RNA from week 5 post-transfusion through week 92 post-transfusion.

TABLE 5

Transfusion-Associated Transmission of HGV: Case BIZ

| Draw Date | Time | ALT in IU/L | 470 PCR Result |
|---|---|---|---|
| 10/30/78 | −4 days | 23 | − |
| 11/01/78 | −1 day | 31 | − |
| 11/03/78 | +1 day | 29 | + |
| 11/17/78 | 2 weeks | 51 | + |
| 03/22/79 | +20 weeks | 135 | + |
| 06/28/79 | +34 weeks | 133 | + |
| 04/06/81 | +127 weeks | 141 | + |
| 08/20/82 | +198 weeks | 39 | + |

TABLE 6

Transfusion-Associated Transmission of HGV: Case STO

| Draw Date | Time | ALT in IU/L | 470 PCR Result |
|---|---|---|---|
| 06/15/83 | −1 day | 23 | − |
| 07/18/83 | +5 weeks | 80 | + |
| 10/31/83 | +20 weeks | 75 | + |
| 12/31/83 | +28 weeks | 30 | + |
| 01/02/85 | +81 weeks | 90 | − |
| 03/20/85 | +92 weeks | 23 | + |

The fourth case, also prospectively-defined, was a cardiac surgery patient who participated in a post-transfusion hepatitis study conducted in Sydney, Australia. The patient (PA-124), having no other identifiable risk factors, received 14 units of blood during surgery (4 units packed red cells, 10 units of platelets). Of these 14 units one was HGV positive; the other 13 were HGV negative. HBV and HCV serologies of the 14 blood donors were negative with the exception of a reactive HCV EIA (first generation test). No other HCV test confirmed the positive finding.

In patient PA-124 (Table 7), serum ALT was elevated beginning with a sample taken two weeks post-operation, and was observed to be at least 10 times the pre-operation level for a period of 14 weeks. PCR results for HCV performed on pre-transfusion, 4 week, and 8 week sera from PA-124, were all negative. Serum from this patient was tested for HGV RNA using the 470-20-1 PCR primers. A pre-transfusion sample was negative for HGV RNA. Positive results were demonstrated following transfusion, coinciding with and succeeding the ALT elevation. The presence of HGV RNA was detected out to one year post-transfusion. These data support the conclusion that HGV may be parenterally transmitted.

TABLE 7

Transfusion-Associated Transmission of HGV: Case PA-124

| Weeks Post-Operation | ALT in IU/L | 470 PCR Result |
|---|---|---|
| pre-transfusion | 7 | − |
| 2 | 74 | + |
| 4 | 86 | + |
| 8 | 135 | + |
| 12 | 179 | + |
| 14 | 78 | + |
| 18 | 9 | + |
| 24 | 6 | + |
| 36 | 11 | + |
| 52 | 11 | + |
| 64 | 23 | − |
| 84 | 10 | − |

In addition to prospectively-defined post-transfusion transmission cases, additional cases of HGV infection were identified in risk groups defined by multiple transfusions and intravenous drug use (IVDU) (Table 8).

TABLE 8

HGV RT-PCR Testing of Coded Sera: Selected Hepatitis and Parenteral Risk Groups

| Group | Number Tested | Number Positive |
|---|---|---|
| Autoimmune Hepatitis | 10 | 0 |
| Primary Biliary Cirrhosis | 20 | 0 |
| Suspected Acute NonA-E Hepatitis | 24 | 2 |
| Chronic Hepatitis (NonA-C (confirmed by liver biopsy) | 34 | 3 |
| Heptaocellular Carcinoma | 20 | 2 |
| Chronic HBV | 20 | 2 |
| Chronic HCV | 50 | 6 |
| Hemophilia | 49 | 9 |
| IVDU | 54 | 15 |
| Multiply Transfused Anemia | 100 | 19 |

Among 100 multiply-transfused sickle cell anemia and thalassemia patients, 19 (19%) were found to have detectable serum HGV RNA. Similarly, 9 of 49 hemophilia patients (18%) were HGV positive with 470-20-1 and NS5 primers. Significantly, 15 of 54 (28%) IVDU were found to be PCR positive for HGV RNA. Infection rates in these parenteral risk groups (18–28%) appear to be higher than rates in blood donors with elevated ALT (1–2%). These results reinforce the significance of the parenteral route for HGV transmission.

5. PCR SCREENING OF SELECTED HEPATITIS DISEASE GROUPS

Sera from patients with acute and chronic hepatitis, hepatocellular carcinoma, HBV infection or HCV infection were tested for the presence of HGV using polymerase chain reaction (data presented in Table 8). In each of sets of specimens from patients with liver disease, HGV positive specimens were demonstrated (with the exception of specimens from patients with autoimmune hepatitis and primary biliary cirrhosis, both conditions not thought to be exclusively associated with an infectious agent).

As shown in the collections of sera from post-transfusion hepatitis patients (Example 4F-4), HGV infection is established during acute hepatitis, but circulating viral RNA continues to be detected during chronic infection for periods of time measured in months to years.

Approximately 10–20% co-infection rates were observed in patients with HBV and HCV infection. HGV infection is thus shown to be associated with hepatitis with or without co-infection with other hepatitis viruses. Co-infection may reflect similar risk factors and routes of transmission for these hepatitis viruses. As noted above, there is a higher prevalence of HGV in parenteral risk groups, such as hemophiliacs, IVDU's, and multiply transfused anemia patients (compared with other hepatitis risk groups).

6. PERSISTENT INFECTION BY HGV IN HUMANS

Post-transfusion hepatitis cases BIZ, STO, and PA-124 were show to have PCR-detectable viral RNA up to 3.8, 1.8, and 1.0 years, respectively, following transfusion and acute infection. Additional serum samples were obtained from donor JC (Example 4F-1), one year and 1.5 years following the initial positive sample. These follow-up serum samples were also HGV positive. Additional sera from other high-ALT donors (T55806, T55875, R25342), obtained several months following the serum sample in which HGV infection was originally detected, were also positive. Similarly, when HGV infection was established in an experimental primate (CH1356, Example 4H), HGV RNA was detected over 1.5 years following innoculation. These data establish persistent HGV viremia in humans and experimental primates.

G. Amplification of Long Fragments from Patient RNA for Sequencing.

PCR primers were designed to amplify several informative regions of the HGV genome in order to obtain sequence information on varied HGV isolates. The primers 470EXT4-2189R (SEQ ID NO:119) and 470EXT4-29F (SEQ ID NO:120) were designed to amplify a 2.2 kb fragment that contained the original 470-20-1 sequence. RNA from samples was reverse-transcribed using "SUPERSCRIPT II" reverse transcriptase (Gibco/BRL, Gaithersburg, Md.). The resulting cDNA was amplified using reagents for efficient long-range PCR ("XL PCR BUFFERS" and "rTth-XL", Perkin Elmer/Applied Biosystems Div., Foster City, Calif.).

The amplification reaction was considered to be positive if a band of the correct size on agarose gel electrophoresis was detected. The sample was confirmed as positive by preliminary DNA sequencing of the amplification product. The following sera samples tested positive for HGV RNA by this amplification method: PNF2161; R10291 (JC); and specimens from each of the North American, Egyptian, and Japanese groups. However, no positive samples were detected from the Peruvian sera.

Successful amplification from a variety of HGV-positive specimens provides confirmation of the results obtained by PCR amplification using the 470-20-1 primer pair discussed above. Failure to obtain amplification, however, may reflect poor RNA quality or low copy number or local sequence differences among isolates such that the selected primer sets would not function universally.

In order to obtain sequence information from the putative 5'-untranslated region of the HGV genome, primers were designed to amplify fragments from the 5'-untranslated region (based on the HGV PNF 2161-variant). The two fragments were defined by the following primer sets: FV94-22F (SEQ ID NO:124) and FV94-724R (SEQ ID NO:125), yielding a 728 base pair fragment; and FV94-94F (SEQ ID NO:126) and FV94-912R (SEQ ID NO:127), yielding an 847 base pair fragment.

The conditions just described to promote efficient long-range PCR were used. Products were obtained from most of the samples tested, providing additional confirmation of the presence of HGV RNA in the samples.

H. Infectivity of HGV in Primates.

Two chimpanzees (designated CH1323 and CH1356), six cynomolgus monkeys (CY143, CY8904, CY8908, CY8912, CY8917, and CH8918), and six Mystax (MY29, MY131, MY98, MY187, MY229, MY254) subjects were inoculated with PNF 2161. Pre-inoculation and post-inoculation sera were monitored for ALT and for the presence of HGV RNA sequences (as determined by PCR screening—described above).

One cynomologous monkey (CY8904) showed a positive RNA PCR result (39 days post-inoculation) and one indeterminant result from a total of 17 seperate blood draws. In one chimpanzee, designated CH1356, was sustained viremia observed by RT-PCR. As shown in Table 9, no significant ALT elevation was observed, and circulating virus was detected only at time points considerably after inoculation. Viremia was observed at and following 118 days post-inoculation. Suggestive reactivity was also observed in the first post-inoculation time-point (8 days), which may indicate residual inoculum.

TABLE 9

ALT and PCR Results from CH1356 Following Inoculation with PNF 2161

| Days Post-Inoculation | ALT* | HGV PCR |
| --- | --- | --- |
| 0 | 59 | – |
| 8 | 65 | ± |
| 15 | 85 | – |
| 22 | 89 | – |
| 29 | 89 | – |
| 36 | 86 | – |
| 39 | 31 | – |
| 47 | 74 | – |
| 54 | 40 | – |
| 61 | 57 | – |
| 84 | 65 | ± |
| 89 | 63 | + |
| 98 | 64 | – |
| 118 | 84 | + |
| 125 | 73 | + |
| 134 | 74 | + |
| 159 | 80 | + |
| 610 | (ALT not available) | + |

*average ALT base-line before inoculation was 50.

The data presented above indicate that HGV infection was persistent up to 1.7 years in an experimental primate.

I. Characterization of the Viral Genome.

The isolation of 470-20-1 from a cDNA library (Example 1) suggests that the viral genome detected in PNF 2161 is RNA. Further experiments to confirm the identity of the HGV viral genome as RNA include the following.

Selective degradation of either RNA or DNA (e.g., by DNase-free RNase or RNase-free DNase) in the original cloning source followed by amplification with HGV specific primers and detection of the amplification products serves to distinguish RNA from DNA templates.

An alternative method makes use of amplification reactions (nucleic acids from the original cloning source as template and HGV specific primers) that employ (i) a DNA-dependent DNA polymerase, in the absence of any RNA-dependent DNA polymerase (i.e., reverse transcripase) in the reactions, and (ii) a DNA-dependent DNA polymerase and an RNA-dependent DNA polymerase in the reactions. In this method, if the HGV genome is DNA or has a DNA intermediate, then amplified product is detected in both types of amplification reactions. If the HGV genome is only RNA, the amplified product is detected in only the reverse transcriptase-containing reactions.

Total nucleic acid (i.e., DNA or RNA) was extracted from PNF 2161, using proteinase K and SDS followed by phenol extraction, as described in Example 4C. The purified nucleic acid was then amplified using polymerase chain reaction (PCR) where either (i) the PCR was preceded by a reverse transcription step, or (ii) the reverse transcription step was omitted. Amplification was reproducibly obtained only when the PCR reactions were preceded by reverse transcription. As a control, DNA templates were successfully amplified in separate reactions. These results demonstrate that the nature of the HGV viral genome is RNA.

The strand of the cloned, double-stranded DNA sequence that was originally present in PNF 2161 may be deduced by various means, including the following. Northern or dot blotting of the unamplified genomic RNA from an infected source serum can be performed, followed by hybridization of duplicate blots to probes corresponding to each strand of the cloned sequence. Alternatively, single-stranded cDNA probes isolated from M13 vectors (Messing), or multiple strand-specific oligonucleotide probes are used for added sensitivity. If the source serum contains single-stranded RNA, only one probe (i.e., sequences from one strand of the 470-20-1 clones) yield a signal, under appropriate conditions of hybridization stringency. If the source serum contains double-stranded RNA, both strand-probes will yeild a signal.

The polymerase chain reaction, prefaced by reverse transcription using one or the other specific primer, represents a much more sensitive alternative to Northern blotting. Genomic RNA extracted from purified virions present in PNF 2161 serum is used as the input template into each RT/PCR. Rather than cDNA synthesis with random hexamers, HGV sequence-specific primers were used. One cDNA synthesis reaction was performed with a primer complementary to one strand of the cloned sequence (e.g., 470-20-1-77F); a second cDNA synthesis reaction was also performed using a primer derived from the opposite strand (e.g., 470-20-1-211R).

The resulting first strand cDNA was amplified in using two HGV specific primers. Controls were included for successful amplification by PCR (e.g., DNA controls). RNA transcripts from each strand of the cloned sequence was also used, to control also for the reverse transcription efficiency obtained when using the specific primers which are described.

Specific products were detected by agarose gel electrophoresis with ethidium bromide staining. DNA controls (i.e., double-stranded DNA controls for the PCR amplifcation) were successfully amplified regardless of the primer used for reverse transcription. Single-stranded RNA transcripts (i.e., controls for reverse transcription efficiency and strand specificity) were amplified only when the opposite-strand primer was used for cDNA synthesis.

The PNF-derived HGV polynucleotide gave rise to a specific amplified product only when the primer 470-20-1-211R was used for reverse transcription, thus indicating that the original HGV polynucleotide sequence present in the serum is complementary to 470-20-1-211R and is likely a single-strand RNA.

EXAMPLE 5

Sucrose Density Gradient Separation of PNF2161

A. Banding of PNF-2161 Agent.

A continuous gradient of 10–60% sucrose ("ULTRAPURE", Gibco/BRL) in TNE (50 mM Tris-Cl, pH 7.5, 100 mM NaCl, 1 mM EDTA) was prepared using a gradient maker from Hoefer Scientific (San Francisco, Calif.). Approximately 12.5 ml of the gradient was overlaid with 0.4 ml of PNF serum which had been stored at −70° C., rapidly thawed at 37° C., then diluted in TNE.

The gradient was then centrifuged in the SW40 rotor (Beckman Instruments) at 40,000 rpm (approximately 200,000×g at $r_{av}$) at 4° C. for approximately 18 hours. Fractions of volume approximately 0.6 ml were collected from the bottom of the tube, and 0.5 ml was weighed directly into the ultracentrifuge tube, for calculation of density.

TABLE 10

Measured Densities of PNF Fractions and Presence of 470-20-1

| Fraction | Density | 470-20-1 Detected* |
|---|---|---|
| 1 | 1.274 | − |
| 2 | 1.274 | − |
| 3 | 1.266 | − |
| 4 | 1.266 | − |
| 5 | 1.260 | − |
| 6 | 1.254 | − |
| 7 | 1.248 | + |
| 8 | 1.206 | + |
| 9 | 1.146 | + |
| 10 | 1.126 | +++ |
| 11 | 1.098 | ++++ |
| 12 | 1.068 | +++ |
| 13 | 1.050 | + |
| 14 | 1.034 | + |
| 15 | 1.036 | + |
| 16 | 1.018 | − |
| 17 | 1.008 | + |
| 18 | 1.020 | + |

*"+" and "−" scores were initially based on 40-cycle PCR. In order to distinguish "+", "++", "+++", and "++++", fractions giving initial positive scores (7–18) were amplified with 30 cycles of PCR.

The putative viral particles were then pelleted by centrifugation at 40,000 rpm in the Ti70.1 rotor (approximately 110,000×g) at 4° C. for 2 hours, and RNA was extracted using the acid guanidinium phenol technique ("TRI REAGENT", Molecular Research Center, Cincinnati, Ohio), and alcohol-precipitated using glycogen as a carrier to improve recovery. The purified nucleic acid was dissolved in an RNase-free buffer containing 2 mM DTT and 1 U/μl recombinant RNasin.

Analysis of the gradient fractions by RNA PCR (Example 4C) showed a distinct peak in the 470-20-1 specific signal, localized in fractions of density ranging from 1.126 to 1.068 g/ml (Table 10). The 470-20-1 signal was thus shown, under these conditions, to form a discrete band, consistent with the expected behavior of a viral particle in a sucrose gradient.

B. Relative Viral Particle Densities.

PNF 2161 has been demonstrated to be co-infected with HCV (see above). In order to compare the properties of the 470-20-1 viral particle to other known hepatitis viral particles, the serum PNF 2161 and a sample of purified Hepatitis A Virus were layered on a sucrose gradient (as described above). Fractions (0.6 ml) were collected, pelleted and the RNA extracted. The isolated RNA from each fraction was subjected to amplification reactions (PCR) using HAV (SEQ ID NO:5; SEQ ID NO:6), HCV (SEQ ID NO:7; SEQ ID NO:8) and 470-20-1 (SEQ ID NO:9, SEQ ID NO:10) specific primers.

Product bands were identified by electrophoretic separation of the amplification reactions on agarose gels followed by ethidium bromide staining. The results of this analysis are presented in Table 11.

TABLE 11

| Average Density | HAV | HCV | 470-20-1 |
|---|---|---|---|
| 1.269 | − | − | − |
| 1.263 | + | − | − |
| 1.260 | + | − | − |
| 1.246 | ++ | − | − |
| 1.238 | ++ | − | − |
| 1.240 | + | − | − |
| 1.207 | + | − | − |
| 1.193 | + | − | − |
| 1.172 | + | ± | − |
| 1.150 | + | ± | ± |
| 1.134 | + | + | ± |
| 1.118 | + | + | + |
| 1.103 | + | + | + |
| 1.118 | + | + | + |
| 1.103 | + | + | + |
| 1.088 | ± | + | + |
| 1.084 | − | + | + |
| 1.080 | − | + | + |
| 1.070 | − | + | + |
| 1.057 | − | + | + |
| 1.035 | − | ± | − |
| 1.017 | − | − | − |
| 1.009 | − | − | − |

These results suggest that 470-20-1 particles are more similar to HCV particles than to HAV.

Further, serum PNF 2161 and HAV particles were treated with chloroform before sucrose gradient centrifugation. The results of these experiments suggest that 470-20-1 agent may be an enveloped virus since it has more similar properties to an enveloped Flaviviridae member (HCV) than a non-enveloped virus (HAV).

EXAMPLE 6

Generation of 470-20-1 Extension Clones

A. Anchor PCR.

RNA was extracted directly from PNF2161 serum as described in Example 1. The RNA was passed through a "CHROMA SPIN" 100 gel filtration column (Clontech) to remove small molecular weight impurities. cDNA was synthesized using a BMB cDNA synthesis kit. After cDNA synthesis, the PNF cDNA was ligated to a 50 to 100 fold excess of KL-1/KL-2 SISPA or JML-A/JML-B linkers (SEQ ID NO:11/SEQ ID NO:12, and SEQ ID NO:17/SEQ ID NO:18, respectively) and amplified for 35 cycles using either the primer KL-1 or the primer JML-A.

The 470 extension clones were generated by anchored PCR of a 1 µl aliquot from a 10 µl ligation reaction containing EcoRI digested (dephosphorylated) lambda gt11 arms (1 µg) and EcoRI digested PNF cDNA (0.2 µg). PCR amplification (40 cycles) of the ligation reaction was carried out using the lambda gt11 reverse primer (SEQ ID NO:13) in combination with either 470-20-77F (SEQ ID NO:9) or 470-20-1-211R (SEQ ID NO:10). All primer concentrations for PCR were 0.2 µM.

The amplification products (9 µl/100 µl) were separated on a 1.5% agarose gel, blotted to "NYTRAN" (Schleicher and Schuell, Keene, N.H.), and probed with a digoxygenin labelled oligonucleotide probe specific for 470-20-1. The digoxygenin labeling was performed according to the manufacturer's recommendations using terminal transferase (BMB). Bands that hybridized were gel-purified, cloned into the "TA CLONING VECTOR pCR II" (Invitrogen), and sequenced.

Numerous clones having both 5' and 3' extensions to 470-20-1 were identified. All sequences are based on a consensus sequence from the sequencing of at least two independent isolates. This Anchor PCR approach was repeated in a similar manner to obtain further 5' and 3' extension sequences. These PCR amplification reactions were carried out using the lambda gt11 reverse primer (SEQ ID NO:13) in combination with HGV specific primers derived from sequences obtained from previous extension clones. The substrate for these reactions was unpackaged PNF 2161 2-cDNA source DNA.

Sequencing was carried out using "DYEDEOXY TERMINATOR CYCLE SEQUENCING" (a modification of the procedure of Sanger, et al.) on an Applied Biosystems model 373A DNA sequencing system according to the manufacturer's recommendations (Applied Biosystems, Foster City, Calif.). Sequence data is presented in the Sequence Listing. Sequences were compared with "GENBANK", EMBL database and dbEST (National Library of Medicine) sequences at both nucleic acid and amino acid levels. Search programs FASTA, BLASTP, BLASTN and BLASTX (Altschul, et al.) indicated that these sequences were novel as both nucleic acid and amino acid sequences.

Individual clones obtained using a selected primer pair were aligned to yield a consensus sequence. The series of consensus sequences used to construct the sequence for the HGV-PNF 2161 variant was as follows: 4E3, SEQ ID NO:26; 3E3, SEQ ID NO:27; 2E5, SEQ ID NO:28; 1E5, SEQ ID NO:29; 4E5, SEQ ID NO:30; 3E5, SEQ ID NO:31; 2E3, SEQ ID NO:32; 1E3, SEQ ID NO:33; 4E5-20, SEQ ID NO:34; 5E3, SEQ ID NO:39; 6E3, SEQ ID NO:40; 7E3, SEQ ID NO:42; 5E5, SEQ ID NO:43; 6E5(44F), SEQ ID NO:44; 8E3, SEQ ID NO:98; 9E3, SEQ ID NO:109; 10E3, SEQ ID NO:110; 11E3, SEQ ID NO:116; 12E3, SEQ ID NO:118; 5'-end, SEQ ID NO:175; and 3'-END, SEQ ID NO:167.

The individual consensus sequences were aligned, overlapping sequences identified and a consensus sequence for the HGV-PNF 2161 variant was determined. This consensus sequence was compared with the sequences obtained for four other HGV variants: JC (SEQ ID NO:182), BG34 (SEQ ID NO:176), T55806 (SEQ ID NO:178), and EB20-2 (SEQ ID NO:180).

Figure 11:
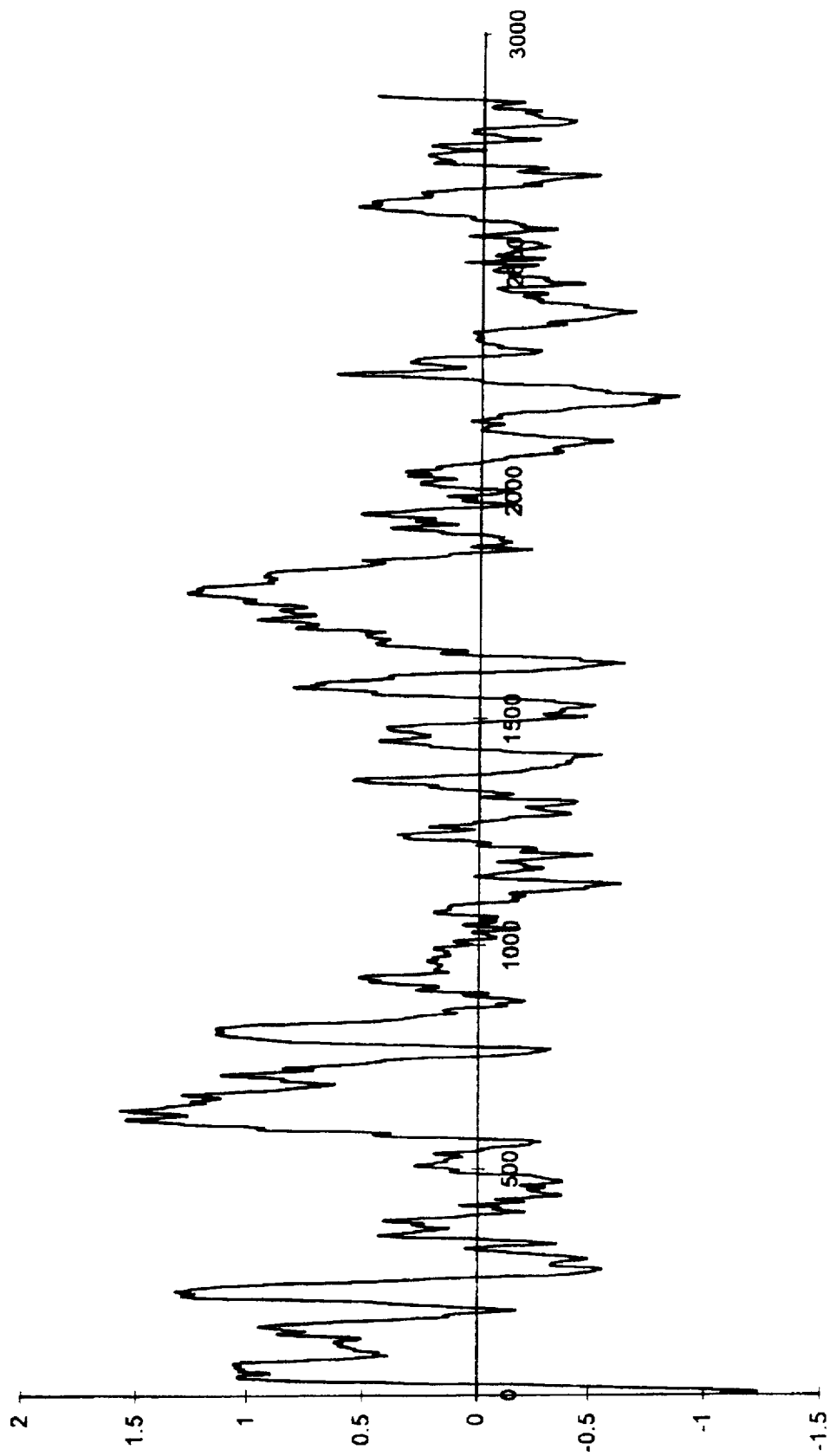

The consensus sequence of the HGV-PNF 2161 variant consists of 9391 base pairs presented as SEQ ID NO:14. This sequence represents a continuous open reading frame (SEQ ID NO:15). A Kyte-Doolittle hydrophobicity plot of the polyprotein is presented as FIG. 11.

The relationship between the original 470-20-1 clone and the sequences obtained by extension is shown schematically in FIG. 1. As seen in the figure, the DNA strand having opposite polarity to the protein coding sequence of 470-20-1 comprising a long continuous open reading frame.

The amino acid sequence of HGV was compared against the sequences of all viral sequence in the PIR database (IntelliGenetics, Inc., Mountain View, Calif.) of protein sequences. The comparison was carried out using the "SSEARCH" program of the "FASTA" suite of programs version 1.7 (Pearson, et al.). Regions of local sequence similarities were found between the HGV sequences and two viruses in the Flaviviridae family of viruses. The similarity alignments are presented in FIGS. 5A and 5B.

Present in these alignments are motifs for the RNA dependent RNA polymerase (RDRP) of these viruses. Conserved RDRP amino acid motifs are indicated in FIGS. 5A and 5B by stars and uppercase, bold letters (Koonin and Dolja). These alignments demonstrate that this portion of the HGV coding sequence correspond to RDRP. This alignment data combined with the data concerning the RNA genome of HGV supports the placement of HGV as a member of the Flaviviridae family.

The global amino acid sequence identities of the HGV polyprotein (SEQ ID NO:15) with HOCV (Hog Cholera Virus) and HCV are 17.1% and 25.5%, respectively. Such levels of global sequence identity demonstrates that HGV is a separate viral entity from both HOCV and HCV. To illustrate, in two members of the Flaviviridae family of viruses BVDV (Bovine Diarrhea Virus) and HCV, 16.2% of the amino acids can be globally aligned with HGV.

Members within a genus generally show high homology when aligned globally, for example, BVDV vs. HoCV show 71.2% identity. Various members (variants) of the un-named genus of which HCV is a member are between 65% and 100% identical when globally aligned.

B. Race PCR: 5' End Cloning.

Clones representing the 5'-end of the HGV genome were obtained by a modified Anchor PCR approach that utilized RACE (Rapid Amplification of cDNA Ends) technology. The RACE method was originally described by Frohman, et al., (1988) and Belyausky, et al., (1989). Briefly, the 5'-end clones of HGV were obtained as follows.

First-strand cDNA synthesis was primed using random hexamers and synthesis was carried out using either "SUPERSCRIPT II" or "rTth" reverse transcriptase (GIBCO/BRL). After first-strand synthesis, the RNA template was degraded by base hydrolysis (NaOH). The cDNA sample was neutralized by the addition of acetic acid and purified by absorption to a glass matrix support ("GENO-BIND," Clontech, Palo Alto, Calif.). Following purification, the cDNA was concentrated by ethanol precipitation and washed twice with 80% ethanol.

The originally described RACE method was modified as follows. A single-stranded oligonucleotide anchor (SEQ ID NO:174) (Clontech) was ligated to the 3' end of the first-strand cDNA using T4 RNA ligase in the presence of cobalt chloride. The oligonucleotide anchor was obtained from the manufacturer with two modifications: (i) the 3'-end of the anchor was modified with an amino group which prevents concatamer formation, and (ii) the 5'-end contains a phosphate group which allows ligation to the first-strand cDNA.

After ligation of the anchor, the cDNA was used as a template for PCR amplification using several HGV-specific primers in combination with a primer complementary to the anchor sequence (AP primer, SEQ ID NO:134). The resulting amplification products were separated by agarose gel electrophoresis, transferred to filters and hybridized with a nested, HGV-specific oligonucleotide probe. Bands that hybridized to the HGV-probe were isolated, cloned into "pCR-II" (Invitrogen, San Diego, Calif.) and sequenced.

C. HGV 3' End Cloning.

Clones representing the 3'-end of the HGV genome were obtained by a modified anchored RT-PCR method. Briefly, poly A polymerase (GIBCO/BRL, Gaithersburg, Md.) was used to catalyze the addition of a poly(A) tail to PNF 2161 RNA prior to cDNA synthesis. The poly(A) addition was performed according to the manufacturer's recommendations. Following purification of the poly(A) modified RNA, reverse transcription with "SUPERSCRIPT II" (GIBCO/BRL) was carried out using primer GV-5446IRT (SEQ ID NO:184). The resulting cDNA was amplified by PCR using the following primer set: GV59-5446F (SEQ ID NO:171) and GV-5446IR (SEQ ID NO:172).

After amplification, the products were separated by agarose gel electrophoresis, transferred to filters and hybridized with a digoxigenin-labelled oligonucleotide probe (E5-7-PRB, SEQ ID NO:173). Products that hybridized with the oligonucleotide were isolated, purified, cloned into "pCR-II" and sequenced. The two clones isolated by this method were MP3-3 (SEQ ID NO:168) and MP3-7 (SEQ ID NO:169).

EXAMPLE 7

Isolation of 470-20-1 Fusion Protein

A. Expression and Purification of 470-20-1/Glutathione-S-Transferase Fusion Protein Expression of a glutathione-S-transferase (sj26) fused protein containing the 470-20-1 peptide was achieved as follows. A 237 base pair insert (containing 17 nucleotides of SISPA linkers on both sides) corresponding to the original lambda gt11 470-20-1 clone was isolated from the lambda gt11 470-20-1 clone by polymerase chain reaction using primers gt11 F(SEQ ID NO:25) and gt11 R(SEQ ID NO:13) followed by Eco RI digestion.

The insert was cloned into a modified pGEX vector, pGEX MOV. pGEX MOV encodes sj26 protein fused with six histidines at the carboxy terminal end (sj26his). The 470-20-1 polypeptide coding sequences were introduced into the vector at a cloning site located downstream of sj26his coding sequence in the vector. Thus, the 470-20-1 polypeptide is expressed as sj26his/470-20-1 fusion protein. The sj26 protein and six histidine region of the fusion protein allow the affinity purification of the fusion protein by dual chromatographic methods employing glutathione-conjugated beads (Smith, D. B., et al.) and immobilized metal ion beads (Hochula; Porath).

E. coli strain W3110 (ATCC catalogue number 27352) was transformed with pGEX MOV and pGEX MOV containing 470-20-1 insert. Sj26his protein and 470-20-1 fusion protein were induced by the addition of 2 mM isopropyl-β-thiogalactopyranoside (IPTG). The fusion proteins were purified either by glutathione-affinity chromatography or by immobilized metal ion chromatography (IMAC) according to the published methods (Smith, D. B., et al.; Porath) in conjunction with conventional ion-exchange chromatography.

The purified 470-20-1 fusion protein was immunoreactive with PNF 2161. However, purified sj26his protein was not immunoreactive with PNF 2161, indicating the presence of specific immunoreaction between the 470-20-1 peptide and PNF 2161.

B. Isolation of 470-20-1/B-Galactosidase Fusion Protein

KM392 lysogens infected either with lambda phage gt11 or with gt11/470-20-1 are incubated in 32° C. until the culture reaches to an O.D. of 0.4. Then the culture is incubated in a 43° C. water bath for 15 minutes to induce gt11 peptide synthesis, and further incubated at 37° C. for 1 hour. Bacterial cells are pelleted and lysed in lysis buffer (10 mM Tris, pH 7.4, 2% "TRITON X-100" and 1% aprotinin). Bacterial lysates are clarified by centrifugation (10K, for 10 minutes, Sorvall JA20 rotor) and the clarified lysates are incubated with Sepharose 4B beads conjugated with anti-β-galactosidase (Promega).

Binding and elution of β-galactosidase fusion proteins are performed according to the manufacturer's instruction. Typically binding of the proteins and washing of the column are done with lysis buffer. Bound proteins are eluted with 0.1M carbonate/bicarbonate buffer, pH 10. The purified 470-20-1/b-galactosidase protein is immunoreactive with both PNF2161 and anti-b-galactosidase antibody. However, β-galactosidase, expressed by gt11 lysogen and purified, is not immunoreactive with PNF2161 but immunoreactive with anti-β-galactosidase antibody.

EXAMPLE 8

Purification of the 470-20-1 Fusion Protein and Preparation of Anti-470-20-1 Antibody A. Glutathione Affinity Purification Materials included 50 ml glutathione affinity matrix reduced form (Sigma), XK 26/30 Pharmacia column, 2.5×10 cm Bio-Rad "ECONO-COLUMN" (Richmond, Calif.), Gilson (Middleton, Wis.) HPLC, DTT (Sigma), glutathione reduced form (Sigma), urea, and sodium phosphate dibasic.

The following solutions were used in purification of the fusion protein:

Buffer A: phosphate buffer saline, pH 7.4, and

Buffer B: 50 mM Tris Ph 8.5, 8 mM glutathione, (reduced form glutathione)

Strip buffer: 8M urea, 100 mM Tris pH 8.8, 10 mM glutathione, 1.5 NaCl.

*E. coli* carrying the plasmid pGEX MOV containing 470-20-1 insert, were grown in a fermentor (20 liters). The bacteria were collected and lysed in phosphate buffered saline (PBS) containing 2 mM phenylmethyl sulfonyl fluoride (PMSF) using a micro-fluidizer. Unless otherwise noted, all of the following procedures were carried out at 4° C.

The crude lysate was prepared for loading by placing lysed bacteria into "OAKRIDGE" tubes and spinning at 20K rpms (40k ×g) in a Beckman model JA-20 rotor. The supernatant was filtered through a 0.4 μm filter and then through a 0.2 μm filter.

The 2.5×10 cm "ECONO-COLUMN" was packed with the glutathione affinity matrix that was swelled in PBS for two hours at room temperature. The column was brought into equilibrium by washing with 4 bed volumes of PBS.

The column was loaded with the crude lysate at a flow rate of 8 ml per minute. Subsequently, the column was washed with 5 column volumes of PBS at the same flow rate.

Figure 2:
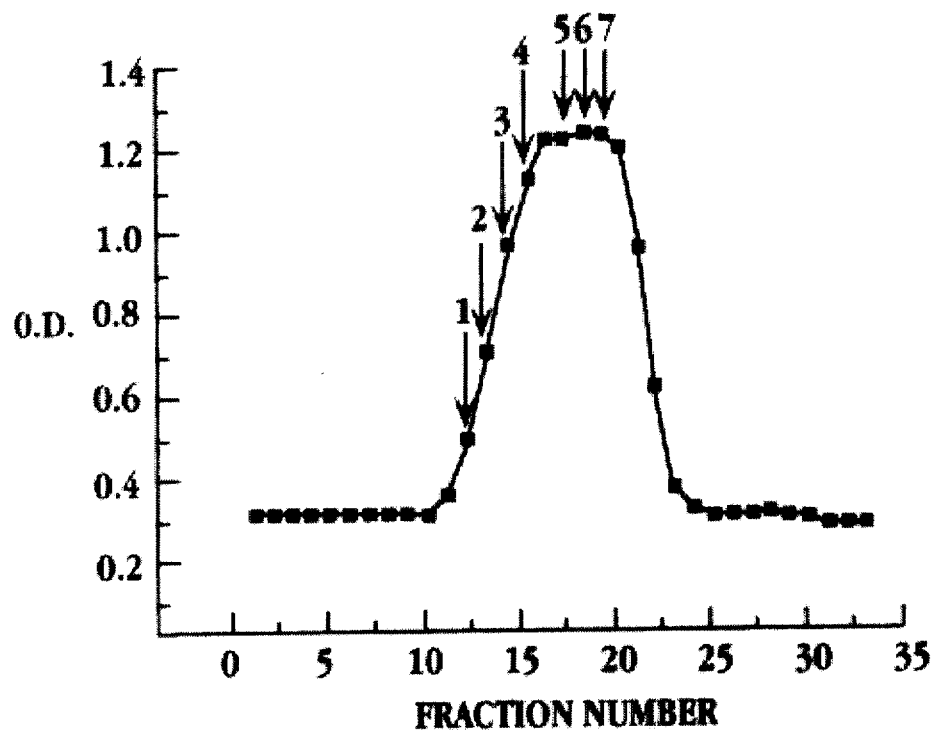
FIG. 2: shows an exemplary protein profile from gradient fractions eluted from a glutathione affinity column.
Figure 3:
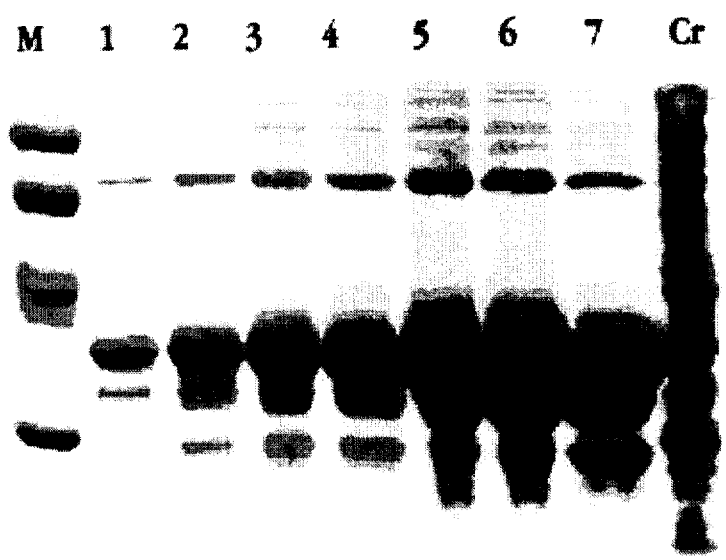
FIG. 3: shows an exemplary Sodium dodecyl sulfate polyacrylamide gel electrophoresis analysis of fraction samples from FIG. 2.

The column was eluted by setting the flow rate to 0.75–1 ml/min. and introducing Buffer B. Buffer B was pumped through the column for 5 column volumes and two-minute fractions were collected. An exemplary elution profile is shown in FIG. 2. The content and purity of the proteins present in the fractions were assessed by standard SDS PAGE (FIG. 3). The 470-20-1/sj26his fusion protein was identified based on its predicted molecular weight and its immunoreactivity to PNF 2161 serum. For further manipulations, the protein can be isolated from fractions containing the fusion protein or from the gel by extraction of gel regions containing the fusion protein.

B. Purification of Clone 470-20-1 Fusion Protein by Anion Exchange.

Solutions include the following:

Buffer A (10 mM sodium phosphate pH 8.0, 4M urea, 10 mM DTT);

Buffer B (10 mM sodium phosphate pH 8.0, 4M urea, 10 mM DTT, 2.0M NaCl); and

Strip Buffer (8M urea, 100 mM Tris pH 8.8, 10 mM glutathione, 1.5 NaCl).

Crude lysate (or other protein source, such as pooled fractions from above) was loaded onto "HIGH-Q-50" (Biorad, Richmond, Calif.) column at a flow rate of 4.0 ml/min. The column was then washed with Buffer A for 5 column volumes at a flow rate of 4.0 ml/min.

Figure 4A:
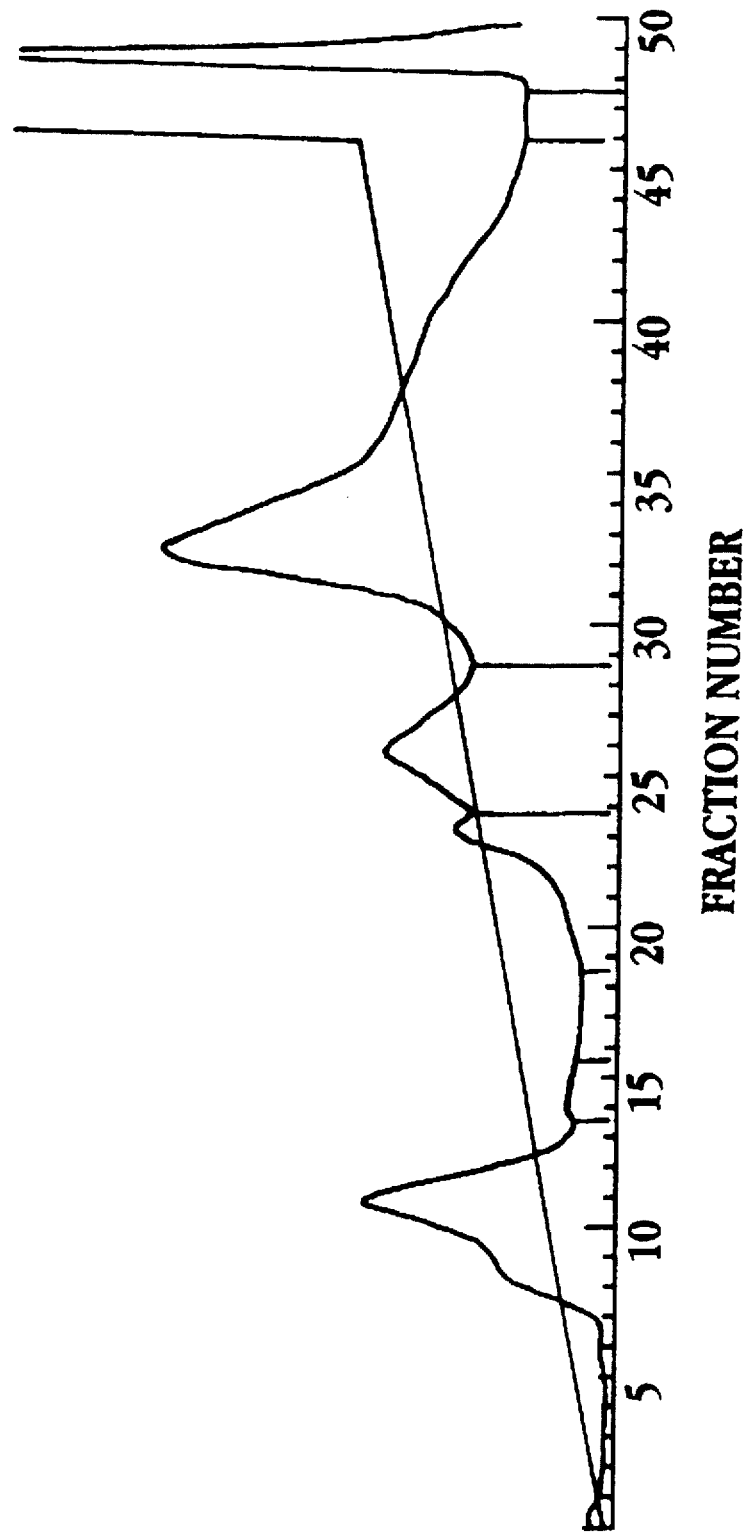
FIG. 4A: shows an exemplary protein profile from gradient fractions eluted from an anion exchange column.
Figure 4B:
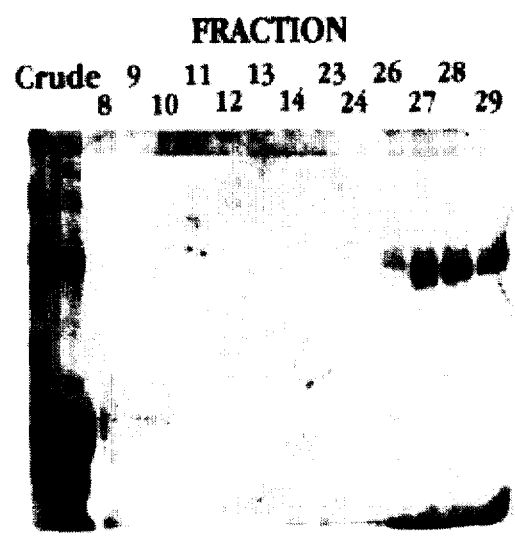
FIGS. 4B and 4C: show exemplary Sodium dodecyl sulfate polyacrylamide gel electrophoresis analysis of fraction samples from FIG. 4A.
Figure 4C:
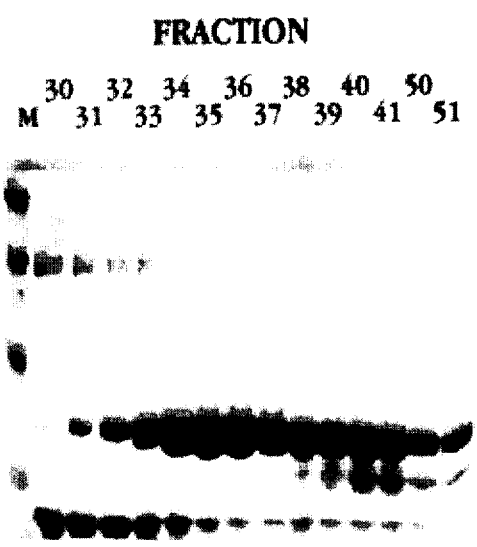

After these washes, a gradient was started and ran from Buffer A to Buffer B in 15 column volumes. The gradient then stepped to 100% Buffer B for one column volume. An exemplary gradient is shown in FIG. 4A. Fractions were collected every 10 minutes. Purity of the 470-20-1/sj26his fusion protein was assessed by standard SDS-PAGE (FIGS. 4B and 4C) and relevant fractions were pooled (approximately fractions 34 through 37, FIG. 4C).

C. Preparation of Anti-470-20-1 Antibody

The purified 470-20-1/sj26his fusion protein is injected subcutaneously in Freund's adjuvant in a rabbit. Approximately 1 mg of fusion protein is injected at days 0 and 21, and rabbit serum is typically collected at 6 and 8 weeks.

A second rabbit is similarly immunized with purified sj26his protein.

Minilysates are prepared from bacteria expressing the 470-20-1/sj26his fusion protein, sj26his protein, and β-galactosidase/470-20-1 fusion protein. The lysates are fractionated on a gel and transfered to a membrane. Separate Western blots are performed using the sera from the two rabbits.

Serum from the animal immunized with 470-20-1 fusion protein is immunoreactive with all sj26his fusion protein in minilysates of IPTG induced *E. coli* W3110 that are transformed either with PGEX MOV or with pGEX MOV containing 470-20-1 insert. This serum is also immunoreactive with the fusion protein in the minilysate from the 470-20-1 lambda gt11 construct.

The second rabbit serum is immunoreactive with both sj26his and 470-20-1/sj26his fusion proteins in the minilysates. This serum is not expected to immunoreactive with 470-20-1/β-galactosidase fusion protein in the minilysate from the 470-20-1 lambda gt11 construct. None of the sera are expected to be immunoreactive with β-galactosidase.

Anti-470-20-1 antibody present in the sera from the animal immunized with the fusion protein is purified by affinity chromatography (using the 470-20-1 ligand).

Alternatively, the fusion protein can be cleaved to provide the 470-20-1 antigen free of the sj-26 protein sequences. The 470-20-1 antigen alone is then used to generate antibodies as described above.

EXAMPLE 9

Rabbit Anti-Peptide Sera

Peptides were designed to cover the entire HGV sequence, in particular, to cover each of the functional groups in the non-structural and structural genes. Peptides were synthesized commercially by conventional techniques. Representative peptides are presented in Table 12.

TABLE 12

| Desgination | Size of Peptide (aa) | End Points Relative to SEQ ID NO:14 |
|---|---|---|
| PEP1/NS2a | 30 | 2674/2763 |
| PEP2/E1 | 16 | 733/780 |
| PEP3/E2 | 18 | 1219/1272 |
| PEP4/NS2B | 18 | 3061/3114 |
| PEP5/NS3 | 21 | 3571/3633 |
| PEP6/NS3** | 18 | 4909/4959 |
| PPE7/NS4A | 18 | 5275/5328 |

TABLE 12-continued

| Desgination | Size of Peptide (aa) | End Points Relative to SEQ ID NO:14 |
|---|---|---|
| PEP8/NS4B | 16 | 6097/6144 |
| PEP9/NS5A | 16 | 7033/7080 |
| PEP10/NS5B | 18 | 7783/7836 |

**The NS3 peptide has an extraneous Cysteine on the C terminal end that is not in the HGV-PNF 2161 variant polypeptide sequence; the actual sequence was a Q.

The peptides were coupled to KLH. Using rabbits as host, the conjugated peptides were injected subcutaneously at multiple sites. Anti-peptide rabbit serum were generated by a commercial facility. A two-week immunization protocol was used with bleeds taken at alternate weeks.

Rabbit anti-peptide sera were shown to be peptide specific and to have high titer. Rabbit anti-peptide sera also recognize corresponding recombinant proteins expressed in *E. coli* and baculovirus. Antibody endpoint titers range from 1:50,000 dilution to 1:625,000 dilution. Rabbit anti-peptide 7 (NS4a) had low end point titers of only 1:1,000. Accordingly, rabbit anti-serum to the NS4a protein expressed in, for example, the baculovirus system may be a more useful reagent.

Rabbit anti-peptide sera are useful for immunoprecipitating corresponding HGV proteins expressed, for example, in baculovirus and vaccinia. Rabbit anti-peptide sera are also useful as capture antibody in EIAs to detect HGV antigen. Rabbit anti-peptide sera are further useful in the characterization of the HGV proteins.

EXAMPLE 10

Serology

A. Western Blot analysis of Sera Panels

The 470-20-1 fusion antigen (described above) was used to screen panels of sera. Many of the panels were of human sera derived both from individuals suffering from hepatitis and uninfected controls.

Affinity purified 470-20-1 fusion antigen (Example 8) was loaded onto a 12% SDS-PAGE at 2 µg/cm. The gel was run for two hours at 200V. The antigen was transfered from the gel to a nitrocellulose filter.

The membrane was then blocked for 2 hours using a solution of 1% bovine serum albumin, 3% normal goat serum, 0.25% gelatin, 100 mM NaPO$_4$, 100 mM NaCl, and 1% nonfat dry milk. The membrane was then dried and cut into 1–2 mm strips; each strip contained the 470-20-1 fusion antigen. The strip was typically rehydrated with TBS (150 mM NaCl; 20 mM Tris HCl, pH 7.5) and incubated in panel sera (1:100) overnight with rocking at room temperature.

The strips were washed twice for five minutes each time in TBS plus "TWEEN 20" (0.05%), and then washed twice for five minutes each time in TBS. The strips were then incubated in secondary antibody (Promega anti-human IgG-Alkaline Phosphatase conjugate, 1:7500), for 1 hour with rocking at room temperature. The strips were then washed twice×5 minutes in TBS+"TWEEN 20", then twice×5 minutes in TBS.

Bound antibody was detected by incubating the strips in a substrate solution containing BCIP (Example 2) and NBT (Example 2) in pH 9.5 buffer (100 mM Tris, 100 mM NaCl, 5 mM MgCl$_2$). Color development was allowed to proceed for approximately 15 minutes at which point color development was halted by 3 washes in distilled H$_2$O.

Test sera were derived from the following groups of individuals: (i) blood donors, negative for HBV Ab, surface Ag, negative for HCV, HIV, HTLV-1 Abs; (ii) HBV, sera from individuals who are infected with Hepatitis B virus; (iii) HCV, sera from individuals infected with Hepatitis C virus by virtue of being reactive in a second-generation HCV ELISA assay; and (iv) HXV, individuals serologically negative for HAV, HBV, HCV, or HEV.

The results of these screens are presented in Table 13.

TABLE 13

470-20-1 Sera Panelling Result Summary

| Sample | No. Human* Sera Tested | + | IND* | – |
|---|---|---|---|---|
| blood donor | 30 | 1 (3.3%) | 2 (6.7%) | 27 (90.0%) |
| HBV | 40 | 7 (17.5%) | 4 (10.0%) | 29 (72.5%) |
| HCV | 38 | 11 (28.95%) | 11 (28.95%) | 16 (42.1%) |
| HXV | 122 | 20 (16.4%) | 12 (9.8%) | 90 (73.8%) |

*Indeterminate, weak reactivity

These results suggest the presence of the 470-20-1 antigen in a number of different sera samples. The antigen is not immunoreactive with normal human sera.

B. General Elisa Protocol for Detection of Antibodies

Polystyrene 96 well plates ("IMMULON II" (PGC)) are coated with 5 µg/ml (100 µL per well) antigen in 0.1M sodium bicarbonate buffer, pH 9.5. Plates are sealed with "PARAFILM" and stored at 4° C. overnight.

Plates are aspirated and blocked with 300 uL 10% normal goat serum and incubated at 37° C. for 1 hr.

Plates are washed 5 times with PBS 0.5% "TWEEN-20".

Antisera is diluted in 1×PBS, pH 7.2. The desired dilution(s) of antisera (0.1 mL) are added to each well and the plate incubated 1 hour at 37° C. The plates are then washed 5 times with PBS 0.5% "TWEEN-20".

Horseradish peroxidase (HRP) conjugated goat anti-human antiserum (Cappel) is diluted 1/5,000 in PBS. 0.1 mL of this solution is added to each well. The plate is incubated 30 min at 37° C., then washed 5 times with PBS.

Sigma ABTS (substrate) is prepared just prior to addition to the plate.

The reagent consists of 50 ml 0.05M citric acid, pH 4.2, 0.078 ml 30% hydrogen peroxide solution and 15 mg ABTS. 0.1 ml of the substrate is added to each well, then incubated for 30 min at room temperature. The reaction is stopped with the addition of 0.050 mL 5% SDS (w/v). The relative absorbance is determined at 410 nm.

EXAMPLE 11

Expression of Selected HGV Antigens

The entire coding sequence of HGV was subcloned into greater than 50 distinct overlapping cDNA fragments. The length of most cDNA fragments ranged from about 200 bp to about 500 bp. The cDNA fragments were cloned separately into the expression vector, pGEX-HisB. This vector is similar to pGEX-MOV, described above.

pGEX-hisB is a modification of pGEX-2T (Genbank accession number A01438; a commercially available expression vector). The vector pGEX-2T has been modified by insertion of a NcoI site directly downstream from the thrombin cleavage site. This site is followed by a BamHI site, which is followed by a poly-histidine (six histidines) encoding sequence, followed by the EcoRI site found in pGEX-2T. Coding sequences of interest are typically inserted between the NcoI site and the BamHI site. In FIG. 6 (SEQ ID NO:115), the inserted sequence encodes the GE3-2 antigen. The rest of the vector sequence is identical to pGEX-2T. Expression of fusion protein is carried out essentially as described above with other pGEX-derived expression vectors.

Cloning of all 50 fragments was carried out essentially as described below, where specific primers were selected for each of the 50 coding regions. Each HGV insert DNA is PCR amplified from RNA extracted from PNF 2161 or other HGV(+) sera using a specific set of primers as described in Example 4C. Typically, the 5' primer contained a NcoI restriction site and the 3' primer contained a BamHI restriction site. The NcoI primers in the amplified fragments allowed in-frame fusion of amplified coding sequences to the GST-Sj26 coding sequence in the expression vectors pGEX-Hisb or pGEX MOV.

Amplified HGV insert DNA is digested with restriction enzymes NcoI and Bam HI. Digested insert DNA is gel purified and ligated with NcoI and BamHI digested pGEX hisB or pGEX MOV. *E. coli* strain W3110 (ATCC #27325, American Type Culture Collection, Rockville, Md.) was transformed with the ligation product. Ampicillin resistant colonies were selected. Presence of the insert was confirmed by the PCR amplification of the insert from the ampicillin resistant colony using primers homologous to PGEX vector sequences flanking the inserted molecules (primers GLI F (SEQ ID NO:235) and GLI R (SEQ ID NO:236).

The size of the PCR amplification product is the insert size plus approximately 160 bp derived from vector. Transformants with appropriate inserts were selected and subjected to protein induction by IPTG as described in Example 7. Expressed recombinant proteins were analyzed for specific immunoreactivity against putative HGV-infected human sera by Western blot.

Eight fragments designated GE3, GE9, GE15, GE17, GE4, EXP3, GE1-N and GE-57 encoded antigens that gave a clear immunogenic response when reacted with putative HGV-infected human sera.

A. CLONING OF GE3, GE9, GE15, GE17, GE4, EXP3, GE1-N AND GE57.

The coding sequence inserts for clones GE3, GE9, GE15, GE17, GE4, EXP3, GE1-N and GE57 were generated by polymerase chain reaction from SISPA-amplified double-stranded cDNA or RNA obtained from PNF 2161 or T55806 using PCR primers specific for each fragment. Following Table 14 lists the coordinates of each clone relative to SEQ ID NO:14 and the primer sets used for generation of each clone insert.

TABLE 14

| Clone | Serum Source | Coordinate on SEQ ID NO:14 | F Primer (SEQ ID NO:) | R Primer (SEQ ID NO:) |
|---|---|---|---|---|
| GE3 | PNF 2161 | 6615-6977 | GE-3F (SEQ ID NO:46) | GE-3R (SEQ ID NO:47) |
| GE9 | PNF 2161 | 8154-8441 | GE-9F (SEQ ID NO:48) | GE-9R (SEQ ID NO:49) |
| GE15 | PNF 2161 | 3615-3935 | GE-15F (SEQ ID NO:111) | GE-15R (SEQ ID NO:112) |
| GE17 | PNF 2161 | 3168-3305 | GE-17F (SEQ ID NO:113) | GE-17R (SEQ ID NO:114) |
| GE4 | PNF 2161 | 6825-7226 | GE4F (SEQ ID NO:149) | GE4R (SEQ ID NO:150) |
| EXP3 | PNF 2161 | 6648-7658 | 470EXP3F (SEQ ID NO:151) | 470EXP3R (SEQ ID NO:152) |
| GE1-N | PNF 2161 | 5850-6239 | GE1-NF (SEQ ID NO:237) | GE1-NR (SEQ ID NO:238) |
| GE57 | T55806 | 271*-456* | GE57F (SEQ ID NO:239) | GE57R (SEQ ID NO:240) |

TABLE 14-continued

*These sequences are given relative to SEQ ID NO:178.

The amino acid sequence of GE57 is presented as SEQ ID NO:241.

In the GE3-5' primer (GE-3F, SEQ ID NO:46) a silent point mutation was introduced to modify a natural NcoI restriction site. Using the above-described primers, PCR amplification products were generated. The amplification products were gel purified, digested with NcoI and BamHI, and gel purified again. The purified NcoI/BamHI GE3, GE9, GE15, GE17, GE4, GE1-N and GE57 fragments were independently ligated into dephosphorylated, NcoI/BamHI cut pGEX-HisB vectors. The purified NcoI/BamHI EXP3 fragment was ligated into dephosphorylated, NcoI/BamHI cut PGEX-MOV vector.

Each ligation mixture was transformed into *E. coli* W3110 strain and ampicillin resistant colonies were selected. The ampicillin resistant colonies were resuspended in a Tris/EDTA buffer and analyzed by PCR, using primers GLI F (SEQ ID NO:235) and GLI R (SEQ ID NO:236) to confirm the presence of insert sequences. Eight candidate clones were designated GE3-2, GE9-2, GE15-1, GE17-2, GE4-8, EXP3-7, GE1-N and GE57, respectively.

B. Expression of the GE3-2, GE9-2, GE15-1, GE17-2, GE4-8, EXP3-7, GE1-N and GE57 Fusion Proteins.

Colonies of ampicillin resistant bacteria carrying GE3-2, GE9-2, GE15-1, and GE17-2, GE4-8, EXP3-7, GE1-N and GE57 containing-vectors were individually inoculated into LB medium containing ampicillin. The cultures were grown to OD of 0.8 to 0.9 at which time IPTG (isopropylthio-beta-galactoside; Gibco-BRL) was added to a final concentration of 0.3 to 1 mM, for the induction of protein expression. Incubation in the presence of IPTG was continued for 3 to 4 hours.

Bacterial cells were harvested by centrifugation and resuspended in SDS sample buffer (0.0625M Tris, pH 6.8, 10% glycerol, 5% mercaptoethanol, 2.3% SDS). The resuspended pellet was boiled for 5 min. and then cleared of insoluble cellular debris by centrifugation. The supernatants obtained from IPTG-induced cultures of GE3-2, GE9-2, GE15-1, GE17-2, GE4-8, EXP3-7, GE1-N and GE57 were analyzed by SDS-polyacrylamide gel electrophoresis (PAGE) together with uninduced lysates. The proteins from these gels were then transferred to nitrocellulose filters (i.e., by Western blotting).

The filters were first incubated with rabbit polyclonal antibody or mouse monoclonal antibody (RM001 from Sierra Biosource, Calif.) directed to GST protein to detect the expression of appropriate size GST-fusion protein expression. Expected protein sizes of above clones are 40, 38, 39, 32, 42, 64, 42 and 33 KDa, respectively. Immunoreactivity of RM001 with bands at the appropriate molecular weight for the fusion proteins demonstrated the successful expression of the fusion proteins of above clones by the bacterial cells. Expression of the clone proteins were also monitored by the appearance of over-expressed proteins of appropriate sizes upon IPTG induction on the Coomassie brilliant blue stained gel.

C. Western Blot Analysis of HGV Proteins.

Once the expression of the HGV clone protein was confirmed by Western blot analysis with anti-GST antibody a second set of filters, prepared as above, were then exposed to several HGV(+) and HGV(−) human sera. Human sera used for Western blot analyses of whole cell lysates were pre-absorbed with the lambda-gt11-nitrocellulose filters. Lambda-gt11-nitrocellulose filters were prepared as follows. Briefly, an overnight culture of KM392 culture was prepared in LB. The culture was diluted 10 fold in fresh LB containing 0.2% maltose and incubated for 1 hour at 37° C. with shaking.

After 1 hour the culture was mixed with an equal volume of MgCa solution (0.01M $MgCl_2$ and 0.01M $CaCl_2$). To this mixture lambda gt11 was added to a titer of $2 \times 10^4$ PFU/ml and incubated for 30 min without shaking. After 30 minutes (per each ml of this phage/*E.coli* mixture) 15 ml of molten (55° C.) LB top agar (LB with 0.8% agar) was added: 8 ml of this mixture was spread onto each 15 cm LB agar plate. After the top agar solidified the plate was incubated at 37° C. for 3–5 hr.

After plaques developed, a nitrocellulose filter was placed on the plate and the plate further incubated at 37° C. overnight. The nitrocellulose filter was removed and washed thoroughly with TBS (50 mM Tris-HCl, pH 7.5, 150 mM NaCl) plus 0.05% "TWEEN 20." The washed filter was then blocked with 1% gelatin in TBS overnight. The filter was washed three times (5 minutes each wash) with TBS.

For the pre-absorption of human sera each serum was diluted 100 fold in blocking solution (described in Example 10). Ten mls. of diluted serum was then incubated overnight with two lambda gt11 filters prepared as above. Lambda gt11 filters were removed and the pre-absorbed serum used for Western blot analysis.

Western blot analyses demonstrated that clones GE3-2, GE9-2, GE15-1, GE17-2, GE4-8, EXP3-7, GE1-N and GE57 showed specific immunoreactivity toward HGV(+) sera. The GE-4-8 protein was immunoreactive with J21689 serum. J21689 is HGV (+) serum as determined by HGV PCR (Example 4) and HCV (+) as determined by HCV PCR and serological analyses. The EXP3-7 protein was immunoreactive with JC and T55806. JC is the HGV-positive serum identified in Example 4F that was rejected by the blood bank for being high ALT. A second JC sample, taken one year after the initial serum sample, was also positive for HGV by PCR analysis. T55806 is also the HGV-positive serum identified in Example 4F that was rejected by the blood bank for being High ALT. This serum is co-positive with HCV.

Further, GE15-1 and GE-17 showed weak but specific immunoreactivity toward PNF 2161 and T55806. GE1-N was immunoreactive with PNF2161, JC, T55806, T56633, T27034 and R0001. T56633, T27034 and R0001 are HGV (+) sera identified in Example 4F. GE57 was immunoreactive with E57963 and R0001. E57963 is HGV and HCV co-positive serum. GE3-2 and GE9-2 were also immunoreactive with HGV sera specifically. However, none of the eight antigens were immunoreactive with HGV negative sera T43608 and R05072.

The GE3-2 and GE9-2 fusion proteins were purified from bacterial cell lysates essentially as in Example 7 using dual chromatographic methods employing glutathione-conjugated beads (Smith, D. B., et al.) and immobilized metal ion beads (Hochuli; Porath). The purified proteins were subjected to Western blot analysis as follows.

Various amounts of the purified HGV proteins (e.g., GE3-2 and GE9-2 proteins) were loaded on 12% acrylamide gels. Following PAGE, proteins were transferred from the gels to nitrocellulose membranes, using standard procedures. Individual membranes were incubated with one of a number of human or mouse sera. Excess sera were removed by washing the membranes.

These membranes were incubated with alkaline phosphatase-conjugated goat anti-human antibody (Promega) or alkaline phosphatase-conjugated goat anti-mouse antibodies (Sigma), depending on the serum being used for screening. The membranes were washed again, to remove excess goat anti-human IgG antibody, and exposed to NBT/BCIP. Photographs of exemplary stained membranes having the GE3 fusion protein are shown in FIGS. 7A to 7D.

Figures 7A, 7B, 7C, 7D:
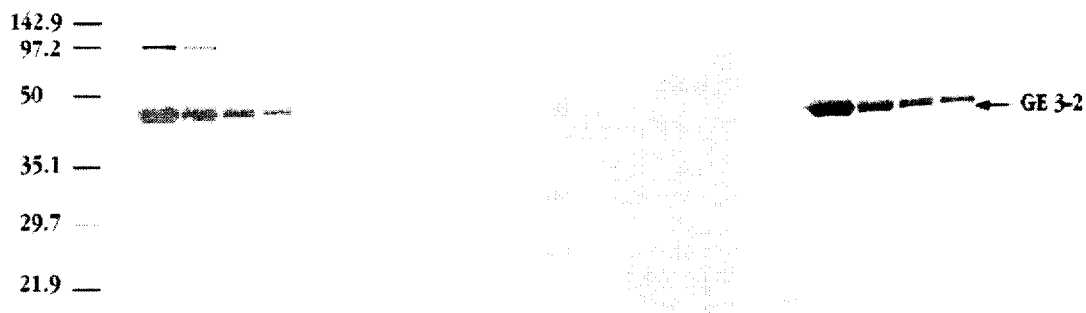
FIGS. 7A to 7D show the results of Western blot analysis of the purified HGV GE3-2 protein.

The Figures show the results of Western blot analysis of the purified GE3-2 protein using the following sera: N-(ABCDE) human (JC) serum (FIG. 7A), N-(ABDE) human (PNF 2161) serum (FIG. 7B), a super normal (SN2) serum (FIG. 7C), and mouse monoclonal antibody (RM001) directed against GST-Sj26 protein (FIG. 7D).

In each of the figures, lane 1 contains pre-stained molecular weight standards(Bio-Rad), and lanes 2–5 contain, respectively, the following amounts of the GE3-2 fusion protein: 4 µg, 2 µg, 1 µg, and 0.5 µg. Numbers represent loading amounts in micrograms per 0.6 centimeter of gel (well size). Dilutions of the human JC, PNF 2161 and Super Normal 2 sera were 1:100. The anti-sj26 dilution was 1:1000. The band seen at about 97K in the JC blot is reactivity against a minor contaminant in the GE3.2 fusion protein preparation. Protein marker sizes are 142.9, 97.2, 50, 35.1, 29.7 and 21.9 KD.

As shown in FIGS. 7A to 7D, GE3-2 showed specific immunoreactivity with JC serum. GE3-2 reacted weakly with PNF 2161 serum and would be scored as an indeterminant or negative.

In parallel experiments, GE9-2 showed weak but specific immunoreactivity toward PNF 2161 serum.

EXAMPLE 12

Construction of Exemplary Epitope Libraries

A. The Y5 Library.

Polymerase Chain Reactions were employed to amplify 3 overlapping DNA fragments from PNF 2161 SISPA-amplified cDNA. The PNF 2161 SISPA-amplified cDNA was prepared using the JML-A/B linkers (SEQ ID NO:54 and SEQ ID NO:55). One microliter of this material was re-amplified for 30 cycles (1 minute at 94° C., 1.5 minutes at 55° C. and 2 minutes at 72° C.) using 1 µM of the JML-A primers. The total reaction volume was 100 µl. The products from 3 of these amplifications were combined and separated from excess PCR primers by a single pass through a "WIZARD PCR COLUMN" (Promega) following the manufacturer's instructions. The "WIZARD PCR COLUMN" is a silica based resin that binds DNA in high ionic strength buffers and will release DNA in low ionic strength buffers. The amplified DNA was eluted from the column with 100 µl distilled H20.

The eluted DNA was fractionated on a 1.5% Agarose TBE gel (Maniatis, et al.) and visualized with UV light following ethidium bromide staining. A strong smear of DNA fragments between 150 and 1000 bp was observed. One microliter of the re-amplified cDNA was used as for template in PCR reactions with each primer pair presented in Table 15.

TABLE 15

| Primers | SEQ ID NO: | Size of Amplified Fragment |
|---|---|---|
| 470ep-F1 | SEQ ID NO:56 | 810 |
| 470ep-R1 | SEQ ID NO:57 | |
| 470ep-F2 | SEQ ID NO:58 | 750 |
| 470ep-R3 | SEQ ID NO:59 | |
| 470ep-F4 | SEQ ID NO:60 | 669 |
| 470ep-R4 | SEQ ID NO:61 | |

The primers were designed to result in the amplification of HGV specific DNA fragments of the sizes indicated in Table 15. In the amplification reactions, the primer pairs were used at a concentration of 1 µM. Amplifications were for 30 cycles of 1 minute at 94, 1.5 minutes at 54° C. and 3 minutes at 72° C. in a total reaction volume of 100 µl. Each of the three different primer pair PCR reactions resulted in the specific amplification of products having the expected sizes. For each primer pair reaction, amplification products from 3 independent PCR reactions were combined and purified using a "WIZARD PCR COLUMN" as described above. The purified products were eluted in 50 µl dH20.

Samples from each purified product (14 µl, containing approximately 1-2 µg of each primer-pair amplified DNA fragment) were combined. The combined sample of all three different amplified fragments was added to 5 µl of 10× DNAse Digestion buffer (500 mM Tris PH 7.5, 100 mM $MnCl_2$) and 2 µl of dH20. From this digestion mixture, a 10 µl sample was removed and placed in a tube containing 5 µl of Stop solution (100 mM EDTA, pH 8.0). This sample was the 0 "minutes of digestion" time point. The rest of the digestion reaction was placed at 25° C. To the digestion mixture 1 µl of 1/25 diluted RNase-free DNAse I (Stratagene) was added. At various time points 10 µl aliquots were withdrawn and mixed with 5 µl of Stop solution. The DNAse I digested DNA products were analyzed on a 1.5% Agarose TBE gel.

The results of several digestion experiments showed that 40 minutes of digestion provided a good distribution of DNA fragments in the size range of 100-300 bp. A DNAse I digestion was then repeated with the entire digestion being left for 40 minutes at room temperature. The digestion was stopped by the addition of 18 µl of Stop Buffer and the digested DNA products were purified using a "WIZARD PCR COLUMN." The "WIZARD-PCR COLUMN" was eluted with 50 µl of dH20 and the eluted DNA added to the following reaction mixture: 7 µl of Restriction Enzyme Buffer C (Promega, 10 mM $MgCl_2$, 1 mM DTT, 50 mM NaCl, 10 mM Tris, pH 7.9, 1× concentration); 11 µl of 1.25 mM dNTPs; and 2 µl T4 DNA Polymerase (Boehringer-Mannhiem). This reaction mixture was held at 37° C. for 30 minutes, at which point 70 µl of pH 8.0 phenol/$CHCl_3$ was added and mixed. The phenol/$CHCl_3$ was removed and extracted once to yield a total aqueous volume of 150 µl containing the DNA sample. The DNA was ethanol precipitated using 2 volumes of absolute ethanol and 0.5 volume of 7.5M $NH_4$-acetate. The DNA was pelleted by centrifugation for 15 minutes at 14,000 rpm in an "EPPENDORF MICROFUGE", dried for 5 minutes at 42° C. and resuspended in 25 µl of dH20.

The DNA was ligated to 5' phosphorylated SISPA linkers KL1 (SEQ ID NO:62) and KL2 (SEQ ID NO:63). Several different concentrations of SISPA linkers and DNA was tested. The highest level of ligation (assessed as described below) occurred under the following ligation reaction conditions: 6 µl of DNA, 2 µl of 5.0×10–12M KL1/KL2 linkers, 1 µl of 10× ligase buffer (New England Biolabs), and 1 µl of 400 Units/µl T4 DNA Ligase (New England Biolabs) in a total reaction volume of 10 µl. Ligations were carried out overnight at 16° C.

Two reactions were run in parallel as follows. A 2 µl sample of the ligated material was amplified using the KL1 SISPA primer in a total reaction volume of 100 µl (25 cycles of 1 minute at 94° C., 1.5 minutes at 55° C. and 2 minutes at 72° C.). The degree of ligation was assessed by separating 1/5 of the PCR reaction amplified products by electrophoresis using a 1.5% agarose TBE gel. The gel was stained with ethidium bromide and the bands visualized with UV light.

The amplification products from the duplicate reactions were purified using "WIZARD PCR COLUMNS" and the purified DNA eluted in 50 µl of dH20. A twenty-five microliter aliquot of the PCR KL1/KL2 amplified DNA was digested with 36 Units of EcoRI (Promega) in a total volume of 30 µl. The reaction was carried out overnight at 37° C. The Digested DNA was purified using a "SEPHADEX G25" spin column.

The EcoRI digested DNA was ligated in overnight reactions to λgt11 arms that were pre-digested with EcoRI and treated with calf intestinal alkaline phosphatase (Stratagene, La Jolla, Calif.). The ligation mixture was packaged using a "GIGAPACK GOLD PACKAGING EXTRACT" (Stratagene) following manufacturer's instructions. Titration of the amount of recombinant phage obtained was performed by plating a 1/10 dilution of the packaged phage on a lawn of KM-392, where the plate contained 20 µl of a 100 mg/ml solution of x-gal (5-Bromo-4-chloro-3-indolyl-β-D-galactoside; Sigma) and 20 µl of a 0.1M solution of IPTG (Isopropyl-1-thio-β-D-galactoside; Sigma). A titer was obtained of $1.2 \times 10^6$ phage/ml containing over 75% recombinant phage.

The percentage of recombinant plaques was confirmed by PCR analysis of 8 randomly picked plaques using primers 11F (SEQ ID NO:25) and 11R (SEQ ID NO:13). This packaged library containing the DNA fragments derived from the digestion of the amplified DNAs F1/R1, F2/R3, and F4/R4 amplified DNAs and was designated library Y5.

B. The ENV Library.

An expression library, designated the ENV library, was generated as follows. One microliter of PNF 2161 SISPA amplified DNA was used as the template in polymerase chain amplification reactions utilizing the following primer pairs: GEP-F15 (SEQ ID NO:128) and GEP-R15 (SEQ ID NO:129), which generate a 525 nucleotide HGV fragment; and GEP-F17 (SEQ ID NO:130) and GEP-R16 (SEQ ID NO:131), which generate a 765 nucleotide HGV fragment.

PCR amplification was for 35 cycles of 94° C. for 1 min, 52° C. for 1.5 minutes, and 72° C. for 3 minutes. The amplified products were purified and digested with DNAse I. Ligation of KL1 and KL2 linkers to cDNA, amplification of DNA fragments and construction of libraries in lambda gt11 were performed essentially as described in Example 12A. The recombinant frequency of the library was greater than 70%. Analysis of the inserts by polymerase chain reaction using primers derived from the flanking regions of lambda gt11 confirmed the recombinant frequency and indicated that the insert size range was 150-500 nucleotides.

C. The NS3 Library.

An expression library designated NS3 was constructed as follows. A first fragment was amplified by polymerase chain reaction using the primers 470ep-F9 (SEQ ID NO:132) and 470ep-R9 (SEQ ID NO:133) and, as template, PNF 2161 SISPA amplified nucleic acids. The predicted product of this amplification reaction was 777 base pairs. The amplified fragment was gel purified by separation on a TAE gel. The fragment was further purified using "GENECLEAN" (Bio 101, La Jolla, Calif.).

Fragment F9/R9 was also amplified using the extension clone GE3L-11 (SEQ ID NO:41) as source material. Approximately 25 ng of GE3L-11 was used as template with the F9 and R9 primers in amplification reactions.

Both of the F9/R9 amplifications were for 30 cycles of 94° C., for 1 minute, 52° C. for two minutes, and 72° C. for 3 minutes, using "TAQ START" (Clonetech, Palo Alto, Calif.). The amplification products from both reactions were combined. The products were digested with DNAse I (10 μl GE3L product and 25 ul of PNF SISPA product). The GE3L-based amplification product represented the majority of the amplification product starting material. Ligation of KL1 and KL2 linkers to cDNA, amplification of DNA fragments and construction of libraries in lambda gt11 were performed essentially as described in Example 12A.

The titer obtained was $2.5 \times 10^6$ phage/ml and the percent recombinant phage was determined to be greater than 99%. Polymerase chain reaction analysis of the insert sizes confirmed the recombinant frequency and indicated an insert size range of 150 to 550 nucleotides.

In addition, a second fragment was also amplified using the GEP-F10/GEP-R10 primers (SEQ ID NO:135 and SEQ ID NO:136, respectively). One microliter of PNF 2161 SISPA amplified nucleic acids was used as template. The predicted fragment size of 570 nucleotides was obtained. The resulting amplification products were manipulated as just described for the F9/R9 amplifications. The titer obtained for this fragment when inserted in lambda gt11 was $1.47 \times 10^6$ phage/ml, with a recombinant frequency of 90%.

D. The NS2 Library.

The NS2 epitope library was constructed using the methodologies described in Example 12A. Four DNA fragments containing all or part of the HGV proteins NS2, NS3, and NS5b were amplified from 1 ul of PNF 2161 SISPA DNA (prepared essentially as described in Example 12A). The library was generated using the primers given in Table 16 and SISPA amplified PNF 2162 DNA as template.

TABLE 16

| Fragments | nt | |
|---|---|---|
| 9E-REV (SEQ ID NO:264) | 592 | aa 358 (of 389) of |
| E394-R (SEQ ID NO:265) | | E2 to aa 166 of NS-2 |
| GEP-F12 (SEQ ID NO:266) | 663 | aa 144 (of 313) of |
| GEP-R12 (SEQ ID NO:267) | | NS-2 to aa 51 of NS-3 |
| GEP-F14 (SEQ ID NO:268) | 715 | aa 357–594 of NS-3 |
| GEP-R13 (SEQ ID NO:269) | | |
| 470epF8 (SEQ ID NO:270) | 648 | aa 716–847 of NS-5 |
| GEP-R14 (SEQ ID NO:271) | | (716 to end) |

All amplifications were for 35 cycles of 94° C./1 minute, 48° C./2 minutes, and 73° C./3 minutes. All amplifications yielded at least a fragment of the expected size. The amplified products were mixed and in an approximately 1:1:1:1 ratio and partially digested with DNase I. As above, the digestion products were ligated to KL1 SISPA linkers, amplified and EcoRI digested. The digested fragments were ligated into lambda gt11. The ligation reactions were packaged.

The packaged ligation products were plated. The resulting library was determined to contain ~70% recombinant phage with an observed insert size of 150 to 500 nucleotides.

E. The VNS5A Library.

Primers 470EXT4-2189R (SEQ ID NO:119) and 470EXT4-29F (SEQ ID NO:120) were used to isolate a 2.1 kb DNA fragment that contains the entire coding sequences for the HGV proteins NS4b and NS5a, as well as the 3' end of NS4a and the 5' end of NS5b. PCR amplifications using these primers were performed as described in Example 4G. Successful amplification was observed with multiple HGV-infected sera including the following: T56633 was from a blood donor whose donation was rejected due to an ALT value above the cutoff; samples E21-A and E20 were derived from Egyptian individuals suffering from hepatitis; and sample AH0591 is derived from an Australian individual who developed fulminant hepatitis.

The amplified products of E21-A and E20 were cloned into the T overhang site of the vector T/A (obtained from InVitrogen, San Diego, Calif.) essentially as described in Example 6. The 2.1 kb HGV inserts from these 2 plasmids were then isolated by the digestion of approximately 20 ug of plasmid DNA with approximately 150 units of the restriction enzyme EcoRI. After incubation overnight at 37° C., the products of the digestion were separated by TAE agarose gel electrophoresis. The products were excised from the section of the agarose gel containing the fragment of interest. The agarose was melted and extraction of the liberated DNA was carried out using the "GENECLEAN II" kit according to the manufacturers instructions (Bio 101, La Jolla, Calif.).

The purified 2.1 kb fragments derived from the E21-A and E20 samples, as well as the DNA fragments obtained from PCR amplification of samples T56633 and AH0591, were digested separately with DNAse I as described in Example 12A. For all 4 samples digestion conditions were determined that resulted in the isolation of fragments of between 100 to 1000 nts in size. After purification and trimming (Example 12A) the fragments derived from each of the 4 HGV infected samples were ligated separately to different sets of SISPA linkers. After ligation the DNAs were SISPA amplified.

The amplified DNAs were separately digested overnight at 37° C. with approximately 100 units of EcoRI. The digested DNAs were then purified by spin column chromatography using G25 resin (5'3' Inc, Boulder, Colo.). Digested DNA from the samples T56633, AH0591, and E21-A were combined at a ratio of 1:1:1 and the mixture of DNAs was ligated into the EcoRI site of λgt11 as described in Example 12A. After packaging using the "GIGAPACK III XL" extract (Stratagene, LaJolla, Calif.), the resulting library was plated in the presence of IPTG and XGAL and determined to have a titer of approximately $1.0 \times 10^6$ phage/ml and a recombinant frequency of approximately 70%.

EXAMPLE 13

Immunoscreening of the Epitope Libraries

A. Isolation of Immunoreactive Y5 Clones.

Two HGV positive sera, PNF2161 and JC, were used for immunoscreening of the Y5 library, essentially as described in Example 2. The Y5 phage library was plated onto 20 plates at approximately 15,000 phage per plate. The plates were incubated for approximately 5 hours and were overlaid with nitrocellulose filters (Schleicher and Schuell) overnight. The filters were blocked by incubation in AIB (1% gelatin plus 0.02% Na azide) for approximately 6 hours. The blocked filters were washed once with TBS.

Ten Y5 library filters were incubated overnight, with agitation, with PNF2161 serum and ten filters with JC serum. Both sera were diluted 1:10 in AIB. In order to reduce non-specific antibody binding, the diluted sera had been pre-treated by incubation overnight with nitrocellulose filters to which wild type λgt11 were adsorbed.

The filters were removed from the sera, washed 3 times with TBS and incubated with goat anti-human alkaline phosphatase-conjugated secondary antibody (Promega; diluted 1/7500 in AIB) for one hour. The filters were washed 4 times with TBS. Bound secondary antibody was detected by incubation of the filters in AP buffer (100 mM NaCl, 5 mM MgCl$_2$, 100 mM Tris pH 9.5) containing NBT and BCIP.

Plaques that tested positive in the initial screen were picked and eluted in 500 μl of PDB (100 mM NaCl, 8.1 mM MgSO$_4$, 50 mM Tris pH 7.5, 0.02% Gelatin). The immunoreactive phage were purified by replating the eluted phage at a total density of 100–500 plaques per 100 mm plate. The plates were re-immunoscreened with the appropriate HGV-positive sera, essentially as described above. After color development several isolated, positive plaques were picked and put into 500 μl of PDB. After 1 hour of incubation, 2 μl of the re-purified phage PDB solution was used as template in a PCR reaction containing the 11F (SEQ ID NO:25) and 11R (SEQ ID NO:13) PCR primers. These primers are homologous to sequences located 70 nucleotides (nt) 5' and 90 nt 3' of the EcoRI site of λgt11. The PCR reactions were amplified through 30 cycles of 94° C. for 1 minute, 55° C. for 1.5 minutes and 72° C. for 2 minutes.

The PCR amplification reactions were size-fractionated on agarose gels. PCR amplification of purified plaques resulted in a single band for each single-plaque amplification reaction, where the amplified fragment contained the DNA insert plus approximately 140 bp of 5' and 3' phage flanking sequences. The amplified products, from PCR reactions resulting in single bands, were purified using a "S-300 HR" spin column (Pharmacia), following manufacturers instructions. The DNA was quantitated and DNA sequenced employing an Applied Biosystems automated sequencer 373A and appropriate protocols.

The above-described screening of the Y5 library with JC sera resulted in the purification and DNA sequencing of the positive-strand clones presented in Table 17. Positive-strand clones correspond to the 5' to 3' translation of the HGV sequence presented in SEQ ID NO:14—the polyprotein reading frame.

TABLE 17

| Clone | Screening Sera | Insert Size (base pairs) | Insert Size (amino acids) | Nucleic Acid SEQ ID NO. | Encoded Protein SEQ ID NO. |
|---|---|---|---|---|---|
| Y5-10 | JC | 210 | 62 | 64 | 65 |
| Y5-12 | JC | 333 | 94 | 66 | 67 |
| Y5-26 | JC | 303 | 93 | 68 | 69 |
| Y5-5 | JC | 153 | 36 | 70 | 71 |
| Y5-3 | JC | 162 | 44 | 72 | 73 |
| Y5-27 | JC | 288 | 86 | 74 | 75 |
| Y5-25 | JC | 165 | 36 | 76 | 77 |
| Y5-20 | JC | 165 | 19[1] | 78 | 79 |
| Y5-16 | JC | 234 | 56 | 80 | 81 |

[1]the clone contained a double insert, nt 69 to 126 of the clone insert correspond to HGV sequences.

These clones delineated 2 immunogenic regions within the putative NS5 protein of HGV. These two region, relative to the sequence presented as SEQ ID NO:14 are positions 6636 to 6821 and 7278 to 7385.

Further, screening of the Y5 library with PNF 2161 sera resulted in the purification and DNA sequencing of the following negative-strand clones presented in Table 18. Negative-strand clones correspond to the 5' to 3' translation of the sequence complementary to the HGV sequence presented in SEQ ID NO:14.

TABLE 18

| Clone | Screening Sera | Insert Size (base pairs) | Insert Size (amino acids) | Nucleic Acid SEQ ID NO. | Encoded Protein SEQ ID NO. |
|---|---|---|---|---|---|
| Y5-50 | PNF 2161 | 349 | 104 | 82 | 83 |
| Y5-52 | PNF 2161 | 119 | 20[1] | 84 | 85 |
| Y5-53 | PNF 2161 | 250 | 33[2] | 86 | 87 |
| Y5-55 | PNF 2161 | 143 | 20[3] | 88 | 89 |
| Y5-56 | PNF 2161 | 366 | 110 | 90 | 91 |
| Y5-57 | PNF 2161 | 231 | 65 | 92 | 93 |
| Y5-60 | PNF 2161 | 151 | 38 | 94 | 95 |
| Y5-63 | PNF 2161 | 125[4] | 25 | 96 | 97 |

[1]the clone contained a double insert, nt 46 to 105 of the clone insert correspond to HGV sequences.
[2]the clone contained a double insert, nt 19 to 118 of the clone insert correspond to HGV sequences.
[3]the clone contained a double insert, nt 70 to 126 of the clone insert correspond to HGV sequences.
[4]the insert contains an extra, non-HGV sequence between nucleotides 19 and 35.

All of these sequences contain portions of the original HGV clone 470-20-1 isolated using the PNF 2161 serum.

Additional epitope clones from the Y5 library were isolated as follows. The Y5 library was screened with the HGV infected sera J21689 and T56633 using the methods described in Example 13. Greater than 400 positive plaques were obtained, indicating the presence of a strongly immunogenic sequence recognized by both of these HGV infected sera. Ten of these positive plaques were purified and DNA sequenced. The results obtained from the DNA sequencing are delineated in Table 19.

TABLE 19

| CLONE | HGV VAR | SERA | START* | STOP |
|---|---|---|---|---|
| Y5-114-1A | PNF | J21689 | 6636 | 6827 |
| Y5-114-2B | PNF | J21689 | 6678 | 6935 |
| Y5-121-19A | PNF | T56633 | 6678 | 7063 |
| Y5-121-11A | PNF | T56633 | 6636 | 6917 |
| Y5-121-12A | PNF | T56633 | 6636 | 6959 |
| Y5-121-15A | PNF | T56633 | 6636 | 6917 |
| Y5-121-16A | PNF | T56633 | 6636 | 6989 |
| Y5-121-17A | PNF | T56633 | 6636 | 7082 |
| Y5-121-20A | PNF | T56633 | 6636 | 6929 |
| Y5-121-18A | PNF | T56633 | 6636 | 6896 |

*start/stop locations are given relative to SEQ ID NO:14

Comparison of these sequences with those obtained previously from screening this library indicated that these clones all contained the same epitope(s) that are contained in the previously isolated epitope clone Y5-10. Two of the clones, Y5-114-2B and Y5-121-19A are distinguished by the fact that their 5' ends are located 14 amino acids closer to the carboxy terminal of NS5a than the previously observed start of clones Y5-10, Y5-12, and Y5-26. None of the above clones has its 3' end interior to that observed in the clone Y5-10. Thus a minimal sequence of this epitope is contained within amino acid sequence (SEQ ID NO:272).

B. Antigenic Clones from the ENV Library.

The ENV library was screened with HGV serum J21094. This serum (J21094) was identified as HCV positive based on the first generation (c-100) HCV test. Subsequent testing of the initial J21094 serum sample, and of subsequently obtained J21094 samples, by PCR and with other HCV antigens confirmed that the source individual for the serum was HCV infected. Evidence for the presence of HGV nucleic acid was obtained via PCR analysis using the 470-20-1 and NS5 primer sets.

A number of phage clones were identified as immunoreactive with J21094 serum. The phage were plaque purified and sequenced. Seven of the clones (Q7-12-1, Q7-16-2-2, Q7-15-2, Q7-17-2-1, Q7-19-1, and Q7-19-2-1) contained the same insert. The nucleotide sequence for Q7-12-1 is presented as SEQ ID NO:143 (polypeptide sequence, SEQ ID NO:144).

One additional clone, Q7-16-1, obtained by the method just described, has the same 5' end as Q7-12-1, but is 26 amino acids shorter at the 3' end.

C. Antigenic Clones from the NS3 Library.

A one to one mixture of the F9/R9 phage and F10/R10 phage were screened using the following sera: PNF 2161, J21689 and E57963. Both J21689 and E57963 are sera that test co-positive for HCV and HGV by PCR (using multiple primers). Each immunoscreening was of 10 plates or approximately 150,000 phage. Some of the immunopositive clones identified in these screens are as follows.

Clone Y12-10-3 (polynucleotide sequence, SEQ ID NO:145; polypeptide sequence, SEQ ID NO:146) was identified by its immunoreactivity with J21689 serum. The clone expresses an 88 amino acid insert from HGV NS3.

Clone Y12-15-1 (polynucleotide sequence, SEQ ID NO:147; polypeptide sequence, SEQ ID NO:148) was identified by its immunoreactivity with E57963 serum. The clone expresses a 64 amino acid insert from the NS3 protein of HGV. This sequence is located approximately 70 amino acids 5' to clone Y12-10-3.

D. Antigenic Clones from the NS2 Library.

Multiple positive plaques were isolated by screening the NS2 library with HGV-positive serum T56633. Eleven of these plaques were subsequently purified and DNA sequenced. The locations of the inserts contained within these plaques (relative to SEQ ID NO:14) are delineated in Table 20.

TABLE 20

| CLONE | HGV VAR | SERA | START* | STOP |
|---|---|---|---|---|
| Q9-18-5 | PNF | T56633 | 3071 | 2778 |
| Q9-18-3 | PNF | T56633 | 2951 | 2745 |
| Q9-20-4 | PNF | T56633 | 3002 | 2745 |
| Q9-18-2 | PNF | T56633 | 2990 | 2745 |
| Q9-20-8 | PNF | T56633 | 3062 | 2745 |
| Q9-20-5 | PNF | T56633 | 2972 | 2787 |
| Q9-17-1 | PNF | T56633 | 2990 | 2745 |
| Q9-19-3 | PNF | T56633 | 2982 | 2745 |
| Q9-19-1 | PNF | T56633 | 2982 | 2745 |
| Q9-19-5 | PNF | T56633 | 2984 | 2745 |
| Q9-20-2 | PNF | T56633 | 3027 | 2745 |

*in this table the locations are given with respect to SEQ ID NO:14. The actual sequence of the clones are the complement of the indicated fragment.

All of the immunoclones express portions of the same open reading frame (ORF). This reading frame is encoded by the HGV polynucleotide strand that is complementary to the sequence encoding the polyprotein. This ORF extends between nts 6322 and 6865 of the sequence complementary to SEQ ID NO:14. There is a Methionine that could serve as a site of translation initiation located at nt 6388 of the complementary strand that would allow for the production of a 159 amino acid protein.

The smallest amino acid sequence common to all of the 11 sequenced clones is located between nts 6342 to 6606 (relative to the complementary strand of SEQ ID NO:14). The amino acid sequence encoded by this region of the negative strand of HGV-PNF 2161 is presented as SEQ ID NO:273.

The subcloning and subsequent Western blot analysis of immunoreactive negative strand regions is described below.

E. Antigenic Clones from the VNS5A Library.

Approximately $1.5 \times 10^5$ phage from the VNS5a library was plated out and subsequently screened with the HGV-positive serum J29374 using the procedures described in Example 13. Immunoscreening of the VNS5a library with J29374 resulted in the isolation of multiple positive plaques. Six of these plaques were purified and subsequently DNA sequenced. The original strain of the DNA sequence obtained could be determined by which of the SISPA linker sequences was present at the 5' and 3' ends of the clones. The locations of the starts and stops of the obtained clones (relative to SEQ ID NO:14) and their source sera are summarized in Table 21.

TABLE 21

| Clone | HGV Variant Source | Sera | Start* | Stop |
|---|---|---|---|---|
| Q11-14-2 | AH0591 | J29374 | 6525 | 6749 |
| Q11-16-1 | E21-A | J29374 | 6432 | 6935 |
| Q11-10-2 | T56633 | J29374 | 6579 | 6710 |
| Q11-18-2 | T56633 | J29374 | 6579 | 6758 |
| Q11-22-1 | T56633 | J29374 | 6576 | 6680 |
| Q11-9-1 | T56633 | J29374 | 6531 | 6851 |

All of these clones contain the sequence of the clone Q11-22-1 in common (SEQ ID NO:274). This amino acid sequence is located immediately 5' to the minimal sequence of the Y5-10 epitope. Thus it defines an additional unique epitope in HGV NS5a (along with Y5-10 and Y5-5). Comparison of the observed amino acid sequence of these 3 HGV variants with the sequence of the PNF-2161 and JC isolates reveals few amino acid substitutions.

EXAMPLE 14

Further Characterization of Immunoreactive Clones

A. Subcloning.

1. Y5 CLONES.

Clones Y5-10, Y5-16, and Y5-5 were selected for subcloning into the expression vector pGEX-HisB. PCR primers were designed which removed the extraneous linker sequences at the end of these clones. These primers also introduced (i) a NcoI site at the 5' end (relative to the coding sequence) of each insert, and (ii) a BamHI site at the 3' end of each insert. Using these primers (see Table 22), the DNA fragments were amplified from 2 μl of the plaque pure stocks.

TABLE 22

| Clone | Primer Set | |
|---|---|---|
| Y5-10 | Y5-10-F1 | SEQ ID NO:99 |
|  | Y5-10-R1 | SEQ ID NO:100 |
| Y5-16 | Y5-16F1 | SEQ ID NO:101 |
|  | 470ep-R3 | SEQ ID NO:102 |

TABLE 22-continued

| Clone | Primer Set | |
|---|---|---|
| Y5-5 | Y5-5-F1 | SEQ ID NO:103 |
| | 470ep-R3 | SEQ ID NO:102 |

Amplifications were performed as follows: 30 cycles of 94° C. for 1 minute, 50° C. for 1.5 minutes, and 72° C. for 2 minutes. After amplification the resulting DNAs were purified using "WIZARD PCR," spin columns, the samples eluted in 50 μl, and digested overnight with NcoI and BamHI. A minimum of 30 units of each enzyme was used in the restriction endonuclease digestions (NcoI, Boehringer Mannhiem; BamHI, Promega).

The digested PCR fragments were ligated overnight to expression vector pGEX-HisB that had been digested with NcoI and BamHI. Each set of ligated plasmids was independently used to transform E. coli strain W3110, using a heat shock protocol (Ausubel, et al.; Maniatis, et al.). Transformants were selected on LB plates containing 100 μg/ml ampicillin and resistant colonies were used to inoculate 2 mls of LB containing 100 μg/ml ampicillin. Cultures expressing non-recombinant sj26/his protein were also prepared.

After incubation overnight at 37° C. the cultures were diluted ¹/₁₀ into 2 mls of fresh LB plus ampicillin and grown for an additional 1 hour at 37° C. IPTG was added to a final concentration of 0.2 mM and the cultures were grown for an additional 3 hours at 37° C. The bacteria were pelleted by centrifugation and the bacterial pellet was resuspended in 100 μl PBS. To the pellet, 100 μl of 2× SDS sample buffer (0.125M Tris, pH 6.8, 10% glycine, 5% β-mercaptoethanol, 2.3% SDS) was added. The resulting lysates were vortexed and heated to 100° C. for 5 minutes. Aliquots (15 μl) of each lysate were loaded onto a 12% acrylamide SDS-PAGE gel.

The expressed proteins were size-fractionated by electrophoresis. The separated proteins were transferred from the gel to nitrocellulose filters using standard techniques (Harlow, et al.). An additional gel containing the expressed proteins was stained using coomasie blue protein stain.

Transformants carrying plasmids Y5-10, Y5-5 and Y5-16 expressed significant amounts of correctly sized recombinant fusion proteins. The identity of the recombinant fusions were confirmed by incubating a Western blot (prepared above) with a murine monoclonal antibody that is specifically immunoreactive with sj26 (Sierra BioSource, Gilroy, Calif.).

Additional confirmation that the picked colonies contained the appropriate insert was obtained as follows. A phage solution for each colony was prepared by inoculating 40 μl of TE solution with a toothpick containing a small amount of bacteria putatively expressing a recombinant clone had been inoculated. A 5 μl sample was taken from each solution and separately PCR amplified.

The amplifications employed the appropriate forward primer, (e.g., Y5-10 F for a colony putatively expressing Y5-10) and a reverse primer (SEQ ID NO:104) homologous to a sequence located 3' to the cloning sites of the plasmid pGEX-HisB. The PCR amplifications were for 25 cycles as follows: 94° C. for 1 minute, 50° C. for 1.5 minutes and 72° C. for 2 minutes. All of the colonies selected for further analysis produced a correctly sized DNA band with no other obvious bands under these conditions.

The immunoreactivity of the antigens expressed from the Y5-10, Y5-16, & Y5-5 inserts (expressed as sj26-his fusion proteins) was determined as follows. Aliquots (15 μl) of the crude lysates prepared above were size-fractionated by SDS-PAGE using a 12% acrylamide gel. The proteins were electro-blotted ("NOVEX MINICELL MINIBLOT II," San Diego, Calif.) onto nitrocellulose filters. The filters were then individually incubated with one of the following sera: JC, PNF 2161, and super normal serum 4 (SN4) (R05072) as a negative control. In addition, one filter was incubated with anti-sj26 monoclonal antibodies (RM001; Sierra BioSource).

As expected, the recombinant protein produced by the bacteria expressing the antigens encoded by the Y5-10, Y5-5, and Y5-16 inserts all reacted with JC sera. No reactivity was observed with either PNF 2161 or SN4 sera. All proteins appeared to be expressed at similar levels as determined by their reactivity to the anti-sj26 monoclonal antibody. The Y5-5 and Y5-10 encoded proteins were selected for further purification.

E. coli carrying Y5-5- and Y5-10- containing pGEX-HisB vectors were cultured and expression of the fusion protein induced as described above. The cells were lysed in PBS, containing 2 mM PMSF, using a French Press at 1500 psi. The crude lysate was spun to remove cellular debris. The supernatant was loaded onto the glutathione affinity column at a high flow rate and the column was washed with 10 column volumes of PBS. The Y5-5 and Y5-10 fusion proteins were eluted with 10 mM Tris pH 8.8 containing 10 mM glutathione.

Each of the fusion protein samples was diluted ¹/₁₀ with Buffer A (10 mM Tris pH 8.8, containing 8M urea) and loaded onto a nickel charged-chelating "SEPHAROSE" fast flow column. Each column was repeatedly washed with Buffer A until no further contaminants were eluted. The fusion proteins were eluted using a gradient of imidazole in buffer A. An imidazole gradient was run from 0 to 0.5M imidazole in 20 column volumes. Fractions were collected.

Each set of fractions was analyzed by standard SDS-PAGE using 12% polyacrylamide gels. Pools of the Y5-5 and Y5-10 fusion protein-containing fractions were separately made.

Figures 8A, 8B, 8C, 8D:
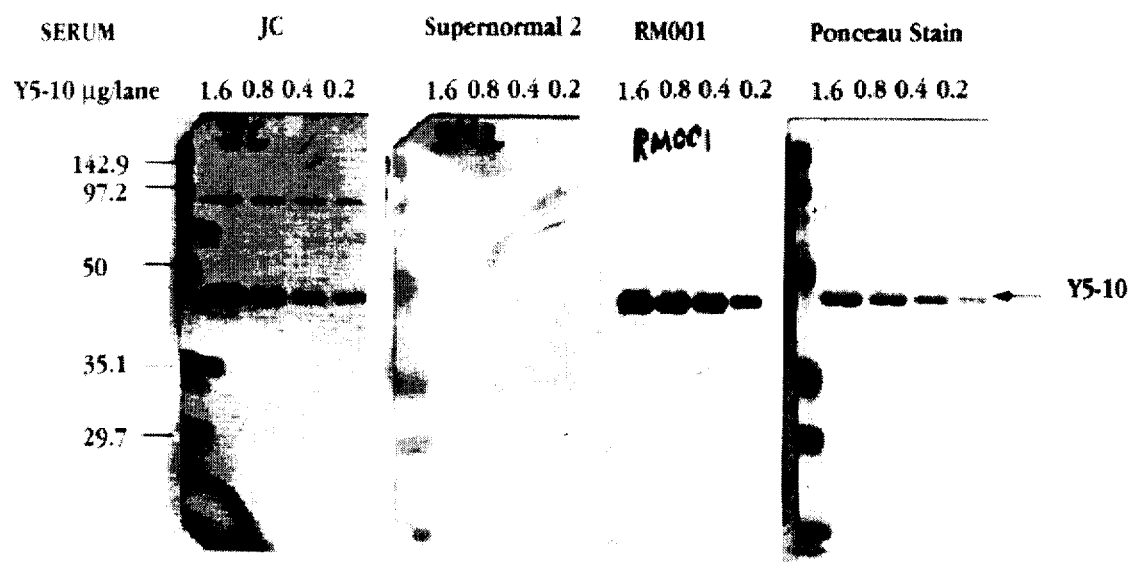
FIGS. 8A to 8D show the results of Western blot analysis of the purified HGV Y5-10 antigen.
Figures 9A, 9B, 9C, 9D:
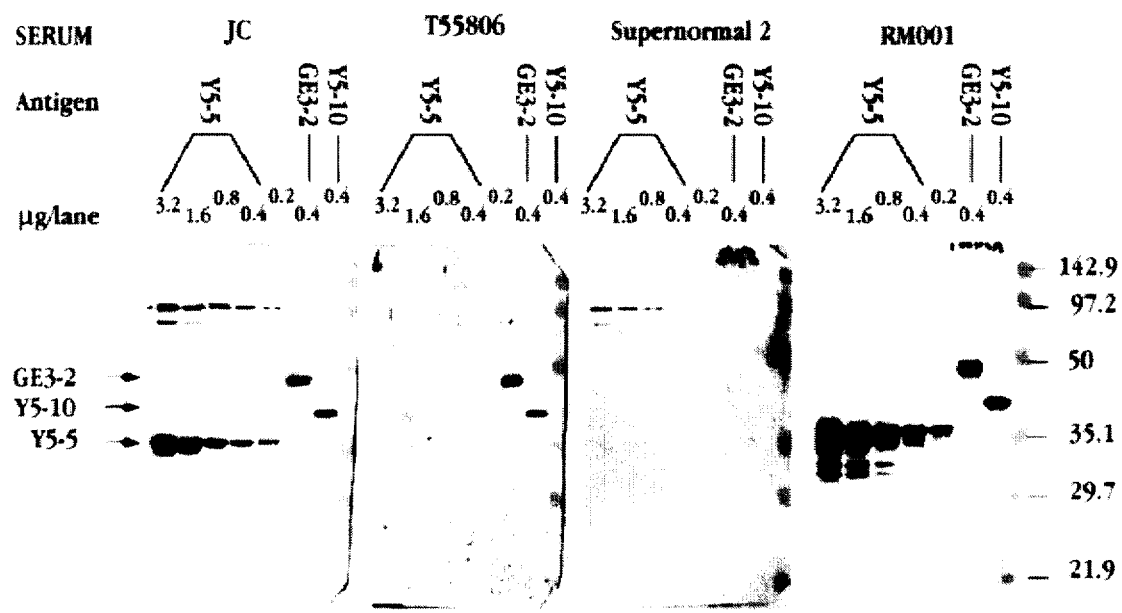
FIGS. 9A to 9D show the results of Western blot analysis of the following antigens: Y5-5, GE3-2 and Y5-10.

FIGS. 8A to 8D show the results of Western blot analysis of the following samples (μg/lane): lane 1, Y5-10 antigen 1.6 μg; lane 2, Y5-10 antigen 0.8 μg; lane 3, Y5-10 antigen 0.4 μg; and lane 4, Y5-10 antigen 0.2 μg. Human serum JC (FIG. 8A) and Super Normal 2 serum (FIG. 8B) were diluted 1:100. The anti-GST mouse monoclonal antibody RM001 (FIG. 8C) was diluted 1:1000. FIG. 8D shows the Y5-10 antigen resolved by SDS-PAGE, transferred onto the nitrocellulose membrane and stained with Ponceau S protein stain (Kodak, Rochester, N.Y.; Sigma). Arrow indicates the location of Y5.10 antigen. These results demonstrate that Y5-10 is specifically immunoreactive with N-(ABCDE) human serum JC.

FIGS. 9A to 9D show the results of Western blot analysis of the following samples: lane 1, Y5-5 antigen 3.2 μg; lane 2, Y5-5 antigen 1.6 μg; lane 3, Y5-5 antigen 0.8 μg; lane 4, Y5-5 antigen 0.4 μg; lane 5, Y5-5 antigen 0.2 μg; lane 6, GE3-2 antigen 0.4 μg; and lane 7, Y5-10 antigen 0.4 μg. Human serum JC (FIG. 9A), T55806 (FIG. 9B), and Super Normal 2 serum (FIG. 9C) were diluted 1:100. RM001, the anti-GST mouse monoclonal antibody, (FIG. 9D) was diluted 1:1000. Arrows indicate the locations of antigens Y5.5, GE3.2 and Y5.10. These results show specific immunoreactivity of the Y5-5 antigen with the JC serum. Further, the antigens GE3-2 and Y5-10 were reactive with T55806. However, the Y5-5 antigen was not reactive with the HGV-positive sera T55806.

The Y5-10 antigen was also size-fractionated by SDS polyacrylamide gel electrophoresis. The gel was stained using coomasie blue protein stain. The gel was scanned for purity with a laser densitometer. The purity of the Y5-10 fusion protein was approximately 95%.

2. ENV CLONES.

The immunoclone Q7-12-1 was originally isolated by screening the ENV epitope library with the HGV positive sera J21094. Sequence specific primers were employed to isolate the HGV insert contained within the Q7-12-1 λgt11 clone. The Q7-12-1 insert was excised and cloned into pGEX-Nde. The sequence of the insert was confirmed by the DNA sequencing (SEQ ID NO:275).

3. NS3 CLONES.

The immunoclone Y12-15-1 was originally isolated by screening the NS3 epitope library with the HGV positive sera E57963. Sequence specific primers were employed to isolate the HGV insert contained within the Y12-15-1 λgt11 clone. The Y12-15-1 insert was excised and cloned into pGEX-Nde. The sequence of the insert was confirmed by the DNA sequencing (SEQ ID NO:276).

The immunoclone Y12-10-3 was originally isolated by screening the NS3 epitope library with the HGV positive sera J21689. Sequence specific primers were employed to isolate the HGV insert contained within the Y12-10-3 λgt11 clone. The Y12-10-3 insert was excised and cloned into pGEX-Nde. Production of fusion proteins by selected clone was evaluated by Western blot analysis. The sequence of the insert was confirmed by the DNA sequencing (SEQ ID NO:277).

4. NS2 CLONES.

Multiple negative strand immunoclones derived from sequences complementary to the sequences of the NS2 region of SEQ ID NO:14 were isolated. There are at least 2 significant ORFs encoded by the negative strand of HGV. The first of these ORFs, represented by the Q9 series of clones was described above. The second of these ORFs is located between nts 6723 and 7259 of the complement of SEQ ID NO:14 and also possess a 5' methionine at nt 6774. The second ORF encodes a 162 amino acid protein.

Selected portions of the sequences of both of these negative strand ORFs were cloned into the expression vector pGEX-Nde. All of these subclones were obtained by the PCR amplification of PNF 2161 SISPA material using appropriate oligonucleotide primers, thus they contain the sequence of the HGV-PNF 2161 variant. Table 23 indicates the names, size of the ORF and locations relative to the complement of SEQ ID NO:14.

TABLE 23

| NAME/ORF | ORF | FROM NT (ATG) | TO NT |
|---|---|---|---|
| 5' NEG ORF | 159 AA | 6388 | 6865 |
| 3' NEG ORF | 162 AA | 6722 | 7258 |
| NORF-F1/R1 | 3' | 7107 | 7259 |
| NORF-F4/R1 | 3' | 6900 | 7259 |
| NORF-F4/KR2 | 3' | 6901 | 7172 |
| NORF-F2/R1 | 3' | 6744 | 7259 |
| NORF-KF2/R4 | 5' | 6684 | 6865 |
| NORF-KF1/R2 | 5' | 6881 | 6742 |
| NORF-F3/R2 | 5' | 6389 | 6742 |
| NORF-F2/R3 | 3' | 6744 | 6899 |
| K3P-KF2/KR1 | 5' | 6684 | 6772 |
|  | 3' | 6744 | 6791 |

The first 2 lines of this table identify the locations of the NS2 region 5' and 3' negative strand ORFs relative to the complement of SEQ ID NO:14. The remaining lines indicate the specific nucleotide sequences expressed by all of the 9 clones. Note that several of the clones express amino acids located 5' to the hypothetical HGV initiating methionine of the ORF. Also note that the last clone listed, K3p-KF2/KR1, is a chimera expressing the indicated portions of the 5' ORF followed by the indicated portions of the 3' ORF.

All of the DNA fragments were subsequently cloned into pGEX-Nde. Insert containing clones were also identified and confirmed.

5. NS5A CLONES.

Table 24 lists a number of NS5a clones and the regions of SEQ ID NO:14 to which they correspond.

TABLE 24

| Name | HGV Source | Start | Stop |
|---|---|---|---|
| EXY10-F2 | PNF | 6416 | 6827 |
| EXY10-F3 | PNF | 6537 | 6827 |
| Q11-F1-R1 | T56633 | 6537 | 6680 |
| Q11-F1-R2 | T56633 | 6537 | 6827 |
| Q11-F2-R1 | T56633 | 6576 | 6680 |
| Q11-F2-R2 | T56633 | 6576 | 6827 |
| Y5-12 | PNF | 6633 | 6917 |
| EXY12 | PNF | 6918 | 6977 |
| EXY10F14 | PNF | 6822 | 6977 |

These sequences were cloned into the vector pGEX-Nde for expression of the encoded protein antigens.

B. Western Blot Analysis of Selected HGV Subclones.

To determine the reactivity of both the negative and positive strand constructs described above whole cell lysates from bacteria expressing the various HGV subclones were prepared essentially as described in Example 13B. Aliquots of the expressed proteins were then fractionated by SDS-PAGE, the proteins transferred to nitrocellulose filters, and the filters probed with HGV-positive or control sera (e.g., anti-SJ26 MAB RM01). The blots were incubated with an appropriate reporter antibody.

With respect to the HGV proteins tested, clear immunoreactivity to the protein NORF-F3/R2 was detected with the HGV sera J21689 and T56633. The NORF-F3/R2 subclone expresses the amino acid sequences that were also encoded by the Q9 series of negative strand epitope clones. The observed strong reactivity with HGV sera T56633 confirms the immunoreactivity of this region of the negative strand of HGV. Reactivity to the NORF-F3/R2 protein was not observed with the sera from the HGV negative individual R04316 or any of 5 other HGV negative supernormal sera tested.

Additional blots indicated that the other major 5' ORF clone NORF KF2-R4, which expresses amino acids of the carboxy terminal half of the 5' negative strand ORF located does not react with the HGV-positive sera T56633. This observation in conjunction with the locations of the Q9 epitope clones described above suggest that the immunogenic epitope of this portion of the negative strand is contained within the 55 amino acid delineated above (SEQ ID NO:273). The fact that this sequence is recognized by other HGV antisera, including J21689, indicates that immunoreactivity towards this sequence is relatively widespread among HGV infected individuals.

Further, clear immunoreactivity with the Y12-10-3 protein was observed with the HGV-infected sera J21689, J29374, and E57963. The specificity of this reactivity is additionally supported by the failure to observe immunoreactivity with the HGV antisera J29374 or E57963 in the absence of the induction of Y12-10-3 protein expression by IPTG. No reactivity to Y12-10-3 was observed with any of 7 supernormal sera tested.

EXAMPLE 15

A Multi-Antigen HGV Diagnostic Assay

Although the epitope clones described above do not appear to be reactive with all HGV PCR-positive sera, many of these clones react with a substantial fraction of the HGV infected sera they have been tested against. Additionally these proteins have not exhibited substantial cross reactivity with HGV-negative sera. It is therefore possible to construct a diagnostic assay in which several of these proteins are combined so that the individual reactivities of the protein are summed. Such an assay is expected to have a relatively high sensitivity for the detection of HGV-positive sera and a relatively low background reactivity with HGV-negative sera.

Exemplary epitopes/antigens useful in such an assay include, but are not limited to, NORF-F3/R2 (NS2-Neg strand), Y12-10-3 (NS3), Q11-F2-R1 (NS5a), Y5-10 (NS5a), Y5-5 (NS5a), Q11-F2-R2 (combines 2 epitopes of NS5a).

For this assay, individual antigens are typically selected that contain different unique epitopes that recognized different subset of HGV-positive sera. Further, such antigens typically do not significantly react with HGV-negative sera. Following the guidance of the present invention, additional useful immunogenic clones can be isolated.

A multi-antigen diagnostic assay can take many formats. In one embodiment, the assay might entail immobilizing each of, et al., 5 HGV proteins and control proteins at separate locations on a nitrocellulose strip or other convenient solid phase format. Alternatively the non-viral portions of, for example, an HGV-fusion protein could be modified, either by insertions or deletions such that they would naturally migrate to easily distinguishable locations upon SDS PAGE and subsequent Western blot analysis. Strips are then incubated in test sera. After detection of bound antibody, a serum may then be scored based on (i) the number of antigens with which it is immunoreactive, and (ii) the strength of the immunological reactions. Reactivity to a non-HGV control protein would render a serum un-typeable. Reactivity with no HGV protein would classify a serum as HGV-negative.

ELISA-based screening assay can be formed by combining purified antigen proteins in a single reaction zone or by creating protein constructs that express 2 or more of the reactive epitopes as a single protein (e.g., a HGV mosaic polypeptide). The methods to construct mosaic polypeptides is described herein. Q11-F2-R2 construct described above, in fact, represents a "matrix protein" that encodes 2 individual epitopes in a single polypeptide chain. Western blot assays may serve as a confirmatory assay for such an ELISA screening test.

Alternatively or in addition, full length HGV proteins, such as E2, NS5a and NS3 might be placed in a single reaction zone. Sera reactive with such proteins may also be confirmed as HGV positive by Western blot assay.

EXAMPLE 16

Expression of Large HGV Polypeptides

A. Expression of Larger HGV Antigens in *E. coli*

1. Cloning and Expression.

To identify conformational HGV epitopes (not covered by small overlapping HGV constructs or by phage library screening) larger HGV protein constructs were generated in the pET-21a(+) vector (Novagen, Wis.) based on the prediction of cleavage sites (Bazan, et al., 1989; Chambers, et al., 1990b; Grakoui, et al., 1993; Kyte and Doolittle, 1982). Individual HGV protein constructs were generated in a similar fashion to HGV sequences cloned into pGEX vectors.

Briefly, selected HGV sequences were RT-PCR amplified from a HGV(+) human sera source using HGV sequence specific primers. The primers were engineered to contain appropriate restriction sites for cloning manipulations in the pET vector. Coding sequences of interest were typically inserted between the EcoRI site and the HindIII sites in the vector to produce 5' in-frame fusions with T7.Tag leader sequence and 3' in-frame fusion with a hexamer histidine sequence. T7.Tag (an 11 amino acid sequence) allows the detection of the fusion proteins using an anti-T7.Tag monoclonal antibody (Novagen, Wis.). The histidine hexamer at the carboxyl end of the fusion protein allows the purification of the protein using immobilized metal ion affinity chromatography.

HGV fragments were ligated into appropriately digested pET-21a(+) vectors. Ligated products were transformed into competent *E.coli* (HMS174; Novagen, Wis.). Plasmid DNA from transformed HMS174 was analyzed for the presence of HGV sequences by PCR, using primers T7F(SEQ ID NO:157) and T7R(SEQ ID NO:158), which are homologous to pET-21a(+) vector sequences flanking the inserted molecule. The size of the PCR product was the insert size plus approximately 260 bp derived from the vector.

For each construct the PCR results confirmed the presence of the insert sequences. Transformants with appropriate inserts were selected, plasmid DNAs with HGV inserts prepared and introduced into HMS174(DE3) competent *E.coli* (Novagen, Wis.) for the expression of HGV proteins.

Expression of HGV proteins was induced with 1 mM IPTG. Expression of the T7.Tag fusion proteins was monitored by the appearance of the predicted size proteins on the Coomassie blue stained gel. Expression of the fusion proteins was confirmed by Western blot analysis using anti-T7.Tag antibody (Novagen, Wis.). HGV proteins expressed in pET-21a(+) vector are shown in the Table 25. The start and end points of the expressed sequences are given relative to SEQ ID NO:14. The amino acid sequence of GE-Cap is shown in SEQ ID NO:185.

TABLE 25

| Name | Domain | Serum Source | Start | End | HGV aa | Size (KDa) |
| --- | --- | --- | --- | --- | --- | --- |
| GE-Cap | capsid | T55806 | 271* | 480* | 70 | 11 |
| GE-E1a | E1 | PNF | 594 | 1148 | 185 | 24 |
| GE-E2 | E2/NS1 | PNF | 1149 | 2183 | 345 | 41 |
| GE-NS2b | NS2b | PNF | 2904 | 3254 | 117 | 16 |
| GE-NS3 | NS3 | PNF | 3255 | 5081 | 609 | 70 |
| GE-NS4a | NS4a | PNF | 5082 | 6083 | 334 | 40 |
| GE-NS4b | NS4b | PNF | 6084 | 6536 | 151 | 20 |
| GE-NS4 | NS4 | PNF | 5082 | 6536 | 485 | 57 |

TABLE 25-continued

| Name | Domain | Serum Source | Start | End | HGV aa | Size (KDa) |
|---|---|---|---|---|---|---|
| GE-NS5a | NS5a | PNF | 6537 | 7529 | 331 | 39 |
| GE-NS5b | NS5b | PNF | 7530 | 9044 | 505 | 59 |

*These sequences are given relative to SEQ ID NO:178

Figure 12:
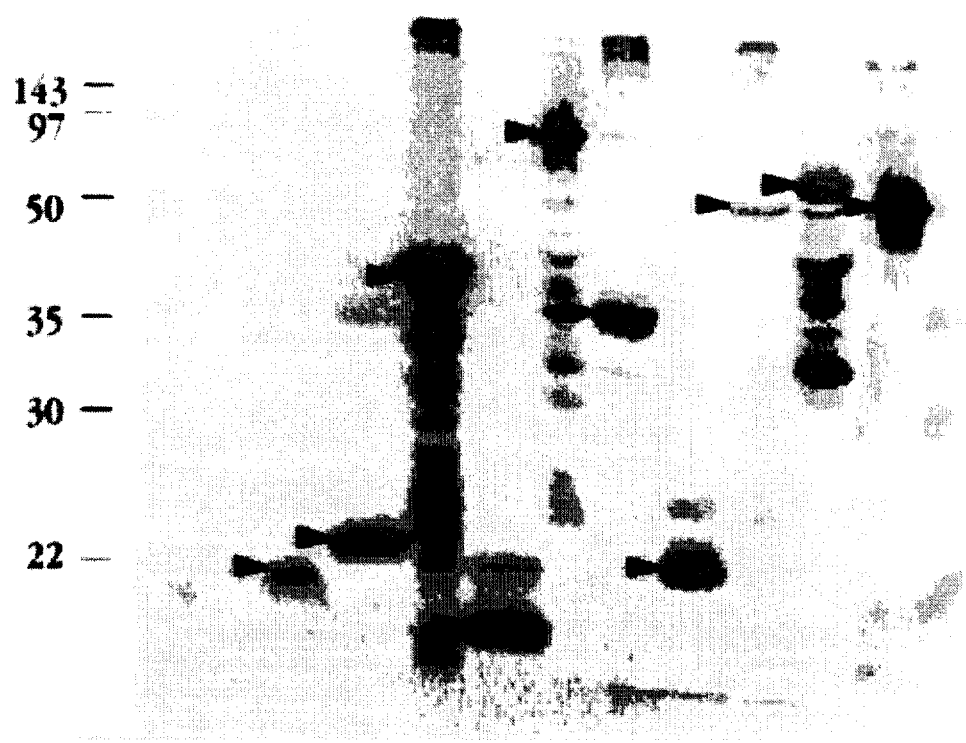
FIG. 12 shows the results of Western blot analysis of HGV pET clones with anti-T7.Tag monoclonal antibody.

FIG. 12 shows the expression of each HGV proteins demonstrated by Western blot analysis with T7.Tag monoclonal antibody. The lanes in FIG. 12 are as follows: Lane 1, pre-stained molecular weight marker (Bio-Rad); Lane 2, uninduced GE-Cap lysate; Lanes 3–11, IPTG induced lysates of GE-Cap, E1a, E2, NS2b, NS3, NS4a, NS4b, NS4, and NS5b lysate, respectively. Lane 12 contained 1 µg of purified NS5a. Locations of each antigen are marked with arrow heads. As shown in FIG. 12 all the HGV proteins were expressed in E.coli.

2. Western Blot Analyses of HGV proteins expressed in pET vector

Western blot analyses of the HGV protein expressed in pET vector were performed as described in Example 11C using E. coli whole cell lysates and pre-absorbed sera. The results of these analyses demonstrated that several of pET HGV proteins are specifically immunoreactive with HGV-positive human sera but not with HGV-negative human sera. GE-NS2b-1 protein was immunoreactive with J21689 serum. The GE-NS5a-3 protein was immunoreactivity with several HGV (+) sera on Western blot analysis, including JC, T55806, T56633, J21689, E57963 and R0001. Among these sera T55806, J21689 and E57963 are HCV co-positive (by the PCR analysis). Neither GE-NS2b-1 nor GE-NS5a-3 were immunoreactive with several HGV negative sera tested.

FIGS. 10A to 10F show the exemplary results of a series of Western blot experiments examining the reactivity of antigens GE-NS2b and GE-NS5a3. The lanes in each blot of FIGS. 10A to 10F are as follows: Lane 1, uninduced GE-NS2b lysate; Lane 2, IPTG induced GE-NS2b lysate; Lane 3, uninduced GE-NS5a lysate; and Lane 4, IPTG induced GE-NS5a lysate. Each blot was incubated with a human serum or mouse monoclonal antibody: FIG. 10A, J29374; FIG. 10B, J21689; FIG. 10C, T56633; FIG. 10D, T43608 (super normal serum); FIG. 10E, Anti-T7.Tag; and FIG. 10F, coomassie stained gel. The serum or monoclonal antibody that was used is indicated above each blot. Human sera were diluted 1:100 and anti-T7.Tag mouse monoclonal antibody was diluted 1:1000.

In addition to the sera listed above, additional HGV-PCR positive sera have been screened using GE-NS5a. The results of all these analyses have demonstrated the reactivity of the GE-NS5a antigen with multiple HGV-infected sera. GE-NS5b was immunoreactive with HGV(+) sera JC and T55806 but was not immunoreactive with HGV(–) negative sera tested. FIGS. 13A to 13E show the results of a series of Western blot experiments examining the reactivity of antigen GE-NS5b. The lanes in each blot the figures are as follows: Lane 1, pre-stained molecular weight marker (Bio-Rad); Lane 2, uninduced GE-NS5b lysate; Lane 3, IPTG induced GE-NS5b lysate.

Figures 13A, 13B, 13C, 13D, 13E:
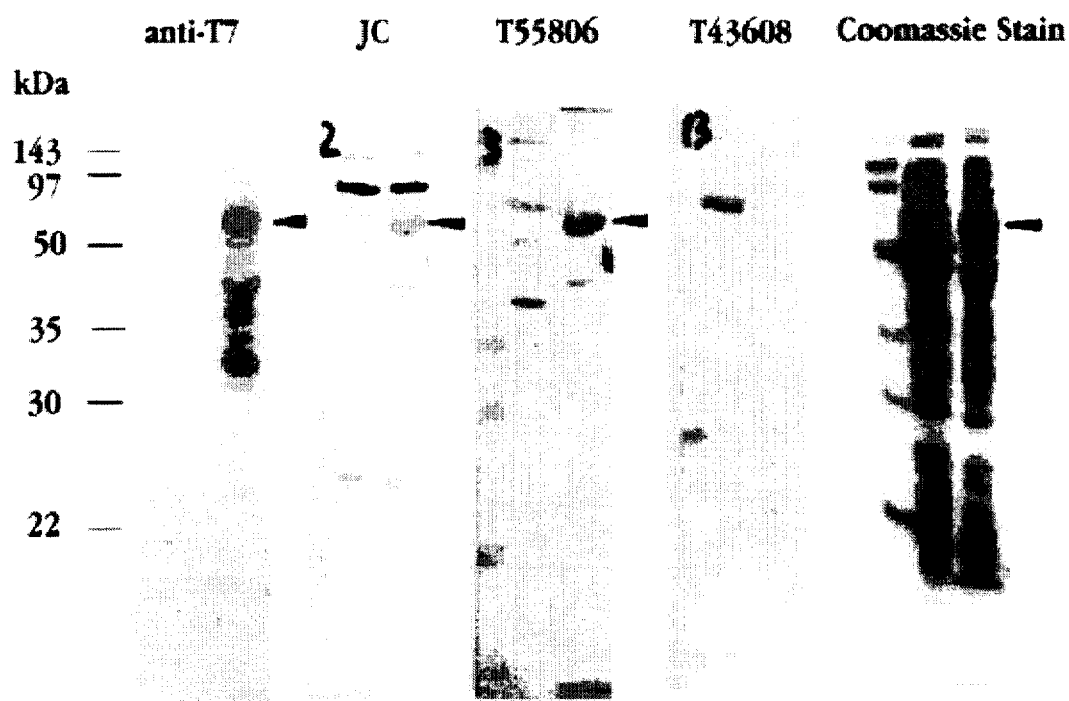
FIGS. 13A to 13D show the results of Western blot analysis of HGV pET clone GE-NS5b.
FIG. 13E shows a corresponding coomassie stained gel.

Each blot was incubated with a human serum or mouse monoclonal antibody: FIG. 13A, anti-T7.Tag monoclonal antibody; FIG. 13B, JC; FIG. 13C, T55806; and FIG. 13D, T43608 (super normal serum). FIG. 13E is a Coomassie Stain.

FIGS. 14A to 14D show the results of a series of Western blot experiments examining the reactivity of antigen GE-E2. The lanes in each of FIGS. 14A to 14D are as follows: Lane 1, pre-stained molecular weight marker (Bio-Rad); Lane 2, uninduced GE-E2 lysate; Lane 3, IPTG induced GE-E2 lysate. Each blot was incubated with a human serum or mouse monoclonal antibody: FIG. 14A, anti-T7.Tag monoclonal antibody; FIG. 14B, 3831781; and FIG. 14C, T43608 (super normal serum). FIG. 14D is Coomassie Stain. The serum or monoclonal antibody that was used is indicated above each blot. GE-E2 protein was immunoreactive with HGV-positive serum 3831781 but was not immunoreactive with supernormal serum T43608 (FIGS. 14B and 14C, respectively).

Antigens GE-Cap and GE-NS4a were also specifically immunoreactive with HGV(+) serum J21689.

B. Expression larger HGV Antigens in Insect Cells.

Expression of proteins using recombinant baculoviruses offers the following advantages (i) a high level of recombinant protein expression, and (ii) the benefits of a higher eucaryotic system, including efficient protein translocation and modification. This system is particularly useful for expression of translocated proteins, e.g., HGV E1, E2 and NS2a.

1. Cloning and Expression.

Spodoptera frugiperda insect cell culture Sf21 and a derivative of Autografa californica nuclear polyhedrosis virus "BACULOGOLD" (Pharmingen, San Diego, Calif.) were used for expression of HGV polypeptides. Established protocols were used for insect cell cultivation and for generation of recombinant baculoviruses by co-transfection of baculovirus plasmid transfer vectors with linearized baculovirus DNA (King, 1992). Conventional techniques were used for construction of baculovirus plasmid transfer vectors (Maniatis, et al.; Sambrook, et al.).

The baculovirus transfer vector pAcYM1 (King, et al., 1992) was modified by ligating a double-stranded oligonucleotide coding for a Histidine hexamer into the vector's BamHI cloning site (vector designated pAcYMIH). A stop codon (TAA) was placed after the Histidine hexamer sequence. This provides a histidine hexamer on the carboxy-termini of expressed proteins. The BamHI cloning site of the pAcYMI parent vector remained intact in the pAcYMIH and could be used for cloning various genes in-frame with the Histidine hexamer. The histidine hexamer provides a method of rapid and efficient purification of the expressed protein (Janknecht, et al., 1991).

A second baculovirus transfer vector, pVT-Bac, was also modified in a similar manner to provide a histidine hexamer on the carboxy-termini of expressed proteins. pVT-Bac like the pAcYMI vector contains a strong late polyhedrin promoter. In addition, pVT-Bac also provides a strong insect translocation signal sequence to ensure efficient translocation of the expressed proteins (Tessier, et al., 1991). The pVT-Bac vector was modified by ligating a double-stranded oligonucleotide coding for a histidine hexamer into the vector's BamHI cloning site (yielding the pVT-BacH vector). The BamHI cloning site of the pVT-Bac parent vector remains intact in the obtained pVT-BacH vector and can be used for cloning genes in-frame with the insect leader sequence and the histidine hexamer sequence.

DNA fragments coding for various HGV genes were obtained by reverse transcription PCR. Regions of the HGV genome were selected according to predicted cleavage sites (Bazan, et al., 1989; Chambers, et al., 1990b; Grakoui, et al., 1993; Kyte and Doolittle, 1982). The following primer pairs were used in RT-PCR amplification reactions using PNF 2161 source nucleic acid: E1, SEQ ID NO:242, SEQ ID NO:243; E2B (HGV signal sequence), SEQ ID NO:246, SEQ ID NO:247; E2C (insect signal sequence), SEQ ID NO:244, SEQ ID NO:245; NS2a, SEQ ID NO:248, SEQ ID NO:249; NS2b, SEQ ID NO:250, SEQ ID NO:251; NS3, SEQ ID NO:252, SEQ ID NO:253; NS4a, SEQ ID NO:254, SEQ ID NO:255; NS4b, SEQ ID NO:256, SEQ ID NO:257; NS5a, SEQ ID NO:258, SEQ ID NO:259; NS5b, SEQ ID NO:260, SEQ ID NO:261; and E1-E2-NS2a, SEQ ID NO:262, SEQ ID NO:263.

Amplified DNA fragments were digested with BamHI or BglII endonucleases and cloned into BamHI cut pAcYMI, pAcYMIH, pVT-Bac or pVT-BacH vectors. Sequences coding for the E1 and E2 carboxy-terminal anchors as well as a hydrophobic sequence at the carboxy-terminus of NS5b were deleted in order to facilitate subsequent protein purification.

The recombinant baculovirus plasmid transfer vectors containing HGV sequences were co-transfected with linearized baculovirus DNA and the recombinant viruses were selected as white foci in presence of X-gal (King, et al., 1992). Recombinant viruses were twice plaque-purified and propagated. Monolayers of Sf21 cells were infected with the recombinant baculoviruses at the multiplicity 5 p.f.u. per cell and incubated at 27° C. for 60 h. The cells were washed with PBS and lysed in TNN buffer (50 mM Tris-HCl pH 8.0, 150 mM NaCl, 0.5% "NONIDET-P40"). Inclusion bodies were isolated by spinning the cell samples at 14k for 5 minutes. The inclusion bodies were resuspended in protein dissociation buffer (10% 2-mercaptoethanol, 10% SDS, 25% glycerol, 10 mM Tris-HCl pH 6.8, 0.02% Bromphenol blue) and incubated at 100° C. for 10 minutes.

The protein expression patterns analyzed by SDS-PAGE. Proteins were separated by 0.1% SDS-18% PAGE and stained with Coomassie brilliant blue. The majority of the HGV proteins were expressed to a high level and could be easily detected on the Coomassie blue stained gels. NS5a and NS2a polypeptides were detected by $^{35}$S methionine protein labeling (King, et al., 1992).

HGV E2 protein glycosylation was examined as follows. Sf21 cells were infected with recombinant baculoviruses and processed as described above. Proteins were separated by 0.1% SDS-12% PAGE, electroblotted onto an "IMMOBILON-P" (Millipore, Bedford Mass.) membrane and reacted with *Galanthus nivalis* agglutinin (Boehringer Mannheim DIG Glycan differentiation kit) which is specific for mannose residues. The HGV E2 protein that was expressed with its own signal sequence was extensively glycosylated, indicating that the predicted E2 signal sequence can function as such.

2. Immunofluorescence Assay Analysis.

SF21 insect cells were infected with the baculovirus-HGV constructs described above. Cells were harvested, spun at 1.5K rpm for 3 minutes, washed in 1× PBS, and spun again.

For Immunofluorescence Assay (IFA) (King, et al., 1992) the cells were resuspended in PBS and layered into the wells of glass slides such that the cells formed a sub-confluent layer in the wells of the slides. The slides were air-dried. The cells fixed with pre-chilled −70° C. acetone for 10 minutes and rehydrated with PBS for 5 minutes. The excess PBS was removed by blotting. The fixed cells were treated for one hour with the following "Blocking" buffer: 40 mM Tris HCl pH 7.5, 3% goat serum, 1% BSA, 1% nonfat milk and 0.1% gelatin.

Primary antibody was then added to the fixed cells. Primary antibodies included a series of human HGV-positive sera and a positive control monoclonal antibody.

Before use, the sera were pre-absorbed for non-specific proteins using insect cell lysate. Pre-absorption was carried out overnight at 4° C. Uninfected SF21 cells were used as a negative control. After addition of a selected primary antibody (sera), the slides were incubated for 2 hours then washed several times with PBS and excess buffer removed. A secondary antibody conjugated with fluorescein (0.5 µg/ml conc.) was then added to the samples on the slides. The incubation time and temperature for the secondary antibody was the same as for the primary antibody. After incubation, slides were washed in PBS and mounted with a cover slip. The fluorescence of the cells was then determined using a fluorescence microscope.

The results of this analysis were as follows. Cells expressing HGV antigen E1-E2-NS2A were immunoreactive with 4/10 HGV-positive sera and weakly immunoreactive with an additional 2/10 sera. Cells expressing E1 were weakly immunoreactive with 1/10 sera. Cells expressing E2 were immunoreactive with 3/10 sera and weakly immunoreactive with 1/10 sera. None of the cells carrying HGV antigens were immunoreactive with supernormal control sera.

3. Western Blot Analyses of HGV proteins expressed in baculo vector

Western blot analyses of the HGV proteins expressed in recombinant baculo virus infected Sf21 insect cells were also performed. Inclusion bodies were prepared as described above and subjected to Western blot analysis. Western blot analysis was performed using pre-absorbed sera. The results of the analyses demonstrated that E2 proteins (one variant having the endogenous HGV signal sequence, E2B, and a second variant carrying an insect signal sequence, E2C) were specifically immunoreactive with HGV(+) serum 3831781.

FIGS. 15A to 15D show the results of a series of Western blot experiments examining the reactivity of baculo antigens E2B and E2C. The lanes in each blot of FIGS. 15A to 15D were as follows: Lane 1, pre-stained molecular weight marker (Bio-Rad); Lane 2, E2B lysate; Lane 3, E2C lysate; Lane 4, β-galactosidase lysate. Each blot was incubated with a human or rabbit serum : FIG. 15A, rabbit anti-E2 antibody; FIG. 15B, 3831781 (an HGV-PCR-positive serum); FIG. 15C, 3838857 (an HGV-negative serum). FIG. 15D a Coomassie Stain. The serum or rabbit antibody that was used is indicated above each blot. Human sera were diluted 1:100 and rabbit serum was diluted 1:1000.

Further, HGV antigen NS2b protein expressed in insect cells was immunoreactive with J21689. These results are consistent with the results obtained with pET expressed HGV proteins.

C. Expression of Larger Antigens in Vaccinia.

1. Cloning and Expression.

Figure 16:
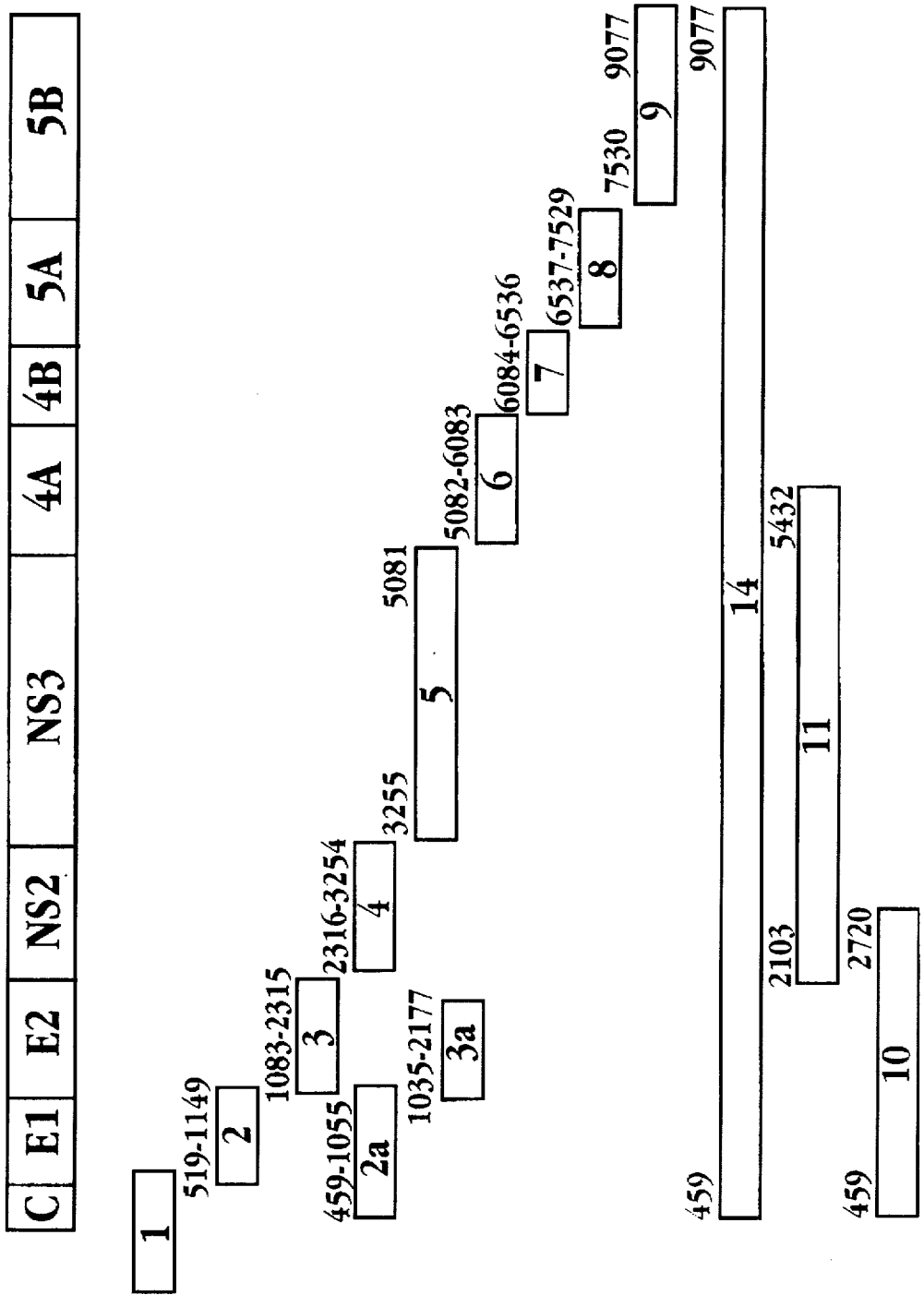
FIG. 16 shows a schematic representation of the coding regions of HGV.

Various regions of HGV genome were integrated into vaccinia virus genome for expression. An exemplary HGV polypeptide expression strategy is given in FIG. 16. HGV (PNF 2161 variant) proteins expressed in vaccinia virus are schematically illustrated in FIG. 16. Full length polyprotein is drawn (not to scale) by an open box indicating regions of predicted proteins: C=highly basic protein, 4A=NS4A, 4B=NS4B, 5a=NS5A, 5b=NS5B. The individual boxes with nucleotide locations (below the polyprotein) represents exemplary regions of HGV for expression in vaccinia virus. The number in the box stands for recombinant virus nomenclature. Virus #1 was derived from the highly basic protein region of HGV Stain T55806 (SEQ ID NO:185).

Two sets of recombinant viruses were generated. The first set contained HGV sequences that correspond to individual protein domains based on sequence analysis of HGV cDNA (FIG. 16, fragments #1 to #9). The second set contained HGV sequences that spanned multiple protein domains, up to full length of HGV genome (FIG. 16, #10, #11, #14).

The various regions of the HGV genome were cloned into the multicloning site of the vaccinia expression vector. A recombinant vaccinia virus expression system was used that included bacterial phage T7 system and *E. coli* lac repressor for high level inducible expression (Fuerst, 1986; Elroy-Stein, 1989; Alexander, 1992; Moss, et al.). Therefore, recombinant protein is expressed only in the presence of an inducer, such as isopropyl beta-D-thiogalactoside (IPTG). Both direct cloning and PCR were used for plasmid construction. In the latter, restriction endonuclease sites suitable for cloning into the vaccinia vector were incorporated into primers used to amplify individual DNA fragment.

A polyhistidine tag was also incorporated into every clone covering individual domains of HGV for use in purifying the expressed proteins. HGV-PCR amplification products were digested with the appropriate restriction enzymes and ligated into the vaccinia vector. Target HGV cDNA fragments were integrated into vaccinia virus genome through homologous recombination and drug (mycophenolic acid) selection (Falkner, 1988, Earl, 1991). Recombinant virus were plaque purified 4 times before a viral stock was generated.

The length of each clone in nucleotides is indicated in FIG. 16. The group of smaller clones (#1 to #9) are useful for HGV epitope mapping. The larger clones (e.g., #10, #11 and #14) are also useful for mapping the HGV polyprotein cleavage sites experimentally. In addition to the clones shown in FIG. 16, additional recombinant viruses covering multiple domains from NS3 to NS5b can be constructed.

Expression plasmids were transfected into mammalian cells which had been infected with a parent vaccinia virus. CV-1 and BS-C-1 cells were maintained in Minimum Essential Medium (MEM) supplemented with 10% fetal bovine serum. The cells were used for transfection (CV-1) and recombinant virus selection and propagation (BS-C-1).

2. Evaluation of recombinant protein expression.

BS-C-1 cells were infected with recombinant virus in the presence or absence of IPTG for 7 hours after which cells were labeled with $^{35}$S-methionine for another one hour (Zhang, 1991). Briefly, 1×10$^6$ BS-C-1 cells were infected with recombinant virus at a multiplicity of infection (MOI) of 10 plaque forming unit (PFU) per cell for 1 h and then supplemented with medium in the presence or absence of 5 mM IPTG for another 6 h. Cells were pulse-labeled with 600 ul Methionine-free medium supplemented with 2.5% dialyzed fetal bovine serum plus 60 uCi 35S-methionine ("TRAN $^{35}$S-LABEL", ICN, Costa Mesa, Calif.) in the presence or absence of 5 mM IPTG for another 60 min. Labeled cells were then lysed on ice for 10 min in the presence of 100 mM Tris pH8.0, 150 mM NaCl, and 1% "TRITON X-100." Nuclei were spun down and supernatant was collected for analysis.

Cell lysate was analyzed by SDS-polyacrylamide gel electrophoresis (Fling, 1986; Schagger, 1987). Gels were fixed with 50% methanol and 10% acetic acid before they were treated with a fluorograph solution "AMPLIFY" (Amersham, Arlington Heights, Ill.). Gels were dried and exposed to X-ray film.

Using this method, expression of HGV polypeptides by viruses containing inserts #4 to #11, and #14 (FIG. 16) has been confirmed. Expression of polypeptides corresponding to other regions is confirmed in a similar manner. For example, in a NS5a construct, upon induction by IPTG, a unique polypeptide was produced that migrated just below a 46 KDa protein standard. This protein was not seen in the infection in the absence of IPTG induction, establishing the identity of the protein as NS5a recombinant protein.

Further, limited immunoprecipitations using HGV region-specific antisera (for example, rabbit anti-sera raised against an isolated HGV polypeptide from the region of interest) against $^{35}$S-Met labeled cell lysate from individual virus infections was carried out to evaluate the protein expression from recombinant viruses. For example, expression of NS2, NS3, NS4B, NS5A and NS5B has been confirmed. An alternative method, to evaluate recombinant protein expression is to perform western blot analysis with HGV-region-specific antisera.

When the full length HGV polyprotein was expressed in #14 virus (FIG. 16), processed products of NS2, NS3 and NS5A were detected using immunoprecipitation with HGV region-specific antisera, demonstrating the usefulness of the full length HGV clone to evaluate polyprotein processing.

Using an expression strategy similar to that shown in FIG. 16, candidate HGV proteins/antigens can be expressed in yeast or CHO cells. Yeast offers high level of expression, economical operation, and ease of scaling up for commercial production. CHO cell lines allow secretion of the recombinant proteins into growth media for large scale protein production and purification useful, for example, for vaccine development.

EXAMPLE 17

HGV Encoded Highly Basic Proteins

A. Determination of the Methionine used for Initiation in the translation of HGV from PNF and T55806.

The methionine located at nucleotide (nt) 459 (relative to SEQ ID NO:14) in the HGV-PNF 2161 variant is in-frame with the polyprotein. The "capsid" region appears to be 32 amino acid long. In other HGV isolates, such as T55806, this region is longer (e.g., about 83 amino acids). The methionine located at nt 349 (relative to SEQ ID NO:14) in HGV-PNF 2161 variant is not in-frame with the polyprotein sequence, but a methionine at the same position in HGV-T55806 variant is in frame with the polyprotein. To see if there is a read-through or a ribosomal frame shift at this position in HGV-PNF 2161, the following experiments were carried out.

Constructs were made containing (i) HGV genomic sequences having all the MET codons upstream of the HGV E1 region (e.g., in HGV-PNF 2161 there are six such METs and five such in T55806), (ii) two different 3' ends for each construct to allow determination of whether a ribosome shift of read-through occurs. For a given genomic DNA, if both translated products are the same size, that suggests they are terminated prematurely at the stop codon. On the other hand, if read-through or frameshift occurs two products that differ by 55 amino acids are expected.

A total of 21 constructs containing sequences from variants HGV-PNF 2161 and HGV-T55806 were subcloned in a pGEX vector and corresponding proteins expressed in *E. coli*. Sizes of the resulting translation products were determined by both Coomassie stained gels and Westerns that were blotted with monoclonal anti-GST antibody. Induced and un-induced samples were prepared for each construct.

The results demonstrated that the size of the protein products corresponded to that expected by translation initiating at the first MET in-frame with the polyprotein. There was no evidence of frame-shifting or read-through.

B. Alternative Encoded Highly Basic Proteins.

The method of Fickett (1982) was used to scan the genomic sequences HGV-PNF 2161 and HGV-JC for sequences that potentially encode proteins (i) alternative to the previously described polyprotein, (ii) showing conservation between HGV-PNF 2161 and HGV-JC, and (iii) having predicted isoelectric points in excess of pH 10. Two such potential proteins were identified.

The first protein is encoded by residues 628 through 882 (relative to SEQ ID NO:14) in HGV-PNF 2161 and by residues 556 through 810 (relative to SEQ ID NO:182) in HGV-JC. This protein is 85 amino acids long, is greater than 75% homologous between HFV94-1 and JC9B, and has a predicted pI of 11.6–12.3.

The second protein is encoded by residues 6844 through 7125 in HGV-PNF 2161 (relative to SEQ ID NO:14) and by 6772 to 7053 in HGV-JC (relative to SEQ ID NO:182). This protein is 94 amino acids long, is greater than 88% homologous between HGV-PNF 2161 and HGV-JC, and has a predicted pI of 12.4–12.7.

These exemplary two proteins represent potentially expressed highly basic proteins of HGV.

EXAMPLE 18

Cloning Further HGV Isolates and Design of Diagnostic Primers

A. Construction of a cDNA Clone of HGV-PNF 2161.

A cDNA clone of the nearly full-length HGV genome from PNF 2161 was constructed by cloning three overlapping PCR products into the plasmid vector pGEM3Z (Promega, Madison, Wis.). The PCR products used in this construction were obtained by reverse transcription with "SUPERSCRIPT II" (Gibco/BRL, Gaithersburg, Md.) followed by PCR using reaction conditions that allowed for the amplification of long target sequences ("rTth-XL" polymerase and "XL PCR BUFFERS", Applied Biosystems, Foster City, Calif.). The rTth enzyme used for these "long-range" PCR reactions has proof-reading activity (i.e. 3' to 5' exonuclease activity) that corrects mis-incorporated nucleotides, thus providing for high fidelity PCR.

The three products used to construct the HGV genome included (i) an internal 6.7 kb product (nt 2101 to 8834 of SEQ ID NO:14) amplified using the primers GV75-36FE (SEQ ID NO:228) and GV75-7064RLE (SEQ ID NO:229), (ii) a 2.8 kb 5'-end product (nt 38 to 2899 of SEQ ID NO:14) amplified using 28F (SEQ ID NO:230) and FV94-2864R (SEQ ID NO:231), and (iii) a 2.9 kb 3'-end product (nt 6449 to 9366 of SEQ ID NO:14) amplified using FV94-6439F (SEQ ID NO:232) and FV94-9331R (SEQ ID NO:233).

Initially, the 6.7 kb internal fragment was cloned into the "TA-vector" pCRII to create the clone HGV7. Subsequently, a 6.1 kb KpnI/EcoRI fragment was removed from HGV7 and combined with the KpnI/XbaI digested 2.8 kb 5'-end product (the primer 28F contains an artificial XbaI site) and cloned into XbaI/EcoRI digested pGEM3Z. This 8.8 kb clone, which lacks about 0.6 kb of the 3' portion of the HGV genome, was designated HGV-KEX-2. To construct the nearly full-length HGV genome, the 3'-end HGV product was digested with NheI and EcoRI (the primer FV94-9331R contains an artificial EcoRI site) and cloned into NheI/EcoRI digested HGV-KEX-2 plasmid creating a cloned HGV-PNF2161 sequence of 9329 nt (nt 38 to 9366 of SEQ ID NO:14) that is designated 3Z-HGV94-6. The complete sequence of 3Z-HGV94-6 is presented as SEQ ID NO:234.

The clone 3Z-HGV94-6 may be used to generate in vitro-transcribed full-length HGV RNA or portions thereof (e.g., using SP6 polymerase). The RNA molecules can be used to transfect human cell lines. This approach could be used to map the various regions of the viral genome, study its replication, and understand the mechanisms of HGV pathogenicity in human cells (Rice, et al., 1989; Sumiyoshi, et al., 1992; Yoo, et al., 1995).

B. Cloning the JC Variant.

One milliliter of JC serum was spun at 40,000 rpms (Beckman, Spinco Rotor 70.1Ti) for 2 hours. The resulting pellet was extracted using "TRIREAGENT" (MRC, Cincinnati, Ohio), resulting in the formation of 3 phases. The upper phase contained RNA only. This phase was taken and RNA recovered by ethanol precipitation.

HGV cDNA molecules were generated from the JC sample by two methods. The first method was amplification (RT-PCR) of the JC nucleic acid sample using specific and nested primers. The primer sequences were based on the HGV sequence obtained from PNF 2161 serum. The criteria used to select the primers were (i) regions having a high G/C content, and (ii) no repetitious sequences.

The second method used to generate HGV cDNA molecules was amplification using HGV (PNF 2161) specific primers followed by identification of HGV specific sequences with $^{32}$P-labelled oligonucleotide probes. Such DNA hybridizations were carried out essentially as described by Sambrook, et al. (1989). The PCR derived clones were either (i) cloned into the "TA" vector (Invitrogen, San Diego, Calif.) and sequenced with vector primers (TAR and TAF), or (ii) sequenced directly after PCR amplification. Both the probe and primer sequences were based on the HGV variant obtained from the PNF 2161 serum.

These two approaches yielded multiply-overlapping HGV fragments from the JC serum. Each of these fragments were cloned and sequenced. The sequences were aligned to obtain the HGV (JC-variant) consensus sequence presented as SEQ ID NO:182 (polypeptide sequence, SEQ ID NO:183). The sequence of each region of the HGV (JC-variant) virus was based on a consensus from at least three different, overlapping, independent clones.

C. Other HGV Variants.

In addition to the HGV PNF 2161-variant and JC-variant sequences, three partial HGV isolates have been obtained from the sera BG34, T55806 and EB20 by methods similar to those described above. The partial sequences of these isolates are presented as SEQ ID NO:176 (BG34 nucleic acid), SEQ ID NO:177 (BG34 polypeptide), SEQ ID NO:178 (T55806 nucleic acid), SEQ ID NO:179 (T55806 polypeptide), SEQ ID NO:180 (EB20-2 nucleic acid) and SEQ ID NO:181 (EB20-2 polypeptide).

D. Alternative Primers for Diagnostic PCR.

PCR primers and corresponding assay development may be derived from regions of the HGV genome(s) typically based on the analysis of conserved regions. Based on comparisons of the HGV-JC variant and the HGV-PNF 2161 variant, the 5' untranslated region of HGV was selected as one such region for development of a further PCR-based diagnostic test for the detection of HGV isolates. Two exemplary primers are FV-94-22F (SEQ ID NO:124) and FV94-724R (SEQ ID NO:125). These primers amplify an approximately 728 bp fragment of the HGV genome.

Sequence analysis was performed on amplification products from reactions employing these two primers for 36 isolates of HGV (including PNF 2161 and JC, see Table 26). An approximately 400 bp region (nt 69 to 469 of SEQ ID NO:14) of the approximately 728 bp amplification product was used for multiple sequence alignments (Table 26) and further determination of conserved regions (see below).

TABLE 26

| SEQ ID NO: | Serum Code | Country | % ID PNF 2161 |
|---|---|---|---|
| 186 | S59 | England | 96.8 |
| 187 | S368 | England | 98.8 |
| 188 | S309 | England | 95.5 |
| 189 | FZ | Australia | 96 |
| 190 | G21 | Greece | 97.8 |
| 191 | G23 | Greece | 94.3 |
| 192 | G59 | Greece | 93.6 |
| 193 | E36 | Egypt | 94 |
| 194 | R38730 | USA | 94.8 |
| 195 | G281 | Greece | 97.8 |
| 196 | G157 | Greece | 94.3 |
| 197 | G154 | Greece | 96 |
| 198 | G213 | Greece | 94.8 |
| 199 | G204 | Greece | 98.3 |
| 200 | G191 | Greece | 94.8 |
| 201 | G299 | Greece | 94.8 |
| 202 | T56957 | USA | 95.3 |
| 203 | C01698 | USA | 98.8 |
| 204 | T27034 | USA | 93.5 |
| 205 | E57963 | USA | 98.5 |
| 206 | R37166 | USA | 97.5 |
| 207 | B5 | Germany | 95.5 |
| 208 | B33 | Germany | 95.5 |
| 209 | FH010 | Australia | 95 |
| 210 | PNF2161 | USA | 100 |
| 211 | JC | USA | 96.3 |
| 212 | 7155 | Peru | 89.8 |
| 213 | 7244 | Peru | 89 |
| 214 | K27 | Korea | 89.5 |
| 215 | K30 | Korea | 89.5 |
| 216 | T55875 | USA | 97.3 |
| 217 | T56633 | USA | 93.5 |
| 218 | EB20 | Egypt | 94.1 |
| 219 | T55806 | USA | 95.6 |
| 220 | BG34 | Greece | 94.8 |
| 221 | BE12 | Egypt | 95 |

The development of an amplification-based (e.g., PCR) or probe-based method/assay for the detection of HGV isolates in samples involves the selection of appropriate primer/probe sequences. Two criteria for such an assay are low copy sensitivity and specificity for HGV sequences. Alignments of sequences (such as just described) can help guide primer/probe selection and design.

Several criteria for selecting primers are as follows: (i) forward and reverse primers of a pair should not be significantly complementary in sequence, and (ii) primers should not have significant self complementarity or the potential to form secondary structures. These precautions minimize the potential for generation of primer dimers or oligomers.

Primers may optimally be designed from sequence regions showing no variation among different isolates but may also be designed from regions of less homology by incorporating mixed base synthesis or neutral bases, such as inosine, at those positions to account for known isolate divergence. The following two groups of primers are examples of primers may be employed in development of a PCR-based assay for detection of HGV genomes: forward primers SEQ ID NO:222, SEQ ID NO:223 and SEQ ID NO:224; and reverse primers SEQ ID NO:225, SEQ ID NO:226 and SEQ ID NO:227.

Various combinations of primers, may be employed in development of an HGV diagnostic assay. Optimal combinations of primers are experimentally determined and typically address considerations for assay sensitivity and specificity. Such considerations include the following: (i) a PCR product length of 100–300 bp for efficient amplification and ease of product detection; (ii) an ability to reproducibly detect at least 10 copies of target HGV, and (iii) an ability to reproducibly detect a majority of HGV variants.

In addition, probe sequences may be similarly designed with mixed base or neutral base syntheses and/or may be used at reduced stringency so as to detect a majority of HGV variants.

While the invention has been described with reference to specific methods and embodiments, it will be appreciated that various modifications and changes may be made without departing from the invention.

It is claimed:

1. A purified antibody preparation made against a polypeptide of SEQ ID NO: 15 or a fragment thereof which is specifically immunoreactive with Non-A Non-B Non-C Non-D Non-E Hepatitis G Virus (HGV), where HGV is characterized by the following: (i) elevated serum alanine aminotransferase levels in an infected primate, (ii) serologic distinctness from hepatitis A virus (HAV), hepatitis B virus (HBV), hepatitis C virus (HCV), hepatitis D virus (HDV) and hepatitis E virus (HEV), and (iii) a viral genome comprising a polynucleotide region that is selectively hybridizable with SEQ ID NO:19.

2. The preparation of claim 1 comprising an anti-Non-A Non-B Non-C Non-D Non-E Hepatitis G Virus (HGV) polyclonal antibody.

3. The preparation of polyclonal antibodies of claim 2, where said polyclonal antibodies are obtained by affinity chromatography.

4. A method for producing an antibody to Non-A Non-B Non-C Non-D Non-E Hepatitis G Virus (HGV), comprising
  administering to a test subject a polypeptide of SEQ ID NO: 15 or a fragment thereof which is specifically immunoreactive with antibodies directed against Non-A Non-B Non-C Non-D Non-E Hepatitis G Virus (HGV) in an amount sufficient to produce an immune response,
  wherein HGV is characterized by the following: (i) elevated serum alanine aminotransferase levels in an infected primate, (ii) serologic distinctness from hepatitis A virus (HAV), hepatitis B virus (HBV), hepatitis C virus (HCV), hepatitis D virus (HDV) and hepatitis E virus (HEV), and (iii) a viral genome comprising a polynucleotide region that is selectively hybridizable with SEQ ID NO: 19, and
  obtaining from the subject, said antibody.

5. A diagnostic kit for use in screening a biological fluid sample containing a Non-A Non-B Non-C Non-D Non-E Hepatitis G Virus (HGV) polypeptide antigen, comprising
  the anti-HGV antibody preparation of claim 1, and
  a reporter for detecting the binding of said polypeptide antigen to said antibody.

6. The kit of claim 5, where said antibody is a monoclonal antibody.

7. The kit of claim 5, where said antibody is attached to a solid support.

8. The kit of claim 5, wherein said reporter comprises a second antibody preparation consisting of a labeled monoclonal antibody.

9. The kit of claim 5, where said reporter comprises a labeled, competing antigen.

10. The method of detecting Non-A Non-B Non-C Non-D Non-E Hepatitis G Virus (HGV) in a test subject, comprising
  reacting a biological fluid sample from a test subject with an antibody of the kit of claim 5, and
  examining the antibody for the presence of bound antigen.

11. The preparation of claim 1 comprising an anti- Non-A Non-B Non-C Non-D Non-E Hepatitis G Virus (HGV) monoclonal antibody.

12. The kit of claim 5 where said antibody is a polyclonal antibody.

* * * * *